US007547759B2

(12) United States Patent
Ioannides et al.

(10) Patent No.: US 7,547,759 B2
(45) Date of Patent: Jun. 16, 2009

(54) INDUCTION OF TUMOR IMMUNITY BY VARIANTS OF FOLATE BINDING PROTEIN

(75) Inventors: Constantin G. Ioannides, Houston, TX (US); George E. Peoples, Jr., Fulton, MD (US)

(73) Assignees: Board of Regents, The University of Texas System, Austin, TX (US); Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 0 days.

(21) Appl. No.: 10/094,097

(22) Filed: Mar. 8, 2002

(65) Prior Publication Data

US 2003/0185840 A1 Oct. 2, 2003

Related U.S. Application Data

(60) Provisional application No. 60/274,676, filed on Mar. 9, 2001.

(51) Int. Cl.
*C07K 17/00* (2006.01)

(52) U.S. Cl. ........................ 530/328; 530/300; 530/350

(58) Field of Classification Search ................. 530/300, 530/328, 350, 327, 326, 325, 324; 514/2, 514/15; 424/185.1, 277.1
See application file for complete search history.

(56) References Cited

U.S. PATENT DOCUMENTS

| | | | | |
|---|---|---|---|---|
| 5,830,755 | A | 11/1998 | Nishimura et al. | |
| 5,846,538 | A | 12/1998 | Cheever et al. | |
| 6,153,430 | A * | 11/2000 | Pastan et al. | 435/325 |
| 6,514,942 | B1 * | 2/2003 | Ioannides et al. | 514/15 |
| 2003/0027766 | A1 * | 2/2003 | Ioannides et al. | 514/13 |
| 2003/0077248 | A1 * | 4/2003 | Moriarty et al. | 424/85.2 |

OTHER PUBLICATIONS

Greenspan et al., (Nat Biotechnol. Oct. 1999;17 (10) :936-937).*
Yu et al. (Mol Med. Mar. 2002; 8 (3):137-148).*
McCoullough et al. (ILAR J. 2005; 46 (3): 230-240).*
Bowie et al. (Science. 1990; 257: 1306-1310).*
Holmes (Expert Opinion on Investigational Drugs. 2001, 10: 511-519).*
Huard et al. (Int. Immunol. 1997; 9 (11):1701-1707).*
Fisk et al. (J. Immunother. Emphasis Tumor Immunol. Nov. 1995: 18 (4): 197-209).*
Ruppert et al. (Cell. Sep. 10, 1993; 74 (5): 929-937).*
Valmori et al. (J. Immunol. 1998; 163: 6956-6962).*
Guichard et al. (J. Med. Chem. 2000; 43: 3803-3808).*
Schirle et al. (J. Immunol. Methods. 2001; 257: 1-16).*
Anderson et al. (Tissue Antigens. Jun. 2000; 55 (6): 519-531).*
Feltkamp et al. (Mol. Immunol. Dec. 1994; 31 (18): 1391-1401).*
van der Burg et al. (J. Immunol. May 1, 1996; 156 (9): 3308-3314).*
Valmori et al. (Journal of Immunology. 1998; 160: 1750-1758).*
Campbell et al. (Cancer Res. Oct. 1991; 51 (19): 5329-5338).*
Yamshchikov, et al (Clinical Cancer Research. 2001; 7: 909s-916s).*
Bodey et al. (Anticancer Research 20: 2665-2676, 2000).*
Ezzell (Journal of NIH Research 7: 46-49, 1995).*
Spitler (Cancer Biotherapy 10: 1-3, 1995).*
Lee et al. (Journal of Immunology 163:6292-6300, 1999).*
Zaks et al. (Cancer Research 58: 4902-4908, 1998).*
Gao et al. (Journal of Immunotherapy 23:643-653, 2000).*
Lu et al. (J. Controlled Release. 2003; 91; 17-29).*
Lollini et al. (Trends in Immunology. Feb. 2003; 24 (2): 62-66).*
Gura (Science. 1997; 278:1041-1042).*
Saijo et al. (Cancer Sci. Oct. 2004; 95 (10): 772-776).*
Forni et al. (Int. Immunopharmacol. 2003; 3: 1151-1158).*
Skolnick et al. (Trends in Biotechnology 2000; 18 (1): 34-39).*
De Plaen et al. (Immunogenetics. 1994; 40:360-369).*
Li, Pei Yong, et al.; Local Concentration of Folate Binding Protein GP38 in Sections of Human Ovarian Carcinoma by In Vitro Quantitative Autoradiography; J Nucl Med 1996; 37:665-672.
Ioannides, Constantin G., et al.; Lymphocytes Infiltrating Ovarian Malignant Ascites: Modulation of IL-2-Induced Proliferation by IL-4 and of Selective Increase in CD8+ T Cells by TNF-a; Lymphokine and Cytokine Research, vol. 10 (4), 1991, pp. 307-315.
Ioannides, Constantin G., et al.; Induction of interleukin—2 receptor by tumor necrosis factor a on cultured ovarian tumor-associated lymphocytes; Cancer Immunol Immunother (1992) 35:83-91.
Ioannides, Constantin G., et al.; Cytotoxic T Cells from Ovarian Malignant Tumors Can Recognize Polymorphic Epithelial Mucin Core Peptides; The Journal of Immunology, vol. 151 (7), pp. 3693-3703, Oct. 1, 1993.
Falk, Kirsten, et al.; Allele-specific motifs revealed by sequencing of self-peptides eluted from MHC molecules; Nature, vol. 351, pp. 290-296, May 23, 1991.
Alexander, Richard B., et al.; Adoptively Transferred Tumor-Infiltrating Lymphocytes Can Cure Established Metastatic Tumor in Mice and Persist Long-Term In Vivo as Functional Memory T Lymphocytes; Journal of Immunotherapy 10:389-397, 1991.
Bednarek, Maria A., et al.; Soluble HLA-A2.1 restricted peptides that are recognized by influenza virus specific cytotoxic T lymphocytes; Journal of Immunological Methods, 139 (1991) 41-47.
Buelow, Roland, et al.; Localization of the immunologic activity in the superantigen staphylococcal enterotoxin B using truncated recombinant fusion proteins; The Journal of Immunology, vol. 148 (1), pp. 1-6, Jan. 1, 1992.
Pietersz, G. A., et al.; Generation of Cellular Immune Responses to Antigenic Tumor Peptides; CMLS Cellular and Molecular Life Sciences 57 (2000) 290-310.
Pardoll, Drew M.; Therapeutic Vaccination for Cancer; Clinical Immunology, vol. 95, No. 1, April, pp. S44-S62. 2000.
Rosenberg, Steven A., The Identification of Cancer Antigens: Impact on the Development of Cancer Vaccines; The Cancer Journal; S142-S149.

(Continued)

*Primary Examiner*—Stephen L Rawlings
(74) *Attorney, Agent, or Firm*—Fulbright & Jaworski, LLP

(57) ABSTRACT

The present invention is directed to variants of antigens comprising folate binding protein epitopes as a composition associated with providing immunity against a tumor in an individual. The variant is effective in inducing cytotoxic T-lymphocytes but preferably not to the extent that they become sensitive to silencing by elimination, such as by apoptosis, or by energy, as in unresponsiveness.

2 Claims, 6 Drawing Sheets

OTHER PUBLICATIONS

Lee, Tom V., et. al.; Identification of Activated Tumor Antigen-Reactive CD8+ Cells in Healthy Individuals; Onocoloy Reports 7: 455-466, 2000.

Dalgleish, AG; Cancer Vaccines; British Journal of Cancer (2000) B2(10), 1619-1624.

Abrams, Scott, et al.; Rational Antigen Modification as a Strategy to Upregulate of Downregulate Antigen Recognition; Immunology 2000, 12:85-91.

Kim, Dong-Kyu, et al.; Folate Binding Protein Peptide 191-199 Presented on Dendritic Cells Can Stimulate CTL from Ovarian and Breast Cancer Patients; Anticancer Research 19:2907-2916 (1999).

Peoples, George E., et al.; Ovarian Cancer-Associaed Lymphocyte Recognition of Folate Binding Protein Peptides; Annals of Surgical Oncology, 5(8): 743-750, Published by Lippincott Williams & Wilkins, copyright 1998 The Society of Surgical Oncology, Inc.

Peoples, George, E., et al.; Vaccine Implications of Folate Binding Protein, a Novel Cytotoxic T Lymphocyte-recognized Antigen System in Epithelial Cancers; Texas Medical Association Library, vol. 5, 4314-4223, Dec. 1999.

Hudson, J. Michael, et al.; Growth and Antigen Recognition of Tumor-Infiltrating Lumphocytes from Human Breast Cancer; Journal of Interferon and Cytokine Research 18:529-536 (1998).

Ioannides, Constantin G., et al.; Cytotoxic T Cell Clones Isolated From Ovarian Tumor-Infiltrating Lymphocytes Recognize Multiple Antigenic Epitopes on Autologous Tumor Cells; The Journal of Immunology, vol. 146 (5), 1700-1707, Mar. 1, 1991.

Ioannides, Constantin G., et al.; T-Cell Recognition of Oncogene Products: A New Straategy for Immunotherapy; Molecular Carcinogenesis 6:77-82 (1992).

Ioannides, Constantin G., et al.; Cytotoxic T Cells Isolated from Ovarian Malignant Ascites.

Kos, Ferdynand J., et al,; Specific epitope-induced conversion of CD8+ memory cells into effector cytotoxic T lymphocytes in vitro: presentation of peptide antigen by CD8+ T cells; Eur. J. Immunol. 1992, 22:1595-1601.

Kim, Dong-Kyu, et al.; The Comparison of Cytotoxic T-Lymphocyte Effects of Dendritic Cells Stimulated by the Folate Binding Protein Peptide Cultured with IL-15 and IL-2 in Solid Tumor, Yonsei Medical Journal, (Sep. 2002), vol. 43, No. 6, pp. 691-700.

National Center for Biotechnology Information GenBank Accession No. 1011184A, submitted Jun. 21, 1996; downloaded Sep. 7, 2004.
National Center for Biotechnology Information GenBank Accession No. 0908212A, submitted May 2, 1996; downloaded Sep. 7, 2004.
National Center for Biotechnology Information GenBank Accession No. CAA44610, submitted Feb. 19, 1992; downloaded Sep. 7, 2004.
National Center for Biotechnology Information GenBank Accession No. CAA83553, submitted Apr. 15, 1994; downloaded Sep. 7, 2004.
National Center for Biotechnology Information GenBank Accession No. AAA74896, submitted Aug. 25, 1995; downloaded Sep. 7, 2004.
National Center for Biotechnology Information GenBank Accession No. AAA49056, submitted Apr. 28, 1993; downloaded Sep. 7, 2004.
National Center for Biotechnology Information GenBank Accession No. AAA37599, submitted Apr. 27, 1993; downloaded Sep. 7, 2004.
National Center for Biotechnology Information GenBank Accession No. AAA37598, submitted Apr. 27, 1993; downloaded Sep. 7, 2004.
National Center for Biotechnology Information GenBank Accession No. AAA37597, submitted Apr. 27, 2003; downloaded Sep. 7, 2004.
National Center for Biotechnology Information GenBank Accession No. AAA37594, submitted Apr. 19, 1994; downloaded Sep. 7, 2004.
National Center for Biotechnology Information GenBan Accession No. AAA37596, submitted Apr. 27, 1993; downloaded Sep. 7, 2004.
National Center for Biotechnology Information GenBank Accession No. AAA37595, submitted Apr. 27, 1993; downloaded Sep. 7, 2004.
National Center for Biotechnology Information GenBank Accession No. AAA35824, submitted Apr. 27, 1993; downloaded Sep. 7, 2004.

Castilleja et al., "Induction of Tumor-Reactive CTL by C-Side Chain Variants of the CTL Epitope HER-2/neu Protooncogene (369-377) Selected by Molecular Modeling of the Peptide: HLA-A2 Complex", The Journal of Immunology, 2002, 3545-3554, vol. 169(7).

Ioannides, "Clarification of the Functional Significance of Human Folate-binding Protein-•, Peptide 191-199, based on a Correct GenBank Sequence and on Other FBP (191-199) Sequences", Anticancer Res.; 2251-2, vol. 27 (4B).

Mazzoni et al., "CD3-CD28 Costimulation as a Means to Avoiding T Cell Preactivation in Bispecific Monoclonal Antibody-based Treatment of Ovarian Carcinoma", Cancer Research, Dec. 1, 1996, 5443-5449, 56(23).

* cited by examiner

CTL Activity
E39 µg/mL
(% Specific Lysis)

|                | 0µg/mL | 5µg/mL | 25µg/mL |
|----------------|--------|--------|---------|
| 1. J65x3, E39  | 0      | 24.5   | 17.4    |
| 2. J65x3, J77  | 0      | 4.2    | 8.2     |
| 3. J65x3, J65  | 0      | 20.9   | 23.2    |
| 4. E39x3, E39  | 0      | 11.1   | 14.6    |

Figure 2B

INDUCTION OF TUMOR IMMUNITY BY VARIANTS OF FOLATE BINDING PROTEIN

The present invention claims priority to U.S. Provisional Patent Application Ser. No. 60/274,676 filed Mar. 9, 2001, incorporated by reference herein in its entirety.

The government owns rights in the present invention pursuant to United States Army grant number DAMD 17-94-J-4313.

FIELD OF THE INVENTION

The present invention is directed to the fields of cancer and immunology. Specifically, the present invention is directed to compositions and methods for tumor vaccines directed to tumor antigens and is directed to specific epitopes on these antigens that are recognized by cytotoxic T-lymphocytes (CTL). More specifically, the present invention regards compositions and methods for variants of folate binding protein (FBP).

BACKGROUND OF THE INVENTION

Tumor reactive T-cells have been reported to mediate therapeutic responses against human cancers (Rosenberg et al., 1988). In certain instances, in human immunotherapy trials with tumor infiltrating lymphocytes (TIL) or tumor vaccines, these responses correlated either with in vitro cytotoxicity levels against autologous tumors (Aebersold et al., 1991) or with expression of certain HLA-A,B,C gene products (Marincola et al., 1992). Recent studies (Ioannides et al., 1992) have proposed that in addition to virally encoded and mutated oncogenes, overexpressed self-proteins may elicit some degree of tumor-reactive cytotoxic T-lymphocytes (CTLs) in patients with various malignancies (Ioannides et al., 1992; Ioannides et al., 1993; Brichard et al., 1993; Jerome et al., 1991). Autologous tumor reactive CTLs can be generated from lymphocytes infiltrating ovarian malignant ascites (Ioannides et al., 1991), and overexpressed proteins, such as HER-2, may be targets for CTL recognition (Ioannides et al., 1992).

T-cells play an important role in tumor regression in most murine tumor models. Tumor infiltrating lymphocytes (TIL) that recognize unique cancer antigens can be isolated from many murine tumors. The adoptive transfer of these TIL in addition to interleukin-2 can mediate the regression of established lung and liver metastases (Rosenberg et al., 1986). In addition, the secretion of IFN-γ by injected TIL significantly correlates with in vivo regression of murine tumors suggesting activation of T-cells by the tumor antigens (Barth et al., 1991). The known ability of TIL to mediate the regression of metastatic cancer in 35 to 40% of melanoma patients when adoptively transferred into patients with metastatic melanoma attests to the clinical importance of the antigens recognized (Rosenberg et al., 1988; Rosenberg, 1992).

Strong evidence that an immune response to cancer exists in humans is provided by the existence of tumor reactive lymphocytes within melanoma deposits. These lymphocytes, when isolated, are capable of recognizing specific tumor antigens on autologous and allogeneic melanomas in an MHC restricted fashion. (Itoh et al., 1986; Muul et al., 1987; Topalian et al., 1989; Darrow et al., 1989; Hom et al., 1991; Kawakami et al., 1992; Hom et al., 1993; O'Neil et al., 1993). TIL from patients with metastatic melanoma recognize shared antigens including melanocyte-melanoma lineage specific tissue antigens in vitro (Kawakami et al., 1993; Anichini et al. 1993). Anti-melanoma T-cells appear to be enriched in TIL, probably as a consequence of clonal expansion and accumulation at the tumor site in vivo (Sensi et al., 1993). The transduction of T-cells with a variety of genes, such as cytokines, has been demonstrated. T-cells have been shown to express foreign gene products. (Blaese, 1993; Hwu et al., 1993; Culver et al., 1991) The fact that individuals mount cellular and humoral responses against tumor associated antigens suggests that identification and characterization of additional tumor antigens is important for immunotherapy of patients with cancer.

T-cell receptors on CD8$^+$ T-cells recognize a complex consisting of an antigenic peptide (9-10 amino acids for HLA-A2), β2 microglobulin and class I major histocompatibility complex (MHC) heavy chain (HLA-A, B, C, in humans). Peptides generated by digestion of endogenously synthesized proteins are transported into the endoplastic reticulum, bound to class I MHC heavy chain and β2 microglobulin, and finally expressed in the cell surface in the groove of the class I MHC molecule.

Information on epitopes of self-proteins recognized in the context of MHC Class I molecules remain limited, despite a few attempts to identify epitopes capable of in vitro priming and Ag-specific expansion of human CTLs. For example, peptide epitopes have been proposed which are likely candidates for binding on particular MHC Class I Ag (Falk et al., 1991), and some studies have attempted to define peptide epitopes which bind MHC Class I antigens.

Synthetic peptides have been shown to be a useful tool for T-cell epitope mapping. However in vivo and in vitro priming of specific CTLs has encountered difficulties (Alexander et al., 1991; Schild et al., 1991; Carbone et al., 1988). It is generally considered that in vitro CTL priming cannot necessarily be achieved with peptide alone, and in fact, a high antigen density is thought to be required for peptide priming (Alexander et al., 1991). Even in the limited instances when specific priming was achieved, APC or stimulators were also required at high densities (Alexander et al., 1991).

Short synthetic peptides have been used either as target antigens for epitope mapping or for induction of in vitro primary and secondary CTL responses to viral and parasitic Ags (Bednarek et al., 1991; Gammon et al., 1992; Schmidt et al., 1992; Kos and Müllbacher, 1992; Hill et al., 1992). Unfortunately, these studies failed to show the ability of protooncogene peptide analogs to stimulate in vitro human CTLs to lyse tumors endogenously expressing these antigens.

Identification of tumor antigens (Ag) and of specific epitopes on these Ag recognized by cytotoxic T-lymphocytes enables the development of tumor vaccines (for review of tumor antigens, see Rosenberg (2000), incorporated by reference herein). Tumor Ag are weak or partial agonists for activation of low-avidity (low-affinity) CTL. Attempts to activate CTL by increasing the affinity of peptide for MHC (by modifications in the anchor residues) has produced mixed successes even with powerful APC (dendritic cells, DC) and added B7 costimulation. Some of the resulting cross-reactive CTL recognized tumors with lower affinity than CTL induced by wild type Ag.

The limited ability of anchor-fixed immunogens to induce and expand high-affinity CTL raises the need for alternative approaches for CTL induction. One approach to this question is to design immunogens which activate "high-affinity" CTL from the existent pool of responders. In human tumor immunlogy, this approach has been successful in some instances. However, high-affinity CTL are expected to be more sensitive to silencing by elimination (e.g apoptosis) or by anergy (unresponsiveness or diminished reactivity to a specific antigen).

These processes occur as a consequence of recurrent stimulations with Ag (tumor Ag) and are amplified by a number of cytokines. The general mechanism of activation induced cell death (AICD) is that repeated stimulations with an Ag in the presence of cytokines such as IL-2 activates cell death pathways. This is because stimulation with Ag and IL-2 transduces a signal which is too strong to induce proliferation and instead leads to premature senescence. An alternative death pathway, passive cell death (PCD) occurs when cytokines involved in survival (IL-2, IL-4, IL-7, etc.) are withdrawn. Since tumor Ag are self-Ag, the corresponding responding cells should be even more sensitive to deletion than CTL responding to foreign Ag, because the body's defense mechanisms are programmed to avoid autoimmunity. There is little known as to how the survival of responders to tumor Ag can be induced, and how they can be protected from AICD or PCD.

Preclinical and clinical trials are underway for the utilization of tumor-specific peptide epitopes for melanoma (Rivoltini et al., 1999; Parkhurst et al., 1998; Kawakami et al., 1998; Lustgarten et al., 1997; Zeng et al., 1997; Reynolds et al., 1998; Nestle et al., 1998; Chakraborty et al., 1998; Rosenberg et al., 1998); breast cancer, such as with MUC1 (Gendler et al., 1998; Xing et al., 1989; Xing et al., 1990; Jerome et al., 1993; Apostolopoulos et al., 1994; Ding et al., 1993; Zhang et al., 1996; Acres et al., 1993; Henderson et al., 1998; Henderson et al., 1996; Samuel et al., 1998; Gong et al., 1997; Apostolopoulos et al., 1995; Pietersz et al., 1998; Lofthouse et al., 1997; Rowse et al., 1998; Gong et al., 1998; Acres et al., 1999; Apostolopoulos et al., 1998; Lees et al., 1999; Xing et al., 1995; Goydos et al., 1996; Reddish et al., 1998; Karanikas et al., 1997), p53 (DeLeo, 1998; McCarty et al., 1998; Hurpin et al., 1998; Gabrilovich et al., 1996), and Her-2/neu (Disis and Cheever, 1998; Ioannides et al., 1993; Fisk et al., 1995; Peoples et al., 1995; Kawashima et al., 1999; Disi et al., 1996); and colon cancer (Kantor et al., 1992; Kantor et al., 1992; Tsang et al., 1995; Hodge et al., 1997; Conry et al., 1998; Kass et al., 1999; Zaremba et al., 1997; Nukaya et al., 1999).

Recently, peptides of folate binding protein (FBP) were recognized by tumor-associated lymphocytes (Peoples et al., 1998; Peoples et al., 1999; Kim et al., 1999). FBP is a membrane-associated glycoprotein originally found as a mAb-defined Ag in placenta and trophoblastic cells but rarely in other normal tissues (Retrig et al., 1985; Elwood, 1989; Weitman et al., 1992; Garin-Chesa et al., 1993). Of interest, this protein has been found in greater than 90% of ovarian and endometrial carcinomas; in 20-50% of breast, colorectal, lung, and renal cell carcinomas; and in multiple other tumor types. When present in cancerous tissue, the level of expression is usually greater than 20-fold normal tissue expression and has been reported to be as high as 80-90-fold in ovarian carcinomas (Li et al., 1996).

U.S. Pat. No. 5,846,538 is directed to immune reactivity to peptides of HER-2/neu protein for treatment of malignancies.

Folate binding protein provides an ideal target for and satisfies a long-felt need in the art for compositions and methods of utilizing the compositions directed to tumor immunity.

SUMMARY OF THE INVENTION

It is an object of the present invention to provide as a composition of matter an antigen comprising a folate binding protein epitope of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

It is another object of the present invention to provide a composition comprising an antigen which includes a folate binding protein epitope of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof in a pharmaceutically acceptable excipient.

It is another object of the present invention to provide a method for stimulating cytotoxic T-lymphocytes, comprising the step of contacting the cytotoxic T-lymphocytes with an amount of an antigen comprising a folate binding protein epitope selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and a combination thereof, wherein the amount is effective to stimulate the cytotoxic T-lymphocytes. In a specific embodiment of the present invention, the cytotoxic T-lymphocytes are located within a human. In another specific embodiment, the method further comprises the step of administering to the human an antigen comprising a folate binding protein epitope selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and a combination thereof. In another specific embodiment of the present invention, the epitope is formulated for administration parenterally, topically, or as an inhalant, aerosol or spray.

It is an additional object of the present invention to provide a method of generating an immune response, comprising the step of administering to a human a pharmaceutical composition comprising an immunologically effective amount of a composition comprising an antigen comprising a folate binding epitope of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof.

It is another object of the present invention to provide a method of inducing immunity against a tumor in an individual, comprising the steps of administering to the individual an antigen comprising a folate binding protein epitope of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof; and administering to the individual a cancer vaccine. In a specific embodiment of the present invention, the an antigen comprising a folate binding protein epitope is administered prior to the administration of the cancer vaccine. In a specific embodiment of the present invention, an antigen comprising a folate binding protein epitope is administered subsequent to the administration of the cancer vaccine. In another specific embodiment of the present invention, the antigen comprising a folate binding protein epitope is administered both prior to and subsequent to the administration of the cancer vaccine. In a further specific embodiment, the cancer vaccine comprises a polypeptide selected from the group consisting of SEQ ID NO:268 (E39) and SEQ ID NO:269 (E41).

It is another object of the present invention to provide a method of inducing memory cytotoxic T-lymphocytes in an individual comprising the step of administering an antigen comprising a folate binding epitope of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof. In a specific embodiment, the individual is substantially susceptible to recurrence of cancer.

It is another object of the present invention to provide a method of providing immunity against a tumor comprising the step of administering an antigen comprising a folate binding epitope vaccine of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof.

It is another object of the present invention to provide a method of treating an individual for cancer comprising the steps of administering to the individual a first cancer vaccine; and administering to the individual a second cancer vaccine comprising a peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof. In a specific embodiment, the first cancer vaccine administration step precedes the second cancer vaccine administration step. In another specific embodiment, the first cancer vaccine administration step is subsequent to the second cancer vaccine administration step.

It is an additional object of the present invention to provide a pharmaceutical composition comprising an antigen comprising a folate binding protein epitope selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof in a pharmaceutically acceptable excipient.

It is another object of the present invention to provide a method of treating a proliferative cell disorder in a human, comprising administering to the human a therapeutically effective amount of a pharmaceutical composition comprising an antigen comprising a folate binding protein epitope selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof in a pharmaceutically acceptable excipient. In a specific embodiment, the proliferative cell disorder is cancer. In an additional specific embodiment, the cancer is breast cancer, ovarian cancer, endometrial cancer, colorectal cancer, lung cancer, renal cancer, melanoma, kidney cancer, prostate cancer, brain cancer, sarcomas, or a combination thereof.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 2B illustrates CTL activity in PBMC with multiple stimulations with J65 or E39.

DETAILED DESCRIPTION OF THE INVENTION

I. Definitions

Figure 1:
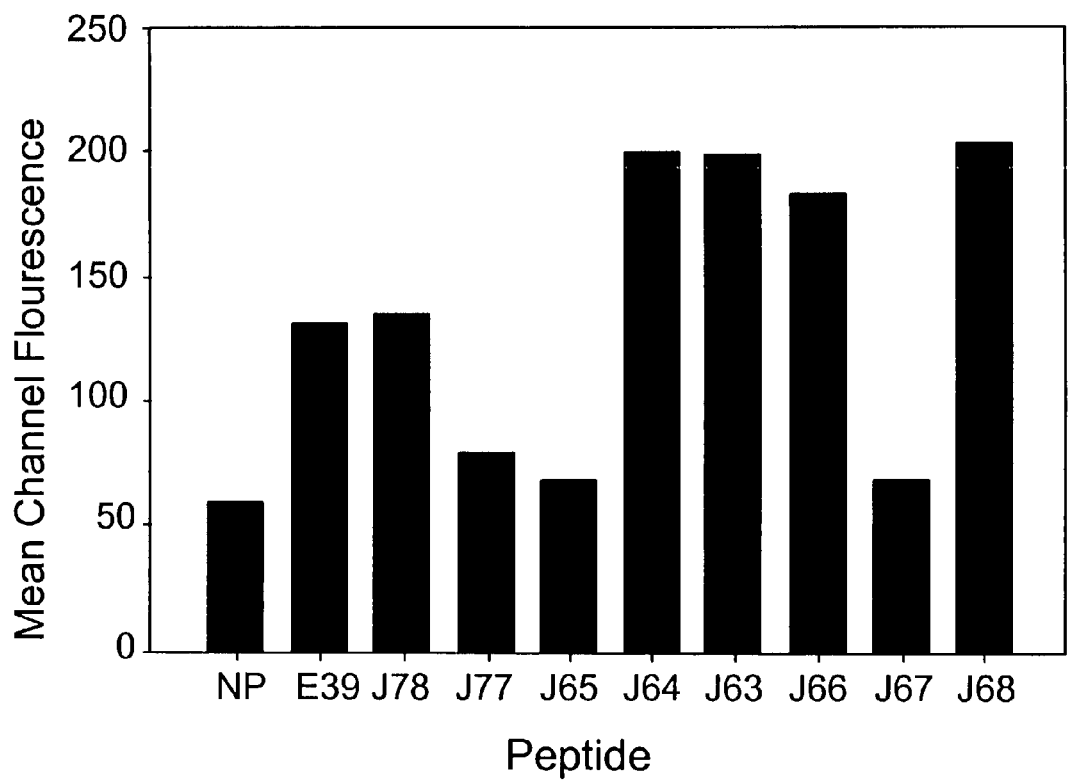
FIG. 1 demonstrates HLA-A2 stabilization by FBP epitope E39 variants.

As used herein the specification, "a" or "an" may mean one or more. As used herein in the claim(s), when used in conjunction with the word "comprising", the words "a" or "an" may mean one or more than one. As used herein "another" may mean at least a second or more.

The term "antigen" as used herein is defined as an entity which elicits an immune system response. The term herein may be abbreviated to "Ag."

The term "cancer" as used herein is defined as a tissue of uncontrolled growth or proliferation of cells, such as a tumor. In a specific embodiment, the cancer is an epithelial cancer. In specific embodiments, the cancer is breast cancer, ovarian cancer, endometrial cancer, colorectal cancer, lung cancer, renal cancer, melanoma, kidney cancer, prostate cancer, brain cancer, sarcomas, or a combination thereof. In specific embodiments, such cancers in mammals are caused by chromosomal abnormalities, degenerative growth and/or developmental disorders, mitogenic agents, ultraviolet radiation (uv), viral infections, inappropriate tissue expression of a gene, alterations in expression of a gene, carcinogenic agents, or a combination thereof. The term melanoma includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. The aforementioned cancers can be treated by methods described in the present application.

The term "epitope" as used herein is defined as a short peptide derived from a protein antigen which binds to an MHC molecule and is recognized by a particular T cell.

The term "folate binding protein variant" as used herein is defined as a folate binding protein and peptides thereof which are preferably recognized by helper T cells or cytotoxic T cells and may be naturally derived, synthetically produced, genetically engineered, or a functional equivalent thereof, e.g where one or more amino acids may be replaced by other amino acid(s) or non-amino acid(s) which do not substantially affect function. In specific embodiments, the peptides are epitopes which contain alterations, modifications, or changes in comparison to SEQ ID NO:268 (E39) or SEQ ID NO:269 (E41). In further specific embodiments, the variants are of SEQ ID NO:1 through SEQ ID NO:8.

The term "immune response" as used herein refers to a cellular immune response, including eliciting stimulation of T lymphocytes, macrophages, and/or natural killer cells.

The term "immunity" as used herein is defined as the ability to provide resistance to a tumor resulting from exposure to an antigen that is a folate binding protein epitope, such as the folate binding protein variants described herein.

The term "vaccine" as used herein is defined as a composition for generating immunity to a cancer. In specific embodiments, the cancer vaccine is a wild-type epitope of folate binding protein, such as E39 (FBP amino acid residues 191-199) (SEQ ID NO:268) or E41 (FBP amino acid residues 245-253) (SEQ ID NO:269). In other specific embodiments, the cancer vaccine comprises SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or a combination thereof. In a preferred embodiment, administration of the vaccine alternates the signaling through the T cell receptor, thereby reducing the possibility of apoptosis.

The term "variant" as used herein is defined as a modified or altered form of a wildtype sequence, such as the folate binding protein E39 epitope (SEQ ID NO:268). The variant may contain replacement of at least one amino acid residue or may contain an altered side chain for at least one amino acid residue.

II. The Present Invention

A. Specific Embodiments

The present invention is directed to folate binding protein tumor Ag modified to attenuate the signaling through T cell receptors, compared with a wild-type folate binding protein tumor Ag, particularly for reducing the possibility of apoptosis that results following repeated exposure to strong antigens. Thus, variants of folate binding protein epitopes such as E39 (SEQ ID NO:268) and E41 (SEQ ID NO:269), which are "strong" antigens, are modified to act as a "weak" antigen. Thus, the present invention utilizes compositions and methods to attenuate signaling through the T cell receptors.

The invention works as (1) prestimulation prevaccine, to be administered before the tumor Ag; (2) as post vaccine to be given after the tumor Ag; and/or (3) in certain individuals will work as a priming vaccine. The situations (1) and (2) are more related to a protective role for SEQ ID NO:6 (J65) and its analogs for tumor reactive CTL. The situation (3) can be encountered in certain individuals where mutations in the histocompatibility Ag binding pocket may transform an attenuator into a strong immunogen.

The invention allows protection before and after vaccination of either precursors (stand-in) or activated effectors. In specific embodiments, administration of the variants of folate binding protein provide targeted induction of memory CTL.

The variants described herein, in a particular embodiment SEQ ID NO:6, are intended to attenuate the signaling at recurrent stimulation, thus inducing protection of CTL precursors as of activated T-cells from apoptosis, thereby enabling the immune response to expand, and, in preferred embodiments, have important implications in induction of memory CTL.

It is well known that the two major arms of the immune system are: (1) cell-mediated immunity with immune T cells; and (2) humoral immunity with antibodies. Further, the immune system normally functions to recognize and destroy any foreign or aberrant cells in the body. Since FBP is expressed by some normal cells, tolerance and/or anergy is expected.

Development of molecular therapies for cancer have historically focused on specific recognition of Ags by cellular immune effectors. The present invention discloses novel strategies aimed at identification of peptide targets for CTLs, and generation of T-cell immunity against specific epitopes (for a review of T-cell specific immunity, see, e.g, Ioannides et al., 1992; Houbiers et al., 1993).

To achieve this, the present invention provides novel naturally- and synthetically-derived peptides which bind human leucocyte antigen-(HLA) class I heavy chains. Appropriate criteria for epitope selection in vitro have been defined, and synthetic peptides based on immunogenic epitopes of FBP have also been produced.

Although the dominant anchors for peptide binding to HLA-A2 are Leu (P2) and Val (P9), a number of residues with similar charge and side chains, such as Ile and/or Met, were identified in CTL epitopes from viral proteins (Falk et al., 1991; Bednarek et al., 1991).

B. General Embodiments

1. CTL Epitopes

CTL epitopes reported to date are mainly derived from foreign (viral) proteins with little or no homology to self-proteins. With respect to CTL responses to self-proteins, it is expected that T-cells expressing TCR with high affinity for self-peptide-MHC class I complexes are eliminated in the thymus during development. Self-peptides eluted from HLA-A2.1 molecules of various cell lines show residues at P3-P5 and P7-P8 which are different from the sequences of viral epitopes recognized by human CTLs. Since these residues are likely to contact and interact with TCR, they may reflect peptides for which autologous T-cells are already tolerant/anergic.

For T-cell recognizing self-epitopes to be eliminated or anergized, a precondition exists that the peptide-MHC complex is stable enough to engage a sufficient number of TCRs, or at least more stable than other HLA-A2 peptide complexes, where one peptide can be easily displaced by other peptides. Consequently, this would suggest that for self-proteins with extension to FBP, the ones that can bind TCR with high affinity during development will be less likely to be recognized later when expressed on a tumor other target, than peptides that bind HLA-A2 with low affinity, which under appropriate conditions (e.g, high protein concentration) may occupy a higher number of HLA-A2 molecules. For low-affinity peptides, modification of the anchors resulting in stabilization of peptide-HLA-A2 interaction by replacing weak with dominant anchor residues (e.g, (P9) M⇒V, should facilitate the reactivity of CTL with targets expressing such antigens, because TCR interacts mainly with the sequence P4-P8.

Tumor progression and metastasis are often associated with overexpression of specific cellular proteins. Epitopes of non-mutated overexpressed proteins can be targets of a specific cellular immune response against tumor mediated by T-cells. Moreover, when T-cell epitopes are present, distinction between tumor immunity/autoimmunity and unresponsiveness can be predicated on the protein concentration as a limiting factor of epitope supply.

2. Epitopic Core Sequences

The present invention is also directed to protein or peptide compositions, free from total cells and other peptides, which comprise a purified protein or peptide which incorporates an epitope that is immunologically recognized by a CTL.

As used herein, the term "incorporating an epitope(s) that is immunologically recognized by a CTL" is intended to refer to a peptide or protein antigen which includes a primary, secondary or tertiary structure similar to an epitope located within a FBP polypeptide. The level of similarity will generally be to such a degree that the same population of CTLs will also bind to, react with, or otherwise recognize, the cross-reactive peptide or protein antigen.

The identification of CTL-stimulating immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of 8 to 20 amino acids in length, and more preferably about 8 to about 15 amino acids in length. It is proposed that shorter antigenic CTL-stimulating peptides will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to FBP sequences. These epitopic core sequences are identified herein in particular aspects as hydrophilic regions of the FBP polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, receptors on CTLs. It will be understood that in the context of the present disclosure, the term "complementary" refers to amino acids or peptides that exhibit an attractive force towards each other.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 9 or 10 being more preferred. Thus, this size will generally correspond to the smallest peptide antigens prepared in accordance with the invention. However, the size of the antigen may be larger where desired, so long as it contains a basic epitopic core sequence.

A skilled artisan recognizes that numerous computer programs are available for use in predicting antigenic portions of proteins (see e.g, Jameson & Wolf, 1988; Wolf et al., 1988). Computerized peptide sequence analysis programs (e.g, DNAStar Software, DNAStar, Inc., Madison, Wisc.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g, through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g, up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4□C, or more preferably, frozen. Of course, where the peptides are stored in a lyophilized or powdered state, they may be stored virtually indefinitely, e.g, in metered aliquots that may be rehydrated with a predetermined amount of water (preferably distilled) or buffer prior to use.

3. T Lymphocytes

T lymphocytes recognize antigen in the form of peptide fragments that are bound to class I and class II molecules of the major histocompatibility complex (MHC) locus. Major Histocompatibility Complex (MHC) is a generic designation meant to encompass the histocompatibility antigen systems described in different species including the human leucocyte antigens (HLA). The T-cell receptor for antigen (TCR) is a complex of at least 8 polypeptide chains. ("Basic and Clinical Immunology" (1994) Stites, Terr and Parslow (eds) Appleton and Lange, Nenmack Conn.) Two of these chains (the alpha and beta chains) form a disulfide-linked dimer that recognizes antigenic peptides bound to MHC molecules and therefore is the actual ligand-binding structure within the TCR. The TCR alpha and beta chains are similar in many respects to immunoglobulin proteins. The amino-terminal regions of the alpha and beta chains are highly polymorphic, so that within the entire T-cell population there are a large number of different TCR alpha/beta dimers, each capable of recognizing or binding a particular combination of antigenic peptide and MHC.

In general, $CD4^+$ T cell populations are considered to function as helpers/inducers through the release of lymphokines when stimulated by a specific antigen; however, a subset of $CD4^+$ cells can act as cytotoxic T lymphocytes (CTL). Similarly, $CD8^+$ T cells are considered to function by directly lysing antigenic targets; however, under a variety of circumstances they can secrete lymphokines to provide helper or DTH function. Despite the potential of overlapping function, the phenotypic CD4 and CD8 markers are linked to the recognition of peptides bound to class II or class I MHC antigens. The recognition of antigen in the context of class II or class I MHC mandates that $CD4^+$ and $CD8^+$ T cells respond to different antigens or the same antigen presented under different circumstances. The binding of immunogenic peptides to class II MHC antigens most commonly occurs for antigens ingested by antigen presenting cells. Therefore, $CD4^+$ T cells generally recognize antigens that have been external to the tumor cells. By contrast, under normal circumstances, binding of peptides to class I MHC occurs only for proteins present in the cytosol and synthesized by the target itself, proteins in the external environment are excluded. An exception to this is the binding of exogenous peptides with a precise class I binding motif which are present outside the cell in high concentration. Thus, $CD4^+$ and $CD8^+$ T cells have broadly different functions and tend to recognize different antigens as a reflection of where the antigens normally reside.

As disclosed within the present invention, the protein product expressed by FBP is recognized by T cells. Such a protein expression product "turns over" within cells, i.e., undergoes a cycle wherein a synthesized protein functions and then eventually is degraded and replaced by a newly synthesized molecule. During the protein life cycle, peptide fragments from the protein bind to major histocompatibility complex (MHC) antigens. By display of a peptide bound to MHC antigen on the cell surface and recognition by host T cells of the combination of peptide plus self MHC antigen, a malignant cell will be immunogenic to T cells. The exquisite specificity of the T cell receptor enables individual T cells to discriminate between protein fragments which differ by a single amino acid residue.

During the immune response to a peptide, T cells expressing a T cell receptor with high affinity binding of the peptide-MHC complex will bind to the peptide-MHC complex and thereby become activated and induced to proliferate. In the first encounter with a peptide, small numbers of immune T cells will secrete lymphokines, proliferate and differentiate into effector and memory T cells. Subsequent encounters with the same antigen by the memory T cell will lead to a faster and more intense immune response.

Intact folate binding protein or peptides thereof which are recognized by cytotoxic T cells may be used within the present invention. The peptides may be naturally derived or produced based upon an identified sequence. The peptides for $CD8^+$ T cell responses (elicited by peptides presented by folate binding protein class I MHC molecules) are generally about 8-10 amino acids in length. Peptides for $CD8^+$ T cell responses vary according to each individual's class I MHC molecules. Examples of peptides suitable within the present invention for CD8+ T cell responses include peptides comprising or consisting of SEQ ID NO:1 through SEQ ID NO:8.

It will be evident to those of ordinary skill in the art that other peptides may be produced for use within the present invention, both for class I MHC molecules as well as for class II molecules. A variety of techniques are well known for isolating or constructing peptides. Suitable peptides are readily identified based upon the disclosure provided herein. Additional suitable peptides include those which are longer in length. Such peptides may be extended (e.g, by the addition of one or more amino acid residues and/or truncated (e.g., by the deletion of one or more amino acid residues from the carboxyl terminus). Alternatively, suitable peptides may be variations on other preferred peptides disclosed herein. Although this particular peptide variation may result in a peptide with the same number of total amino acids (such as nine), a peptide variation on a preferred peptide need not be identical in length. Variations in amino acid sequence that yield peptides having substantially the same desired biological activity are within the scope of the present invention.

Immunization of an individual with a FBP peptide (i.e., as a vaccine) can induce continued expansion in the number of T cells necessary for therapeutic attack against a tumor in which FBP is associated. Typically, about 0.01 µg/kg to about 100 mg/kg body weight will be administered by the intradermal, subcutaneous or intravenous route. A preferred dosage is about 1 µg/kg to about 1 mg/kg, with about 5 µg/kg to about 200 µg/kg particularly preferred. It will be evident to those skilled in the art that the number and frequency of administrations will be dependent upon the response of the patient. It may be desirable to administer the FBP peptide repetitively. It will be evident to those skilled in this art that more than one FBP peptide may be administered, either simultaneously or sequentially. For example, a combination of about 8-15 peptides may be used for immunization. Preferred peptides for immunization are those that include all or a portion of at least one FBP amino acid SEQ ID NO:1 through SEQ ID NO:68, or variants thereof. One or more peptides from other portions of the amino acid-sequence shown in SEQ ID NO:1 through SEQ ID NO:68 may be added to one or more of the preferred peptides.

In addition to the FBP peptide (which functions as an antigen), it may be desirable to include other components in the vaccine, such as a vehicle for antigen delivery and immunostimulatory substances designed to enhance the protein's immunogenicity. Examples of vehicles for antigen delivery include aluminum salts, water-in-oil emulsions, biodegradable oil vehicles, oil-in-water emulsions, biodegradable microcapsules, and liposomes. Examples of immunostimulatory substances (adjuvants) include N-acetylmuramyl-L-alanine-D-isoglutamine (MDP), lipopoly-saccharides (LPS), glucan, IL-12, GM-CSF, gamma interferon and IL-15. It will be evident to those skilled in this art that a FBP peptide may be prepared synthetically or that a portion of the protein (naturally-derived or synthetic) may be used. When a peptide is used without additional sequences, it may be desirable to couple the peptide hapten to a carrier substance, such as keyhole limpet hemocyanin.

The methods and compositions of the present invention are particularly well-suited for inducing an immune response in a patient who has developed resistance to conventional cancer treatments or who has a high probability of developing a recurrence following treatment. A skilled artisan recognizes that cancer cells are able to evade the immune system or evade an effective immune response because they look like self, they actively anergize the immune system to any antigens which may potentially differentiate between self and tumor, and they may create an immunosuppressive environment by secreting immunosuppressive factors and/or by expressing factors which can induce apoptosis of an offensive tumor antigen-specific killer cell.

A skilled artisan is aware of multiple reviews concerning cancer vaccines and the generation of cellular immune responses to antigenic tumor peptides (Pietersz et al., 2000; Pardoll, 2000;.Rosenberg, 2000; Dalgleish, 2000, each of which are incorporated by reference herein).

A skilled artisan recognizes that the antigen can be produced in large amounts by recombinant technology, either as soluble molecules in eukaryotic systems or as fusion proteins in bacterial systems. In a specific embodiment, synthetic peptides are made from the tumor antigen. Furthermore, monoclonal antibodies to the tumor antigens are useful in their identification and purification.

In a peptide approach to tumor immunotherapy, peptides (such as about 8-9mers) are presented by MHC class I molecules, leading to the generation of CD8+-mediated cellular responses comprising CTLs and cytokine secretion, mostly in the form of IFN-γ and TNF-α.

A skilled artisan recognizes that the dendritic cell is important in generating CD8+ CTLs following class I presentation. Esche et al. (1999) demonstrated techniques whereby dendritic cells are obtained from patients, isolated, expanded in vitro, exposed to the peptides and reintroduced into the patient. Others utilize similarly treated dendritic cells for generation of specifically activated T cells in vitro before transfer.

A crucial initial step in CD8+T cell generation is the uptake and presentation of peptides by MHC molecules by antigen-presenting cells. MHC class I proteins consist of three subunits, all of which are important for the formation of a stable complex. X-ray crystallography of MHC class I molecules has demonstrated that interaction of peptides with the MHC class I groove is determined by the peptide sequence, with discrete amino acids interacting with pockets in the MHC groove (which have a fixed spacing from each other) and also have specificity for anchoring amino acid side chains. Although there are exceptions, the amino and carboxy termini of the peptides are anchored at either end of the groove, often in positions 2 or 3, 5 or 7 (Apostolopoulos et al., 1997a; Apostolopoulos et al., 1997b). The peptides also interact with the T cell receptor, yet only a small amount of the peptide is exposed (Apostolopoulos et al., 1998).

Given that multiple peptide tumor antigens, such as folate binding protein, have been identified in addition to characterization of T cell epitopes, in a specific embodiment of the present invention peptide antigens are generated synthetically for immunization. The immunogenicity of small peptides can be improved upon by increasing the peptide size, by binding to carriers and also by using adjuvants to activate macrophages and other immune system factors. A skilled artisan is cognizant of recombinant cytokines being used to increase immunogenicity of a synthetic peptide (Tao and Levy, 1993) and furthermore that cytokines can also be directly fused to peptides (Nakao et al., 1994; Disis et al., 1996; Chen et al., 1994).

In specific embodiments of the present invention, mixtures of separate peptides are administered as a vaccine. Alternatively, multiple epitopes may be incorporated into the same molecule by recombinant technology well known in the art (Mateo et al., 1999; Astori and Krachenbuhl, 1996). In another embodiment, a combinatorial peptide library is used to increase binding peptides by utilizing different amino acids at least one anchor location.

In another embodiment of the present invention, natural amino acids of a peptide are replaced with unnatural D-amino acids; alternatively, the peptide residues are assembled in reverse order, which renders the peptides resistant to proteases (Briand et al., 1997; Herve et al., 1997; Bartnes et al., 1997; Guichard et al., 1996). In another embodiment, unnatural modified amino acids are incorporated into a peptide, such as α-aminoisobutyric acid or N-methylserine.

A skilled artisan recognizes that the binding strength of the 8- or 9-mer to the MHC complex and the subsequent recognition by the T cell receptor determines the immunogenicity of CTL peptides. Van Der Burg et al. (1993) determined that the longer the peptide remains bound to the MHC complex, the better the chance it will induce a T cell response. A skilled artisan also recognizes that there are methods for introducing extraneous peptides directly into the cytoplasm of a cell to allow generation of class I-restricted cellular immune responses. One example includes microbial toxins, which can carry peptides in their cytoplasm for delivery because they enter cells by receptor-mediated endocytosis and thereby deposit cellular toxins into the cytoplasm. Specific examples include shiga toxin (Lee et al., 1998), anthrax toxin (Goletz et al., 1997), diphtheria toxin (Stenmark et al., 1991), *Pseudomonas* exotoxin (Donnelly et al., 1993), and *Bordetella pertussis* toxin (Fayolle et al., 1996).

In alternative embodiments, peptides enter cells through membrane fusion and are beneficial for delivering tumor or other peptides into a cell cytoplasm, including *Antennapedia* (Derossi et al., 1994; Derossi et al., 1996; Schutze-Redelmeier et al., 1996), Tat protein (Kim et al., 1997), and Measles virus fusion peptide (Partidos et al., 1997).

In other embodiments, peptides are introduced into a cytoplasm through lipopeptides, which comprise both a lipid and a peptide, by direct insertion into the lipophilic cell membrane (BenMohamed et al., 1997; Obert et al., 1998; Deprez et al, 1996; Beckman et al., 1997). In alternative embodiments, the peptides are delivered in liposomes (for examples, see Nakanishi et al., 1997; Noguchi et al., 1991; Fukasawa et al., 1998; Guan et al., 1998), whereby the immunogenicity is dependent on the size, charge, lipid composition of the liposome itself, and whether or not the antigen is present on the surface of the liposome or within its interior.

A skilled artisan also recognizes that immune-stimulating complexes (ISCOMs), which comprise Quill A (a mixture of saponins), cholesterol, phospholipid, and proteins, are useful for delivering naturally hydrophobic antigens or antigens made hydrophobic by the addition of myristic or palmitic acid tails (for examples, see Hsu et al., 1996; Sjolander et al., 1997; Villacres-Eriksson, 1995; Tarpey et al., 1996; Rimmelzwaan et al., 1997). ISCOMs facilitate penetration into cells by fusion with their membranes, by endocytosis, or by phagocytosis.

Antigens may also be directed to particular subcellular compartments through incorporation of sorting signals to the antigen by recombinant technology, including Class II LAMP-I (Rowell et al., 1995; Wu et al., 1995), ER targeting peptide (Minev et al., 1994); CLIP (Malcherik et al., 1998), and heat shock proteins (Udono and Srivastava, 1993; Heike et al., 1996; Zhu et al., 1996; Suzue et al., 1997; Ciupitu et al., 1998).

A skilled artisan recognizes that the present invention provides anti-cancer therapeutic compositions comprising a variety of peptides designated for CD8$^+$ T cell responses comprising SEQ ID NO:1 through SEQ ID NO:8, or a combination thereof. A skilled artisan also recognizes that the present invention provides anti-cancer therapeutic compositions comprising a variety of peptides designated for CD8+T cell responses consisting essentially of SEQ ID NO:1 through SEQ ID NO:8, or a combination thereof.

A skilled artisan recognizes that references such as Abrams and Schlom (2000) summarize the current views on rational Ag modification. Two types of peptides are described: (1) agonistic peptides which upregulate Ag-specific responses; (2) antagonistic/partial agonistic peptides which downregulate the same responses. However, it is an object of the present invention to provide therapy which stimulate Ag-specific immune responses while at the same time does not elicit activation induced-cell death or death by neglect.

A skilled artisan recognizes that sequences that encode folate binding protein epitopes for induction of tumor immunity can be obtained from databases such as the National Center for Biotechnology Informations's GenBank® database or commercially available databases, such as that of Celera Genomics, Inc. (Rockville, Md.). Examples of folate binding protein sequences which may comprise an epitope or which can be altered to comprise an epitope include the following, denoted by GenBank® Accession numbers:

| | |
|---|---|
| P14207; | (SEQ ID NO:9) |
| P15328; | (SEQ ID NO:10) |
| P13255; | (SEQ ID NO:11) |
| NP_000793; | (SEQ ID NO:12) |
| AAB05827; | (SEQ ID NO:13) |
| AAG36877; | (SEQ ID NO:14) |
| S42627; | (SEQ ID NO:15) |
| S00112; | (SEQ ID NO:16) |
| BFBO; | (SEQ ID NO:17) |
| S62670; | (SEQ ID NO:18) |
| S62669; | (SEQ ID NO:19) |
| A55968; | (SEQ ID NO:20) |
| A45753; | (SEQ ID NO:21) |
| A33417; | (SEQ ID NO:22) |
| B40969; | (SEQ ID NO:23) |
| A40969; | (SEQ ID NO:24) |
| NP_057943; | (SEQ ID NO:25) |
| NP_057942; | (SEQ ID NO:26) |
| NP_057941; | (SEQ ID NO:27) |
| NP_057937; | (SEQ ID NO:28) |
| NP_057936; | (SEQ ID NO:29) |
| NP_037439; | (SEQ ID NO:30) |
| NP_032061; | (SEQ ID NO:31) |
| NP_032060; | (SEQ ID NO:32) |
| NP_000795; | (SEQ ID NO:33) |
| NP_000794; | (SEQ ID NO:34) |
| AAF66225; | (SEQ ID NO:35) |
| BAA37125; | (SEQ ID NO:36) |

| | |
|---|---|
| P02752; | (SEQ ID NO:37) |
| Q05685; | (SEQ ID NO:38) |
| P35846; | (SEQ ID NO:39) |
| P02702; | (SEQ ID NO:40) |
| AAD53001; | (SEQ ID NO:41) |
| AAD33741; | (SEQ ID NO:42) |
| AAD33740; | (SEQ ID NO:43) |
| AAD19354; | (SEQ ID NO:44) |
| AAD19353; | (SEQ ID NO:45) |
| AAC98303; | (SEQ ID NO:46) |
| AAB81938; | (SEQ ID NO:47) |
| AAB81937; | (SEQ ID NO:48) |
| AAB49703; | (SEQ ID NO:49) |
| AAB35932; | (SEQ ID NO:50) |
| 1011184A; | (SEQ ID NO:51) |
| 0908212A; | (SEQ ID NO:52) |
| CAA44610; | (SEQ ID NO:53) |
| CAA83553; | (SEQ ID NO:54) |
| AAA74896; | (SEQ ID NO:55) |
| AAA49056; | (SEQ ID NO:56) |
| AAA37599; | (SEQ ID NO:57) |
| AAA37598; | (SEQ ID NO:58) |
| AAA37597; | (SEQ ID NO:59) |
| AAA37594; | (SEQ ID NO:60) |
| AAA37596; | (SEQ ID NO:61) |
| AAA37595; | (SEQ ID NO:62) |
| AAA35824; | (SEQ ID NO:63) |
| AAA35823; | (SEQ ID NO:64) |
| AAA35822; | (SEQ ID NO:65) |
| AAA35821; | (SEQ ID NO:66) |
| AAA18382; and | (SEQ ID NO:67) |
| AAA17370. | (SEQ ID NO:68) |

A skilled artisan also recognizes that epitopes of folate binding protein, nucleic acid sequences are encoded by, or altered to encode a variant of, for example, one of the following:

| | |
|---|---|
| U02715; | (SEQ ID NO:69) |
| BE518506; | (SEQ ID NO:70) |
| BG058247; | (SEQ ID NO:71) |
| BG017460; | (SEQ ID NO:72) |
| NM_000802; | (SEQ ID NO:73) |
| U20391; | (SEQ ID NO:74) |
| NM_016731; | (SEQ ID NO:75) |
| NM_016730; | (SEQ ID NO:76) |
| NM_016729; | (SEQ ID NO:77) |
| NM_016725; | (SEQ ID NO:78) |
| NM_016724; | (SEQ ID NO:79) |
| NM_013307; | (SEQ ID NO:80) |
| NM_008035; | (SEQ ID NO:81) |
| NM_008034; | (SEQ ID NO:82) |
| BF153292; | (SEQ ID NO:83) |
| BF114518; | (SEQ ID NO:84) |
| BE940806; | (SEQ ID NO:85) |
| BE858996; | (SEQ ID NO:86) |
| AF219906; | (SEQ ID NO:87) |
| AF219905; | (SEQ ID NO:88) |
| AF219904; | (SEQ ID NO:89) |
| BE687177; | (SEQ ID NO:90) |
| BE636622; | (SEQ ID NO:91) |
| BE627230; | (SEQ ID NO:92) |
| BE506561; | (SEQ ID NO:93) |
| BE505048; | (SEQ ID NO:94) |
| BE496754; | (SEQ ID NO:95) |
| BB114010; | (SEQ ID NO:96) |
| BB109527; | (SEQ ID NO:97) |
| BB107219; | (SEQ ID NO:98) |
| BE206324; | (SEQ ID NO:99) |
| BE448392; | (SEQ ID NO:100) |
| BE207596; | (SEQ ID NO:101) |
| BE206635; | (SEQ ID NO:102) |
| BE240998; | (SEQ ID NO:103) |
| BE228221; | (SEQ ID NO:104) |
| BE225416; | (SEQ ID NO:105) |
| BE225404; | (SEQ ID NO:106) |
| BB214040; | (SEQ ID NO:107) |
| BE199619; | (SEQ ID NO:108) |
| BE199597; | (SEQ ID NO:109) |
| BE198610; | (SEQ ID NO:110) |
| BE198571; | (SEQ ID NO:111) |
| BE188055; | (SEQ ID NO:112) |

-continued

| | |
|---|---|
| BE187804; | (SEQ ID NO:113) |
| BB032646; | (SEQ ID NO:114) |
| BE037278; | (SEQ ID NO:115) |
| BE037125; | (SEQ ID NO:116) |
| BE037110; | (SEQ ID NO:117) |
| BE037009; | (SEQ ID NO:118) |
| BE036024; | (SEQ ID NO:119) |
| BE035828; | (SEQ ID NO:120) |
| BE035751; | (SEQ ID NO:121) |
| BE019724; | (SEQ ID NO:122) |
| AW913291; | (SEQ ID NO:123) |
| AW912445; | (SEQ ID NO:124) |
| AW823912; | (SEQ ID NO:125) |
| AW823418; | (SEQ ID NO:126) |
| AB023803; | (SEQ ID NO:127) |
| AB022344; | (SEQ ID NO:128) |
| AW475385; | (SEQ ID NO:129) |
| AW323586; | (SEQ ID NO:130) |
| AW319308; | (SEQ ID NO:131) |
| AW239668; | (SEQ ID NO:132) |
| AV253136; | (SEQ ID NO:133) |
| AW013716; | (SEQ ID NO:134) |
| AW013704; | (SEQ ID NO:135) |
| AW013702; | (SEQ ID NO:136) |
| AW013696; | (SEQ ID NO:137) |
| AW013669; | (SEQ ID NO:138) |
| AW013647; | (SEQ ID NO:139) |
| AW013501; | (SEQ ID NO:140) |
| AW013484; | (SEQ ID NO:141) |
| AW013428; | (SEQ ID NO:142) |
| AW013404; | (SEQ ID NO:143) |
| AW013386; | (SEQ ID NO:144) |
| AW013284; | (SEQ ID NO:145) |
| AW013183; | (SEQ ID NO:146) |
| AF061256; | (SEQ ID NO:147) |
| AI956572; | (SEQ ID NO:148) |
| AI882550; | (SEQ ID NO:149) |
| AI822932; | (SEQ ID NO:150) |
| AI785988; | (SEQ ID NO:151) |
| AI744273; | (SEQ ID NO:152) |

-continued

| | |
|---|---|
| AI727302; | (SEQ ID NO:153) |
| AI725714; | (SEQ ID NO:154) |
| AF137375; | (SEQ ID NO:155) |
| AF137374; | (SEQ ID NO:156) |
| AF137373; | (SEQ ID NO:157) |
| AF096320; | (SEQ ID NO:158) |
| AF096319; | (SEQ ID NO:159) |
| AI663857; | (SEQ ID NO:160) |
| AI647841; | (SEQ ID NO:161) |
| AI646950; | (SEQ ID NO:162) |
| AI607910; | (SEQ ID NO:163) |
| AI529173; | (SEQ ID NO:164) |
| AI509734; | (SEQ ID NO:165) |
| AI506267; | (SEQ ID NO:166) |
| AI498269; | (SEQ ID NO:167) |
| AI000444; | (SEQ ID NO:168) |
| AA956337; | (SEQ ID NO:169) |
| AA955042; | (SEQ ID NO:170) |
| AA899838; | (SEQ ID NO:171) |
| AA899718; | (SEQ ID NO:172) |
| AA858756; | (SEQ ID NO:173) |
| AI311561; | (SEQ ID NO:174) |
| AI385951; | (SEQ ID NO:175) |
| AI352406; | (SEQ ID NO:176) |
| AF100161; | (SEQ ID NO:177) |
| AI326503; | (SEQ ID NO:178) |
| AI325517; | (SEQ ID NO:179) |
| AI325453; | (SEQ ID NO:180) |
| AI325382; | (SEQ ID NO:181) |
| AI323700; | (SEQ ID NO:182) |
| AI323374; | (SEQ ID NO:183) |
| AI313973; | (SEQ ID NO:184) |
| AI196928; | (SEQ ID NO:185) |
| AE091041; | (SEQ ID NO:186) |
| AI156212; | (SEQ ID NO:187) |
| AI120374; | (SEQ ID NO:188) |
| AI119000; | (SEQ ID NO:189) |
| AA408670; | (SEQ ID NO:190) |
| AA408072; | (SEQ ID NO:191) |
| AA407615; | (SEQ ID NO:192) |

-continued

| | |
|---|---|
| AA995272; | (SEQ ID NO:193) |
| C78593; | (SEQ ID NO:194) |
| AA999910; | (SEQ ID NO:195) |
| AA991491; | (SEQ ID NO:196) |
| X99994; | (SEQ ID NO:197) |
| X99993; | (SEQ ID NO:198) |
| X99992; | (SEQ ID NO:199) |
| X99991; | (SEQ ID NO:200) |
| X99990; | (SEQ ID NO:201) |
| AA958985; | (SEQ ID NO:202) |
| AA873222; | (SEQ ID NO:203) |
| AA930051; | (SEQ ID NO:204) |
| AA895334; | (SEQ ID NO:205) |
| AA796142; | (SEQ ID NO:206) |
| AA798223; | (SEQ ID NO:207) |
| AA734325; | (SEQ ID NO:208) |
| AA690871; | (SEQ ID NO:209) |
| AA674988; | (SEQ ID NO:210) |
| AA674863; | (SEQ ID NO:211) |
| AA674821; | (SEQ ID NO:212) |
| AA674744; | (SEQ ID NO:213) |
| AA671558; | (SEQ ID NO:214) |
| AF000381; | (SEQ ID NO:215) |
| AF000380; | (SEQ ID NO:216) |
| AA637071; | (SEQ ID NO:217) |
| AA616314; | (SEQ ID NO:218) |
| AA109687; | (SEQ ID NO:219) |
| AA608235; | (SEQ ID NO:220) |
| AA589050; | (SEQ ID NO:221) |
| AA544782; | (SEQ ID NO:222) |
| AA522095; | (SEQ ID NO:223) |
| AA386821; | (SEQ ID NO:224) |
| AA386818; | (SEQ ID NO:225) |
| AA386495; | (SEQ ID NO:226) |
| AA289278; | (SEQ ID NO:227) |
| AA286342; | (SEQ ID NO:228) |
| AA276302; | (SEQ ID NO:229) |
| AA276123; | (SEQ ID NO:230) |
| AA277280; | (SEQ ID NO:231) |
| AA273543; | (SEQ ID NO:232) |

-continued

| | |
|---|---|
| U89949; | (SEQ ID NO:233) |
| AA208306; | (SEQ ID NO:234) |
| AA208089; | (SEQ ID NO:235) |
| AA242285; | (SEQ ID NO:236) |
| AA139715; | (SEQ ID NO:237) |
| AA139709; | (SEQ ID NO:238) |
| AA139675; | (SEQ ID NO:239) |
| AA139593; | (SEQ ID NO:240) |
| AA124010; | (SEQ ID NO:241) |
| AA108790; | (SEQ ID NO:242) |
| AA108350; | (SEQ ID NO:243) |
| AA028831; | (SEQ ID NO:244) |
| AA061275; | (SEQ ID NO:245) |
| W82933; | (SEQ ID NO: 246) |
| AA015571; | (SEQ ID NO:247) |
| W71715; | (SEQ ID NO:248) |
| W59165; | (SEQ ID NO:249) |
| X62753; | (SEQ ID NO:250) |
| Z32564; | (SEQ ID NO:251) |
| T29279; | (SEQ ID NO:252) |
| M25317; | (SEQ ID NO:253) |
| M86438; | (SEQ ID NO:254) |
| J03922; | (SEQ ID NO:255) |
| M64817; | (SEQ ID NO:256) |
| L25338; | (SEQ ID NO:257) |
| M97701; | (SEQ ID NO:258) |
| M97700; | (SEQ ID NO:259) |
| M64782; | (SEQ ID NO:260) |
| M35069; | (SEQ ID NO:261) |
| J05013; | (SEQ ID NO:262) |
| M28099; | (SEQ ID NO:263) |
| J02876; | (SEQ ID NO:264) |
| U08471; | (SEQ ID NO:265) |
| U02714; and | (SEQ ID NO:266) |
| U02716. | (SEQ ID NO:267) |

A skilled artisan also recognizes that the scope of the invention is not limited to the specific nonapeptides described in SEQ ID NO:1 through SEQ ID NO:8. The antigens comprising a FBP epitope may be at least about 7, 8, 9, 10, 11, 12, 13, 14, 15, 16, 17, 18, 19, 20, 25, or up to about 30. It is contemplated that any amino acid may be used for additions or filling in for the remainder of sequences in addition to the specific variant sequence provided herein. However, it is preferred that they will be those that will maintain the underlying sequence of FBP.

III. Rational Vaccine Design

The goal of rational vaccine design is to produce structural analogs of biologically active compounds. By creating such analogs, it is possible to fashion vaccines which are more active or stable than the natural molecules, which have different susceptibility to alteration or which may affect the function of various other molecules. In one approach, a skilled artisan generates a three-dimensional structure for the folate binding protein variant of the invention or a fragment thereof. This could be accomplished by X-ray crystallography, computer modeling, or by a combination of both approaches. An alternative approach involves the random replacement of functional groups throughout the folate binding protein variant, and the resulting affect on function is determined.

It also is possible to isolate a folate binding protein variant specific antibody, selected by a functional assay, and then solve its crystal structure. In principle, this approach yields a pharmacore upon which subsequent vaccine design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the vaccine.

Thus, one may design vaccines which have enhanced and improved biological activity, for example, anti-tumor activity, relative to a starting folate binding protein variant of the invention. By virtue of standard chemical isolation procedures and other descriptions herein, sufficient amounts of the folate binding protein variants of the invention can be produced to perform crystallographic studies. In addition, knowledge of the chemical characteristics of these compounds permits computer-employed predictions of structure-function relationships.

IV. Immunological Reagents

It is well known in the art that the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as g-interferon, IL-2, or IL-12 or genes encoding proteins involved in immune helper functions, such as B-7.

A variety of routes can be used to administer the vaccines including but not limited to subcutaneous, intramuscular, intradermal, intraepidermal, intravenous and intraperitoneal.

An individual, such as a patient, is injected with vaccine generally as described above. The antigen may be mixed with adjuvant, such as Freund's complete or incomplete adjuvant. Booster administrations with the same vaccine or DNA encoding the same may occur at approximately two-week intervals.

V. Immunotherapeutic Agents

An immunotherapeutic agent generally relies on the use of immune effector cells and molecules to target and destroy cancer cells. The immune effector may be, for example, a folate binding protein variant which is or is similar to a tumor cell antigen. The variant alone may serve as an effector of therapy or it may recruit other cells to actually effect cell killing. The variant also may be conjugated to a drug or toxin (e.g, a chemotherapeutic, a radionuclide, a ricin A chain, a cholera toxin, a pertussis toxin, etc.) and serve merely as a targeting agent. Such antibody conjugates are called immunotoxins, and are well known in the art (see U.S. Pat. No. 5,686,072, U.S. Pat. No. 5,578,706, U.S. Pat. No. 4,792,447, U.S. Pat. No. 5,045,451, U.S. Pat. No. 4,664,911, and U.S. Pat. No. 5,767,072, each incorporated herein by reference). Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist in addition to folate binding protein described herein, and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

The disclosures presented herein have significant relevance to immunotherapy of human diseases and disorders, including cancer. In using the immunotherapeutic compositions derived from the antigen of the present invention in treatment methods, other standard treatments also may be employed, such as radiotherapy or chemotherapy. However, it is preferred that the immunotherapy be used alone initially as its effectiveness can be readily assessed. Immunotherapies of cancer can broadly be classified as adoptive, passive and active, as described in the following sections, and may be used or produced with the folate binding protein variant antigen of the present invention.

A. Immune Stimulators

A specific aspect of immunotherapy is to use an immune stimulating molecule as an agent, or more preferably in conjunction with another agent, such as, for example, a cytokine such as IL-2, IL-4, IL-12, GM-CSF, tumor necrosis factor; interferons alpha, beta, and gamma; F42K and other cytokine analogs; a chemokine such as, for example, MIP-1, MIP-1beta, MCP-1, RANTES, IL-8; or a growth factor such as, for example, FLT3 ligand.

One particular cytokine contemplated for use in the present invention is tumor necrosis factor. Tumor necrosis factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-a also has been found to possess anti-cancer activity.

Another cytokine specifically contemplate is interferon alpha. Interferon alpha has been used in treatment of hairy cell leukemia, Kaposi's sarcoma, melanoma, carcinoid, renal cell cancer, ovary cancer, bladder cancer, non-Hodgkin's lymphomas, mycosis fungoides, multiple myeloma, and chronic granulocytic leukemia.

B. Passive Immunotherapy

A number of different approaches for passive immunotherapy of cancer exist. They may be broadly categorized into the following: injection of vaccine alone; injection of vaccine coupled to toxins or chemotherapeutic agents; injection of vaccine coupled to radioactive isotopes; injection of anti-idiotype vaccine; and finally, purging of tumor cells in bone marrow.

It may be favorable to administer more than one vaccine associated with two different antigens or even vaccine with multiple antigen specificity. Treatment protocols also may include administration of lymphokines or other immune enhancers (Bajorin et al. 1988).

C. Active Immunotherapy

In some embodiments of the invention, active immunotherapy may be employed. In active immunotherapy, a folate binding protein variant (e.g., a peptide or polypeptide), a nucleic acid encoding a folate binding protein variant, and/or additional vaccine components, such as for example, a cell expressing the folate binding protein variant (e.g a dendritic cell fused with a tumor cell, or an autologous or allogeneic tumor cell composition expressing the antigen), an adjuvant, a recombinant protein, an immunomodulator, and the like is administered (Ravindranath and Morton, 1991; Morton and Ravindranath, 1996; Morton et al., 1992; Okamoto et al., 1997; Kugler et al., 2000; Trefzer et al., 2000; Mitchell et al., 1990; Mitchell et al., 1993).

An antigenic peptide, polypeptide or protein, or an autologous or allogenic tumor cell composition or "vaccine" is administered generally with a distinct bacterial adjuvant (Ravindranath and Morton, 1991; Morton and Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anti-carbohydrate antibodies.

D. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. In certain embodiments, the patient's lymphocytes are cultured or expanded in number or selected for activity, such as immunoreactivity to the antigen. This form of immunotherapy has produced several cases of regression of melanoma and renal carcinoma.

VI. Vaccines

The present invention contemplates vaccines for use in both active and passive immunization embodiments. Immunogenic compositions, proposed to be suitable for use as a vaccine, may be prepared most readily directly from immunogenic CTL-stimulating peptides prepared in a manner disclosed herein. Preferably the antigenic material is extensively dialyzed to remove undesired small molecular weight molecules and/or lyophilized for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

The peptides of the present invention may be formulated into the vaccine as neutral or salt forms. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g, the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide mono-oleate (Aracel A) or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

For an antigenic composition to be useful as a vaccine, an antigenic composition must induce an immune response to the antigen in a cell, tissue or animal (e.g., a human). As used herein, an "antigenic composition" may comprise an antigen (e.g., a peptide or polypeptide), a nucleic acid encoding an antigen (e.g., an antigen expression vector), or a cell expressing or presenting an antigen. In particular embodiments, the antigenic composition comprises or encodes a folate binding protein variant, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In certain embodiments, an antigenic composition or immunologically functional equivalent, may be used as an effective vaccine in inducing an anti-folate binding protein variant humoral and/or cell-mediated immune response in an animal. The present invention contemplates one or more antigenic compositions or vaccines for use in both active and passive immunization embodiments.

A vaccine of the present invention may vary in its composition of proteinaceous, nucleic acid and/or cellular components. In a non-limiting example, a nucleic acid encoding an antigen might also be formulated with a proteinaceous adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

A. Proteinaceous Antigens

It is understood that an antigenic composition of the present invention may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an antigen of the present invention in an in vitro translation system or in a living cell. Preferably the antigenic composition is isolated and extensively dialyzed to remove one or more undesired small molecular weight molecules and/or lyophilized for more ready formulation into a desired vehicle. It is further understood that additional amino acids, mutations, chemical modification and the like, if any, that are made in a vaccine component will preferably not substantially interfere with the antibody recognition of the epitopic sequence.

A peptide or polypeptide corresponding to one or more antigenic determinants of the folate binding protein variant of the present invention should generally be at least five or six amino acid residues in length, and may contain up to about 10, about 15, about 20, or more. A peptide sequence may be synthesized by methods known to those of ordinary skill in the art, for example, peptide synthesis using automated peptide synthesis machines, such as those available from Applied Biosystems (Foster City, Calif.).

Longer peptides or polypeptides also may be prepared, e.g., by recombinant means. In certain embodiments, a nucleic acid encoding an antigenic composition and/or a component described herein may be used, for example, to produce an antigenic composition in vitro or in vivo for the various compositions and methods of the present invention. For example, in certain embodiments, a nucleic acid encoding an antigen is comprised in, for example, a vector in a recombinant cell. The nucleic acid may be expressed to produce a peptide or polypeptide comprising an antigenic sequence. The peptide or polypeptide may be secreted from the cell, or comprised as part of or within the cell.

B. Genetic Vaccine Antigens

In certain embodiments, an immune response may be promoted by transfecting or inoculating an animal with a nucleic acid encoding an antigen. One or more cells comprised within a target animal then expresses the sequences encoded by the nucleic acid after administration of the nucleic acid to the animal. Thus, the vaccine may comprise "genetic vaccine" useful for immunization protocols. A vaccine may also be in the form, for example, of a nucleic acid (e.g, a cDNA or an RNA) encoding all or part of the peptide or polypeptide sequence of an antigen. Expression in vivo by the nucleic acid may be, for example, by a plasmid type vector, a viral vector, or a viral/plasmid construct vector.

In preferred aspects, the nucleic acid comprises a coding region that encodes all or part of the sequences disclosed as SEQ ID NO:1 through SEQ ID NO:9, or an immunologically functional equivalent thereof. Of course, the nucleic acid may comprise and/or encode additional sequences, including but not limited to those comprising one or more immunomodulators or adjuvants. The nucleotide and protein, polypeptide and peptide encoding sequences for various genes have been previously disclosed, and may be found at computerized databases known to those of ordinary skill in the art. One such database is the National Center for Biotechnology Information's Genbank® and GenPept databases. The coding regions for these known genes may be amplified, combined with the nucleic acid sequences encoding the folate binding protein variant disclosed herein (e.g, ligated) and/or expressed using the techniques disclosed herein or by any technique that would be know to those of ordinary skill in the art (e.g, Sambrook et al., 1987). Though a nucleic acid may be expressed in an in vitro expression system, in preferred embodiments the nucleic acid comprises a vector for in vivo replication and/or expression.

C. Cellular Vaccine Antigens

In another embodiment, a cell expressing the antigen may comprise the vaccine. The cell may be isolated from a culture, tissue, organ or organism and administered to an animal as a cellular vaccine. Thus, the present invention contemplates a "cellular vaccine." The cell may be transfected with a nucleic acid encoding an antigen to enhance its expression of the antigen. Of course, the cell may also express one or more additional vaccine components, such as immunomodulators or adjuvants. A vaccine may comprise all or part of the cell.

D. Immunologically Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | F | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |

TABLE 1-continued

| Amino Acids | | | Codons |
|---|---|---|---|
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA GGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode the peptides without appreciable loss of their biological utility or activity. Amino acid substitutions may be based on the relative similarity of the amino acid side-chain substituents, for example, their hydrophobicity, hydrophilicity, charge, size, and the like. Exemplary substitutions which take various of the foregoing characteristics into consideration are well known to those of skill in the art.

Numerous scientific publications have also been devoted to the prediction of secondary structure, and to the identification of an epitope, from analyses of an amino acid sequence (Chou and Fasman, 1974a,b; 1978a,b, 1979). Any of these may be used, if desired, to supplement the teachings of U.S. Pat. No. 4,554,101.

Moreover, computer programs are currently available to assist with predicting an antigenic portion and an epitopic core region of one or more proteins, polypeptides or peptides. Examples include those programs based upon the Jameson-Wolf analysis (Jameson & Wolf, 1988; Wolf et al., 1988), the program PepPlot® (Brutlag et al., 1990; Weinberger et al., 1985), and other new programs for protein tertiary structure prediction (Fetrow & Bryant, 1993). Another commercially available software program capable of carrying out such analyses is MacVector® (IBI, New Haven, Conn.).

As modifications and changes may be made in the structure of an antigenic composition (e.g, a folate binding protein variant) of the present invention, and still obtain molecules having like or otherwise desirable characteristics, such immunologically functional equivalents are also encompassed within the present invention.

For example, certain amino acids may be substituted for other amino acids in a peptide, polypeptide or protein structure without appreciable loss of interactive binding capacity with structures such as, for example, antigen-binding regions of antibodies, binding sites on substrate molecules or receptors, DNA binding sites, or such like. Since it is the interactive capacity and nature of a peptide, polypeptide or protein that defines its biological (e.g., immunological) functional activity, certain amino acid sequence substitutions can be made in a amino acid sequence (or, of course, its underlying DNA coding sequence) and nevertheless obtain a peptide or polypeptide with like (agonistic) properties. It is thus contemplated by the inventors that various changes may be made in the sequence of an antigenic composition such as, for example a folate binding protein variant peptide or polypeptide, or underlying DNA, without appreciable loss of biological utility or activity.

Accordingly, antigenic composition, particularly an immunologically functional equivalent of the sequences disclosed herein, may encompass an amino molecule sequence comprising at least one of the 20 common amino acids in naturally synthesized proteins, or at least one modified or unnatural amino acid, including but not limited to those shown on Table 2 below.

TABLE 2

Modified, Unnatural or Rare Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, b-Amino-propionic acid | Ahyl | Allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | Allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In terms of immunologically functional equivalent, it is well understood by the skilled artisan that, inherent in the definition is the concept that there is a limit to the number of changes that may be made within a defined portion of the molecule and still result in a molecule with an acceptable level of equivalent immunological activity. An immunologically functional equivalent peptide or polypeptide are thus defined herein as those peptide(s) or polypeptide(s) in which certain, not most or all, of the amino acid(s) may be substituted.

In particular, where a shorter length peptide is concerned, it is contemplated that fewer amino acid substitutions should be made within the given peptide. A longer polypeptide may have an intermediate number of changes. The full-length protein will have the most tolerance for a larger number of changes. Of course, a plurality of distinct polypeptides/peptides with different substitutions may easily be made and used in accordance with the invention.

It also is well understood that where certain residues are shown to be particularly important to the immunological or structural properties of a protein or peptide, e.g, residues in binding regions or active sites, such residues may not generally be exchanged. This is an important consideration in the present invention, where changes in the folate binding protein variant antigenic site should be carefully considered and subsequently tested to ensure maintenance of immunological function (e.g, antigenicity), where maintenance of immunological function is desired. In this manner, functional equivalents are defined herein as those peptides or polypeptides which maintain a substantial amount of their native immunological activity.

Amino acid substitutions are generally based on the relative similarity of the amino acid side-chain substituents, for example, their hydrophobicity, hydrophilicity, charge, size, and the like. An analysis of the size, shape and type of the amino acid side-chain substitueuts reveals that arginine, lysine and histidine are all positively charged residues; that alanine, glycine and serine are all a similar size; and that phenylalanine, tryptophan and tyrosine all have a generally similar shape. Careful selection of a particular amino acid substitution for a peptide, as opposed to a protein, must be considered given the differences in size between peptides and proteins.

In further embodiments, major antigenic determinants of a peptide or polypeptide may be identified by an empirical approach in which portions of a nucleic acid encoding a peptide or polypeptide are expressed in a recombinant host, and the resulting peptide(s) or polypeptide(s) tested for their ability to elicit an immune response. For example, PCR™ can be used to prepare a range of peptides or polypeptides lacking successively longer fragments of the C-terminus of the amino acid sequence. The immunoactivity of each of these peptides or polypeptides is determined to identify those fragments or domains that are immunodominant. Further studies in which only a small number of amino acids are removed at each iteration then allows the location of the antigenic determinant(s) of the peptide or polypeptide to be more precisely determined.

Another method for determining a major antigenic determinant of a peptide or polypeptide is the SPOTs™ system (Genosys Biotechnologies, Inc., The Woodlands, Tex.). In this method, overlapping peptides are synthesized on a cellulose membrane, which following synthesis and deprotection, is screened using a polyclonal or monoclonal antibody. An antigenic determinant of the peptides or polypeptides which are initially identified can be further localized by performing subsequent syntheses of smaller peptides with larger overlaps, and by eventually replacing individual amino acids at each position along the immunoreactive sequence.

Once one or more such analyses are completed, an antigenic composition, such as for example a peptide or a polypeptide is prepared that contain at least the essential features of one or more antigenic determinants. An antigenic composition is then employed in the generation of antisera against the composition, and preferably the antigenic determinant(s).

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. Nucleic acids encoding these antigenic compositions also can be constructed and inserted into one or more expression vectors by standard methods (Sambrook et al., 1987), for example, using PCR™ cloning methodology.

In addition to the peptidyl compounds described herein, the inventors also contemplate that other sterically similar compounds may be formulated to mimic the key portions of the peptide or polypeptide structure or to interact specifically with, for example, an antibody. Such compounds, which may be termed peptidomimetics, may be used in the same manner as a peptide or polypeptide of the invention and hence are also immunologically functional equivalents.

Certain mimetics that mimic elements of protein secondary structure are described in Johnson et al. (1993). The underlying rationale behind the use of peptide mimetics is that the peptide backbone of proteins exists chiefly to orientate amino acid side chains in such a way as to facilitate molecular interactions, such as those of antibody and antigen. A peptide mimetic is thus designed to permit molecular interactions similar to the natural molecule.

E. Antigen Mutagenesis

In particular embodiments, an antigenic composition is mutated for purposes such as, for example, enhancing its immunogenicity or producing or identifying an immunologically functional equivalent sequence. Methods of mutagenesis are well known to those of skill in the art (Sambrook et al., 1987).

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In a preferred embodiment, site directed mutagenesis is used. Site-specific mutagenesis is a technique useful in the preparation of an antigenic composition (e.g, a folate binding protein variant-comprising peptide or polypeptide, or immunologically functional equivalent protein, polypeptide or peptide), through specific mutagenesis of the underlying DNA. In general, the technique of site-specific mutagenesis is well known in the art. The technique further provides a ready ability to prepare and test sequence variants, incorporating one or more of the foregoing considerations, by introducing one or more nucleotide sequence changes into the DNA. Site-specific mutagenesis allows the production of a mutant through the use of specific oligonucleotide sequence(s) which encode the DNA sequence of the desired mutation, as well as a sufficient number of adjacent nucleotides, to provide a primer sequence of sufficient size and sequence complexity to form a stable duplex on both sides of the position being mutated. Typically, a primer of about 17 to about 75 nucleotides in length is preferred, with about 10 to about 25 or more residues on both sides of the position being altered, while primers of about 17 to about 25 nucleotides in length being more preferred, with about 5 to 10 residues on both sides of the position being altered.

In general, site-directed mutagenesis is performed by first obtaining a single-stranded vector, or melting of two strands of a double stranded vector which includes within its sequence a DNA sequence encoding the desired protein. As will be appreciated by one of ordinary skill in the art, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

This mutagenic primer is then annealed with the single-stranded DNA preparation, and subjected to DNA polymerizing enzymes such as, for example, *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

Alternatively, a pair of primers may be annealed to two separate strands of a double stranded vector to simultaneously synthesize both corresponding complementary strands with the desired mutation(s) in a PCR™ reaction. A genetic selection scheme to enrich for clones incorporating the mutagenic oligonucleotide has been devised (Kunkel et al., 1987). Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector (Tomic et al., 1990; Upender et al., 1995). A PCR™ employing a thermostable ligase in addition to a thermostable polymerase also may be used to incorporate a phosphorylated mutagenic oligonucleotide into an amplified DNA fragment that may then be cloned into an appropriate cloning or expression vector (Michael 1994).

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

Additionally, one particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

F. Vectors

In order to effect replication, expression or mutagenesis of a nucleic acid, the nucleic acid may be delivered ("transfected") into a cell. The tranfection of cells may be used, in certain embodiments, to recombinately produce one or more vaccine components for subsequent purification and preparation into a pharmaceutical vaccine. In other embodiments, the nucleic acid may be comprised as a genetic vaccine that is administered to an animal. In other embodiments, the nucleic acid is transfected into a cell and the cell administered to an animal as a cellular vaccine component. The nucleic acid may consist only of naked recombinant DNA, or may comprise, for example, additional materials to protect the nucleic acid and/or aid its targeting to specific cell types.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g, YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell.

The nucleic acid encoding the antigenic composition or other vaccine component may be stably integrated into the genome of the cell, or may be stably maintained in the cell as a separate, episomal segment of DNA. Such nucleic acid segments or "episomes" encode sequences sufficient to permit maintenance and replication independent of or in synchronization with the host cell cycle. Vectors and expression vectors may contain nucleic acid sequences that serve other functions as well and are described infra. How the expression construct is delivered to a cell and where in the cell the nucleic acid remains is dependent on the type of expression construct employed.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Table 3 lists non-limiting examples of elements/promoters that may be employed, in the context of the present invention, to regulate the expression of a RNA. Table 4 provides non-limiting examples of inducible elements, which are regions of a nucleic acid sequence that can be activated in response to a specific stimulus.

TABLE 3

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et at., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 4

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Samow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferasc (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, $E.$ $coli$ is often transformed using derivatives of pBR322, a plasmid derived from an $E.$ $Coli$ species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEMTMλ11 may be utilized in making a recombinant phage vector which can be used to transform host cells, such as, for example, $E.$ $coli$ LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, $E.$ $coli$, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g, by adding IPTG to the media or by switching incubation to a higher temperature. After culturing the bacteria for a further period, generally of between 2 and 24 h, the cells are collected by centrifugation and washed to remove residual media.

10. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Vaccine components of the present invention may be a viral vector that encode one or more folate binding protein variant antigenic compositions or other components such as, for example, a folate binding protein variant immunomodulator or adjuvant.

Non-limiting examples of virus vectors that may be used to deliver a nucleic acid of the present invention are described below.

a. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

b. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system for use in the folate binding protein variant vaccines of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

C. Retroviral Vectors

Retroviruses have promise as folate binding protein variant antigen delivery vectors in vaccines due to their ability to integrate their genes into the host genome, transferring a large amount of foreign genetic material, infecting a broad spectrum of species and cell types and of being packaged in special cell lines (Miller, 1992).

In order to construct a folate binding protein variant vaccine retroviral vector, a nucleic acid (e.g, one encoding an folate binding protein variant antigen of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g, by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant antiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

d. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

e. Vaccine Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989). Thus, it is contemplated that antibodies, specific binding ligands and/or other targeting moieties may be used to specifically transfect APC types.

11. Vector Delivery and Cell Transformation

Suitable methods for nucleic acid delivery for transformation of an organelle, a cell, a tissue or an organism for use with the current invention are believed to include virtually any method by which a nucleic acid (e.g, DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulileh et al., 1993; U.S. Pat. Nos. 4,684,611 and 4,952, 500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Injection

In certain embodiments, a nucleic acid may be delivered to an organelle, a cell, a tissue or an organism via one or more injections (i.e., a needle injection). Methods of injection of nucleic acids are described herein, and are well known to those of ordinary skill in the art. Further embodiments of the present invention include the introduction of a nucleic acid by direct microinjection to a cell. Direct microinjection has been used to introduce nucleic acid constructs into *Xenopus* oocytes (Harland and Weintraub, 1985). The amount of folate binding protein variant used may vary upon the nature of the antigen as well as the organelle, cell, tissue or organism used b. Electroporation In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

d. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

e. Liposome-Mediated Transfection

In a further embodiment of the invention, one or more vaccine components or nucleic acids may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

f. Receptor Mediated Transfection

One or more vaccine components or nucleic acids, may be employed to delivered using a receptor-mediated delivery vehicle. These take advantage of the selective uptake of macromolecules by receptor-mediated endocytosis that will be occurring in the target cells. In view of the cell type-specific distribution of various receptors, this delivery method adds another degree of specificity to the present invention. Specific delivery in the context of another mammalian cell type has been described (Wu and Wu, 1993, incorporated herein by reference).

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

g. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

12. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a folate binding protein variant. The tissue may be part or separated from an organism. In certain embodiments, a tissue may comprise, but is not limited to, adipocytes, alveolar, ameloblasts, axon, basal cells, blood (e.g, lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, ascite tissue, cobs, ears, flowers, husks, kernels, leaves, meristematic cells, pollen, root tips, roots, silk, stalks, and all cancers thereof.

In certain embodiments, the host cell or tissue may be comprised in at least one organism. In certain embodiments, the organism may be, but is not limited to, a prokayote (e.g, a cubacteria, an archaea) or an eukaryote, as would be understood by one of ordinary skill in the art.

Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as E. coli (e.g, E. coli strain RR1, E. coli LE392, E. coli B, E. coli X 1776 (ATCC No. 31537) as well as E. coli W3110 (F', lambda, prototrophic, ATCC No. 273325), bacilli such as Bacillus subtilis; and other enterobacteriaceae such as Salmonella typhimurium, Serratia marcescens, various Pseudomonas specie, DH5a, JM109, and KC8, as well as a number of commercially available bacterial hosts such as SURE® Competent Cells and SOLOPACKä Gold Cells (STRATAGENE®, La Jolla). In certain embodiments, bacterial cells such as E. coli LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

13. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROLä Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radiolabeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g, visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

G. Vaccine Component Purification

In any case, a vaccine component (e.g, an antigenic peptide or polypeptide or nucleic acid encoding a proteinaceous composition) may be isolated and/or purified from the chemical synthesis reagents, cell or cellular components. In a method of producing the vaccine component, purification is accomplished by any appropriate technique that is described herein or well known to those of skill in the art (e.g, Sambrook et al., 1987). Although preferred for use in certain embodiments, there is no general requirement that an antigenic composition of the present invention or other vaccine component always be provided in their most purified state. Indeed, it is contemplated that a less substantially purified vaccine component, which is nonetheless enriched in the desired compound, relative to the natural state, will have utility in certain embodiments, such as, for example, total recovery of protein product, or in maintaining the activity of an expressed protein. However, it is contemplate that inactive products also have utility in certain embodiments, such as, e.g., in determining antigenicity via antibody generation.

The present invention also provides purified, and in preferred embodiments, substantially purified vaccines or vaccine components. The term "purified vaccine component" as used herein, is intended to refer to at least one vaccine component (e.g., a proteinaceous composition, isolatable from cells), wherein the component is purified to any degree relative to its naturally-obtainable state, e.g, relative to its purity within a cellular extract or reagents of chemical synthesis. In certain aspects wherein the vaccine component is a proteinaceous composition, a purified vaccine component also refers to a wild-type or mutant protein, polypeptide, or peptide free from the environment in which it naturally occurs.

Where the term "substantially purified" is used, this will refer to a composition in which the specific compound (e.g., a protein, polypeptide, or peptide) forms the major component of the composition, such as constituting about 50% of the compounds in the composition or more. In preferred embodiments, a substantially purified vaccine component will constitute more than about 60%, about 70%, about 80%, about 90%, about 95%, about 99% or even more of the compounds in the composition.

In certain embodiments, a vaccine component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g., antigenicity), or assessing the number of polypeptides within a fraction by gel electrophoresis.

Various techniques suitable for use in chemical, biomolecule or biological purification, well known to those of skill in the art, may be applicable to preparation of a vaccine component of the present invention. These include, for example, precipitation with ammonium sulfate, PEG, antibodies and the like or by heat denaturation, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography ion exchange, gel filtration, reverse phase, hydroxylapatite, lectin affinity; isoelectric focusing and gel electrophoresis (see for example, Sambrook et al. 1989; and Freifelder, Physical Biochemistry, Second Edition, pages 238-246, incorporated herein by reference).

Given many DNA and proteins are known (see for example, the National Center for Biotechnology Information's Genbank® and GenPept databases, or may be identified and amplified using the methods described herein, any purification method for recombinately expressed nucleic acid or proteinaceous sequences known to those of skill in the art can now be employed. In certain aspects, a nucleic acid may be purified on polyacrylamide gels, and/or cesium chloride centrifugation gradients, or by any other means known to one of ordinary skill in the art (see for example, Sambrook et al. 1989, incorporated herein by reference). In further aspects, a purification of a proteinaceous sequence may be conducted by recombinately expressing the sequence as a fusion protein. Such purification methods are routine in the art. This is exemplified by the generation of an specific protein-glutathione S-transferase fusion protein, expression in *E. coli*, and isolation to homogeneity using affinity chromatography on glutathione-agarose or the generation of a polyhistidine tag on the N- or C-terminus of the protein, and subsequent purification using Ni-affinity chromatography. In particular aspects, cells or other components of the vaccine may be purified by flow cytometry. Flow cytometry involves the separation of cells or other particles in a liquid sample, and is well known in the art (see, for example, U.S. Pat. Nos. 3,826,364, 4,284,412, 4,989,977, 4,498,766, 5,478,722, 4,857,451, 4,774,189, 4,767,206, 4,714,682, 5,160,974 and 4,661,913). Any of these techniques described herein, and combinations of these and any other techniques known to skilled artisans, may be used to purify and/or assay the purity of the various chemicals, proteinaceous compounds, nucleic acids, cellular materials and/or cells that may comprise a vaccine of the present invention. As is generally known in the art, it is believed that the order of conducting the various purification steps may be changed, or that certain steps may be omitted, and still result in a suitable method for the preparation of a substantially purified antigen or other vaccine component.

H. Additional Vaccine Components

It is contemplated that an antigenic composition of the invention may be combined with one or more additional components to form a more effective vaccine. Non-limiting examples of additional components include, for example, one or more additional antigens, immunomodulators or adjuvants to stimulate an immune response to an antigenic composition of the present invention and/or the additional component(s).

1. Immunomodulators

For example, it is contemplated that immunomodulators can be included in the vaccine to augment a cell's or a patient's (e.g., an animal's) response. Immunomodulators can be included as purified proteins, nucleic acids encoding immunomodulators, and/or cells that express immunomodulators in the vaccine composition. The following sections list non-limiting examples of immunomodulators that are of interest, and it is contemplated that various combinations of immunomodulators may be used in certain embodiments (e.g., a cytokine and a chemokine).

In another aspects of the invention, it is contemplated that the folate binding protein variant composition may further comprise a therapeutically effective composition of an immunomodulator. It is envisioned that an immunomodulator would constitute a cytokine, hematapoietin, colony stimulating factor, interleukin, interferon, growth factor or combination thereof. As used herein certain embodiments, the terms "cytokine" are the same as described in U.S. Pat. No. 5,851,984, incorporated herein by reference in its entirety, which reads in relevant part:

"The term 'cytokine' is a generic term for proteins released by one cell population which act on another cell as intercellular mediators. Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-.alpha. and -.beta.; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-.alpha. and TGF-.beta.; insulin-like growth factor-I and -II; erythropoietin (EPO); osteoinductive factors; interferons such as interferon-a, -.b, and -g; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL-9, IL-11, IL-12; IL-13, IL-14, IL-15, IL-16, IL-17, IL-18, LIF, G-CSF, GM-CSF, M-CSF, EPO, kit-ligand or FLT-3. As used herein, the term cytokine includes proteins from natural sources or from recombinant cell culture and biologically active equivalents of the native sequence cytokines.

a. β-Interferon

β-interferon (IFN-b) is low molecular weight protein that is produced by many cell types, including epithelial cells, fibroblasts and macrophages. Cells that express endogenous IFN-b are resistant to viral infection and replication. The b-interferon genes from mouse (GenBank® accession numbers X14455, X14029) and human (GenBank® accession numbers J00218, K00616 and M1029) have been isolated and sequenced. IFN-b is a multifunctional glycoprotein that can inhibit tumor growth both directly, by suppressing cell replication and inducing differentiation or apoptosis and indirectly by activating tumoricidal properties of macrophages and NK cells, by suppressing tumor angiogenesis and by stimulating specific immune response.

b. Interleukin-2

Interleukin-2 (IL-2), originally designated T-cell growth factor I, is a highly proficient inducer of T-cell proliferation and is a growth factor for all subpopulations of T-lymphocytes. IL-2 is an antigen independent proliferation factor that induces cell cycle progression in resting cells and thus allows clonal expansion of activated T-lymphocytes. Since freshly isolated leukemic cells also secrete IL2 and respond to it IL2 may function as an autocrine growth modulator for these cells capable of worsening ATL. IL2 also promotes the proliferation of activated B-cells although this requires the presence of additional factors, for example, IL4. In vitro IL2 also stimulates the growth of oligodendroglial cells. Due to its effects on T-cells and B-cells IL2 is a central regulator of immune responses. It also plays a role in anti-inflammatory reactions, in hematopoiesis and in tumor surveillance. IL-2 stimulates the synthesis of IFN-g in peripheral leukocytes and also induces the secretion of IL-1, TNF-a and TNF-b. The induction of the secretion of tumoricidal cytokines, apart from the activity in the expansion of LAK cells, (lymphokine-activated killer cells) are probably the main factors responsible for the antitumor activity of IL2.

c. GM-CSF

GM-CSF stimulates the proliferation and differentiation of neutrophilic, eosinophilic, and monocytic lineages. It also functionally activates the corresponding mature forms, enhancing, for example, to the expression of certain cell surface adhesion proteins (CD-11A, CD-11C). The overexpression of these proteins could be one explanation for the observed local accumulation of granulocytes at sites of inflammation. In addition, GM-CSF also enhances expression of receptors for fMLP (Formyl-Met-Leu-Phe) which is a stimulator of neutrophil activity.

d. Cytokines

Interleukins, cytokines, nucleic acids encoding interleukins or cytokines, and/or cells expressing such compounds are contemplated as possible vaccine components. Interleukins and cytokines, include but are not limited to interleukin I (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH-1, METH-2, tumor necrosis factor, TGFb, LT and combinations thereof.

e. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

f. Immunogenic Carrier Proteins

In certain embodiments, an antigenic composition's may be chemically coupled to a carrier or recombinantly expressed with a immunogenic carrier peptide or polypetide (e.g, a antigen-carrier fusion peptide or polypeptide) to enhance an immune reaction. Exemplary and preferred immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m-maleimidobenzoyl-N-hydroxysuccinimide ester, carbodiimide and bis-biazotized benzidine.

g. Biological Response Modifiers

It may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m2) (Johnson/Mead, NJ), or a gene encoding a protein involved in one or more immune helper functions, such as B-7.

2. Adjuvants

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

In one aspect, an adjuvant effect is achieved by use of an agent such as alum used in about 0.05 to about 0.1% solution in phosphate buffered saline. Alternatively, the antigen is made as an admixture with synthetic polymers of sugars (Carbopol®) used as an about 0.25% solution. Adjuvant effect may also be made my aggregation of the antigen in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cell(s) such as *C. parvum* or an endotoxin or a lipopolysaccharide components of Gram-negative bacteria, emulsion in physiologically acceptable oil vehicles such as mannide monooleate (Aracel A) or emulsion with a 20% solution of a perfluorocarbon (Fluosol-DA®) used as a block substitute also may be employed.

Some adjuvants, for example, are certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

Adjuvants have been used experimentally to promote a generalized increase in immunity against unknown antigens (e.g, U.S. Pat. No. 4,877,611). This has been attempted particularly in the treatment of cancer. For many cancers, there is compelling evidence that the immune system participates in host defense against the tumor cells, but only a fraction of the likely total number of tumor-specific antigens are believed to have been identified to date. However, using the present invention, the inclusion of a suitable adjuvant into the membrane of an irradiated tumor cell will likely increase the anti-tumor response irrespective of the molecular identification of the prominent antigens. This is a particularly important and time-saving feature of the invention.

In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is the to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

Another adjuvant contemplated for use in the present invention is BCG. BCG (*bacillus* Calmette-Guerin, an attenuated strain of *Mycobacterium*) and BCG-cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945.

BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990).

Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE™ BCG (Organon Inc., West Orange, N.J.).

In a typical practice of the present invention, cells of Mycobacterium bovis-BCG are grown and harvested by methods known in the art. For example, they may be grown as a surface pellicle on a Sauton medium or in a fermentation vessel containing the dispersed culture in a Dubos medium (Dubos et al., 1947; Rosenthal, 1937). All the cultures are harvested after 14 days incubation at about 37° C. Cells grown as a pellicle are harvested by using a platinum loop whereas those from the fermenter are harvested by centrifugation or tangential-flow filtration. The harvested cells are resuspended in an aqueous sterile buffer medium. A typical suspension contains from about $2 \times 10^{10}$ cells/ml to about $2 \times 10^{12}$ cells/ml. To this bacterial suspension, a sterile solution containing a selected enzyme which will degrade the BCG cell covering material is added. The resultant suspension is agitated such as by stirring to ensure maximal dispersal of the BCG organisms. Thereafter, a more concentrated cell suspension is prepared and the enzyme in the concentrate removed, typically by washing with an aqueous buffer, employing known techniques such as tangential-flow filtration. The enzyme-free cells are adjusted to an optimal immunological concentration with a cryoprotectant solution, after which they are filled into vials, ampoules, etc., and lyophilized, yielding BCG vaccine, which upon reconstitution with water is ready for immunization.

Amphipathic and surface active agents, e.g, saponin and derivatives such as QS21 (Cambridge Biotech), form yet another group of adjuvants for use with the immunogens of the present invention. Nonionic block copolymer surfactants (Rabinovich et al., 1994; Hunter et al., 1991) may also be employed. Oligonucleotides are another useful group of adjuvants (Yamamoto et al., 1988). Quil A and lentinen are other adjuvants that may be used in certain embodiments of the present invention.

One group of adjuvants preferred for use in the invention are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

In other embodiments, the present invention contemplates that a variety of adjuvants may be employed in the membranes of cells, resulting in an improved immunogenic composition. The only requirement is, generally, that the adjuvant be capable of incorporation into, physical association with, or conjugation to, the cell membrane of the cell in question. Those of skill in the art will know the different kinds of adjuvants that can be conjugated to cellular vaccines in accordance with this invention and these include alkyl lysophosphilipids (ALP); BCG; and biotin (including biotinylated derivatives) among others. Certain adjuvants particularly contemplated for use are the teichoic acids from Gram positive cells. These include the lipoteichoic acids (LTA), ribitol teichoic acids (RTA) and glycerol teichoic acid (GTA). Active forms of their synthetic counterparts may also be employed in connection with the invention (Takada et al., 1995a).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g, as may occur using non-irradiated tumor cells, is irrelevant in such circumstances.

One group of adjuvants preferred for use in some embodiments of the present invention are those that can be encoded by a nucleic acid (e.g, DNA or RNA). It is contemplated that such adjuvants may be encoded in a nucleic acid (e.g, an expression vector) encoding the antigen, or in a separate vector or other construct. These nucleic acids encoding the adjuvants can be delivered directly, such as for example with lipids or liposomes.

3. Excipients, Salts and Auxiliary Substances

An antigenic composition of the present invention may be mixed with one or more additional components (e.g., excipients, salts, etc.) which are pharmaceutically acceptable and compatible with at least one active ingredient (e.g, antigen). Suitable excipients are, for example, water, saline, dextrose, glycerol, ethanol and combinations thereof.

An antigenic composition of the present invention may be formulated into the vaccine as a neutral or salt form. A pharmaceutically-acceptable salt, includes the acid addition salts (formed with the free amino groups of the peptide) and those which are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, 2-ethylamino ethanol, histidine, procaine, and combinations thereof.

In addition, if desired, an antigentic composition may comprise minor amounts of one or more auxiliary substances such as for example wetting or emulsifying agents, pH buffering agents, etc. which enhance the effectiveness of the antigenic composition or vaccine.

1. Vaccine Preparations

Once produced, synthesized and/or purified, an antigen or other vaccine component may be prepared as a vaccine for administration to a patient. The preparation of a vaccine is generally well understood in the art, as exemplified by U.S. Pat. Nos. 4,608,251, 4,601,903, 4,599,231, 4,599,230, and 4,596,792, all incorporated herein by reference. Such methods may be used to prepare a vaccine comprising an antigenic composition comprising folate binding protein epitopes and/or variants as active ingredient(s), in light of the present disclosure. In preferred embodiments, the compositions of the present invention are prepared to be pharmacologically acceptable vaccines.

Pharmaceutical vaccine compositions of the present invention comprise an effective amount of one or more folate binding protein epitopes and/or variants or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one folate binding protein epitope or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g, human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g, antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The folate binding protein variant may comprise different types of carriers depending on whether it is to be administered in solid, liquid or aerosol form, and whether it need to be sterile for such routes of administration as injection. Except insofar as any conventional carrier is incompatible with the active ingredient, its use in the therapeutic or pharmaceutical compositions is contemplated.

In any case, the composition may comprise various antioxidants to retard oxidation of one or more component. Additionally, the prevention of the action of microorganisms can be brought about by preservatives such as various antibacterial and antifungal agents, including but not limited to parabens (e.g, methylparabens, propylparabens), chlorobutanol, phenol, sorbic acid, thimerosal or combinations thereof.

The folate binding protein variant may be formulated into a composition in a free base, neutral or salt form. Pharmaceutically acceptable salts, include the acid addition salts, e.g, those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g, glycerol, propylene glycol, liquid polyethylene glycol, etc.), lipids (e.g, triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the folate binding protein variant is prepared for administration by such routes as oral ingestion. In these embodiments, the solid composition may comprise, for example, solutions, suspensions, emulsions, tablets, pills, capsules (e.g, hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

J. Vaccine Administration

The manner of administration of a vaccine may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in cremes, in lipid compositions (e.g, liposomes), or by other method or any combination of the forgoing as would be known to one of ordinary skill in the art (see, for example, Remington's Pharmaceutical Sciences, 18th Ed. Mack Printing Company, 1990, incorporated herein by reference).

A vaccination schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g, the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/ kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/ kg/body weight to about 500 milligram/kg/body weight, etc., can be administered, based on the numbers described above. A suitable regime for initial administration and booster administrations (e.g, innoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the folate binding protein variant can be performed, following immunization.

K. Enhancement of an Immune Response

The present invention includes a method of enhancing the immune response in a subject comprising the steps of contacting one or more lymphocytes with a folate binding protein variant antigenic composition, wherein the antigen comprises as part of its sequence a sequence in accordance with SEQ ID NO:1 through SEQ ID NO:8, or a immunologically functional equivalent thereof. In certain embodiments the one or more lymphocytes is comprised in an animal, such as a human. In other embodiments, the lymphocyte(s) may be isolated from an animal or from a tissue (e.g, blood) of the animal. In certain preferred embodiments, the lymphocyte(s) are peripheral blood lymphocyte(s). In certain embodiments, the one or more lymphocytes comprise a T-lymphocyte or a B-lymphocyte. In a particularly preferred facet, the T-lymphocyte is a cytotoxic T-lymphocyte.

The enhanced immune response may be an active or a passive immune response. Alternatively, the response may be part of an adoptive immunotherapy approach in which lymphocyte(s) are obtained with from an animal (e.g, a patient), then pulsed with composition comprising an antigenic composition. In a preferred embodiment, the lymphocyte(s) may be administered to the same or different animal (e.g, same or different donors).

1. Cytotoxic T Lymphocytes

In certain embodiments, T-lymphocytes are specifically activated by contact with an antigenic composition of the present invention. In certain embodiments, T-lymphocytes are activated by contact with an antigen presenting cell that is or has been in contact with an antigenic composition of the invention.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a T cytotoxic cell that recognizes an antigen-MHC complex proliferates and differentiates into an effector cell called a cytotoxic T lymphocyte (CTL). CTLs eliminate cells of the body displaying antigen by producing substances that result in cell lysis.

CTL activity can be assessed by methods described herein or as would be known to one of skill in the art. For example, CTLs may be assessed in freshly isolated peripheral blood mononuclear cells (PBMC), in a phytohaemaglutinin-stimulated IL-2 expanded cell line established from PBMC (Bernard et at., 1998) or by T cells isolated from a previously immunized subject and restimulated for 6 days with DC infected with an adenovirus vector containing antigen using standard 4 h $51^{Cr}$ release microtoxicity assays. In another fluorometric assay developed for detecting cell-mediated cytotoxicity, the fluorophore used is the non-toxic molecule ALAMARBLUE (dye) (Nociari et at., 1998). The ALAMARBLUE (dye) is fluorescently quenched (i.e., low quantum yield) until mitochondrial reduction occurs, which then results in a dramatic increase in the alamarBlue fluorescence intensity (i.e., increase in the quantum yield). This assay is reported to be extremely sensitive, specific and requires a significantly lower number of effector cells than the standard 51Cr release assay.

In certain aspects, T helper cell responses can be measured by in vitro or in vivo assay with peptides, polypeptides or proteins. In vitro assays include measurement of a specific cytokine release by enzyme, radioisotope, chromaphore or fluorescent assays. In vivo assays include delayed type hypersensitivity responses called skin tests, as would be known to one of ordinary skill in the art.

2. Antigen Presenting Cells

In general, the term "antigen presenting cell" can be any cell that accomplishes the goal of the invention by aiding the enhancement of an immune response (i.e., from the T-cell or -B-cell arms of the immune system) against an antigen (e.g, a folate binding protein variant or a immunologically functional equivalent) or antigenic composition of the present invention. Such cells can be defined by those of skill in the art, using methods disclosed herein and in the art. As is understood by one of ordinary skill in the art (see for example Kuby, 1993, incorporated herein by reference), and used herein certain embodiments, a cell that displays or presents an antigen normally or preferentially with a class II major histocompatability molecule or complex to an immune cell is an "antigen presenting cell." In certain aspects, a cell (e.g, an APC cell) may be fused with another cell, such as a recombinant cell or a tumor cell that expresses the desired antigen. Methods for preparing a fusion of two or more cells is well known in the art, such as for example, the methods disclosed in Goding, pp. 65-66, 71-74 1986; Campbell, pp. 75-83, 1984; Kohler and Milstein, 1975; Kohler and Milstein, 1976, Gefter et al., 1977, each incorporated herein by reference. In some cases, the immune cell to which an antigen presenting cell displays or presents an antigen to is a $CD4^+TH$ cell. Additional molecules expressed on the APC or other immune cells may aid or improve the enhancement of an immune response. Secreted or soluble molecules, such as for example, immunomodulators and adjuvants, may also aid or enhance the immune response against an antigen. Such molecules are well known to one of skill in the art, and various examples are described herein.

VII. Peptide Formulations

Peptides containing the epitope motifs described herein are contemplated for use in therapeutics to provide universal FBP targets and antigens for CTLs in the HLA-A2 system. The development of therapeutics based on these novel sequences provides induction of tumor reactive immune cells in vivo through the formulation of synthetic cancer vaccines, as well as induction of tumor-reactive T-cells in vitro through either peptide-mediated (e.g, lipopeptide) or cell-mediated (e.g, EBV-B lines using either autologous or HLA-A2 transfectants where the gene for the peptide of interest is introduced, and the peptide is expressed associated with HLA-A2 on the surface). The use of these novel peptides as components of vaccines to prevent, or lessen the chance of cancer progression is also contemplated.

The peptides contemplated for use, being smaller than other compositions, such as envelope proteins, will have improved bioavailability and half lives. If desired, stability examinations may be performed on the peptides, including, e.g, pre-incubation in human serum and plasma; treatment with various proteases; and also temperature- and pH-stability analyses. If found to be necessary, the stability of the synthetic peptides may be enhanced by any one of a variety of methods such as, for example, employing D-amino acids in place of L-amino acids for peptide synthesis; using blocking groups like t-boc and the like; or encapsulating the peptides within liposomes. The bio-availability of select mixtures of peptides may also be determined by injecting radio-labeled peptides into experimental animals, such as mice and/or Rhesus monkeys, and subsequently analyzing their tissue distribution.

If stability enhancement was desired, it is contemplated that the use of dextrorotary amino acids (D-amino acids) would be advantageous as this would result in even longer bioavailability due to the inability of proteases to attack these types of structures. The peptides of the present invention may also be further stabilized, for example, by the addition of groups to the N- or C-termini, such as by acylation or amination. If desired, the peptides could even be in the form of lipid-tailed peptides, formulated into surfactant-like micelles, or other peptide multimers. The preparation of peptide multimers and surfactant-like micelles is described in detail in U.S. Ser. No. 07/945,865, incorporated herein by reference. The compositions of the present invention are contemplated to be particularly advantageous for use in economical and safe anti-tumor/anti-cancer therapeutics, and specific therapeutic formulations may be tested in experimental animal models, such as mice, rats, rabbits, guinea pigs, cats, goats, Rhesus monkeys, chimpanzees, and the like, in order to determine more precisely the dosage forms required.

In addition to the peptidyl compounds described herein, the inventors also contemplate that other sterically similar compounds may be formulated to mimic the key portions of the peptide structure and that such compounds may also be used in the same manner as the peptides of the invention. This may be achieved by the techniques of modelling and chemical design known to those of skill in the art. For example, esterification and other alkylations may be employed to modify the terminus of a peptide to mimic a particular terminal motif structure. It will be understood that all such sterically similar constructs fall within the scope of the present invention.

Therapeutic or pharmacological compositions of the present invention will generally comprise an effective amount of a CTL-stimulating peptide or peptides, dissolved or dispersed in a pharmaceutically acceptable medium. The phrase "pharmaceutically acceptable" refers to molecular entities and compositions that do not produce an allergic, toxic, or otherwise adverse reaction when administered to a human. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated.

Supplementary active ingredients can also be incorporated into the therapeutic compositions of the present invention. For example, the stimulatory peptides may also be combined with peptides including cytotoxic T-cell- or T-helper-cell-inducing epitopes (as disclosed in U.S. Ser. No. 07/945,865; incorporated herein by reference) to create peptide cocktails for immunization and treatment.

The preparation of pharmaceutical or pharmacological compositions containing a CTL-stimulating peptide or peptides, including dextrorotatory peptides, as active ingredients will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Sterile solutions suitable for intravenous administration are preferred in certain embodiments and are contemplated to be particularly effective in stimulating CTLs and/or producing an immune response in an animal. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

A peptide or peptides can be formulated into a composition in a neutral or salt form. Pharmaceutically acceptable salts, include the acid addition salts (formed with the free amino groups of the peptide) and which are formed with inorganic acids such as, e.g, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

The carrier can also be a solvent or dispersion medium containing, e.g, water, ethanol, polyol (for example, glycerol, propylene glycol, and liquid polyethylene glycol, and the like), suitable mixtures thereof, and vegetable oils. The proper fluidity can be maintained by inter alia the use of a coating, such as lecithin, by the maintenance of the required particle size in the case of dispersion and by the use of surfactants. The prevention of the action of microorganisms can be brought inter alia by various antibacterial ad antifungal agents, for example, parabens, chlorobutanol, phenol, sorbic acid, thimerosal, and the like. In many cases, it will be preferable to include isotonic agents, e.g, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more- or highly-concentrated solutions for intramuscular injection is also contemplated. This is envisioned to have particular utility in facilitating the treatment of needle stick injuries to animals or even humans. In this regard, the use of DMSO as solvent is preferred as this will result in extremely rapid penetration, delivering high concentrations of the active peptide, peptides or agents to a small area.

The use of sterile formulations, such as saline-based washes, by veterinarians, technicians, surgeons, physicians or health care workers to cleanse a particular area in the operating field may also be particularly useful. Therapeutic formulations in accordance with the present invention may also be reconstituted in the form of mouthwashes, including the peptides alone, or in conjunction with antifungal reagents. Inhalant forms are also envisioned, which again, may contain active peptides or agents alone, or in conjunction with other agents, such as, e.g, pentamidine. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9±0.2%. Suitable antioxidants and stabilizers include sodium bisulfite, sodium metabisulfite, sodium thiosulfate, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethyl-propylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed. As used herein, "pharmacologically effective amount" means an amount of composition is used that contains an amount of a peptide or peptides sufficient to significantly stimulate a CTL or generate an immune response in an animal.

In this context, the quantity of peptide(s) and volume of composition to be administered depends on the host animal to be treated, such as, the capacity of the host animal's immune system to produce an immune response. Precise amounts of active peptide required to be administered depend on the judgment of the practitioner and are peculiar to each individual.

A minimal volume of a composition required to disperse the peptide is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580).

In certain embodiments, active compounds may be administered orally. This is contemplated for agents that are generally resistant, or have been rendered resistant, to proteolysis by digestive enzymes. Such compounds are contemplated to include chemically designed or modified agents; dextrorotatory peptides; and peptide and liposomal formulations in timed-release capsules to avoid peptidase, protease and/or lipase degradation.

Oral formulations may include compounds in combination with an inert diluent or an edible carrier which may be assimilated; those enclosed in hard- or soft-shell gelatin capsules; those compressed into tablets; or those incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should generally contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

Tablets, troches, pills, capsules and the like may also contain the following: a binder, as gum tragacanth, acacia, corn starch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparaben as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The peptides may be used in their immunizing capacity by administering an amount effective to generate an immune response in an animal. In this sense, such an "amount effective to generate an immune response" means an amount of composition that contains a peptide or peptide mixture sufficient to significantly produce an antigenic response in the animal.

VIII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Rationale for Variant Design

Studies in experimental models regarding lymphocyte development in the thymus show that interaction of thymocytes with weak or null (no apparent effect) agonists lead to positive selection (i.e. survival) of responders for a specific Ag, while stimulation with strong agonists leads to negative selection (deletion of reactive CTL). Similarly, recent studies on CD8+ cell responses from peripheral blood show that Ag variants with null or weak agonistic activity induced expansion of precursors of CTL responding to a model Ag, but not effector function. These results were obtained with transgenic animals, and the recipients for the CTL were heavily irradiated. There is little information concerning how the responders to tumor, and/or their precursors, can be maintained and avoid elimination in healthy individuals, or patients without evidence of disease. However, the presence of such precursors, or of activated CTL recognizing tumor Ag, (Peoples et al., 1998; Hudson et al., 1998; Peoples et al, 1998; Kim et al., 1999; Lee et al., 2000) is proof that such responders exist in the peripheral blood. Approaches to promote their survival, expansion and induction of lytic formation is beneficial for the patients. If the responders targeted for survival are low-affinity CTL, the weak affinity is expected to be compensated by a significant increase in effector numbers. If the responders are of high affinity, protection from AICD will also allow their expansion.

To design "survival inducing" Ag, the present invention focuses on the FBP epitope E39: EIWTHSYKV (SEQ ID NO:268). This epitope is recognized, although with low affinity, by ovarian and breast tumor reactive CTL. It was predicted that improved immunogenicity in terms of net gain in cell numbers reacting with the wild-type Ag is achieved by reducing the positive charge at the amino acid in position 5 (histidine) and replacement of histidine with phenylalanine (Phe). Phe is not charged, but its benzene aromatic ring is a close substitution for the imidazole ring of histidine. To ensure a better flexibility of the residues in the peptide, the phenolic structure of tyrosine was replaced with the aliphatic core chain of Threonine (Thr). Both Tyr and Thr contain an OH (hydroxyl) side chain group. Thus, the positive charge in position 5 and the rigid structure of Tyr were eliminated. In a specific embodiment, this increases the flexibility of the residues 5-9 (SYKV) (SEQ ID NO:270) in the peptide and allows for a better fitting of the TCR with the peptide MHC complex. The variant: E I W T F S T K V (SEQ ID NO:5) was designated J65. Additional variants of J65 were created with changes in position 7 (Tyr)→Thr only=designated J77, in position 5 only Phe→His=designated J78, and in positions 1 and 6. These analogs/variants are listed in Table 5.

TABLE 5

Variants of Folate Binding Protein

| VARIANT | SEQUENCE | CHANGE |
|---------|----------|--------|
| E39 | EIWTHSYKV (SEQ ID NO:268) | wild type |
| J77 | EIWTHSTKV (SEQ ID NO:1) | Y7→T |
| J78 | EIWTFSYKV (SEQ ID NO:2) | H5→F |
| J68 | FIWTFATKV (SEQ ID NO:3) | E1→F, H5→F, Y7→T |
| J67 | EIWTHATKV (SEQ ID NO:4) | S6→A, Y7→T |
| J66 | FIWTFSTKV (SEQ ID NO:271) | E1→F, H5→F, Y7→T |
| J65 | EIWTFSTKV (SEQ ID NO:5) | H5→F, Y7→T |
| J64 | GIWTHSTKV (SEQ ID NO:7) | E1→G, Y7→T |
| J63 | FIWTHSTKV (SEQ ID NO:8) | E1→F, Y7→T |

Selection of these Ag variants was made on the principle of Ag alteration aiming to alternate signaling. In addition to substitutions H→F (Pos. 5) and Y→T (pos. 7), substitutions were introduced in the other positions: S→A (Pos. 6 and Glu (B)→F and E→Gly (G) (in Pos. 1). The purpose of these substitutions was to remove potential reacting groups with the TCR. In the substitution S→A (Pos. A), this change removes a side chain OH group. In position 1, the substitution E (glutamic acid)→glycine, removes the entire aliphatic side chain plus the charged COO group. Also in position 1, the substitution E→F (removes the charged group COO, but introduces an aromatic ring). These substitutions aim to diminish the reactivity of the peptide with the TCR.

Example 2

IFN-γ Induction and CTL Activity

Figure 2A:
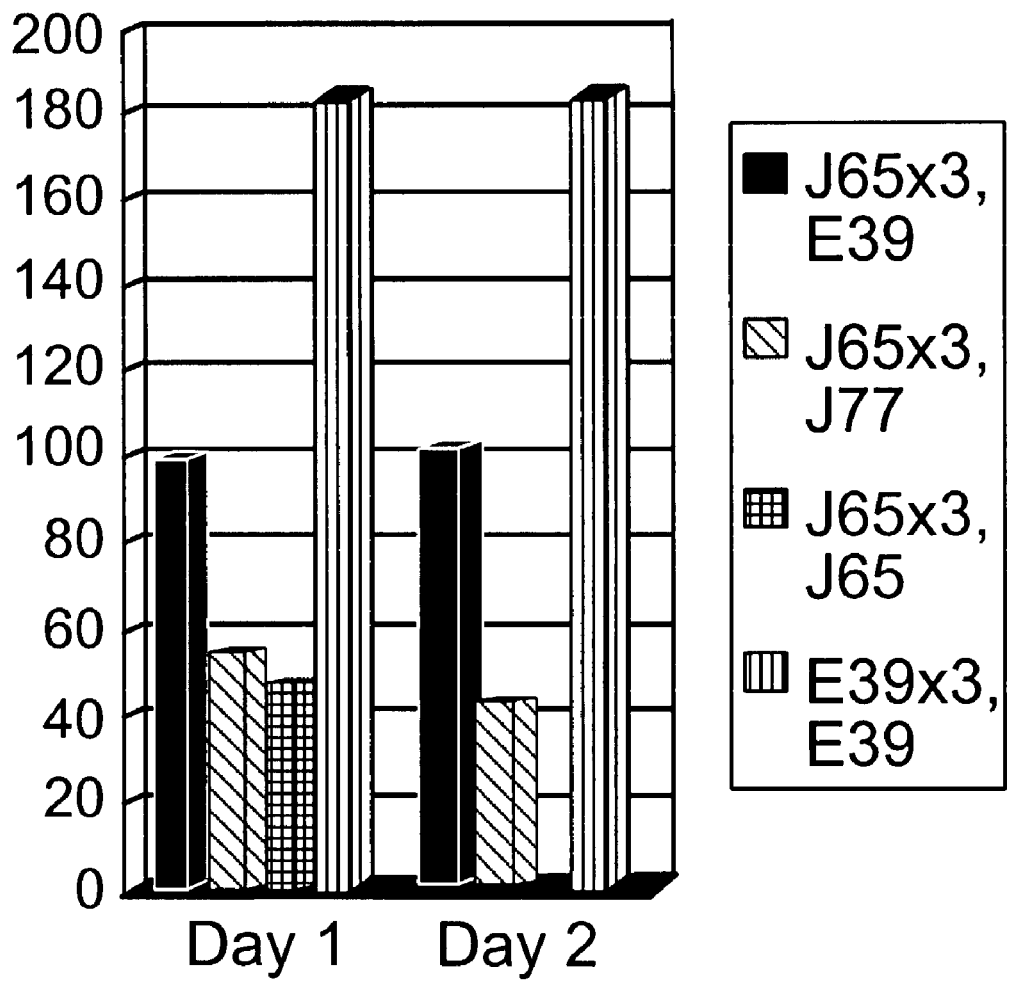
FIG. 2A illustrates IFN-γ induction in peripheral blood mononuclear cells (PBMC) with multiple stimulations with J65 or E39.

The HLA-A2 stabilizing ability of the variant peptides has also been determined (FIG. 1). The results show that the stabilizing ability of J65 is almost half of the stabilizing ability of E39. In contrast, substitutions at position 1 increase the binding affinity of the peptide. The results in FIG. 2 show the cytolytic activity of J65-induced CTL compared with E39-induced CTL. The results indicate that J65 was a weaker inducer of IFN-γ from 3×J65 stimulated cultures than J77 and E39, suggesting that the changes in the sequence had cumulative effects in decreasing IFN-γ induction.

To address the effects of FBP variants on induction of CTL activity, PBMC cultures from the healthy donor stimulated three times with J65 were split in three and restimulated with either E39 or J65 or J77. A control culture was made of the same PBMC stimulated three times with E39 and restimulated with E39 for the fourth time. PBMC stimulated three times with E39 (3×E39) followed by E39 showed moderate weak recognition of E39. In contrast, 3×J65 stimulated CTL showed significantly higher recognition of E39 after stimulation with E39. A similar picture was observed with 3×J65 cells restimulated with J65, while 3×J65 restimulated with J77 showed significantly lower CTL activity than 3×J65 stimulated with the other peptides. It was recently reported that memory CTL reacting with the tumor Ag such as FBP are present in the blood of healthy individuals (Lee et al., 2000). These cells can be easily activated by stimulation with the corresponding peptide presented on dendritic cells (Kim et al., 1999). To evaluate the stimulating ability of the analogs J65 and J77, PBMC from a responding donor were stimulated with E39, J65 and J77. These results show that the potentiating role of J65 in responder proliferation and cytotoxicity does not reflect enhanced IL-2 and/or IFN-γ secretion compared with the wild-type Ag, but its weaker cytokine-inducing activity appears to protect CTL of higher affinity from apoptosis by avoiding overstimulation.

Example 3

Specific IL-2 Induction by Priming with FBP Variants

Figure 3:
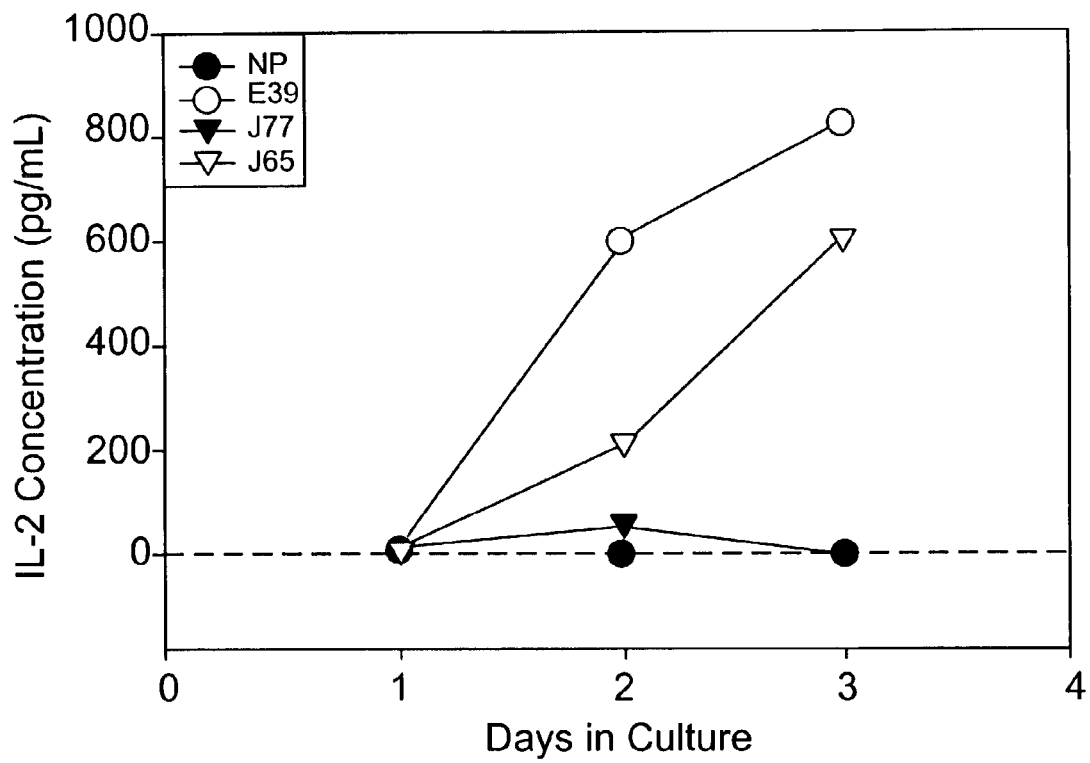
FIG. 3 illustrates specific interleukin 2 (IL-2) induction in PBMCs by priming with E39 variants.
Figure 4:
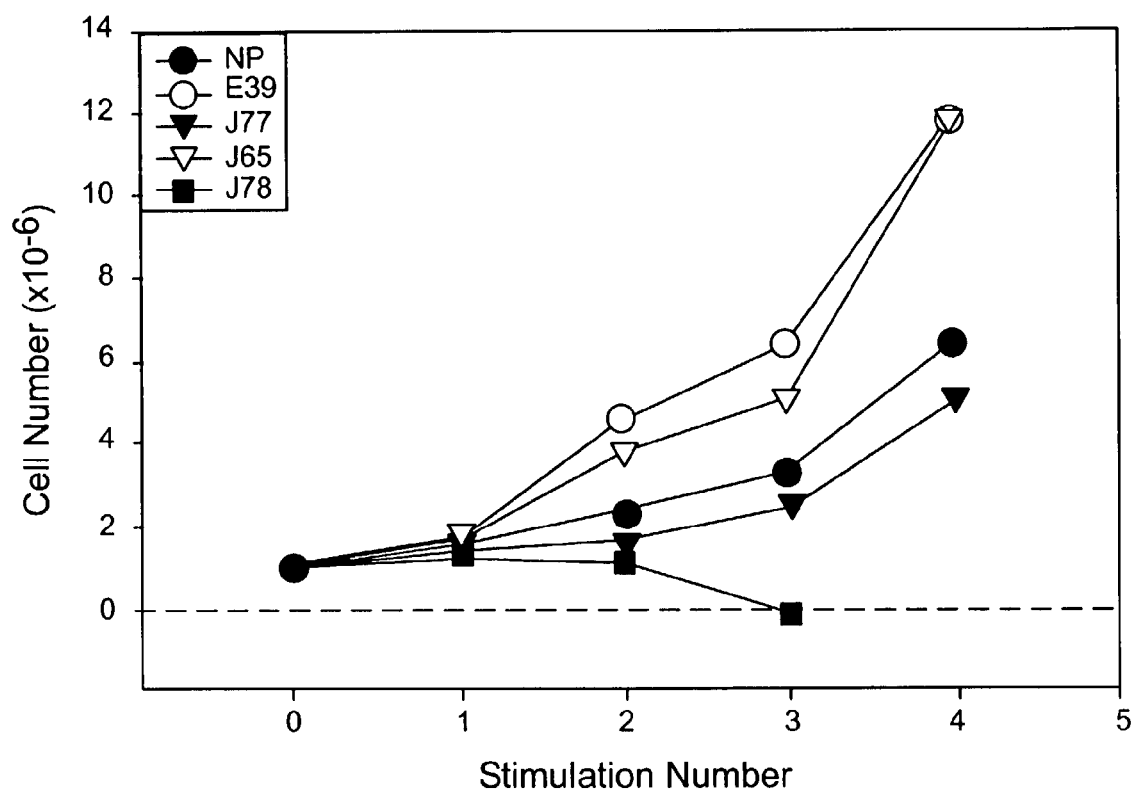
FIG. 4 illustrates expansion of PBMCs stimulated with FBP peptide E39 and its variants.
Figure 5:
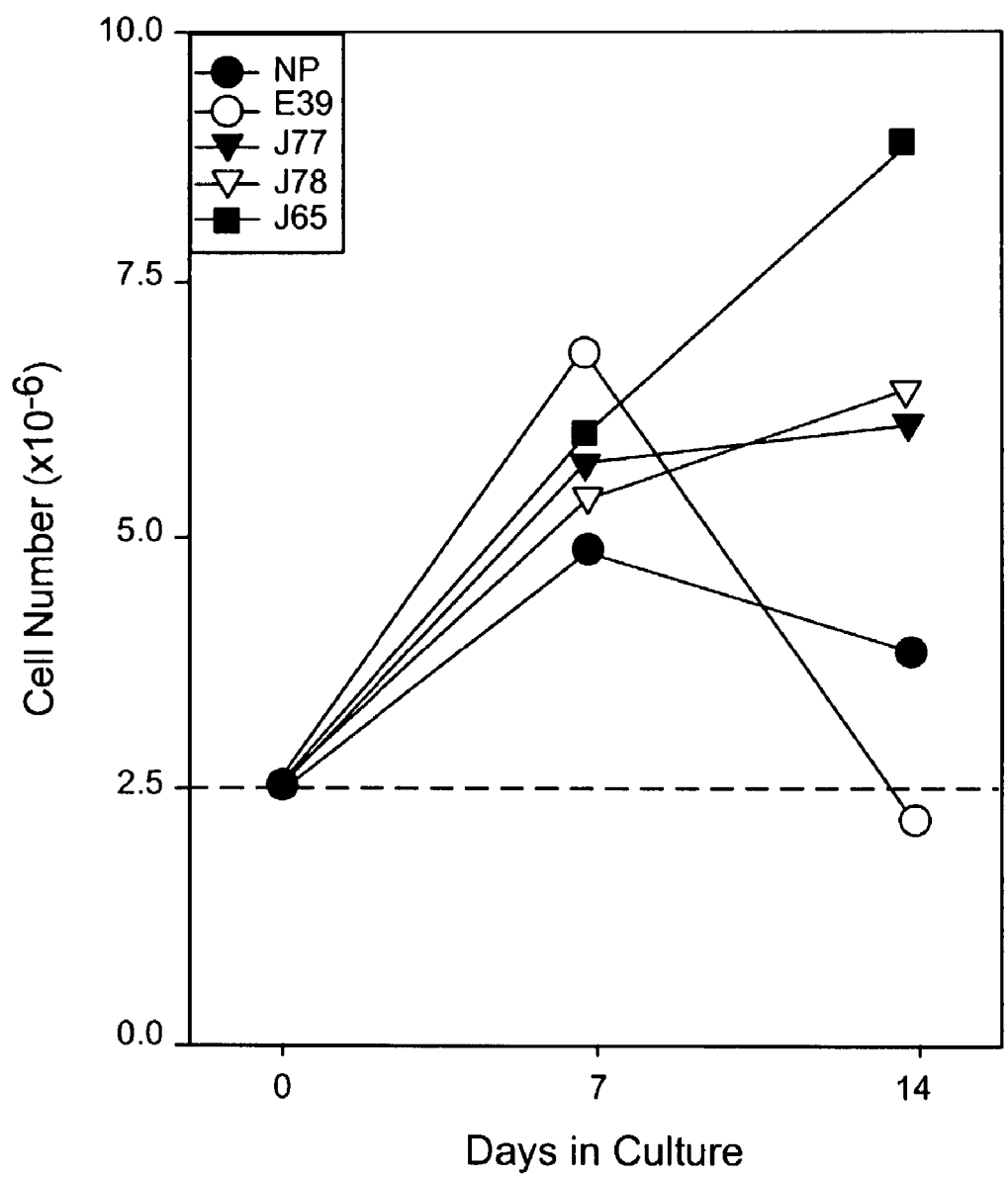
FIG. 5 demonstrates expansion of PBMC stimulated with variants of the FBP peptide E39.

In J65-primed CTL, higher CTL activity and IFN-γ secretion can be elicited by the wild-type epitope E39, suggesting a protective effect of the previous stimulations. The results in FIG. 3 show that J65 and J77 induced lower levels of IL-2 in the PBMC of this donor compared with the wild-type peptide E39. To identify which of E39 variants induced higher cell expansion, PBMC from the same donor were stimulated three times with the corresponding peptide, and the resulting live cells were counted a week after each stimulation. The results in FIG. 4 show that cultures stimulated with E39 initially expanded faster than other cultures; however, after the third stimulation, cultures stimulated with J65 increased faster in numbers. In contrast, cultures stimulated with J78 (H→F) and J77 (Y→T) proliferated slower than control cultures which were not stimulated with peptide. Similar results were obtained with J65 in another donor (FIG. 5). In this donor, cells stimulated with E39 died after the third stimulation while cells stimulated by J65 expanded faster. Cells stimulated with J77 and J78 also expanded, but at a slower rate.

TABLE 6

| Accessions/SEQ ID NOs | Sequence |
| --- | --- |
| P14207<br>SEQ ID NO:9 | M V W K W M P L L L L L V C V A T M C S A Q D R T D L L N V C M<br>D A K H H K T K P G P E D K L H D Q C S P W K K N A C C T A S T<br>S Q E L H K D T S R L Y N F N W D H C G K M E P A C K R H F I Q<br>D T C L Y E C S P N L G P W I Q Q V N Q T W R K E R F L D V P L<br>C K E D C Q R W W E D C H T S H T C K S N W H R G W D W T S G V<br>N K C P A G A L C R T F E S Y F P T P A A L C E G L W S H S Y K<br>V S N Y S R G S G R C I Q M W F D S A Q G N P N E E V A R F Y A<br>A A M H V N A G E M L H G T G G L L L S L A L M L Q L W L L G |
| P15328<br>SEQ ID NO:10 | M A Q R M T T Q L L L L L V W V A V V G E A Q T R I A W A R T E<br>L L N V C M N A K H H K E K P G P E D K L H E Q C R P W R K N A<br>C C S T N T S Q E A H K D V S Y L Y R F N W N H C G E M A P A C<br>K R H F I Q D T C L Y E C S P N L G P W I Q Q V D Q S W R K E R<br>V L N V P L C K E D C E Q W W E D C R T S Y T C K S N W H K G W<br>N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L M L L W L L S |
| P13255<br>SEQ ID NO:11 | M V D S V Y R T R S L G V A A E G I P D Q Y A D G E A A R V W Q<br>L Y I G D T R S R T A E Y K A W L L G L L R Q H G C H R V L D V<br>A C G T G V D S I M L V E E G F S V T S V D A S D K M L K Y A L<br>K E R W N R R K E P A F D K W V I E H A N W L T L D K D V P A G<br>D G F D A V I C L G N S F A H L P D S K G D Q S E H R L A L K N<br>I A S M V R P G G L L V I D H R N Y D Y I L S T G C A P P G K N<br>I Y Y K S D L T K D I T T S V L T V N N K A H M V T L D Y T V Q<br>V P G A G R D G A P G F S K F R L S Y Y P H C L A S F T E L V Q<br>E A F G G R C Q H S V L G D F K P Y R P G Q A Y V P C Y F I H V<br>L K K T G |
| NP_000793<br>SEQ ID NO:12 | M A Q R M T T Q L L L L L V W V A V V G E A Q T R I A W A R T E<br>L L N V C M N A K H H K H K P G P E D K I H E Q C R P W R K N A<br>C C S T N T S Q E A H K D V S Y L Y R F N W N H C G E M A P A C<br>K R H F I Q D T C I Y E C S P N I G P W I Q Q V D Q S W R K E R<br>V L N V P L C K E D C E Q W W E D C R T S Y T C K S N W H K G W<br>N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L M L L W L L S |
| AAB05827<br>SEQ ID NO:13 | M A Q R M T T Q L L L L L V W V A V V G E A Q T R I A W A R T E<br>L L N V C M N A K H H K E K P G P E D K I H E Q C R P W R K N A<br>C C S T N T S Q E A H K D V S Y L Y R F N W N H C G E M A P A C<br>K R H F I Q D T C L Y E C S P N L G P W I Q Q V D Q S W R K E R<br>V L N V P L C K E D C E Q W W E D C R T S Y T C K S N W H K G W |

TABLE 6-continued

| Accessions/SEQ ID NOs | Sequence |
|---|---|
| | N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L M L L W L L S |
| AAG36877<br>SEQ ID NO:14 | M A Q W W Q I L L G L W A V L P T L A G D K L L S V C M N S K R<br>H K Q E P G P B D E L Y Q E C R P W E D N A C C T R S T S W E A<br>H L E E P L L F N F S M M H C G L L T P A C R K H F I Q A I C F<br>H E C S P N L G P W I Q P V V P N G Q E E Q R V W G V P L C Q E<br>D C E D W W R A C H S S L T C K S N W L H G W D W S E E K K H C<br>P A H E P C L P F S Y H F P T P D D L C E K I W N N T F K A S P<br>E R R N S G R C L Q K W F E P T L S N P N V E V A L H F A G S A<br>L A P Q L S Y T L P A F S L C L L F H P |
| S42627<br>SEQ ID NO:15 | M V D S V Y R T R S L G V A A E G L P D Q Y A E C E A A R V W Q<br>L Y I G D T R S R T A E Y K A W L L G L L R Q H G C Q R V L D V<br>A C G T G V D S I M L V E E G F S V T S V D A S D K M L K Y A L<br>K E R W N R R H E P A F D K W V I E E A N W M T L D K D V P Q S<br>A E G G F D A V I C L G N S F A H L P D C K G D Q S E H R L A L<br>K N I A S M V R A G G L L V I D H R N Y D H I L S T G C A P P G<br>K N I Y Y K S D L T K D V T T S V L I V N N K A H M V T L D Y T<br>V Q V P G A G Q D G S P G L S K F R L S Y Y P H C L A S F T E L<br>L Q A A F G C K C Q H S V L G D F K P Y K P G Q T Y I P C Y F I<br>H V L K R T D |
| S00112<br>SEQ ID NO:16 | M V D S V Y R T R S L G V A A E G I P D Q Y A D G E A A R V W Q<br>L Y I G D T R S R T A E Y K A W L L G L L R Q H G C H R V L D V<br>A C G T G V D S I M L V E E G F S V T S V D A S D K M L K Y A L<br>K E R W N R R K E P A F D K W V I E E A N W L T L D K D V P A G<br>D G F D A V I C L G N S F A H L P D S K G D Q S E H R L A L K N<br>I A S M V R P G G L L V I D H R N Y D Y I L S T G C A P P G K N<br>I Y Y K S D L T K D I T T S V L T V N N K A H M V T L D Y T V Q<br>V P G A G R D G A P G F S K F R L S Y Y P H C L A S F T E L V Q<br>E A F G G R C Q H S V L G D F K P Y R P G Q A Y V P C Y F I H V<br>L K K T G |
| BFB0<br>SEQ ID NO:17 | A Q A P R T P R A R T D L L N V C M D A K H H K A E P G P E D S<br>L H E Q C S P W R K N A C C S V N T S I E A X K D I S Y L Y R F<br>N W D H C G K M E P A C K R H F I Q D T C L Y E C S P N L G P W<br>I R E V N Q R W R K E R V L G V P L C K E D C Q S W W E D C R T<br>S Y T C K S N W H K G W N W T S G Y N Q C P V K A A H C R F D F<br>Y F P T P A A L C N E I W S H S Y K V S N Y S R G S G R C I Q M<br>W F D P F Q G N P N E E V A R F Y A E N P T S G S T P Q C I |
| S62670<br>SEQ ID NO:18 | Q A T R A R T E L L N V F A D A K R E K P K |
| S62669<br>SEQ ID NO:19 | Q A T R A E T E N L N V D M D A K H H K E K |
| A55968<br>SEQ ID NO:20 | M V P S S P A V E K Q V P V E P G P D P E L R S W R H L V C Y L<br>C F Y G F M A Q I R P G E S F I T P Y L L G P D K N F T R E Q V<br>T N E I T P V L S Y S Y L A V L V P V F L L T D Y L R Y T P V L<br>L L Q G L S F V S V W L L L L G H S V A H M Q L M E L F Y S V<br>T M A A R I A Y S S Y I F S L V R P A R Y Q R V A G Y S R A A V<br>L L G V F T S S V L G Q L L V T V G R V S F S T L N Y I S L A F<br>L T F S V V L A L F L K R P K R S L F F N R D D R G R C E T S A<br>S E L E R M N P G P G G K L G H A L R V A C G D S V L A R M L R<br>E L G D S L R R P Q L R L W S L W W V F N S A G Y Y L V V Y Y V<br>H I L W N E V D P T T N S A R V Y N G A A D A A S T L L G A I T<br>S F A A G F V K I R W A R W S K L L I A G V T A T Q A G L V F L<br>L A H T R H P S S I W L C Y A A F V L F R G S Y Q F L V P I A T<br>F Q I A S S L S K E L C A L V F G V N T F F A T I V K T I I T F<br>I V S D V R G L G L P V R K P V I L R V L P D P V H H L L L G G<br>H A G W P A A L P A G P P P A A A P G P G P E E C R G G E G S T<br>G T E R A G Q G P R R L Q P A Q S P P L S P E D S L G A V G P A<br>S L E Q R Q S D P Y L A Q A P A P Q A A E F L S P V T T P S P C<br>T L S S A Q A S G P E A A D E T C P Q L A V H P P G V S K L G L<br>Q C L P S D G V Q N V N Q |
| A45753<br>SEQ ID NO:21 | M A Q R M T T Q L L L L L V W V A V V G E A Q T R I A W A R T E<br>L L N V C M N A K H H K E K P G P E D K L H E Q C R P W R K N A<br>C C S T N T S Q E A H K D V S Y L Y R F N W N H C G E M A P A C<br>K R H F I Q D T C L Y E C S P N L G P W I Q Q V N D Q S W R K E R<br>V L N V P L C K E D C E Q W W E D C R T S Y T C K S N W H K G W<br>N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L M L L W L L S |

TABLE 6-continued

| Accessions/SEQ ID NOs | Sequence |
| --- | --- |
| A33417<br>SEQ ID NO:22 | M V W K W M P L L L L L V C V A T M C S A Q D R T D L L N V C M<br>D A K H H K T K P G P E D K L H D Q C S P W K K N A C C T A S T<br>S Q E L H K D T S R L Y N F N W D H C G K M E P A C K R H F I Q<br>D T C L Y E C S P N L G P W I Q Q V N Q T W R K E R F L D V P L<br>C K E D C Q R W W E D C H T S H T C K S N W H R G W D W T S G V<br>N K C P A G A L C R T F E S Y F P T P A A L C E G L W S H S Y K<br>V S N Y S R G S G R C I Q M W F D S A Q G N P N E E V A R F Y A<br>A A M H V N A G E M L H G T G G L L L S L A L M L Q L W L L G |
| B40969<br>SEQ ID NO:23 | M A W K Q T P L L L L V Y M V T T G S G R D R T D L L N V C M D<br>A K H H K T K P G P E D K L H D Q C S P W K K N A C C S V N T S<br>Q E L H K A D S R L Y F N W D H C G K M E P A C K S H F I Q D S<br>C L Y E C S P N L G P W I Q Q V D Q S W R K E R F L D V P L C K<br>E D C H Q W W E A C R T S F T C K R D W H K G W D W S S G I N K<br>C P N T A P C H T F E Y Y F P T P A S L C E G L W S H S Y K V S<br>N Y S R G S G R C I Q M W P D S T Q G N P N E D V V K F Y A S F<br>M T S G T V P H A A V L L V P S L A P V L S L W L P G |
| A40969<br>SEQ ID NO:24 | M A H L M T V Q L L L L V M W M A E C A Q S R A T R A R T E L L<br>N V C M D A K H H K E K P G P E D N L H D Q C S P W K T N S C C<br>S T N T S Q E A H K D I S Y L Y R F N W N H C G T M T S E C K R<br>H F I Q D T C L Y E C S P N L G P W I Q Q V D Q S W R K E R I L<br>D V P L C K E D C Q Q W W E D C Q S S F T C K S N W H K G W N W<br>S S G H N E C P V G A S C H P F T F Y F P T S A A L C E E I W S<br>H S Y K L S N Y S R G S G R C I Q M W F D P A Q G N P N E E V A<br>R F Y A E A M S G A G L H G T W P L L C S L S L V L L W V I S |
| NP_057943<br>SEQ ID NO:25 | M A Q R M T T Q L L L L L V W V A V V G E A Q T R I A W A R T E<br>L L N V C M N A K H H K E K P G P E D K L H E Q C R P W R K N A<br>C C S T N T S Q E A H K D V S Y L Y R F N W N H C G E M A P A C<br>K R H F I Q D T C L Y E C S P N L G P W I Q Q V D Q S W R K E R<br>V L N V P L C K E D C E Q W W E D C R T S Y T C K S N W H K G W<br>N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L F M L W L L S |
| NP_057942<br>SEQ ID NO:26 | M A Q R M T T Q L L L L L V W V A V V G E A Q T R I A W A R T E<br>L L N V C M N A K H H K E K P G P E D K L H E Q C R P W R K N A<br>C C S T N T S Q E A H K D V S Y L Y R F N W N H C G E M A P A C<br>K R H F I Q D T C L Y E C S P N L G P W I Q Q V D Q S W R K E R<br>V L N V P L C K E D C E Q W W E D C R T S Y T C K S N W H K C W<br>N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L M L L W L L S |
| N_057941<br>SEQ ID NO:27 | M A Q R M T T Q L L L L L V W V A V V G E A Q T R I A W A R T E<br>L L N V C M N A K H H K E K P G P E D K L H E Q C R P W R K N A<br>C C S T N T S Q E A H K D V S Y L Y R F N W N H C G E M A P A C<br>K R H F I Q D T C L Y E C S P N L G P W I Q Q V D Q S W R K E R<br>V L N V P L C K E D C E Q W W E D C R T S Y T C K S N W H K G W<br>N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L M L L W L L S |
| N_057937<br>SEQ ID NO:28 | M A Q R M T T Q L L L L L V W V A V V G E A Q T R I A W A R T E<br>L L N V C M N A K H H K E K P G P E D K L H E Q C R P W R K N A<br>C C S T N T S Q E A H K D V S Y L Y R F N W N H C G E M A P A C<br>K R H F I Q D T C L Y E C S P N L G P W I Q Q V D Q S W R K E R<br>V L N V P L C K E D C E Q W W E D C R T S Y T C K S N W H K G W<br>N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L M L L W L L S |
| N_057936<br>SEQ ID NO:29 | M A Q R M T T Q L L L L L V W V A V V G E A Q T R I A W A R T E<br>L L N V C M N A K H H K E K P G P E D K L H E Q C R P W R K N A<br>C C S T N T S Q E A H K D V S Y L Y R F N W N H C G E M A P A C<br>K R H F I Q D T C L Y E C S P N L G P W I Q Q V D Q S W R K E R<br>V L N V P L C K E D C E Q W W E D C R T S Y T C K S N W H K G W<br>N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L M L L W L L S |
| N_037439<br>SEQ ID NO:30 | M A S V P K T N K I E P R S Y S I I P S C S I R R L G P A L N T<br>P I F Q S K R N G P R G H S A Y S I E G R Q R Q G A G R A V V P<br>R A D R P P A P K I Q L R A F Y L Q Q L Y Y T L L E L E L P R L<br>L A P D L P S N G S S L K D L K W T H S N Y R A S K E S C I V I |

TABLE 6-continued

| Accessions/SEQ ID NOs | Sequence |
|---|---|
| | F V T T S P G R E W V I C A P A A F L G C G S L Q A P S P E S E<br>P S F P V T R G H H G R H G D Y H R K L I G Q T F E W V V R R<br>H G G R A I G P R L S R V T K A A G A R P P A G A G E G L R V G<br>F D L I N A P I P P A K G V S A R R H V L A L E L P Q L S K |
| N_032061<br>SEQ ID NO:31 | M A W K Q T P L L L L V Y M V T T G S G R D R T D L L N V C M D<br>A K H H K T K P G P E D K L H D Q C S P W K K N A C C S V N T S<br>Q E L H K A D S R L Y F N W D H C G K M E P A C K S H F I Q D S<br>C L Y E C S P N L G P W I Q Q V D Q S W R K E R F L D V P L C K<br>E D C H Q W W E A C R T S F T C K R D W H K G W D W S S G I N K<br>C P N T A P C H T F E Y Y F P T P A S L C E G L W S H S Y K V S<br>N Y S R G S G R C I Q M W F D S T Q G N P N E D V V K F Y A S F<br>M T S G T V P H A A V L L V P S L A P V L S L W L P G |
| N_032060<br>SEQ ID NO:32 | M A H L M T V Q L L L L V M W M A E C A Q S R A T R A R T E L L<br>N V C M D A K H H K E K P G P E D N L H D Q C S P W K T N S C C<br>S T N T S Q E A H K D I S Y L Y R F N W N H C G T M T S E C K R<br>H F I Q D T C L Y E C S P N L G P W I Q Q V D Q S W R K E R I L<br>D V P L C K E D C Q Q W W E D C Q S S F T C K S N W H K G W N W<br>S S G H N E C P V G A S C H P F T F Y F P T S A A L C E E I W S<br>H S Y K L S N Y S R G S G R C I Q M W F D P A Q G N P N E E V A<br>R F Y A E A M S G A G L H G T W P L L C S L S L V L L W V I S |
| NP_000795<br>SEQ ID NO:33 | M A W Q M M Q L L L L A L V T A A G S A Q P R S A R A R T D L L<br>N V C M N A K H H K T Q P S P E D E L Y G Q C S P W K K N A C C<br>T A S T S Q E L H K D T S R L Y N F N W D H C G K M E P T C K R<br>H F I Q D S C L Y E C S P N L G P W I R Q V N Q S W R K E R I L<br>N V P L C K E D C E R W W E D C R T S Y T C K S N W H K G W N W<br>T S G I N E C P A G A L C S T F E S Y F P T P A A L C E G L W S<br>H S F K V S N Y S R G S G R C I Q M W F D S A Q G N P N E E V A<br>K F Y A A A M N A G A P S R G I I D S |
| NP_000794<br>SEQ ID NO:34 | M V W K W M P L L L L L V C V A T M C S A Q D R T D L L N V C M<br>D A K H H K T K P G P E D K L H D Q C S P W K K N A C C T A S T<br>S Q E L H K D T S R L Y N F N W D H C G K M E P A C K R H F I Q<br>D T C L Y E C S P N L G P W I Q Q V N Q T W R K E R F L D V P L<br>C K E D C Q R W W E D C H T S H T C K S N W H R G W D W T S G V<br>N K C P A G A L C R T F E S Y F P T P A A L C E G L W S H S Y K<br>V S N Y S R G S G R C I Q M W F D S A Q G N P N E E V A R F Y A<br>A A M H V N A G E M L H G T G G L L L S L A L M L Q L W L L G |
| AAF66225<br>SEQ ID NO:35 | M A H L M A G Q W L L L L M W M A E C A Q S R A T R A R T E L L<br>N V C M D A K H H K E K P G P E D K L H D Q C S P W K T N A C C<br>S T N T S Q E D T K D I S Y L Y R F N W N H C G T M T P E C K R<br>H F I Q D T C L Y E C S P N L G P W I Q Q V D Q S W R K E R I L<br>D V P L C K E D C V L W W E D C K S S F T C K S N W L K G W N W<br>T S G H N E C P V G A S C H P F T F Y F P T P A V L C E K I W S<br>H S Y K L S N Y S R G S G R C I Q M W F D P A Q G N P N E E V A<br>R F Y A E V M S G A G L R E A W L L V C S L S L V L F C V V S |
| BAA37125<br>SEQ ID NO:36 | M L R F A I T L F A V I T S S T C Q Q Y G C L E G D T H K A N P<br>S P E P N M H E C T L Y S E |
| P02752<br>SEQ ID NO:37 | M L R F A I T L F A V I T S S T C Q Q Y G C L E G D T H K A N P<br>S P E P N M H E C T L Y S E S S C C Y A N F T E Q L A H S P I I<br>K V S N S Y W N R C G Q L S K S C E D F T K K I E C F Y R C S P<br>H A A R W I D P R Y T A A I Q S V P L C Q S F C D D W Y E A C K<br>D D S I C A H N W L T D W E R D E S G E N H C K S K C V P Y S E<br>M Y A N G T D M C Q S M W G E S F K V S E S S C L C L Q M N K K<br>D M V A I K H L L S E S S E E S S S M S S S E E H A C Q K K L L<br>K F E A L Q Q E E G E E R R |
| Q05685<br>SEQ ID NO:38 | M A W K Q T P L L L L V Y M V T T G S G R D R T D L L N V C M D<br>A K H H K T K P G P E D K L H D Q C S P W K K N A C C S V N T S<br>Q E L H K A D S R L Y F N W D H C G K M E P A C K S H F I Q D S<br>C L Y E C S P N L G P W I Q Q V D Q S W R K E R F L D V P L C K<br>E D C H Q W W E A C R T S F T C K R D W H K G W D W S S G I N K<br>C P N T A P C H T F E Y Y F P T P A S L C E G L W S H S Y K V S<br>N Y S R G S G R C I Q M W F D S T Q G N P N E D V V K F Y A S F<br>M T S G T V P H A A V L L V P S L A P V L S L W L P G |
| P35846<br>SEQ ID NO:39 | M A H L M T V Q L L L L V M W M A E C A Q S R A T R A R T E L L<br>N V C M D A K H H K E K P G P E D N L H D Q C S P W K T N S C C<br>S T N T S Q E A H K D I S Y L Y R F N W N H C G T M T S E C K R<br>H F I Q D T C L Y E C S P N L G P W I Q Q V D Q S W R K E R I L<br>D V P L C K E D C Q Q W W E D C Q S S F T C K S N W H K C W N W<br>S S G H N E C P V G A S C H P F T F Y F P T S A A L C E E I W S<br>H S Y K L S N Y S R G S C R C I Q M W F D P A Q G N P N E E V A<br>R F Y A E A M S G A G L H G T W P L L C S L S L V L L W V I S |

TABLE 6-continued

| Accessions/SEQ ID NOs | Sequence |
|---|---|
| P02702<br>SEQ ID NO:40 | A Q A P R T P R A R T D L L N V C M D A K H H K A E P C P E D S<br>L H E Q C S P W R K N A C C S V N T S I E A X K D I S Y L Y R F<br>N W D H C G K M E P A C K R H F I Q D T C L Y E C S P N L G P W<br>I R E V N Q R W R K E R V L G V P L C K E D C Q S W W E D C R T<br>S Y T C K S N W H K G W N W T S G Y N Q C P V K A A H C R F D F<br>Y F P T P A A L C N E I W S H S Y K V S N Y S R G S C R C I Q M<br>W F D P F Q G N P N E E V A R F Y A E N P T S G S T P Q G I |
| AAD53001<br>SEQ ID NO:41 | M A H L M T Q L L L L L I W V S E C A Q S R A T R A R T E L L<br>N V C M D A K H H K E K P G P E D N L H Q C S P W K K N S C C<br>S T N T S Q E A H E D I S Y L Y R F N W D H C G K M T L E C K R<br>H F I Q D T C L Y E C S P N L C P W I Q Q V D Q S W R K E R I L<br>D V P L C K E D C Q R W W E D C R T S F T C K S N W H K G W N W<br>T S G Y N Q C P V G A S C R H F D F Y F P T P A A L C E E I W S<br>H S Y K L S N Y S R G S G R C I Q M W F D P A Q G N P N E E V A<br>R F Y A E M S G A G L H G A W P L M C S L S L V L L W V F S R<br>V P L T F |
| AAD33741<br>SEQ ID NO:42 | M A L G R A R L L L L L V C V A V T W A A R P D L L N I C M D A<br>K H H K T K P G P E D G L H E Q C S P W E M N A C C S V N T S Q<br>E A H N D I S Y L Y K F N W E H C G K M K P A C K R H F I Q D T<br>C L Y E C S P N L G P W I Q E V N Q K W R R E R I L N V P L C K<br>E D C Q N W W E D C R T S Y T C K S N W H E G W N W S S G Y N R<br>C P A N A A C H P F D F Y F P T P A A L C S Q I W S N S Y K Q S<br>N Y S R G S G R C I Q M W F D P E Q G N P N E V V A R Y Y A Q I<br>M S G A G L S E A W P L Q F G L A L T L L W L L S |
| AAD33740<br>SEQ ID NO:43 | M A W R L T L F V L L G L V A A V G G A R A K S D M L N V C M D<br>A K H H K P K P S P E D K L H D Q C S P W R K N S C C S V N T S<br>L E A H K D I S Y L Y R F N W D H C G K M E P A C K R H F I Q D<br>T C L Y E C S P N L G P W I Q E V N Q K W R R E R I L N V P L C<br>K E D C Q I W W E D C R T S Y T C K S N W H K G W N W T S G Y N<br>Q C P V S A A C H R F D F Y F P T P A A L C N E I W S H S F E V<br>S S Y S R G S G R C I Q M W F D P A Q G N P N E A V A R Y Y A E<br>N G D A G A V A Q G I G P L L T N L T E M V K H W V T G |
| AAD19354<br>SEQ ID NO:44 | M A H L M T Q L L L L V M W M A E C A Q S R A T R A R T E L L<br>N V C M D A K H H K |
| AAD19353<br>SEQ ID NO:45 | M A H L M T Q L L L L V M W M A E C A Q S R A T R A R T E L L<br>N V C M D A K H H K E K P G P E D N L H D Q C S P W K T N S C C<br>S T N T S Q E A H K D I S Y L Y R F N W N H C G K M T S E C K R<br>H F I Q D T C L Y E C S P N L G P W I Q Q V D Q S W R K E R I L<br>D V P L C K E D C Q Q W W E D C Q S S F T C K S N W H K G W N W<br>S S G H N E C P V G A S C H P F T F Y F P T S A A L C E E I W S<br>H S Y K L S N Y S R G S G R C I Q M W F D P A Q G N P N E E V A<br>R F Y A E M S G A G F H G T W P L L C S L S L V L L W V I S |
| AAC98303<br>SEQ ID NO:46 | M A W Q M M Q L L L L A L V T A A G S A Q P R S A R A R T D L L<br>N V C M N A K H H K T Q P S P E D E L Y G Q |
| AAB81938<br>SEQ ID NO:47 | T C L Y E C S P N L G P W I Q Q V D Q S W R K E R V L N V P L C<br>K E D C E Q W W E D C R T S Y T C K S N W H K G C N W T S G F N<br>K C A V G A A C Q P F H F Y F P T P I A R |
| AAB81937<br>SEQ ID NO:48 | M L P A A T E V Q H R L Q G Q K D M V W K W M P L L L L L V C V<br>A T M C S A Q D R T D L L N V C M D A K H H K T K P G P E D K L<br>H D Q C S P W K K N A C C T A S T S Q E L H K D T S R L Y N F N<br>W D H C G K M E P A C S A T S S R T P V S M S A H Q P G A L D P<br>A G E S E L A A K N A S W N C P Y A K S T V S A G G R I V T P P<br>T R A R A T G T E D G T G P Q E L T S A Q L G L S A A P L S P T<br>S P L Q L P F V K A S G V T H T R S A T T A E G A A A A S R C G<br>L L Q P R A T P T R K W R G S M L Q P C M |
| AAB49703<br>SEQ ID NO:49 | M P W K L T A L L L F L A G V V S V C R A R A R T D L L N V C M<br>D A K H H K V E P G P E D E L H D Q C V P W K K N A C C S A R V<br>S H E L H R D K S S L Y N F S W E H C G R M E P A C K R H F I Q<br>N N C L Y E C S P N L G P W F Q E V N Q K W R K E R F L N V P L<br>C K E D C L D W W E D C R T S Y T C K S S W H K G W N W S S G S<br>N Q C P T G T T C D T F E S F F P T P A A L C E G I W N H D Y K<br>F T N Y S R G S G R C I Q M W F D A A E G N P N E E V A R F Y A<br>L A L S A G T M S L G T G P L L L S A A L M L P L G L L D |
| AAB35932<br>SEQ ID NO:50 | Q A T R A E T E N L N V D M D A K H H K E K |

TABLE 6-continued

| Accessions/SEQ ID NOs | Sequence |
|---|---|
| 1011184A SEQ ID NO:51 | A Q A P R T P R A R T D L L N V C M D A K H H K A E P G P E D S<br>L H E Q C S P W R K N A C C S V N T S I E A X K D I S Y L Y R E<br>N W D H C G K M E P A C K R H F I Q D T C L Y E C S P N L G P W<br>I R E V N Q R W R K E R V L G V P L C K E D C Q S W W E D C R T<br>S Y T C K S N W H K G W N W T S G Y N Q C P V K A A H C R F D F<br>Y F P T P A A L C N E I W S H S Y K V S N Y S R G S G R C I Q M<br>W F D P F Q G N P N E E V A R F Y A E N P T S G S T P Q G I |
| 0908212A SEQ ID NO:52 | I A W A R T E L L N V X M N A K H H K E K P G P E D K L H E Q X<br>X P W R K N A X X S T X T X Q E A X K D V S Y L Y R F N A P A C<br>K R H F I Q D T C L Y E X S P N L G P X I Q Q V D Q S X R K E R<br>V L N V W F D P A Q G N P N E Q V A |
| CAA44610 SEQ ID NO:53 | M A Q R M T T Q L L L L L V W V A V V G E A Q T R I A W A R T E<br>L L N V C M N A K H H K E K P G P E D K L H E Q C R P W R K N A<br>C C S T N T S Q E A H K D V S Y L Y R F N W N H C G E M A P A C<br>K R H F I Q D T C L Y E C S P N L G P W I Q Q V D Q S W R K E R<br>V L N V P L C K E D C E Q W W E D C R T S Y T C K S N W H K G W<br>N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L M L L W L L S |
| CAA83553 SEQ ID NO:54 | M A W Q M M Q L L L L A L V T A A G S A Q P R S A R A R T D L L<br>N V C M N A K H H K T Q P S P E D E L Y G Q C S P W K K N A C C<br>T A S T S Q E L H K D T S R L Y N F N W D H C G K M E P T C K R<br>H F I Q D S C L Y E C S P N L G P W I R Q V N Q S W R K E R I L<br>N V P L C K E D C E R W W E D C R T S Y T C K S N W H K G W N W<br>T S G I N E C P A G A L C S T F E S Y F P T P A A L C E G L W S<br>H S F K V S N Y S R G S G R C I Q M W F D S A Q G N P N E E V A<br>K F Y A A A M N A G A P S R G I I D S |
| AAA74896 SEQ ID NO:55 | T R I A W A R T E L L N V C M N A K H H K E K P G P E D K L H E<br>Q C R P W R K N A C C S T N T S Q E A H K D V S Y L Y R F N W N<br>H C G E M A P A C K R H F I Q D T C L Y E C S P N L G P W I Q Q<br>V D Q S W R K E R V L N V P L C K E D C E Q W W E D C R T S Y T<br>C K S N W H K G W N W T S G F N K C A V G A A C Q P F H F Y F P<br>S P T V L C N E I W T H S Y K V S N Y S R G S G R C I Q M W F D<br>P A Q G N P N E E V A R F Y A A A M S G A G P W A A W P F L L S L A |
| AAA49056 SEQ ID NO:56 | M L R F A I T L F A V I T S S T C Q Q Y G C L E G D T H K A K P<br>S P E P N M H E C T L Y S E S S C C Y A N F T E Q L A H S P I I<br>K V S N S Y W N R C G Q L S K S C E D F T K K I E C F Y R C S P<br>H A A R W I D P R Y T A A I Q S V P L C Q S F C D D W Y E A C K<br>D D S I C A H N W L T D W E R D E S G E N H C K S K C V P Y S E<br>M Y A N G T D M C Q S M W G E S F K V S E S S C L C L Q M N K K<br>D M V A I K H L L S E S S E E S S S M S S S E E H A C Q K K L L<br>K F E A L Q Q E E G E E R R |
| AAA37599 SEQ ID NO:57 | M A W K Q T P L L L L V Y M V T T G S G R D R T D L L N V C M D<br>A K H H K T K P G P E D K L H D Q C S P W K K N A C C S V N T S<br>Q E L H K A D S R L Y F N W D H C G K M E P A C K S H F I Q D S<br>C L Y E C S P N L G P W I Q Q V D Q S W R K E R F L D V P L C K<br>E D C H Q W W E A C R T S F T C K R D W H K G W D W S S G I N K<br>C P N T A P C H T F E Y Y F P T P A S L C E G L W S H S Y K V S<br>N Y S R G S G R C I Q M W F D S T Q G N P N E D V V K F Y A S F<br>M T S G T V P H A A V L L V P S L A P V L S L W L P G |
| AAA37598 SEQ ID NO:58 | M A H L M T V Q L L L L V M W M A E C A Q S R A T R A R T E |
| AAA37597 SEQ ID NO:59 | M F G L K F F L V L E A L L F L F T C Y I V L K I G L K I L |
| AAA37594 SEQ ID NO:60 | M A W K Q T P L L L L V Y M V T T G S G R D R T D L L N V C M D<br>A K H H K T K P G P E D K L H D Q |
| AAA37596 SEQ ID NO:61 | M A H L M T V Q L L L L V M W M A E C A Q S R A T R A R T E L L<br>N V C M D A K H H K E K P G P E D N L H D Q |
| AAA37595 SEQ ID NO:62 | M A H L M T V Q L L L L V M W M A E C A Q S R A T R A R T E L L<br>N V C M D A K H H K E K P G P E D N L H D Q C S P W K T N S C C<br>S T N T S Q E A H K D I S Y L Y R F N W N H C G T M T S E C K R<br>H F I Q D T C L Y E C S P N L G P W I Q Q V D Q S W R K E R I L<br>D V P L C K E D C Q Q W W E D C Q S S F T C K S N W H K G W N W<br>S S G H N E C P V G A S C H P F T F Y F P T S A A L C E E I W S<br>H S Y K L S N T S R G S G R C I Q M W F D P A Q G N P N E E V A<br>R F Y A E A M S G A G L H G T W P L L C S L S L V L L W V I S |

TABLE 6-continued

| Accessions/SEQ ID NOs | Sequence |
|---|---|
| AAA35824<br>SEQ ID NO:63 | T R I A W A R T E L L N V C M N A K H H K E |
| AAA35823<br>SEQ ID NO:64 | M A Q R M T T Q L L L L L V W V A V V G E A Q T R I A W A R T E<br>L L N V C M N A K H H K E K P G P E D K L H E Q C R P W R K N A<br>C C S T N T S Q E A H K D V S Y L Y R F N W N H C G E M A P A C<br>K R H F I Q D T C L Y E C S P N L G P W I Q Q V D Q S W R K E R<br>V L N V P L C K E D C E Q W W E D C R T S Y T C K S N W H K G W<br>N W T S G F N K C A V G A A C Q P F H F Y F P T P T V L C N E I<br>W T H S Y K V S N Y S R G S G R C I Q M W F D P A Q G N P N E E<br>V A R F T A A A M S G A G P W A A W P F L L S L A L M L L W L L S |
| AAA35822<br>SEQ ID NO:65 | M A Q R M T T Q L L L L L V W V A V V G E A Q T R I A W A R T E<br>L L N V C M N A K H H K E K P G P E D K L H E Q C R P W R K N A<br>C C S T N T S Q E A H K D V S Y L T R F N W N H C G E M A P A C<br>K R H F I Q D T C L Y E C S P N L G P W I Q Q V D Q S W R K E R<br>V L N V P L C K E D C E Q W W E D C R T S Y T C K S N W H K G W<br>N W T S G F N K C A V G A A C Q P F H F Y F P T P T V L C N E I<br>W T H S Y K V S N Y S R G S G R C I Q M W F D P A Q G N P N E E<br>V A R F Y A A A M S G A G P W A A W P F L L S L A L M L L W L L S |
| AAA35821<br>SEQ ID NO:66 | M V W K W M P L L L L L V C V A T M C S A Q D R T D L L N V C M<br>D A K H H K T K P G P E D K L H D Q C S P W K K N A C C T A S T<br>S Q E L H K D T S R L Y N F N W D H C G K M E P A C K R H F I Q<br>D T C L Y E C S P N L G P W I Q Q V N Q T W R K E R F L D V P L<br>C K E D C Q R W W E D C H T S H T C K S N W H R G W D W T S G V<br>N K C P A G A L C R T F E S Y F P T P A A L C E G L W S H S Y K<br>V S N Y S R G S G R C I Q M W F D S A Q G N P N E E V A R F Y A<br>A A M H V N A G E M L H G T G G L L L S L A L M L Q L W L L G |
| AAA18382<br>SEQ ID NO:67 | M A W Q M M Q L L L L A L V T A A G S A Q P R S A R A R T D L L<br>N V C M N A K H H K T Q P S P E D E L Y G Q C S P W K K N A C C<br>T A S T S Q E L H K D T S R L Y N F N W D H C G K M E P T C K R<br>H F I Q D S C L Y E C S P N L G P W I R Q V N Q S W R K E R I L<br>N V P L C K E D C E R W W E D C R T S Y T C K S N W H K G W N W<br>T S G I N E C P A G A L C S T F E S Y F P T P A A L C E G L W S<br>H S F K V S N Y S R G S G R C I Q M W F D S A Q G N P N E E V A<br>K F Y A A A M N A G A P S R G I I D S |
| AAA17370<br>SEQ ID NO:68 | M V W K W M P L L L L L V C V A T M C S A Q D R T D L L N V C M<br>D A K H H K T K P G P E D K L H D Q C S P W K K N A C C T A S T<br>S Q E L H K D T S R L Y N F N W D H C G K M E P A C K R H F I Q<br>D T C L Y E C S P N L G P W I Q Q V N Q T W R K E R F L D V P L<br>C K E D C Q R W W E D C L T S H T C K S N W H R G W D W T S G V<br>N K C P A G A L C R T F E S Y F P T P A A L C E G L W S H S Y K<br>V S N Y S R G S G R C I Q M W F D S A Q G N P N E E V A R F Y A<br>A A M H V N A G E M L H G T G G L L L R L A L M L Q L W L L G |
| U02715<br>SEQ ID NO:69 | tctcattggg tcccattggc ctgaccctaa agcctgggtt cttttccacc agacctaatc<br>tccatcgagc tggccttatc ctaagaaacca cttgggtat ctataaaatc cagatgcccc<br>ctggtgatga gcaattctct agattttgat gaaagttgaa tgtgtggatg ctggaatgag<br>taaattaaca agtaaggaga tgaatgcaag caggaatgac taaatggaca gactcaggga<br>gccttgaaga gggtggggtc tggaagggaa ggaagagagg aaggagaata gctaagtagg<br>gagatttcac tcagtgctta ccagagcgcg ttgtctaccc tgtaccgaag acagaggctg<br>tggggacagc ctaggggcct ggatctattg cctacttaga gagaggccaa ctcagacaca<br>gccgtgtatg ctcccagcag caacggaggt tcaggcaaga tgcccgaaga gggaaggg |
| BE518506<br>SEQ ID NO:70 | gggggctggg acaggcggta gctcgcctcg cggcggaccg ccagctcgat cccgagatcc<br>aactacgagc ttttttaactg cagcaacttt aagatacgct attggagctg gaattaccgc<br>ggctgctggc accagacttg ccctccaatg aaaggattta aagtgtactc<br>attccaatta cagggcctcg aaaagagtcct gtattgttat ttttcgtcac tacctccccg<br>agtcgggagt gggtaatttg cgcgcctgct gccttccttg gatgtggtag ccgtttctca<br>ggctccctct ccggaatcga accctgattc cccgttaccc gtggtcacca tggtaggcac<br>agaaagtacc atcgaaagtt gataggggcag acattcgaat gagacgtcac cgccacaaag<br>ggcgcgcgat cggctcgagg ttatctagag tcaccaaagc ggccggggca accgagattg<br>gcccgcatgg gtttttgggtc tgataaaatgc acgcatcccc ggaggtcagc gctcgtctgc<br>atgtattagc tctagaattg ccacagttat ccaagtaacg ttggagcgat caaaggaacc<br>ataactgatt taatgagcca ttcgcagttt cactgtaccg gccgtgtgta cttagacttg<br>catggcttaa tctttgagac aagcatatgc tactggcagg a |
| BG058247<br>SEQ ID NO:71 | gcggccgcct actactacta ctactgctcg aattcaagct tctaacgatg tacgggggaca<br>tgccgacggg cgctgacccc cttcgcgggg gggatgcgtg catttatcag atcaaaacca<br>acccggtcag cccctctccg gccccggccg ggggcgggc gccgcggct ttggtgactc<br>tagataacct cgggccgatc gcacgccccc cgtggcggcg acgaccatt cgaacgtctg<br>ccctctccct taccaggacc acagctctgt tccttcggcc tctggtcctc tctggtcccc<br>tcctgggttt cttacgtagt tgattttttcc tctttagtct ccccgacct gcgccc |

TABLE 6-continued

| Accessions/SEQ ID NOs | Sequence |
|---|---|
| BG017460<br>SEQ ID NO:72 | tttttttttt tttcaaagta aacgcttcgg gccccggga cactcagtca agagcatcgg<br>ggaggcgccg agaggcaggg gctgggacag gcggtagctc gcctcgcggc ggaccgccag<br>ctcgatccca agatccaact acgagctttt taact |
| NM_000802<br>SEQ ID NO:73 | tcaagattaa acgcaaagga cagacatggc tcagcggatg acaacacagc tgctgctcct<br>tctagtgtgg gtggctgtag taggggaggc tcagacaagg attgcatggg ccaggactga<br>gcttctcaat gtctgcatga acgccaagca ccacaaggaa aagccaggcc ccgaggacaa<br>gttgcatgag cagtgtcgac cctggaggaa gaatgcctgc tgttctacca acaccagcca<br>ggaagcccat aaggatgttt cctacctata tagattcaac tggaaccact gtggagagat<br>ggcacctgcc tgcaaacggc atttcatcca ggacaccctgc tctacgagt gctcccccaa<br>cttggggccc tggatccagc aggtggatca gagctggcgc aaagagcggg tactgaacgt<br>gcccctgtgc aaagaggact gtgagcaatg gtgggaagat tgtcgcacct cctacacctg<br>caagagcaac tggcacaagg gctggaactg gacttcaggg tttaacaagt gcgcagtggg<br>agctgcctgc caaccttttcc atttctactt cccacacacc actgttctgt gcaatgaaat<br>ctggactcac tcctacaagg tcagcaacta cagccgaggg agtggccgct gcatccagat<br>gtggttcgac ccagcccagg gcaaccccaa tgaggaggtg gcgaggttct atgctgcagc<br>catgagtggg gctgggccct gggcagcctg gccttcctg cttagcctgg ccctaatgct<br>gctgtggctg ctcagctgac ctccttttac cttctgatac ctggaaatcc ctgccctgtt<br>cagccccaca gctcccaact atttggttcc tgctccatgt tcgggcctct gacagccact<br>ttgaataaac cagacaccgc acatgtgtct tgagaattat ttgg |
| U20391<br>SEQ ID NO:74 | taagttgaca cttctcaggt tgtcacaaga ttcaggtatg gctcactgtt gcaggacata<br>agctgggatc tcctgggaat tggtctgctt gcaggcccta gagagccttc cttcttggtt<br>gattttcctc tagagatcca actgtcttct caggctcccc tgcctgcctc ctccttgggt<br>cctttcttgt ggcattgcca gattactggg cccccatttt ccctacactt actgccactc<br>atagtctgat ggttcccaca tctgcatcca acctggactc ttccctgag cttttcccctc<br>tacaaccacc ttcccgggc caagggcaca caggcacctc gacaaaacag tgttctatgt<br>ttcttcctgc ccaaacctgc ccctcctct cctttttccc atctgtggta ccaccatgt<br>ctcagagaat aaaaaaaatg aaggcttctg tcattgactg gggtggagat ggagggaaga<br>gttagcccag aatcacaggt gctgtagaaa ggatacctga gttgccggga gaggggtcc<br>atgagttggg gatggaagga gagcttggcc cttcaaacaa ttgaagatct gatcaaaaga<br>ttcagaacat ctgtgatttt gtggctggtg atgggtgaca cctgggctaa tggggttggg<br>ggagttggtg gctctacaat ttatggcctt gggagatcct tgctctctat agctgactgg<br>gaggttggaa gcctgggctc tagcccttgc cttgatcctc cggatctcat tttcctcatc<br>tgcctaacag gacagagggg ttggaaactg atgagattag ctcaaaggat cctggcagct<br>caggctgcaa gattttttc agacctcagt gtttgggaaa aaattgggta ggtggagctt<br>agggactggc cttaggcctg cactgttaat tcaccccctc ccactacccc atggaggcct<br>ggctggtgct cacatacaat aattaactgc tgagtggcct tcgcccaatc ccaggctcca<br>ctcctgggct ccattcccac tccctgcctg tctcctaggc cactaaacca cagctgtccc<br>ctgaataag gcaaggggga gtgtagagca gagcagaagc ctgagccaga cggagagcca<br>cctcctctcc caggtatgtg acactcccca tccccttca gaggccacac accctatggc<br>attcccacca tgtgttaagg attttctgaa ctggaagggc cctctgttg cctgaaggcc<br>agagaatctt gaagtggaga ctgaggccca gaccagagtg tggcctgctc aagattaaac<br>gacaagttag tgttcatccc cctgaactag tacctgggct ctagcccttc agtccagagc<br>tgagttctca gctcttctag tctggggccc caaggttggg tgtgggggtc atgattgttg<br>gtggggaggg gtcacagctg gactaagacc tgaaggtgag actaggcagg tgggaaagga<br>gcttgcagag tgatgctgct caaaaggaca ggaagagagc ctggcttcag aagcagccac<br>agcaagagga actactgact gaacaggtgg gctccactgg gggctccgga aaggattttc<br>tcagccccca tcccagcac tgtgtgttgg ccgcacccat gagagcctcc gcactctgaa<br>ggtgcagggg gcaaaggcca aaagagctct ggcctgaact tgggtggtcc ctactgtgtg<br>acttgggca tggccctcat ctgtgctgaa atgattccac aaagattaaa ctggctatca<br>tttgttgatt tcccccttct tacatttaat ccttgcagga gaaagctaag cctcaagata<br>gtttgcttct ctttccccca aggccaagga gaaggtggag tgagggctgg ggtcgggaca<br>ggttgaacgg gaaccctgtg ctctaaacag ttagggtttg ttcccgcagg aactgaaccc<br>aaaggatcac ctggtattcc ctgagagtac agatttctcc ggcgtggccc tcaaggttag<br>tgagtgagca ggtccacagg ggcatgattg gatcctgaga tgaatgaatc aaccatgaga<br>gagtgaatga acactggaat caatagagta gcagagtaat ggattgtgga gcaggaaaga<br>gagctgctgg gtgggaattc aattccaggc ttatatgagc cctgctgtgc agtcggcctg<br>gagacagccc agctcaggcc ctgcctagac ccctgtcaag gaggccctgt caagaggaga<br>ggaggggcag cacggggca aggcaagctt gtgagcggga aaggcatgtc cactttagcg<br>actggtatgt ggaagatgag ttagaggaga cagatggaga gaagtcatag gaaataaatt<br>ctgagcattt taggagggcc cagacacctg gtgtccagtg gagtgaagga aacagtcgcc<br>tcccaaaatt cagtgtctga ggtcaaagga ttgaagttct gtgatgacca aggagaagcc<br>agctctgtgg tagggggcac aggagctccc caaggcccca gggctgtcca gctggctgtc<br>ccctgccagc acccatgtcc tgtgacccca ccccaccaag atcccatggt ttccgggaag<br>ggcctactaa actagccttga gtgatgaggc tagaaagggg ctgggaccaa ggtttaaaaa<br>gcaaaacaaa ctaacaaaaa ccacactgca gcccccccaa ctaaaacatt tttataaact<br>tttttttttt ttttgagatg gagtctcgct ctgtcaccca ggctagagtg caatggcaca<br>atcttggctc actgtaacct ccacctcctg gattcaagtg attctcctgc ctcagcctcc<br>cacgtagctg ggactacagg cacacgacac cgcacccagc tcatttgta ttttttagtag<br>agacagggtt tcactatgtt ggccaggctg gtctcaaact tctgacctca ggtgatccac<br>ccacctcagc cttccaaagt gctgggatta caggcatgag ccaccgcgcc cagcccattt<br>ttgtaaactt ttacaatgaa gtaatttggt gtcaaaatct gacctgaaaa ttaatgtgag<br>tttatgtata gttttaattt atcccactag tgtaactgtt tcacccagaa atatacactt<br>gattattggg tatatgaaaa aaatatttc tttgaatcac ctttgatgaa atcctaaaaa<br>attttaaccc tgaaacattt gaataaggca ttgtggacct atggcaaact cctggctatt |

TABLE 6-continued

| Accessions/SEQ ID NOs | Sequence |
|---|---|
| NM_016731<br>SEQ ID NO:75 | agggacagac atggctcagc ggatgacaac acagctgctg ctccttctag tgtgggtggc<br>tgtagtaggg gaggctcaga caaggattgc atgggccagg actgagcttc tcaatgtctg<br>catgaacgcc aagcaccaca aggaaaagcc aggcccgag gacaagttgc atgagcagtg<br>tcgaccctgg aggaagaatg cctgctgttc taccaacacc agccaggaag cccataagga<br>tgtttcctac ctatatagat tcaactggaa ccactgtgga gagatggcac ctgcctgcaa<br>acggcatttc atccaggaca cctgcctcta cgagtgctcc cccaacttgg ggccctggat<br>ccagcaggtg gatcagagct ggcgcaaaga gcgggtactg aacgtgcccc tgtgcaaaga<br>ggactgtgag caatggtggg aagattgtcg cacctcctac acctgcaaga gcaactggca<br>caagggctgg aactggactt caggggttaa caagtgcgca gtgggagctg cctgccaacc<br>tttccatttc tacttcccca cacccactgt tctgtgcaat gaaatctgga ctcactccta<br>caaggtcagc aactacagcc gagggagtgg ccgctgcatc cagatgtggt tcgacccagc<br>ccagggcaac cccaatgagg aggtggcgag gttctatgct gcagccatga gtggggctgg<br>gccctgggca gcctggcctt tctgcttag cctggcccta atgctgctgt ggctgctcag<br>ctgacctcct tttaccttct gatacctgga aatccctgcc ctgttcagcc ccacagctcc<br>caactatttg gttcctgctc catggtcggg cctctgacag ccactttgaa taaaccagac<br>accgcacatg tgtcttgaga attatttgg |
| NM_016730<br>SEQ ID NO:76 | ggaaaggatt ttctcagccc ccatccccag cactgtgtgt tggccgcacc catgagagcc<br>tcagcactct gaaggtgcag ggggcaaagg ccaaaagagc tctggcctga acttgggtgg<br>tccctactgt gtgacttggg gcatggccct catctgtgct gaaatgattc cacaaagatt<br>aaactggcta tcatttgttg atttcccct tcttacattt aatccttgca ggagaaagct<br>aagcctcaag atagtttgct tctcttccc ccaaggccaa ggagaaggtg gagtgagggc<br>tggggtcggg acaggttgaa cgggaaccct gtgctctaaa cagttagggt ttgttcccgc<br>aggaactgaa cccaaaggat cacctggtat tccctgagag tacagattc tccggcgtgg<br>ccctcaaggg acagacatgg ctcagcggat gacaacacag ctgctgctcc ttctagtgtg<br>ggtggctgta gtaggggagg ctcagacaag gattgcatgg gccaggactg agcttctcaa<br>tgtctgcatg aacgccaagc accacaagga aaagccaggc cccgaggaca agttgcatga<br>gcagtgtcga ccctggagga agaatgcctg ctgttctacc aacaccagcc aggaagccca<br>taaggatgtt tcctacctat atagattcaa ctggaaccac tgtggagaga tggcacctgc<br>ctgcaaacgg catttcatcc aggacacctg cctctacgag tgctccccca acttgggggcc<br>ctggatccag caggtggatc agagctggcg caaagagcgg gtactgaacg tgcccctgtg<br>caaagaggac tgtgagcaat ggtgggaaga ttgtcgcacc tcctacacct gcaagagcaa<br>ctggcacaag ggctggaact ggacttcagg gtttaacaag tgcgcagtgg gagctgcctg<br>ccaacctttc catttctact tccccacacc cactgttctg tgcaatgaaa tctggactca<br>ctcctacaag gtcagcaact acagccgagg gagtggccgc tgcatccaga tgtggttcga<br>cccagcccag ggcaacccca atgaggaggt ggcgaggttc tatgctgcag ccatgagtgg<br>ggctgggccc tgggcagcct ggcctttcct gcttagcctg ccctaatgc tgctgtggct<br>gctcagctga cctcctttta ccttctgata cctggaaatc cctgccctgt tcagccccac<br>agctcccaac tatttggttc ctgctccatg gtcggcctc tgacagccac tttgaataaa<br>ccagacaccg c |
| NM_016729<br>SEQ ID NO:77 | cattccttgg tgccactgac cacagctctt tcttcaggga cagacatggc tcagcggatg<br>acaacacagc tgctgctcct tctagtgtgg gtggctgtag taggggaggc tcagacaagg<br>attgcatggg ccaggactga gcttctcaat gtctgcatga acgccaagca ccacaaggaa<br>aagccaggcc ccgaggacaa gttgcatgag cagtgtcgac cctggaggaa gaatgcctgc<br>tgttctacca acaccagcca ggaagcccat aaggatgttt cctacctata tagattcaac<br>tggaaccact gtggagagat ggcacctgcc tgcaaacggc atttcatcca ggacacctgc<br>ctctacgagt gctcccccaa cttgggggccc tggatccagc aggtggatca gagctggcgc<br>aaagagcggg tactgaacgt gcccctgtgc aaagaggact gtgagcaatg gtgggaagat<br>tgtcgcacct cctacacctg caagagcaac tggcacaagg gctggaactg gacttcaggg<br>tttaacaagt gcgcagtggg agctgcctgc caacctttcc atttctactt ccccacaccc<br>actgttctgt gcaatgaaat ctggactcac tcctacaagg tcagcaacta cagccgaggg<br>agtggccgct gcatccagat gtggttcgac ccagcccagg gcaaccccaa tgaggaggtg<br>gcgaggttct atgctgcagc catgagtggg gctgggcct gggcagcctg gcctttcctg<br>cttagcctgg ccctaatgct gctgtggctg ctcagctgac ctccttttac cttctgatac<br>ctggaaatcc ctgccctgtt cagccccaca gctcccaact atttggttcc tgctccatgg<br>tcgggcctct gacagccact ttgaataaac cagacaccg |
| NM_016725<br>SEQ ID NO:78 | tggaggcctg gctggtgctc atacaata attaactgct gagtggcctt cgcccaatcc<br>caggctccac tcctgggctc cattcccact ccctgcctgt ctcctaggcc actaaaccac<br>agctgtcccc tggaataagg caaggggag tgtagagcag agcagaagcc tgagccagac<br>ggagagccac ctcctctccc agggacagac atggctcagc ggatgacaac acagctgctg<br>ctccttctag tgtgggtggc tgtagtaggg gaggctcaga caaggattgc atgggccagg<br>actgagcttc tcaatgtctg catgaacgcc aagcaccaca aggaaaagcc aggcccgag<br>gacaagttgc atgagcagtg tcgaccctgg aggaagaatg cctgctgttc taccaacacc<br>agccaggaag cccataagga tgtttcctac ctatatagat tcaactggaa ccactgtgga<br>gagatggcac ctgcctgcaa acggcatttc atccaggaca cctgcctcta cgagtgctcc<br>cccaacttgg ggccctggat ccagcaggtg gatcagagct ggcgcaaaga gcgggtactg<br>aacgtgcccc tgtgcaaaga ggactgtgag caatggtggg aagattgtcg cacctcctac<br>acctgcaaga gcaactggca caagggctgg aactggactt caggggttta caagtgcgca<br>gtgggagctg cctgccaacc tttccatttc tacttcccca cacccactgt tctgtgcaat<br>gaaatctgga ctcactccta caaggtcagc aactacagcc gagggagtgg ccgctgcatc<br>cagatgtggt tcgacccagc ccagggcaac cccaatgagg aggtggcgag gttctatgct<br>gcagccatga gtggggctgg gccctgggca gcctggcctt tctgcttag cctggcccta<br>atgctgctgt ggctgctcag ctgacctcct tttaccttct gatacctgga aatccctgcc<br>ctgttcagcc ccacagctcc caactatttg gttcctgctc catggtcggg cctctgacag<br>ccactttgaa taaaccagac accg |

TABLE 6-continued

| Accessions/SEQ ID NOs | Sequence |
| --- | --- |
| NM_016724<br>SEQ ID NO: 79 | ggcaaggggg agtgtagagc agagcagaag cctgagccag acggagagcc acctcctctc<br>ccaggaactg aacccaaagg atcacctggt attccctgag agtacagatt tctccggcgt<br>ggccctcaag ggacagacat ggctcagcgg atgacaacac agctgctgct ccttctagtg<br>tgggtggctg tagtagggga ggctcagaca aggattgcat gggccaggac tgagcttctc<br>aatgtctgca tgaacgccaa gcaccacaag gaaaagccag gcccgagga caagttgcat<br>gagcagtgtc gaccctggag gaagaatgcc tgctgttcta ccaacaccag ccaggaagcc<br>cataaggatg tttcctacct atatagattc aactggaacc actgtggaga gatggcacct<br>gcctgcaaac ggcatttcat ccaggacacc tgcctctacg agtgctcccc caacttgggg<br>ccctggatcc agcaggtgga tcagagctgg cgcaaagagc gggtactgaa cgtgcccctg<br>tgcaaagagg actgtgagca atggtgggaa gattgtcgca cctcctacac ctgcaagagc<br>aactggcaca agggctggaa ctggacttca gggtttaaca agtgcgcagt gggagctgcc<br>tgccaacctt tccatttcta cttccccaca cccactgttc tgtgcaatga aatctggact<br>cactcctaca aggtcagcaa ctacagccga gggagtggcc gctgcatcca gatgtggttc<br>gacccagccc agggcaaccc caatgaggag gtggcgaggt tctatgctgc agccatgagt<br>ggggctgggc cctgggcagc ctggccttt ctgcttagcc tggccctaat gctgctgtgg<br>ctgctcagct gacctccttt taccttctga tacctggaaa tccctgccct gttcagcccc<br>acagctccca actatttggt tcctgctcca tggtcgggcc tctgacagcc actttgaata<br>aaccagacac cg |
| NM_013307<br>SEQ ID NO: 80 | atggcctcag ttccgaaaac caacaaaata gaaccgcggt cctattccat tattcctagc<br>tgcagtatca ggcggctcgg gcctgctttg aacactccaa tttttcaaag taaacgcaac<br>gggccccgcg gacactcagc ttacagcatc gaggggcgcc agaggcaagg gggggacgg<br>gcggtggtcc ctcgcgcgga ccgccgccc gctcccaaga tccaactacg agcttttac<br>ctgcagcaac tttactatac gctattggag ctggaattac cgcggctgct ggcaccagac<br>ttgccctcca atggctcctc gttaaaggat ttaaagtgga ctcattccaa ttacagggcc<br>tcgaaagagt cctgtattgt tattttcgtc actacctccc cgggtcggga gtgggtaatt<br>tgcgcgcctg ctgccttcct tggatgtggt agcctccagg ctccctctcc ggaatctgaa<br>ccctcattcc ccgtcacccg tggtcaccat ggtcggcacg gcgactacca tcgaaagttg<br>atagggcaga cgttcgaatg ggtcgtcgtc cgccgccacg gggggcgtgc gatcggcccg<br>aggttatcta gagtcaccaa agccgccggc gcccgcccc cggccgggc cggagagggg<br>ctgagggttg gttttgatct gataaatgca ccgatcrccc ccgcgaaggg ggtcagcgcc<br>cgtcggcatg tattagctct agaattacca cagttatcca agtag |
| NM_008035<br>SEQ ID NO: 81 | gctttagagg cagatcaggg tgtagttttc agctagcgcc gtgccttccc caccatgttc<br>cttgccatga tgataatgta ctagacctct gaaactgtag cttcttttgtt acagagtctc<br>cgtgaatctg gaattcacca attcggcgag tctgaaagcc tcagtgatct ctcaggctcc<br>atctgtctcc actcccagt ggaaggcttg cagctgtgtc accgctccag acttcacaca<br>ggtgctggaa gactgaacta agacagaaag acatggcctg gaaacagaca ccactcttgc<br>ttttggtcta catggtcaca acaggcagtg gccgggacag aacagaccta ctcaacgttt<br>gcatggatgc caaacaccat aagacaaagc cgggcccga ggacaagctg catgaccagt<br>gtagtccatg gaagaaaaat gctgttgct cagtcaacac cagccaggag ctacacaagg<br>ctgactcccg tctgtacttc aactgggatc actgtggcaa gatggagcct gcctgtaaga<br>gtcacttcat ccaagactcc tgcctgtatg agtgctcccc caaccttggg ccttggatcc<br>agcaagtgga ccagagttgg cgtaaagagc gtttcctgga tgtgcccta tgcaaagagg<br>actgtcacca gtggtgggaa gcctgtcgta cctccttac ctgcaagaga gactggcata<br>aaggctggga ctggtcctca ggcattaaca agtgcccaaa cacagcaccc tgtcacacgt<br>ttgagtacta cttcccgaca ccagccgcc tttgcgaagg tctctggagt cactcctaca<br>aggtcagcaa ctacagcaga gggagtggcc gctgcatcca gatgtggttt gactcaaccc<br>agggcaatcc caatgaggac gtggtgaagt tttatgcttc ctttatgaca tctgggactg<br>tgccccatgc agcagtactt cttgtgccca gcctggcccc agtgctgtca ttatggctcc<br>ctggctgaga ggtcagtctt cctctctaga tttctcctct atctaccctt ggtctggttc<br>aactcttcaa agaataagga agtcttgagc ctgcttccac ccctctcctc tgtcatccag<br>ttcctgatcc atgttggggg ttggggtttc tacaatcatt tcaataaat ctatgacaca<br>tctgggccta atgaaaaaaa aaa |
| NM_008034<br>SEQ ID NO: 82 | tggagctgag cacacacttg gaggttccac ttaccttagc tctgccttca gggtctgaca<br>tggctcacct gatgactgtg cagttgttgc tcctggtgat gtggatggcc gaatgtgctc<br>agtccagagc tactcgggcc aggactgaac ttctcaatgt ctgcatggat gccaagcacc<br>acaaagaaaa accgggccct gaggacaatt tacacgacca gtgcagcccc tggaagacga<br>attcctgctg ttccacgaac acaagccagg aagcacataa ggacatttcc tacctgtacc<br>ggttcaactg gaaccactgc ggaactatga atcggaatg caaacggcac tttatccaag<br>acacctgcct ctatgagtgt ccccgaact tgggaccctg gatccagcag gtggaccaga<br>gctggcgcaa agagcggatc cttgatgttc ccctgtgcaa agaggactgt cagcagtggt<br>gggaggactg ccagagctct tttacctgca agagcaattg gcacaaggga tggaactggt<br>cctctgggca taacgagtgt cctgtgggag cctcctgcca tcccttcacc ttctacttcc<br>ccacatctgc tgctctgtgt gaggaaatct ggagtcactc ctacaagctc agcaactaca<br>gccgagggag cggccgctgc attcagatgt ggtttgaccc agcccagggc aaccccaacg<br>aggaagtggc gaggttctat gccgaggcca tgggcttcat tgggcttcat tggactcggtt<br>cactcttgtg cagcctgtcc ttagtgctgc tctgggtgat cagctgagtg cctgttttac<br>cttcagttgt ctggagcgcc accctgcttg gctcagcctc ccagctccca gctcctttg<br>tggtgggct ctgacagcct ctttaataaa ccagacattc cacatgtgcc ttatgaatta<br>aaaaaaaaaa aaaaaaaaa |
| BF153292<br>SEQ ID NO: 83 | ctccgatccc gaaggccaac gtaataggac cgaaatccta taatgttatc ccatgctaat<br>gtatacagag cgtaggcttg ctttgagcac tctaatttct tcaaagtaac agcgccggag<br>gcacgacccg gccaattaag gccaggagcg catcgccgac agaagggacg agacgaccgg |

TABLE 6-continued

| Accessions/SEQ ID NOs | Sequence |
|---|---|
| | tgcacaccta gggcggaccg gccggcccat cccaaagtcc aactacgagc tttttaactg<br>caacaactta aatatacgct attggagctg gaattaccgc ggctgctggc accagacttg<br>ccctccaatg gatcctcgtt aagggattta gattgtactc attccaatta ccagactcat<br>agagcccggt attgttattt attgtcacta cctccccgtg tcaggattgg gtaatttgcg<br>cgcctgctgc cttccttgga tgtggtagcc gtttctcagg ctccctctcc ggaatcgaac<br>cctaattctc cgtcacccgt caccaccatg gtaggccact atcctaccat cgaaagttga<br>tagggcagaa atttgaatga tgcgtcgccg cacgatggc cgtgcgatcc gtcgagttat<br>catgaatcat cgcagcaacg ggcagagccc gcgtcgacct tttatct |
| BF114518<br>SEQ ID NO:84 | cgacgcatca ttcaaattc tgccctatca actttcgatg gtaggatagt ggcctaccat<br>ggtggtgacg ggtgacggag aattagggtt cgattccgga gagggagcct gagaaacggc<br>taccacatcc aaggaaggca gtaggcgcgc aaattaccca atcctgacac ggggaggtag<br>tgacaataaa taacaatacc gggctcttcg agtctggtaa ttggaatgag tacaatctaa<br>atcccttaac gaggatccat tggagggcaa gtctggtgcc |
| BE940806<br>SEQ ID NO:85 | gcacggccct cgtgccggcg acgcatcatt caaatttctg ccctatcaac tttcgatggt<br>aggatagtgg cctactatgg tggtgacggg tgacggagaa ttagggttcg attccggaga<br>gggagcctga gaaacggcta ccacatccaa ggaaggcagc aggcgcgcaa attacccaat<br>cctgatacgg ggaggtagtg acaataaata acaataccgg gctctcagag tctggtaatt<br>ggatgagtac aatctaatcc ttaacgagga tccattggag ggcaagtctg gtgcacgagc |
| BE858996<br>SEQ ID NO:86 | gaagacacac gtttagtatt ttattatgaa tcattatttc aaagtcccat actgcatatt<br>catataaggc aacacggcac aatttcaggc ttcatcacaa aggatgaaaa agactgtttc<br>taactccctc ctaatttgca gacatgcttg aacacttaat ggaaggtgaa gtttattttg<br>tggcccctca gttctctttc aagtcctcta gtagaaagtc tccatggtgt gatcttctga<br>ctgggtagaa cccgcaattc tctgctgttt ttagtctttg ttccagatga ctaattacat<br>gacttggctg catttgtgag gggccgacac caacacaatt aaatcagtgc accattcagg<br>gccataggg aggaggcacc agtggtcacc atggtaggca cggcgactac catcgaaagt<br>tgatagggca gacgttcgaa tgggtcgtcg ccg |
| AF219906<br>SEQ ID NO:87 | gttgaagagt cacctggtgc ttcaacggga ctgatttcct gggcctggag ttggagatca<br>gaggtctgac |
| AF219905<br>SEQ ID NO:88 | cgctgatctg gaagcataaa caagaactga agctgaaggc tctaggggtt cccaacctgt<br>gatctccagc agacactcct ggtgtgtcac cggattcagg ctcctggaat agaggaaagca<br>aaggaagtct ggagctggaga cgaagaaacc ccaggcactc tgagagctgc tacctttttcc<br>atgtgtgctg ccagacactt ctcgtcaggg accaaatacc ccaagggagt ggagagaggc<br>ctgggctggg ccagacttcc tgggctttaa cctgtgctcc aagtaggtgg gtcacatttt<br>ccccagcggg agttgaaagag tcacctggtg cttcaacggg actgatttc c tgggcctgga<br>gttggagatc agaggtctga c |
| AF219904<br>SEQ ID NO:89 | ggggctggag ttggagatca gaggtctgac atggctcacc tgatggctgg gcagtggttg<br>ctcctgctga tgtggatggc cgaatgtgcc cagtccgag ctactcgggc caggaccgaa<br>cttctcaatg tctgcatgga tgccaagcac cacaaagaaa agccaggccc agaggacaag<br>ttacacgacc agtgcagccc ctggaagacg aatgcctgct gctccaccaa cacaagccag<br>gaagacacta aggacatttc ctacctgtac cgattcaact ggaatcactg tggaactatg<br>accccggagt gcaaacgtca ctttatccaa gacacctgcc tctatgagtg ttccccgaac<br>ttgggaccct ggatccagca ggtggaccag agctggccca aagagcggat ccttgatgtt<br>cccctgtgca aagaagactg tgtgctgtgg tgggaggact gcaagagctc ttttacctgc<br>aagagcaact ggctcaaggg atggaactgg acctcggggc ataatgagtg ccctgtggga<br>gcctcctgcc atcccttcac tttctactc cctacacctg ctgtgctgtg tgagaaaatc<br>tggagtcact cctacaagct cagcaactac agccgaggcg gcggccgctg catccagatg<br>tggttcgacc cagcccaagg caaccccaac gaggaagtgg cgaggttcta tgccgaggtc<br>atgagtggag ctgggcttcg cgaggcctgg ctgctggtgt gcagcctgtc cttagtgctg<br>ttctgcgtcg tcagctgagt tcctgttact ccttgtctgg agctccaccc tgcccggctt<br>agcctcccag ctccagcctc ctttgtggtg ggctctgac agcctgttta gtaaaccaga<br>cattctaaaa aaaaaa |
| BE687177<br>SEQ ID NO:90 | acccggtgag ctccctcccg gctccggccg ggggtcgggc gccggcggct ttggtgactc<br>tagataacct cgggccgatc gcacgccccc aggtcaagtt tgtttatgaa ggtattttgg<br>tattgttttc ctttgcttaa ttgcctcaca ttttgttctg aaaaacatgg gtccactgtt<br>aaaaccgaat gtatgtgtag ctttattctg tttcacaggc gcatgtgatt ggaaaactca<br>ttgtctcctc cagcctcagg agacttctaa aaagtttgc gtagctcaag ttgtgcatga<br>attaccgaat atattatttt tcagctttc ttcatgaacg atatttgaca tgtgcttggg<br>tacccttctc tgaaagttga aaacctacct acttagtccg ttctgtgcct tttttatttt<br>gccaaccatg ttttatggaa aagacattag caattacatt ttgcaaatgg aattatgt |
| BE636622<br>SEQ ID NO:91 | ggcaccagag tagtcatatg cttgtgttaa agattaagcc atgcatgcct aagtacaaac<br>tattcttatg gtaaaactgc ggacggctcc atagatcagt aatagttcgt tcagtgattt<br>gaaaagtac ttggataacc ctgttaattg tagagctaat acatgcaccg acggcctgat<br>cggtgaccg agagggtcgc acttgtctta attcacagtg ccccggaact gaggctgttc<br>gacgtggtag gggaggacgc tgaatgggc tggtagaaac aactgggggt ataaaaccaa<br>ggaggaagca aaaaagccat aacccggcga tggcctgga gtaaacctct gggctcaagg<br>ttgttattat gttcattgtg gcctctcggg gttatttga atgtggtaat aaaccgaaag<br>caactctatc agtttggttt ggatgtccgt taatcctgcg tggccagcgg ctttggggac<br>tccaggggac agggcgaaac gaggcaattc aaagctgatc gctttctaac gagggcgaca<br>cactgttcga attcctgacn tatcaactcg atggtaggat agtggcctac catggttata |

TABLE 6-continued

| Accessions/SEQ ID NOs | Sequence |
|---|---|
| | acgggtaacg gggaatcagg gctcgattcc ggagagggag cctgagaaac ggctaccact<br>tccaaggaag gcagcaggcg cgtaaattac tccctgccga cacggcgagg tagtgacgac<br>aaataccaag gaaaaccgcc tttggtggtt ttccattgga atgagcagaa ttcaaacccc<br>tctgcaagta acaattggag ggcaagtctg gtgccagcag c |
| BE627230<br>SEQ ID NO:92 | tccctcgact gtagttgctg agcttgtagg agtgactcca gatttcctca cacagagcag<br>cagatgtggg gaagtagaag gtgaagggat ggcaggaggc tcccacagga<br>tccctcgact gtagttgctg agcttgtagg agtgactcca gatttcctca cacagagcag<br>cagatgtggg gaagtagaag gtgaagggat ggcaggaggc tcccacagga |
| BE506561<br>SEQ ID NO:93 | ctatcgatat ccgatggtac ttgttgtgcc taccatggtg accccagttc atagcgaatg<br>agggtgcgat ggcagagagg gaggatgtga tgcagctatc gcatgcggtg gatgctggag<br>gcgcgcatgt tgcaccctcc cgacggcgag aggtggtgac tacccatatc gtgcaggact<br>ctttcgacgc gctgtagtct gaatgagtac acttttaagtc cgtgagcgcg gatctatcgg<br>ttggcgagtt tagtgccagc agcgcgaggc tttacagcct caatgtcgtg tatgacagtt<br>gcgtgtcctt atggagcgtg agttggatca tggg |
| BE505048<br>SEQ ID NO:94 | gcggccgcct actactacta aattcgcggc cgcgtcgacc gacgacccat tcgatcgtct<br>gccctatcaa ctttcgntgg ttgtcgccgt gcctaccatg gtgaccacgg gtgacgggga<br>ttctgggttc gtttccggtg agggtgcctg tgggggcggtt gcctcttctc tggttggctg<br>caggcgcgct ttttttcctcc tcccggcccg gggtggttgt |
| BE496754<br>SEQ ID NO:95 | ctggctgcag gaattcgcac gaggctatat gctcagttta aagattaagc catgcatgtc<br>gagttcatct ttgaagagaa actgcgaacg gctcattaga gcagatgtca tttattcgga<br>acgtcctttt ggataactgc ggtaattctg gagctaatac atgcaaataa accctgactt<br>ttgaaagggt gcaattatta gagcaaatca atcactttcg ggtgcagttt gctgactctg<br>aataacgcag catatcggcg gcttgttcgc cgatattccg aaaaagtgtc tgccctatca<br>acctgatggt agtctattag tctaccatgg ttattacggg taacggagaa taagggttcg<br>actccggaga gggagcctta gaaacggcta ccacatccaa ggaaggcagc aggcgcgaaa<br>cttatccaat cttgaacaga tgagatagtg actaaaaata aaaagaccat tcctatgaa<br>cggtcatttc aatgagttga tcataaacct ttttttcgagg atcaagtgga gggcaagtct<br>ggtgccagca gccgcggtaa ttccagctcc actagtgtaa atcgtcattg ctgcggttaa<br>aaagctcgta gttggatctg agttacatgc |
| BB114010<br>SEQ ID NO:96 | atcatccaga tttcgtttga tttcaccccg ggccttccgg aggaggacct cctgaaattt<br>tctccttcct atatgacatt agggactgtg ccccaagcag cagtacttttt tgtccccagc<br>ctgccccag tgccgtcatt atggctcccc gctgagaggt cagttttcct ctctagattt<br>ttcctctatt tacccttggt ctggttcaac ttttcaaaga ataaggaagt cttgaccctg<br>cttccacccc tttctctgt catccagttc ctgatccatg tgggggggttg gggtttctac<br>aatcattttc aataaattta tgacacatct gggcctaatg |
| BB109527<br>SEQ ID NO:97 | aggacgtttg atgtcttatg cttcctttat gaaatccggg attgtgcccc atccagcagt<br>attcttgtgc ccagcctggc cccactgcag tcattatgcc tccctggctg agaggtcatt<br>cttcctcttt agatttctcc tcaatctacc cttgttctgg ttcaactctt caaagaataa<br>ggaagtcttg acctgcttc cacccctttc ctctttcatc cagttcctga tccatgttgg<br>gggttgggt ttctacattc attttcaata aatctatgac acac |
| BB107219<br>SEQ ID NO:98 | tccgggcctt tcccccacaca caccaaaaac tttttctgcct actctggccc cagcgctttc<br>cttatgcctc cctggctgag aggtcatttt cttctataga tttctcctct atttaccctc<br>gctctggttc aactcttcaa agaataagga acttttgagc ctgcttccac ccttttcctc<br>tgtcatccag ttcctgatcc atgttgggg ttggggtttc tacaatcatt ttcaataaat<br>ctatgacaca tctgggccta atg |
| BE206324<br>SEQ ID NO:99 | tttttgtgcg gtgtctggtt tattcaaagt ggctgtcaga ggcccgacca tggagcagga<br>accaaatagt tgggagctgt gggctgaac agggcaggga tttccaggta tcagaaggta<br>aaaggaggtc agctgagcag ccacagcagc attagggcca ggctaagcag gaaaggccag<br>gctgccagg gcccagcccc actcatggct gcagcataga acctcgccac ctcctcattg<br>gggttgccct gggctgggtc gaaccacatc tggatgcagc ggccactccc tcggctgtag<br>ttgctgacct tgtaggagtg agtccagatt tcattgcaca gaacagtggg tgtggggaag<br>tagaaatgga aaggttggca ggcagctccc actgcgcact tgttaaaccc tgaagtccag<br>tttcagccct tgtgccagtt gctcttgcag gtgtaggagg tgcgacaatc ttcccaccat<br>tgctcacag |
| BE448392<br>SEQ ID NO:100 | ggatggaact ggtcctcggg gcataacgag tgtcctgtgg gagcctcctg ccatcccttc<br>accttctact tccccacatc tgctgctctg tgtgaggaaa tc |
| BE207596<br>SEQ ID NO:101 | tagtgtgggt ggctgtagta ggggaggctc agacaaggat tgcatgggcc aggactgagc<br>ttctcaatgt ctgcatgaac gccaagcacc acaaggaaaa gccaggcccc gaggacaagt<br>tgcttgtagc agtgtcgacc ctggaggaag aatgctcggt gttctaccaa caccagccag<br>gaagcccata aggatgtttc ctacctatat agattcaact ggaaccactg tggagagatg<br>gcacctgcct gcaaacggca tttcatccag gacacctgcc tctacgagtg ctccccaac<br>ttggggcct ggatccagca ggtggatcag agctggcgca aagagcgggt actgaacgtg<br>ccctgtgca aagaggactg tgagcaatgg tgggaagatt gtcgcacctc ctacacctgc<br>aagagcaact ggcacaaggg ctggaactgg acttcagggt taacaagtg cgcagtggga<br>gctgcctgcc aacctttcca tttctactc cccacaccca ctgttctgtg caatgaaatc<br>tggactcact cctacaggtc agcaactaca gccgagggag tgg |

TABLE 6-continued

| Accessions/SEQ ID NOs | Sequence |
| --- | --- |
| BE206635<br>SEQ ID NO:102 | tgcggtgtct ggtttattca aagtggctgt cagaggcccg accatggagc aggaaccaaa<br>tagttgggag ctgtgggggct gaacagggca tttttatttcc aggtatcata ttgtttgttg<br>taggagctga acagccacag cagcattagg gccaggctaa gcaggaaagg ccaggctgcc<br>cagggcccag ccccactcat ggctgcagca tagaacctcg ccacctcctc attggggttg<br>ccctgggctg ggtcgaacca catctggatg cagcggccac tccctcggct gtagttgctg<br>accttgtagg agtgagtcca gatttcattg cacagaacag tgggtgtggg gaagtagaaa<br>tggaaaggtt ggcaggcagc tcccactgcg cacttgttaa accctgaaga ccagttccag<br>cccttgtgcc agttgctctt ggaggtgtag gaggtgccac aatcttccca ccattgctca<br>cagtccttct tgcacagggg cacgttcaga accc |
| BE240998<br>SEQ ID NO:103 | cgacgcatca ttcaaatttc tgccctatca actttcgatg gtaggatagt ggcctaccat<br>ggtggtgacg ggtgacggga aattagggtt cgattccgga gagggagcct gagaaacggc<br>taccacatcc aaggaaggca gtaggcgcgc aaattaccca atcctgacac ggggaggtag<br>tgacaataaa taacaatacc gggctcttcg agtctggtaa ttggaatgag tacaatctaa<br>atcccttaac gaggatccat tggagggcaa gtctggtgcc agcagccgcg gtaattccag<br>ctccaatagc gtatatttaa g |
| BE228221<br>SEQ ID NO:104 | tatatgctca gtttaaagat taagccatgc atgtcgagtt catctttgaa gagaaactgc<br>gaacggctca ttagagcaga tgtcatttat tcggaacgtc cttttggata actgcggtca<br>ttctggagct aatacatgca aataaaccct gactttttgaa agggtgcaat tattagagca<br>aatcaatcac tttcgggtgc agtttgctga ctctgaataa cgcagcatat cggcggcttg<br>ttcgccgata ttccgaaaaa gtgtctgccc tatcaacctg atggtagtct attagtctac<br>catggttatt acgggtaacg gagaataagg gttcgactcc ggagagggag ccttagaaac<br>ggctaccaca tccaaggaag gcagcaggcg cgaaacttat ccaatcttga acagatgaga<br>tagtgactaa aaataaaaag accattccta tggaacggtc atttcaatga gttgatcata<br>aaccttttttt ccagttaatt ctac |
| BE225416<br>SEQ ID NO:105 | tggccgggat tagaacaaaa ccacgcggct tcggctgctt cttgttgact cagaataact<br>aagctgaccg catggccttg tgccggcggc gtgtctttca agcgtccact ttatcaactt<br>gacgggagca taatcgactc ccgtggtggt gacggataac ggaggatcag ggttcgactc<br>cggagaaggg gcctgagaaa tggccactac gtctaaggat ggcagcaggc gcgcaaatta<br>cccactctcg gctcgaggag gtagtgacga gaaataacga gatcgttctc tttgaggccg<br>gtcatcggaa tgagtacaat ttaaacccttt taacgagtat caagcagagg gcaagtctgg<br>tgccagcagc cgcggtaatt ccagctctgc taatacatag aattattgct gcggttaaaa<br>agctcgtagt tggattcgta tcggtaccct ggaaccctcc gggtgtttct gggtgttatc<br>gatttatcgt aatgttcggt tttgagtcct taacaggatt cttaacaggc attgcaagtt<br>tactttgaac aaatcagagt gcttcaaaca ggcgtttgcg ctgaatgatc gtgcatggat |
| BE225404<br>SEQ ID NO:106 | tgcctaatgt gccaccgctg agtgtgatga tattgacaat cggtagcatt atggccgggt<br>gtgtctattt caaagattaa gccatgcatg tataagttta aatcgttttg acgagaaacc<br>gcgaacggct cattacaatg gccatgattt acttgatctt gattatctaa atggattaac<br>tgtggaaaag ctagagctaa tacatgcacc aaaacttgtt cctctcggaa aagcgcattt<br>attagaacaa aaccacgcgg cttcggctgc ttcttgtgac tcagaataac taagctgacc<br>gcatggcctt gtgccggcgg cgtgtctttc aagcgtccac tttatcaact tgacgggagc<br>ataatcgact cccgtggtgg tgacggataa cggaggatca gggttcgact ccggagaagg<br>ggcctgagaa atggccacta cgtctaagga tggcagcagg cgcgcaaatt acccactctc<br>ggctcgagga ggtagtgacg agaaataacg agatcgttct ctttgaggcc ggtcatcgga<br>atgggtacaa tttaaacccct ttaacgagta tcaagcagag ggcaagtctg gtgccagcag<br>ccgggtattc cagctctgct aatacataga atta |
| BE214040<br>SEQ ID NO:107 | tccccaccct gcccccagtg ctgtcattat ggatccctgn ctgagaggtc aatcttcctt<br>tctagatttt tcctctatct accctttggtc tggttcaaat tttcaaagaa taaggaagtc<br>ttgagcctgc ttccacccct ctcctctttc atccagttcc taatccatgt tgggggttgg<br>ggtttctaca atcattttca ataaatttat gacacatctg gg |
| BE199619<br>SEQ ID NO:108 | gtagttgctg agcttgtagg agtgactcca gatttcctca cacagagcag cagatgtggg<br>gaagtagaag gtgaaggggat ggcaggaggc tcccacagga cactcgttat gccccgagga<br>ccagttccat cccttgtgcc aattgctctt gcaggtaaaa gagctctggc agtcctccca<br>ccactgctga cagtcctctt tgcacagggg aacatcaagg atccgctctt tgcgccagct<br>ctggtccacc tgctggatcc agggtcccaa gttcggggaa cactcataga ggcaggtgtc<br>ttggataaag t |
| BE199597<br>SEQ ID NO:109 | acacagagca gcagatgtgg ggaagtagaa ggtgaaggga tggcaggagg ctcccacagg<br>acactcgtta tgccccgagg accagttcca tcccttgtgc caattgctct tgcaggtaaa<br>agagctctgg cagtcctccc accactgctg acagtcctct ttgcacaggg gaacatcaag<br>gatccgctct tgcgccagct ctggtccacc tgctggatcc agggtcccaa gttcgggga<br>acactcatag aggcaggtgt cttggataaa gt |
| BE198610<br>SEQ ID NO:110 | actgcggaac tatgacatcg gaatgcaaac ggcactttat ccaagacacc tgcctctatg<br>agtgttcccc gaacttggga ccctggatcc agcaggtgga ccagagctgg cgcaaagagc<br>ggatccttga tgttcccctg tgcaaagagg actgtcagca gtggtgggag gactgccaga<br>gctcttttac ctgcangagc aattggcaca agggatggaa ctggtcctcg gggcataacg<br>agtgtcctgt gggagcctcc tgccatccct tcaccttcta cttccccaca tctgctgctc<br>tgtgtgagga aatct |
| BE198571<br>SEQ ID NO:111 | actgcggaac tatgacatcg gaatgcaaac ggcactttat ccaagacacc tgcctctatg<br>agtgttcccc gaacttggga ccctggatcc agcaggtgga ccagagctgg cgcaaagagc<br>ggatccttga tgttcccctg tgcaaagagg actgtcagca gtggtgggag gactgccaga |

TABLE 6-continued

| Accessions/SEQ ID NOs | Sequence |
|---|---|
| | gctcttttac ctgcaagagc aattggcaca agggatggaa ctggtcctcg gggcataacg<br>agtgtcctgt gggagcctcc tgccatccct tcaccttcta cttccccaca tctgctgctc<br>tgtgtgagga aatct |
| BE188055<br>SEQ ID NO:112 | gaggccagta gtcatatgct tgtctcaaag attaagccat gcatgtctaa gtataagcaa<br>ctatacggtg aaactgcgaa tggctcatta aatcagttat cgtttatttg atagtaccct<br>actacatgga taaccgtggt aattctagag ctaatacatg ctaaaaaccc cgacttcgga<br>aggggtgtat ttattanata aaaaaccaac gcccctcggg gctccttggt gaatcataat<br>aacttcacga atcgcatggc cttgcgccgg cgatggttca ttcaaatttc tgccctatca<br>actttcgatg gtaggataga ggcctaccat ggtttcaacg ggtaacgggg aattagggtt<br>cgactccgga gagggagcct gagaaacggc taccacatcc aaggaaggca gcaggcgcgc<br>aaaattccca atcccgaccg ggagggagn gacaataaat actgatncng gctntttggg<br>gtcttgnaat tggaatgagt ncaattaaat cccttaccag gaacaattgg aggcaanttg<br>gngcccccan cncggnattc cactccatag cgttntaaag tttgcaatta aaagttgaat<br>taacttggcc tggtggcggc ccctacgggt ctggccgcg gcnttnttg gggccgnncc<br>tttatgnggg gggaacngct ttntt |
| BE187804<br>SEQ ID NO:113 | tgacaattga atacggatgc ccccgactat ccctattaat cattacgggg gtcctagaaa<br>ccaacaaaat anaaccacnc gtcctattct attattccat gctaatgtat tcgagcaaag<br>gcctgctttg aacactntaa tttttttcaaa gnaaaagtcc tggttccccg acncncccag<br>ngaagggcat gcggctcccc aaaaggaaag gcccggccgg accagtacac gcggngaggn<br>ggaccggcca gccaggccca aggttcaact acgagctttt taactgcaac aactttaata<br>tacgctattg gagctgaat taccgnggnt gctggcacca aacttgccct ccaattgttc<br>ctcgttaagg ggatttaaat tgtactcatt ccaattacaa gacccaaaag agccctgtat<br>cagtatttat tgncactact |
| BB032646<br>SEQ ID NO:114 | tgtgccccat gcaacagtaa ttttgagcc cacccctggcc ccagtgctgt cattatggct<br>ccctggctga gaggtcagtt tcctatcta gattttcct gtatctaccc ttggtctggt<br>tcaaattttc aaagaataag gaagtcttga gcctgcttcc acccctttcc tctgtcatcc<br>agttcctgat ccatgttggg ggttggggtt tctacaatca ttttcaataa atctatgaca<br>catctg |
| BE037278<br>SEQ ID NO:115 | cccctagat gctagtagca gtngncacga ggtcatatgc ttgtctcaaa gattaagcca<br>tgcatgtgta agtatgaact aattcagact gtgaaactgc gaatggctca ttaaatcagt<br>tatagtttgt ttgatggtac ctgctactcg gataaccgta gtaattctag agctaatacg<br>tgcaacaaac cccgacttct ggaagggatg catttattag ataaaaggtc gacgcgggct<br>ttgcccgttg ctctgatgat tcatgataac tcgacggatc gcacggnctt tgcgccggcg<br>acgcatcatt caaatttctg ccctatcaac tttcgatggt aggatagtgg cctaccatgg<br>tggtgacggg tgacggagaa ttagggttcg attccggaga gggagcctga gaaacggcta<br>ccacatccaa ggaaggcagc aggcgcgcaa attacccaat cctgcacggg gaggtaggga<br>caataaaataa caataccggg ctcttcgagt ctggtaattg gaatgagtac aatctaaatc<br>ccttaacgag gatacattgg agggccaagt ctgttgccag cagccgcggt atattccagc<br>ttcaatagnc gtatatttaa agttgttggc agttaaaaag cttgtatttg gactctgggg<br>tgggcgaccc ggtcgtctag cggtgtgcac cggc |
| BE037125<br>SEQ ID NO:116 | gactactcat cagtgncagg ctagctgcac gaggtcatat gctcgtctca tagattaagc<br>catgcatgtg taagtatgaa ctaattcaga ctgtgaaact gcgaatggct cattaaatca<br>gttatagttt gtttgatggt acctgctact aggataaccg tagtaattct agagctaata<br>cgtgcaacaa accccgactt ctggaaggga tgcatttatt agataaaagg tcgacgcggg<br>cttttgcccgt tgctctgatg attcatgata actcgacgga tcgcacggcc tttgcgccgg<br>cgacgcatca ttcaaatttc tgccctatca actttcgatg gtaggatagt ggcctaccat<br>ggtggtgacg ggtgacggag aattagggtt cgattccgga gagggagcct gagaaacggc<br>taccacatcc aaggaaggca tcaggcgcgc atattaccca atcctgacac ggcgaggtag<br>tgacaataaa taacaatacc gggctcttcg agtctcggta atcggaatga gttcaatcta<br>tatccttta cgaggatcca ttggagggca agtcctgctg ccagcagcct gctgtccttt<br>cagctccaat agcgtatatt taagttgttg cagtttaaca agctcttatt cgaccttgtc<br>gtgcgaccgt tctcattacg ctatatgcct catcatatgt ccatatctat tctcgacttc<br>tcgctcccct cgtcttctct agtacttctg cctcttctat tatattcact atgatctatt<br>ctctacgcct cttcctctgc actcttatat tcatcgcact cttcactcta ctctctctta<br>tcgtctgcta gtctttcgct cttcctctt tctactttct catgtctctc atcttatctt<br>accctctctc actctttctg ttcgtctcct ctcactctgc gatttctcca ctgtatcacg<br>cttcgttctc tctactcttc tacttgttct ctctctatct cgtcctcatc tctccgtct<br>cgtctctatc gtcgtctacc gatactcttt cctttctgt catcttcctc tctcttcctc<br>tcttgcttac ttctcgtctc tcttcacgat tatcntctag cacgtcatct ctttactctc<br>tctatcttca tgtctactca ctctctcctg tgcgtactac tcttggctat catcatctcc<br>tagagtggct cgatgaggcg aatgtgcncn tctatctctc tacgttctct tactgatact<br>tctttg |
| BE037110<br>SEQ ID NO:117 | gtcgacgcac tagtgctata gtagcgttca tgcnagcngc acgaggagag agagagagag<br>agagagagag agagagagag agagagagag agagagagag agagagagag agagagagag<br>agagagagag agagagcggc acgagcttgt ctcaaagatt aagccatgca tgtgtaagta<br>tgaactaatt cagactgtga aactgcgaat ggctcattaa atcagttata gtttgtttga<br>tggtacctgc tactaggata accgtagtaa ttctagagct aatacgtgca acaaaccccg<br>acttctggaa gggatgcatt tattagataa aaggtcgacg cgggctttgc ccgttgctct<br>gatgattcat gataactcga cggatcgcac ggcctttgcg ccggcgacgc atcattcaaa<br>tttctgccct atcaactttc gatggtagga tagtggccta ccatggtggt gacgggtgac<br>agagaattag ggttcgattc cggagaggga gcctgagaaa cggctaccac atccaaggaa |

TABLE 6-continued

| Accessions/SEQ ID NOs | Sequence |
|---|---|
| | ggcagcatgc gcgcaaatta cccaatcctg acacggagag gtagtgacaa tatataacaa<br>taccgcgctc ttcgagtctg gtaattggaa tgagtacaat ctatatccct taacgaggat<br>ccattgtagg gcatgtctgg tgccagcagt cgcggtaatt tcagttccaa ttagcgatat<br>ttaattcgtt gcagtaaaaa gctcgtattt gaactttgcg tgggcccacc taccgtctag<br>cggtgtgcac tgtcttctct gcttttttcg gcatagcctc tgccttaaag cttgtctcgc<br>actgctctta cttcgatatt tgatcttcat gcgctctctt ggatctcatc atggatacct<br>aatgatctgc ctttctttgc ttggattcgc atcatcattg tacctggtct ttcgttctan<br>ttagtatttc tcgattttat catcctgcta ccctactcga tttatttaa actatttgtc<br>ttaacctatt tctttctctt cttacttcac tcttcctcgt aatctgtctt attatcactc<br>ttcctcattt cttttattact gttcatttac ttatttactt tatttccttc tacatctttt<br>ctctcatctt ctactcacgt cg |
| BE037009<br>SEQ ID NO:118 | cccacactag ttctagagga ttcggcacga ggtctcaaag attaagccat gcatgtgtaa<br>gtatgaacta attcagactg tgaaactgcg aatggctcat taaatcagtt atagtttgtt<br>tgatggtacc tgctactagg ataaccgtag taattctaga gctaatacgt gcaacaaacc<br>ccgacttctg gaagggatgc atttattaga taaaaggtcg acgcgggctt tgcccgttgc<br>tctgatgatt catgataact cgacggatcg cacggccttt gcgccggcga cgcatcattc<br>aaatttctgc cctatcaact ttcgatggta ggatagtggc ctaccatggt ggtgacgggt<br>gacggagaat taggggttcga ttccggagag ggagcctgag aaacggctac cacatccaag<br>gaaggcagca ggcgcgcaaa ttacccaatc ctgacacggn gaggtagtga acaataataa<br>caataccggg ctcttcgagt ctggtaatgg gaatgagtac aatctaaatt ccttaac |
| BE036024<br>SEQ ID NO:119 | gcacgagcga cgcgggcttt gcccgttgct ctgatgattc atgataactc gacggatcgc<br>acggcctttg cgccggcgac gcatcattca aatttctgcc ctatcaactt tcgatggtag<br>gatagtggcc taccatggtg gtgacgggtg acggagaatt agggttcgat tccggagagg<br>gagcctgaga aacggctacc acatccaagg aaggcagcag gcgcgctaat tacccaatcc<br>tgacacgggg aggtagtgac aataaataac aataccgggc tcttcgagtc tggtaattgg<br>aatgagtaca atctaaatcc cttaacgagg atccattgga gggcaagtct ggtgccagca<br>gccgcggtaa ttccagctcc aatagcgtat atttaagttg ttgcagttaa aaagctcgta<br>gttggacctt ggggtgggc gaccggtccg cctagcggtg tgcaccggtc gtcctgcctc<br>ttctgccggc gatgcgctcc tggcctaac tgggccggtc gtgccaccgg gcgctgtact<br>ttgaagaaat agagtgctca agcaggccta cgctctggat acattagcat gggataacat<br>cataggaatt ccgtcctatt ctgttgccct tcggnattcg agtaattgat aacaggnnac<br>agcggggggca ttcgtatttc atagtcagag gtgaaaatct tggattattg aagaccaaca<br>actgccaaag catttggcca ggatgttttc attattcaag accgaaagtt ggggcttcga<br>agaccaacag attcccgtct aatcttaaac cttaaacata tcccaccagg ggatcggggga<br>tgtaactttt aggacccccgc cggcccctta tgagaaatta aagtttggg gtcccggggg<br>gagtttggtg ccaaggcttt aacttaaggg aattgcgcgg aggggccccc cccgggaatg<br>ggccctgt |
| BE035828<br>SEQ ID NO:120 | gcacgaggtc tcaaagatta agccatgcat gtgtaagtat gaactaattc agactgtgaa<br>actgcgaatg gctcattaaa tcagttatag tttgtttgat ggtacctgct actaggataa<br>ccgtagtaat tctagagcta atacgtgcaa caaacccga cttctggaag ggatgcattt<br>attagataaa aggtcgacgc gggctttgcc cgttgctctg atgattcatg ataactcgac<br>ggatcgcacg gcctttgcgc cggcgacgca tcattcaaat ttctgcccta tcaactttcg<br>atggtaggat agtggcctac catggtggtg acgggtgacg gagaattagg gttcgattcc<br>ggagagggag cctgagaaac ggctaccaca tccaaggaag gcagcaggcg cgcaaattac<br>ccaatcctga cacggggagg tagtgacaat aaataacaat accgggctct tcgagtctgg<br>taattggaat gagtacaatc taaatccctt aacgaggatc cattggaggg caagtctggt<br>gccagcagcc gcggtaattc cagctccaat agcgtatatt taagttgttg cagttaaaaa<br>gctcgtagtt ggaccttggg gtgggccgac cggtccgcct agcggtgtgc accggtcggn<br>cttgcctctt ttgtcggcga tgcgctcctg gcctttaact ggccgggttg tgccaccggc<br>gctgttactt ttgaagaaat aagagtgctc aaagcaagcc ctacgctctg gttacattag<br>catgggataa caatatagga tttccggtcc tattttgttg gcctttggga tcggagttat<br>gaataacagg gaccgtccgg gggcatttct tttttaatat tcaaaggtga aat |
| BE035751<br>SEQ ID NO:121 | agctggtacg cctgcggtac cggtccggaa ttcccgggtc gacccacgcg tccgcggacg<br>cgtgggcgga cgcgtggggc taatacatgc aactcggtct ctaccggaaa tggtagggac<br>gcttttatta gaccaaaacc aatcgggcgt tctcgtccgt tttgccttgg tgactctgaa<br>taaattgtgt gcagatcgca cggtcctcgt accggcgacg catctttcaa atgtctgcct<br>tatcaacttt cgatggtagg tcctgcgcct accatggttg taacgggtaa cggggaatca<br>gggttcgatt ccggagaggg agcctgagaa acggctgcta catccaagga aggcagcagg<br>cgcgcaaatt acccactccc ggcacgggga ggtagtgacg acaaataacg atacgggact<br>catccgagcc cccgtaatcg aactttaaatc ctttaatgag tatccattgg<br>agggcaagtc tggtgccagc agccgcggta attccagctc caatagcgta tattaaagtt<br>gttgcggtta aaaagctcgt agtcggactt gtgtcacacg ctgccggttc accgcccgtc<br>ggtgctaact ggcatgcacg tgttgacgtc ctgctggtgg ccgtagccgg tccgggtgtt<br>ctgggatccc ttcggngttt cccggacccc ggtgcttggt gaaggcctac ttgacctacc<br>cgtcgcggtg ctcttaaccg aagtgtctcga tgggccggca cttttactt gaacaattag<br>agtgcttaaa gcaggcagta tcagccctga tactgagtgc atggaataat ggaataggaa<br>cctcggtcta tttatggt tttcggaatg ccctagatcg cgagcggccg ctctagaaga<br>tccaagctta cgtacgcctg cattgccaag tataagcttt tttatatggg gaaccctaaa<br>ttcaatcaac tggcgcgcgg tttaacacac gcggag |
| BE019724<br>SEQ ID NO:122 | tgctgctcct tctagtgtgg gtggctgtag taggggaggc tcagacaagg attgcatggg<br>ccaggactga gcttctcaat gtctgcatga acgccaagca ccacanagga aaattctttc<br>cccgaggaca agttgcatgt tctgtggggg ccctggagga agaatgcctg ctgttctacc |

TABLE 6-continued

| Accessions/SEQ ID NOs | Sequence |
|---|---|
| | aacaccagcc aggaagccca taaggatgtt tcctacctat atagattcaa ctggaaccac<br>tgtggagaga tggcacctgc ctgcaaacgg catttcatcc aggacacctg cctctacgag<br>tgctccccca acttggggcc ctggatccag caggtggatc agagctggcg caaagagcgg<br>gtactgaacg tgccctgtg caaagaggac tgtgagcaat ggtgggaaga ttgtcgcacc<br>tcctacacct gcaagagcaa ctggcacaag gcctggaac ctggacttca gggttttaac<br>aaggtgcgca ggtgggaggc tgccctgccc accttttcca ttttctactt ctctcacacc<br>cactgttgct gttgcattgc aaatcttgtc ctcacttctt acaaggtaca gcaactacca<br>agaaaaa |
| AW913291<br>SEQ ID NO:123 | aggacatttc ctacctgtac cggttcaact ggaaccactg cggaactatg acatcggaat<br>gcaaacggca ctttatccaa gacacctgcc tctatgagtg ttcccgaac ttgggaccct<br>ggatccagca ggtggaccag agctggcgca aagagcggat ccttgatgtt cccctgtgca<br>aagaggactg tcagcagtgg tgggaggact gccagagctc ttttacctgc aagagcaatt<br>ggcacaaggg atggaactgg tcctcggggc ataacgagtg tcctgtggga gcctcctgcc<br>atcccttcac cttctacttc cccacatctg ctgctctgtg tgaggaaatc t |
| AW912445<br>SEQ ID NO:124 | gcggccgctc cctcgactgt agttgctgag cttgtaggag tgactccaga tttcctcaca<br>cagagcagca gatgtgggga agtagaaggt gaagggatgg caggaggctc ccacaggaca<br>ctcgttatgc cccgaggacc agttccatcc cttgtgccaa ttgctcttgc aggtaaaaga<br>gctctggcag tcctcccacc actgctgaca gtcctctttg cacagggaa catcaaggat<br>ccgctctttg cgccagctct ggtccacctg ctggatccag ggtcccaagt tcggggaaca<br>ctcatagagg caggtgtctt ggataaagtg ccgtttgcat tccgatgtca tagttccgca<br>gtggt |
| AW823912<br>SEQ ID NO:125 | gggctgtgga cgaagactgt agagactacc cagagtctga cctagggaga ggccaactcg<br>gatacccta tgtgcgctcc cagaagctaa ggacattgag acagaaagac atggcctgga<br>aacagacacc actcttgctt ttggtctaca tggtcacaac aggcagtggc cgggacagaa<br>cagacctact caacgttttgc atggatgcca aacaccataa gacaaagccg ggccccgagg<br>acaagctgca tgaccagtgt agtccatgga agaaaaatgc ctgttgctca gtcaacacca<br>gccaggagct acacaaggct gactcccgtc tgtacttcaa ctgggatcac tgtggcaaga<br>tggagcctgc ctgtaagagt cacttcatcc aagctcctg cctgtatgag tgctccccca<br>accttgggcc ttggatccag caagtggacc agagttggcg taaagagcgt gtcctggatg<br>tgcccttatg caaagaggac tgtcaccagt ggtgggaagc ctgtcgtacc tactttacct<br>gcaagagaga ctggcataaa ggctgggact ggtcctcagg catttacaag tgcccaaaca<br>cagcaccctg tcacacgttt gagtactact tcccgacacc agccagccct tgc |
| AW823418<br>SEQ ID NO:126 | tttttttttt ttcccaaatg tgtcatagat ttattgaaaa tgattgtaga aaccccaacc<br>cccaacatgg atcaggaact ggatgacaga ggaaggggg ggaagcaggc tcaagacttc<br>cttattcttt gaagagttga accaaaccaa gggtagatag aggagaaatc tagagaggaa<br>gactgacctc tcagccaggg agccataatg acagcactgg ggccaggctg ggcacaaaaa<br>gtactgctgc atggggcaca gtcccagatg tcataaagga agcataaaac ttcaccacgt<br>cctcattcgg attgccctgg gttgagtcaa accacatttg gatgcagcgg ccactccctc<br>tgctgtagtt gctgaccttg taggagtgac tccagagacc ctcgcaaagg ctggctggtg<br>tcgggaagta gtactcaaac gtgtgacagg gtgctgtgtt tgggcacttg ttaatgcctg<br>aggaccagtc ccagccttta tgccagtctc tcttgcaggt aaaggaggta cgacaggctt<br>cccaccctg gtgacagtcc ttttttgcata agggcaccat ccagaaaacg ctctttacgc<br>caactcttgt tccacttgct gatccaaagg ccaaagttgg gggagcact |
| AB23803<br>SEQ ID NO:127 | cagcctcttg cacacagctt tactctgtca gccccagggt ggaaacaaag ggctggctgt<br>tcatcacact gcactttgtg taatcactcg ctctcacaac tggcaaatct cttttgccag<br>tggtgggact gaataacatt ttaaagggat gaagtacagc acagagctgt acaagatagt<br>ggatgactgc agactttttc ataattttgt gccattttcta aaaaagtgat gtttctcaaa<br>ttactacaag ttgatttttaa ctccattctt tttaaaatgt gattgatgtg tgtttctcat<br>tttacacaca gatgtatgca aatgggaccg acatgtgcca gagtatgtgg ggggaatcct<br>ttaaggtgag cgaatcctcc tgcctctgct tgcaaatgaa caagaaggac atggtggcaa<br>tcaagcacct cctctccgaa agctcagagg aaagctccag tatgagcagc agtgaggagc<br>acgcctgcca aaagaaactc ctgaagtttg aggcactgca gcaagaggaa ggggaagaga<br>gaagatgaat tttggtggat gaatatcagg aggagaggaa tcattgtgga ggttgtgctc<br>ggggcatcac agcagcctgt cttatccctc acttctgaga acacaataaa tcaatggttg<br>gctatatt |
| AB22344<br>SEQ ID NO:128 | acaagcagat taatttcatt agcacgcatc accatatata ataaagctgt aataggccaa<br>atgctccaat ttacacttgt gaaactccgt ctcactccag ccacactgtt gttacacttt<br>catgatgcca aggagggaaa cagatctggc agctgtcaca agttggaagt acaaacaatt<br>tttccttca ccactacagc tttgcagagt taacaaaaat ataaaaccag aaaaagcttac<br>ttcagtcatt agagagatct gcctcactaa aaagggatca ctgtgttgag ttaggagatg<br>tcagtttgac atagatacta actcaatggc cagaagctgt gaagttagca actagctgga<br>gttcttgtat ctcttttgca tttttttccc tcattaccca atggtagctc ttgcagaagg<br>aattcatgca ggcaggtagc ggctcctgag agctcaaata gctgcgtctg tgatttcgga<br>ataaatacat ccttctgcta acatcgctgg ccattatcag atagtcagat gataatgtaa<br>taataataat gtacccgtgc cagaattact gtctgtgca atatctgtaa catcatgcat<br>gctttaacgc tgtataaaaa ctttgagaag atgaaatataa gttcataggg caatgatatt<br>aatgttaaaa ataaatgata acaggagttt tatcagtaca aaaatatgag tcgtacttg<br>caaataaatt cagcattaac aaatgaggtt aacaaccct tcaagtattg aaagcaataa<br>gaaacattct ttaatgaaatt tctcaatata agacttacgg tcttatactg agacttttct<br>tactcagaat aagaaaaaga agactcaaga tgatgaagat gtgtggctga aatctctaga<br>agctcctgtg cttgagcctg cctacatcta ttgttaacca aagccaagtc tgagaaatca |

TABLE 6-continued

| Accessions/SEQ ID NOs | Sequence | |
|---|---|---|
| | caaacatatg acaattttcc ttcctgctgt tagaaattct gcctaatctc ccagcaagtg | |
| | gtcccatttg gctcatattc aaagcttgaa aaagatccca gtctcctata gcttaatata | |
| | atttgtatgt caattccata aacaaaggca ttacatgaaa cctcctggct cctaacacct | |
| | ttacaagagt gaatacattt catacaaacc aagcagtaag gaacagaaca cgtgcttttt | |
| | caccaggctg gctagcacag ccactcatcc tcagattgaa aggggatgtt tatgtggcac | |
| | agtggtcttt actttgtatg aatacactga tcttagtacc aagcaatatg cacaagtcct | |
| | ttacactaca aatcagcaag aagctccatt aatttcagcc agcacaaaat caagccacat | |
| | gaagtgaagg cacaggcaat aaggtcttac atttacttca gtttctccta tacttatatt | |
| | atgtctcttt gtatttgttt taattaaatt cactctggaa agcagaaaac actagggttt | |
| | caaatgatct gaaaatggtc ttgtaaaggc agcagcactt ttgcctcaag gaaggcttca | |
| | gccagagcag gaattggtgc ttacagctca gcagagatca ttatcatact gtgagtttgc | |
| | tcagtgagat tcattccaca cttccactgt gccagtgttt gttttattca agcaaaaaag | |
| | ttttgtaaat actgacccac agttactatt tgacaaacca ctgttgtgtt ttaaaataga | |
| | aacaagagat gctattttcc atttgcatct gaataattgc aaagtagtca gtggcgtgtt | |
| | gctagttagg gagctcactg ggatttgacc tatggaagta agtgcaccta tttgtaatga | |
| | ccacgtctgc tttctgtgat ggtccatgtt cagatgtgga atccctctg cagaaagcac | |
| | acctggtaag gaaatccagt cagcaactgc tgtcagtggt actcgcaaca gtttctccta | |
| | gtgtttgtga cacccttgga aagcacaaac atggcaggta gagaaagaag gacaaacatc | |
| | agcaggttaa aaaaagaatc ttctgggcaa agagcaaagg cctgagaatc aggagaccaa | |
| | ttctccttca ggggctgcag taaaattact gagtaaccca aagcaaactg atatgtttac | |
| | ggtcaaaatt aagccagaca ggttgaaata tgaagagttg tttgaaatgt ctataattca | |
| | gtgaagttgg tgataagaac ccaattaagc tgttgtagaa atgaatctaa taattataac | |
| | aaaaggaatc attgcaaaat caggcagggg gtgggagtga gttgtattgg gtacactgga | |
| | gagctgttgt ttttctaatt ctagtctatg tttgtacttt cctgtttatt atgtccacat | |
| | ttgcaagcaa taaaagggca ttatgtgctg gtcattccat ctgcttttga gataaatcta | |
| | tgttagcatt tcaaagggtc aaggaactct ccagggcaaa caaattctgg agcgctgctg | |
| | ccagatggcg cgtatataaa gtggaaagcg agaaaagcaa tttgctgtgt ttctgttcca | |
| | gggagaagtc tcacccagaa ggacagcaaa agaggtgaga aactaccgag aaattgtaca | |
| | ggcggttttc ttctgtaaca tgttgctttc tttgcatctg aaaagtttag gtacggagag | |
| | aagctcagtt cttgttcagg caaagctctt ccaaaaaggt atcaggaata tttaaccaaa | |
| | gaattgaagg ttaagttaat aacacctata aagaattatg cacttcttta tgtgggaggt | |
| | tctagattta tctgtataac tcactaatat gtagtctgta cttacagaaa ctctatgctc | |
| | gcagaccaaa tggtggttat cttgcatatt tgactgaact ctacaaaagc agacacaaaa | |
| | ccattgatca gattattagg ttcaaataag cgtgacctca acaaaggcaa gttatctgca | |
| | taatttatcc agctcaattg ccaccttatg ctctgctatt agcttgtcaa ttctgtaaac | |
| | agaagcactg caattaaatg ggtaatttcc cagcacacaa aagaactctg taagtttcgg | |
| | agctgatcaa tcttgccttc aaatctagtg tagcagtggg atgggaaatc catatctgca | |
| | tgagaaattt aaaaacctt tgttaaatac tgaaaaccat aacatatagc cttcattctt | |
| | catatagcct gtattcttca taggtcacca agaactaaaa atatgtagca gaagcattaa | |
| | gtgtttggac atgagcaaag gaaagggaga atgagtgacc caatatttat atgcgtacct | |
| | ctcttgagca tatttaattg tatatatatg tagctttttt acagcagccc ttcttttac 3420 | |
| | tatcaggact tttcctacaa ataaaggata tcagtaaaga cttctctccg cacaggaaaa 3480 | |
| AW475385 SEQ ID NO:129 | tttccccagt cagctggctg atctggaagt ataaacaaga aaggaggctg acggctctag aagtcccaa cctgttgtga tcttcagtag acaaacactc ctggtgtgtc acaggattca ggccactaaa cctcggccgg ctgtctcctg gaatgaagaa agcaaaggaa gcctagagtg gagacaaaga aacccgaggc actctgagag ctgccatctt atccttgttt gccgcctgac acttctcagc aggatccaca tacccctaagg agtggaagac tccttggcgc ttggtgcttc aaccggactg acttcctggg cctggagttg gcgattagag gtctgacatg gctcacctga tgactgtgca gttgttgctc ctggtgatgt ggatggccga atgtgctcag tccagagcta ctcgggccag gactgaactt ctcaatgtct gcatggatgc catacaccac agagaaaaac cgggccctga tgacaattta cacgaccagt gcagcctctg gaaacgaatt cctgctgttc cacgaacact agccatgaag cacataagga catgtcctac ctgttccaga tcaactggaa ccactgcggg actatgacat cggaatgcag actgcactgt atgcaagaca cctgcctcta tgagtgtaca cagaacttgg gacgctggat tcatctagtg aaccaaagct ggc | |
| AW323586 SEQ ID NO:130 | cacctgatga ctgtgcagtt gttgctcctg gtgatgtgga tggccgaatg tgctcagtcc agagctactc gggccaggac tgaacttctc aatgtctgca tggatgccaa acaccacaaa gaaaaaccgg gccctgagga caatttacac gaccagtgca gcccctggaa gacgaattcc tgctgttcca cgaacacaag ccaggaagca cataaggaca tttcctacct gtaccggttc aactggaacc actgcggaac tatgacatcg gaatgcaaac ggcactttat ccaagacacc tgcctctatg agtgttcccc gaactgggga ccctggatcc agcaggtgga ccagagctgg cgcaaagagc ggatccttga tgttccctg tgcaaagagg actgtcagca gtggtgggag gactgccaga gtcttttac ctgc | |
| AW319308 SEQ ID NO:131 | caacaaccca ttcaaacatc taccctatca actttcaata atagtcacca tacctaccat aataaccacg aataacaaaa aatcataatt caattccaaa taagaatcct aagaaactac taccacatcc aaataataca gcatacactc aaattcccca ctcccgaccc aagaaaattt aacgaaaaat aacaatacaa tactcttcg aagccctata attaaaataa atccacttta aatcctttaa cgaagatcca ttagagaaca attctgctga tatcac | |
| AW239668 SEQ ID NO:132 | aagattatgc ctcccccaaa ttcggcacga agcggggagc gagcggaccc cctccctgtc cgtcctctgg tcggggtcct tttttaataa cgcgtaaacc tatccaaagg tacacaacga agaagcttgg acaaaaggcg gaaaagcgtc ttgccaaaag ggggactgga agtaaactgg aaaaaaaacta attttccaag agaagaactt ggaagaaagg ggaattgagt tcagggggtg accttctcga tctccgggga cgaaattctg aatacgcaac aagcaaggac caatccaatc ccgggaacgc gggcggaccc aaccgcgaag attttcaaac ccgaaaatcc aaacaatcct | |

TABLE 6-continued

| Accessions/SEQ ID NOs | Sequence |
|---|---|
| | ggccaaagaa atatgcccttt gagtaacaaa ccatcccaat tttttttaata tatcccaaaa<br>tattattatt aaaacaaatg ctaaaaaccc tccactccca aaaggttaaa aaaatgggggt<br>ccaattggca ccaactttaa tgggaagttt gggattaaaa aaaaacaccc cttccatttt<br>cccggggagc gttatttggg gaagcacccc ccccgcactt taattttgtt |
| AV253136<br>SEQ ID NO:133 | atgggaatat cccccataca atagtacttc ttgtgcccaa tctggcccca gtgccgtcat<br>tatgggtccc tgcgtgagag gtcatttttct tctttagatt ttttcctctat ttaccccttgg<br>tctggttcaa ttcttcaaag aataaggaag ttttgagcct gcttccaccc cttcttcttt<br>tcatccagtt cctgatccat gttgggggtt ggggtttcta caatcatttt caataaatct<br>atgacac |
| AW013716<br>SEQ ID NO:134 | gaattcggca cgagccagta gcatatgctt gtctcaaagn ttaagccatg caagtctaag<br>tacacacggc cggtacagtg aaactgcgaa tggctcatta aatcagttat ggttccttttg<br>atcgctctca cgttacttgg ataactgtgg caattccaga gctaatacat gccaacgggc<br>gctgacctcc ggggacgcgt gcatttatca gacccaaaac ccatgcgggg tgctcctcac<br>ggggtgcccc ggccgctttg gtgactctag ataacctcga gctgatcgct ggcctcgtg<br>gcggcgacgt ctcattcgaa tgtctgccct atcaactttc gatggtactt tttgtgccta<br>ccatggtgac cacgggtaac ggggaatcag ggttcgattc cggagaggga gcctgagaaa<br>cggctaccac atccaaggaa ggcagcaggc gcgcaaatta cccactcccg actcggggag<br>gtagtgacga aaaataacaa tacaggactc tttcgaggcc ctgtaattgg aatgagtaca<br>cttttaaatcc tttaacgaag atccattgga gggcaagtct ggtgccagca gccgcnggta<br>attcagctcc aatagcgtat cttaaagttg ctgcaattaa aaagctccgt attggacctc<br>ggatc |
| AW013704<br>SEQ ID NO:135 | gaattcggca cgagcagtag catatgcttg tctcaaagat taagccatgc aagtctaagt<br>acacacgcc ggtacagtga aactgcgaat ggctcattaa atcagttatg gttcctttga<br>tcgctctcac gttacttgga taactgtggc aattccagag ctaatacatg ccaacgggcg<br>ctgacctccg ggacgcgtg catttatcag acccaaaacc catgcgggggt gctcctcacg<br>gggtgccccg gccgctttg tgactctaga taacctcgag ctgatcgctg gcctcgtgg<br>cggcgacgtc tcattcgaat gtctgccccta tcaactttcg atggtacttt ttgtgcctac<br>catggtgacc acgggtaacg gggaatcagg gttcgattcc ggagagggag cctgagaaac<br>ggctaccaca tccaaggaag gcagcaggcg cgcaaattac ccactcccga ctcggggagg<br>tagtgacgaa aaataacaat acaggactct ttcgaggccc tgtaattgga atgagtacac<br>tttaaatcct ttaacgagga tccattggaa ggcaagtctg gtgccagcag ccgcggtaat<br>tccagctcca atagcgtatc ttaaagttgc tgcagttcaa caagcctcgt attggacctc<br>ggattc |
| AW013702<br>SEQ ID NO:136 | gaattcggca cgaggcggta ttcaggcgac cgggcctgct ttgaacactc taattttttc<br>aaagtaaacg cttcggaccc cgcgggacac tcagctaaga gcatcgaggg ggcgccgaga<br>ggcagggggct gggacagacg gtagctcgcc tcgcggcgga ccgtcagctc gatcccgagg<br>tccaactacg agctttttaa ctgcagcaac tttaagatac gctattggag ctggaattac<br>cgcggctgct ggcaccagac ttgccctcca atggatcctc gttaaaggat ttaaagtgta<br>ctcattccaa ttacagggcc tcgaaagagt cctgtattgt tatttttcgt cactacctcc<br>ccgagtcggg agtgggtaat ttgcgcgcct gctgccttcc ttggatgtgg tagccgtttc<br>tcaggctccc tctccggaat cgaaccctga ttccccgtta cccgtggtca ccatggtagg<br>cacaaaaagt accatcgaaa gttgatangg cagacattcg aatgagacgt cccgccacga<br>aggccagcga tcagctcgag gttatctana gtcaccacag cggccgggc cacccgttga<br>ggaaccaccg ccgcattggg ggttttgggt ctgaataaat tgcac |
| AW013696<br>SEQ ID NO:137 | gaattcggca cgaggctnga cctccgggga cgcgtgcatt tatcagaccc aaaacccatg<br>cggggtgctc ctcacggggt gccccggccg ctttggtgac tctagataac ctcgagctga<br>tcgctgcccc tcgtggcgg gacgtctcat ttcgaatgtct gccctatcca cttttcgatgg<br>tactttttgt gcctaccatg gtgaccacgg gtaacgggga atcagggttc gattccgatgg<br>agggagcctg agaaacggct accacatcca aggaaggcag caggcgcgca aattacccac<br>tcccgactcg gggaggtagt gacgaaaaat aacaatacag gactctttcg aggccctgta<br>attggaatga gtacacttta aatcctttaa caaggactcg ttggagggca agtctggtgc<br>catcagccgc ggtaattcca gctccaatan cgtatcttaa agttggctgc acttaaaaag<br>ctcntaattg gacctcggga tccaagctga cggtccgccg ctaagcgaac ttaccgtctg tc |
| AW013669<br>SEQ ID NO:138 | gaattcggca cgagcagtag catatgcttg tctcaaagat taagccatgc aagtctaagt<br>acacacggcc ggtacagtga aactgcgaat ggctcattaa atcagttatg gttcctttga<br>tcgctctcac gttacttgga taactgtggc aattccagag ctaatacatg ccaacgggcg<br>ctgacctccg ggacgcgtg catttatcag acccaaaacc catgcgggggt gctcctcacg<br>gggtgccccg gccgctttg tgactctaga taacctcgag ctgatcgctg gcctcgtgg<br>cggcgacgtc tcattcgaat gtctgccccta tcaactttcg atggtacttt ttgtgcctac<br>catggtgacc acgggtaacg gggaatcagg gttcgattcc ggagagggag cctgagaaac<br>ggctaccaca tccaaggaag gcagcaggcg cgcaaattac ccactcccga ctcggggagg<br>tagtgacgaa aaataacaat acaggactct ttcgaggccc tgtaattgga atgagtacac<br>tttaaatcct ttaacgagga tccattggag gcaagtctg gtgccagcag ccgccggtaa<br>ttccagctcc atagcgtatc ttaaanttgc ctgccagtta aataagcctc |
| AW013647<br>SEQ ID NO:139 | gaattcggca cgagtggccg tccctcttaa tcatggcccc agttcagaga agaaaaccca<br>caaatagaa ccggagtcct attccattat tcctagctgc ggtattcagg cgaccgggcc<br>tgctttgaac actctaatttt ttttcaaagta aacgcttcgg accccgcggg acactcagct<br>aagagcatcg agggggcgcc gagaggcagg ggctgggaca gacggtagct cgcctcgcgg<br>cggaccgtca gctcgatccc gaggtccaac tacgagcttt ttaactgcag caactttaag<br>atacgctatt ggagctggaa ttaccgcggc tgctggcacc agacttgccc tccaatggat |

TABLE 6-continued

| Accessions/SEQ ID NOs | Sequence |
| --- | --- |
| | cctcgttaaa ggatttaaag tgtactcatt ccaattacag ggcctcgaaa gagtcctgta<br>ttgttatttt tcgtcactac ctccccgagt cgggagtggg taatttgcgc gcctcgaaaga<br>ttccttggat gtggtagccg tttctcaggc tccctctccg gaatcgaacc ctgattcccc<br>gttacccgtg gtcaccatgg taggcacaaa aagtaccatc gaaagttgat agggcagaca<br>ttccgaatga gacgtcgccg ccaccgaggg ccagcggatc tagctcgagg ttatctagag<br>tcaccaaaag ccggccgggg caccccgtga ggaacacccc gccattggg |
| AW013501<br>SEQ ID NO:140 | gaattcggca cgaggtcagc tcgatcccga ggtccaacta cgagctttt aactgcagca<br>actttaagat acgctattgg agctggaatt accgcggctg ctggcaccag acttgccctc<br>caatggatcc tcgttaaagg atttaaagtg tactcattcc aattacaggg cctcgaaaga<br>gtcctgtatt gttattttc gtcactacct ccccgagtcg ggagtgggta atttgcgcgc<br>ctgctgcctt ccttggatgt ggtagccgtt tctcaggctc cctctccgga atcgaaccct<br>gattcccgt tacccgtggt caccatggta ggcacaaaaa gtaccatcga aagttgatag<br>ggcagacatt cgaatgagac gtcgccgcca cgagggccag cgatcagctc gagttatct<br>agagtcacca aagcggccgg ggcacccgt gaggagcacc ccgcatgggt tttgggtctg<br>ataaatgcac gcgtccccgg aggtcagcgc ccgttggcat gtattagctc tggaattgcc<br>acagttatcc aagtaacgtg agagcgatca aaggaaccat aactgattta atgagccatt<br>cgcagtttca ctgtaccggc cgtgtgtatt agacttgcat ggcttaatct ttgagacaag<br>catatctcgt gccgaattc |
| AW013484<br>SEQ ID NO:141 | gaattcggca cgaggcccta tcaactttcg atggtacttt ttgtgcctac catggtgacc<br>acgggtaacg gggaatcagg gttcgattcc ggagagggag cctgagaaac ggctaccaca<br>tccaaggaag gcagcaggcg cgcaaattac ccactcccga ctcgggaagg tagtgacgaa<br>aaataacaat acaggactct ttcgaggccc tgtaattgga atgagtacac tttaaatcct<br>ttaacgagga tccattggag ggcaagtctg gtgccagcag ccgcggtaat tccagctcca<br>atagcgtatc ttaaagttgc tgcagttaaa aagctcgtag ttggacctcg ggatcgagct<br>gacggtccgc cgcgaggcga gctaccgtct gtcccagccc ctgcctctcg gcgcccctc<br>gatgctctta gctgagtgtc ccgcggggtc cgaaacgttt actttgaaaa aattagagtg<br>ttcaaagcag gcccggtcgc ctgaataccg catctaggaa taatggaata ggactccggt<br>tctattttgt gggttttctt ctctgaactg gggccatgat taagaaggac ggccgggctc<br>gtgccgaatt c |
| AW013428<br>SEQ ID NO:142 | gaattcggca cgaggtgccc ttccgtcaat tcctttaagt ttcagctttg caaccatact<br>ccccccgaa cccaaagact ttggtttccc ggacgctgcc cggcgggtca tgggaataac<br>gccgccggat cgctagttgg catcgtttac ggtcggaact acgacggtat ctgatcgtct<br>tcgaacctcc gactttcgtt cttgattaat gaaaacattc ttggcaaatg ctttcgcttt<br>cgtccgtctt gcgccggtcc aagaatttca cctctagcgg cacaatacga atgcccccgg<br>ccgtccctct taatcatggc cccagttcag agaanaaaac ccacaaaata gaaccggagt<br>cctattccat tattcctagc tgcggtattc aggcgaccgg gcctgctttg aacactctaa<br>ttttttcaaa gtaaacgctt cggaccccgc gggacactca gcctcgtgcc gaattc |
| AW013404<br>SEQ ID NO:143 | gaattcggca cgaggctgcg gtattcaggc gacccgggcct gctttgaaca ctctaatttt<br>ttcaaagtaa acgcttcgga ccccgcggga cactcagcta agagcatcga gggggcggaa<br>tcggcacga gctgggacag acgtagctc gcctcgcggc ggaccgtcag ctcgatcccg<br>aggtccaact acgagctttt aactgcagc aactttaaga tacgctattg gagctggaat<br>taccgcggct gctggcacca gacttgccct ccaatggatc ctcgttaaag gatttaaagt<br>gtactcattc caattacagg gcctcgaaag agtcctgtat tgttattttt cgtcactacc<br>tccccgagtc gggagtgggt aatttgcgcg cctgctgcct tccttggatg tggtagccgt<br>ttctcaggct ccctctccgg aatcgaaccc tgattccccg ttacccgtgg tcaccatggt<br>aggcacaaaa agtaccatcg aaagttgata gggcagacat tcgaaagaga cgtcgccgcc<br>acgagggcca gcgatcagct cgaggttatc tagagtcacc aaagcggccg ggggcacccg<br>tgaggagcac cccgcatggg ttttgggtct gataaatgca cgcgctctct ctctctctct<br>ctctctctct ctctctctct ctctctctct ctctctctct ctctctctct ctctctctct<br>ctctccctcg tgccgaattc |
| AW013386<br>SEQ ID NO:144 | gaattcggca cgaggctgcg gtattcaggc gacccgggcct gctttgaaca ctctaatttt<br>ttcaaagtaa acgcttcgga ccccgcggga cactcagcta agagcatcga gggggcgccg<br>agaggcaggg gctgggacag acgtagctc gcctcgcggc ggaccgtcag ctcgatcccg<br>aggtccaact acgagctttt aactgcagc aactttaaga tacgctattg gagctggaat<br>taccgcggct gctggcacca gacttgccct ccaatggatc ctcgttaaag gatttaaagt<br>gtactcattc caattacagg gcctcgaaag agtc |
| AW013284<br>SEQ ID NO:145 | gaattcggca cgagtacttg gataactgtg gcaattccag agctaataca tgccaacggg<br>cgctgacctc cggggacgcg tgcatttatc agacccaaaa cccatgcggg gtgctcctca<br>cggggtgccc cggccgcttt ggtgactcta gataacctcg agctgatcgc tggccctcgt<br>ggcggcgacg tctcattcga atgtctgccc tatcaactt cgatggtact ttttgtgcct<br>accatggtga ccacgggtaa cggggaatca gggttcgatt ccggagaggg agcctgagaa<br>acggctacca catccaagga aggcagcagg cgcgcaaatt acccactccc gactcgggga<br>ggtagtgacg aaaaataaca atacaggact ctttcgaggc cctgtaattg gaatgagtac<br>actttaaatc ctttaacgag gatccattgg agggcaagtc tggtgccagc agccgcgta<br>attccagctc caatagcgta tcttaaagtt gcctcntgcc naatcctgca gccgggggat<br>cc |
| AW013183<br>SEQ ID NO:146 | cgtccgtctt gggccggtcc aagaatttca cctctagcgg cacaatacga atgcccccgg<br>ccgtccctct taatcatggc cccagttcag agaagaaaac ccacaaaata gaaccggagt<br>cctattccat tattcctagc tgcggtattc aggcgaccgg gcctgctttg aacactctaa<br>ttttttcaaa gtaaacgctt cggaccccgc gggacactca gctaagagca tcgagggggc |

TABLE 6-continued

| Accessions/SEQ ID NOs | Sequence |
|---|---|
| | gccgagaggc aggggctggg acagacggta gctcgcctcg cggcggaccg tcagctcgat<br>cccgaggtcc aactacgagc tttttaactg cagcaacttt aagatacgct attggagctg<br>gaattaccgc ggctgctggc accagacttg ccctccaatg gatcctcgtt aaaggattta<br>aagtgtactc attccaatta cagggcctcg aaagagtcct gtattgttat ttttcgtcac<br>tacctccccg agtcgggagt gggtaatttg cgcgcctgct gccttccttg ga |
| AF061256<br>SEQ ID NO:147 | gggcggcgac ggtttcctgg tggccgcgcg ctgctctgtg agcggcgggt ggcagacgga<br>cctgggccct caccccagac gcaccgcgga tctggcatgg ctcacctgat gacaatgcag<br>ttgctgctcc tgctgatatg ggtatctgag tgtgcccaat caagagctac tcgggccaga<br>actgaactgc tcaatgtttg catggatgca aagcaccaca aagaaaagcc attggccctgag<br>gacaatttac acaaccagtg cagtccctgg aagaagaatt cctgctgttc caccaacaca<br>agccaggaag cccacgagga catttcctac ctgtaccgat tcaactggga ccactgtgga<br>aagatgacat tggaatgcaa gcgacacttt atccaggata cctgtctcta tgagtgttct<br>cctaacttgg gaccctggat tcagcaggtg gaccagagct ggcgaaaaga gcgaatcctt<br>gatgttcctc tgtgcaaaga ggactgtcag cgatggtggg aggactgccg cacctctttc<br>acctgcaaga gcaactggca caaggggtgg aactggacct cggggtataa ccagtgccct<br>gtgggagcct cctgtcgcca cttcgacttc tatttcccta cacctgctgc tctgtgtgag<br>gaaatctgga gtcactccta caaactcagt aactacagcc gagggagtgg ccgctctatc<br>cagatgtggt tcgacccagc ccaaggcaac cccaacgagg aagtggcaag gttctatgct<br>gaggccatga gtggagctgg gcttcacggg gcctggccac taatgtgcag cctgtctttta<br>gtgctgctct gggtgttcag ccgagttcct ttaaccttct gatccccagg aactccctgc<br>cgggcttaga ctcccagctc ccaacctcct ttgtggtggg gcctctgaca ggcattcaat<br>atctctctta tgaattattt gggtgtgaat gggaatataa ttattttgca tcctacttac<br>cactgattga agttgtttaa acttggttag ttccctgctc taacacttac tgtgggcaag<br>ttaaataaac ttaattttcc tgtgctgttc cacaaaaaaa aaaaaaaaaa aaaaa |
| AI956572<br>SEQ ID NO:148 | atcggacgcc ccccgtgtcg gtgacgaccc attcgaacgt ctgccctatc aactttcgat<br>ggtagtcgct |
| AI882550<br>SEQ ID NO:149 | gtggacgaag actgtagaga ctacccagag tctgacctag ggagaggcca actcggatac<br>ccctatgtgc gctcccagaa gctaaggaca ttgagacaga aagacatgcc ctggaaacag<br>acaccactct tgctttttggt ctacatggtc acaacaggca gtggcgggac agaacagacc<br>tactcaacgt ttgcatggat gccaaacacc ataagacaaa gccgggcccc gaggacaagc<br>tgcatgacca gtgtagtcca tggaagaaaa atgcctgttg ctcagtcaac accagccagg<br>agctacacaa ggctgactcc cgtctgtact tcaactggga tcactgtggc aagtggagc<br>ctgcctgtaa gagtcacttc atccaagact cctgcctgta tgagtgctcc ccaaccttgg<br>ccttggatca gcaagtggac agagttggcg taagagcgtt ctggatgtgc |
| AI822932<br>SEQ ID NO:150 | gagaattagg gttcgattcc ggagagggag cctgagaaac ggctaccaca tccaaggaag<br>gcagcaggcg cgcaaattac ccaatcctga cacggggagg tagtgacaat aaataacaat<br>accgggctct tcgagtctgg taattggaat gagtacaatc taaatccctt aacgaggatc<br>cattggaggg caagtctggt gccagcagcc gcggtaattc cagctccaat agcgtatatt<br>taagttgttg cagttaaaaa gctcgtagtt gctgtcttta ggggactctc actctcctgc<br>ttgtcgttgt gttcttaagg tcttgtctttt attgccggtt gatgtactgc tagtcgtaat<br>tgctctcatt tgccctgtcg tttccgt |
| AI785988<br>SEQ ID NO:151 | cgccgtgcct accatggtga cc |
| AI744273<br>SEQ ID NO:152 | gggcccccgcg ggacactcag ctaaaagcat cgaggggggcg ccgaga |
| AI727302<br>SEQ ID NO:153 | ctaaatccct taacgaggat ccattggagg gcaagtctgt tgccagcagc cgcggtaatt<br>ccagctccaa tagcgtatat ttaagttgtt gcagttaaaa agctcgtagt tggacttagg<br>ggtgggtcgg ccggtccgcc tcacggtgag caccggtctg ctcgtcccta ctgccggcga<br>tgcgctcctg gccttaattg gccgggtcgt tcctccggcg ctgttacttt gaagaaatta<br>gagtgctcaa agcaggccta cgcttgtata cattagcatg ggataacatc ataggatttc<br>gatcctattg tgttggcctt cgggatcgga gtaatgatta acagggacag tcgggggcat<br>tcgtatttca tagtcagagg tgaaattctt ggatttatga agacgaaca actgcgatag<br>catttgccaa ggatgttttc attaatcaag aacgaaagtt ggggggctcga aacgatcag<br>ataccgtcct agtctcaacc ataaatctcc tccagttccg gaaccacatc ctccgccagt<br>tccagtctat aagaaaacac atccnactcc agttccagta tacaagatac catgtcctcc<br>ccagttccag tctataaatc tcctccggtt ccatt |
| AI725714<br>SEQ ID NO:154 | ggataaccgt agtaattcta gagctaatac gtgcaacaaa ccccgacttc tggaagggat<br>gcatttatta aataaaaggt cgacgcgggc tttgcccgtt gctctgatga ttcatgataa<br>ctcgacggat cgcacggcct ttgtgccggc gacgcatcat tcaaatttct gccctatcaa<br>ctttcgatgg taggatagtg gcctactatg gtggtgacgg gtgacggaga attagggttc<br>gattccggag agggagcctg agaaacggct accacatcca aggaaggcag caggcgcgca<br>aattacccaa tcctgacacg gggaggtatt gacaataaat aacaataccg ggctctatga<br>gtctggtaat tggaatgagt acaatctana tcccttaacg aagatccatt ggagggcaat<br>tctggtgcca ncanccgcgg taattccact cccatancgt atatttaagt gtttgcagtc<br>aaaaagctcg taattggact tagggggtggg tcagccggtc ccctccacgg tgagcacggg<br>tctgctcttc cctactgcgg gcgatgcccc cctggcctta attg |
| AF137375<br>SEQ ID NO:155 | ggattcctgc tgcttttgac cacagttctt tctgcaggac aagcatggcc cttgggagag<br>cacgg |

TABLE 6-continued

| Accessions/SEQ ID NOs | Sequence |
|---|---|
| AF137374<br>SEQ ID NO:156 | gatgagggag tccaggagtt ccagcaagct cgacctgctt aacactccca gacggtcaca<br>ggattcagga caagcatggc ccttgggaga gcacggctgc tgctgctctt ggtgtgtgtg<br>gctgtcacat gggcggcccg gcctgatctc ctcaacatct gcatggacgc caagcaccac<br>aagaccaagc ccggcccgga agatggcctg catgagcagt gcagcccctg ggagatgaac<br>gcctgctgct ccgtcaacac cagccaagaa gcccataacg acatctccta cctgtacaaa<br>ttcaactggg agcactgcgg caagatgaag ccggcctgca agcgccactt cattcaagac<br>acctgtctct atgagtgctc gcccaacctg ggccctgga tccaggaggt gaaccagaag<br>tggcgcagag agcggatcct gaacgtgccc ctctgcaaag aggactgtca gaactggtgg<br>gaagactgcc gcacctccta cacctgcaag agcaactggc acgagggctg gaactggagc<br>tcagggtata accggtgccc cgcgaacgcc gcctgccacc ccttcgactt ctacttcccc<br>acgcctgctg ccctgtgcag ccagatctgg agcaactcct acaaacaaag caactacagc<br>cggggcagcg gccgctgcat ccagatgtgg ttcgacccgg aacagggcaa ccccaacgag<br>gtggtggcga gatactacgc ccagatcatg agtggcgctg ggctctccga ggcctggcct<br>ctccagttcg gcctggccct gacgctgctc tggctgctga gctgagcttc tgtcttcgga<br>gagctggaca gccctccct gttcggcccc acagcaccca gctcgtcagt gcctcagtgg<br>tggtggtagt ggtggtggtg gtggcggcgg ggggactctg aataaaccag tcaccccac |
| AF137373<br>SEQ ID NO:157 | gacactgctt ccgggtgggc ctccaggagg gccgaggcag aggagcctct gcctgtgggt<br>gaagcactgg ctggcgaact ccggaagggg aggtccggag aggtggtgcc tccccccgca<br>gcaaagctca gactgcactg tcctcaggtg gcagtggtgt cctaccactt ggcacagacc<br>tccacgggcc cttcatcgct tggctccact gtgctgtggg gtaagcggcg cggggaggga<br>cgacgatctg ggcttggaag ggaaacagga aatctgcctc agaagcttac ggcagctttc<br>tggcagaagt ggatcaacat ggcctggcgg ctgacgctct tcgtgctcct gggtttggtg<br>gctgctgtgg ggggcgcccg ggccaagtcg gacatgctca atgtctgcat ggatgccaag<br>caccacaagc caaagccaag cccggaggac aagctgcacg accagtgcag cccctggagg<br>aagaactcct gctgctcagt caacaccagc ctagaagccc ataaagacat ctcctacctg<br>tacagattca actgggacca ctgcggcaag atggagccgg cctgcaagcg ccacttcatt<br>caagcacct gtctctatga gtgctcgccc aacctggggc cctggatcca ggaggtgaac<br>cagaagtggc gcagagagc gatcctgaac gtgcccctct gcaaagagga ctgtcagatc<br>tggtgggaag actgccgtac ctcctacacc tgcaagagca actggcacaa gggctggaac<br>tggacctcag ggtataacca gtgcccagtg agcgccgcct gccaccgctt cgacttctac<br>ttccccacgc ccgctgccct gtgcaacgag atctggagcc actccttga agtcagcagc<br>tacagccggg gcagcggccg ctgcatccag atgtggttcg acccggccca gggcaacccc<br>aacgaggcgg tggcgagata ctatgcgagg aatggggatg ctggggccgt ggcccagggg<br>atcgggcctc tcctgaccaa cttgacggag atggtgaaac actgggtcac cggctaagct<br>gttccccgc cgacccctgc tttccgccca caccccctgg gttactctcc gggtggcctc<br>agcaccccgg tcattggctc ctgatctaag atccgatggg gagcctctga tggcctcttc<br>caatacaata tccacgtg |
| AF096320<br>SEQ ID NO:158 | ctcagtcgca catagataaa attggccttt atttggagac gggtttgttc ttctatgttt<br>aatcctcggg tgaaatgacc tgaagatatt tgtgtctgtt ttccgcatgg tcaagcaggg<br>agtggagaga ggcctgggct gggccaggtt ttctgggctt tttcctgtgc tccgagtagg<br>tgggttgtat tttacccagt aggagtggaa gacttcgttg cgcttggtgc ttcaaccgga<br>ctgacttcct gggcctggag ttggcgatta gaggtctgac atggctcacc tgatgactgt<br>gcagttgttg ctcctggtga tgtggatggc cgaatgtgct cagtccagag ctactcgggc<br>caggactgaa cttctcaatg tctgcatgga tgccaaacac cacaaa |
| AF096319<br>SEQ ID NO:159 | gctgacggct ctagaagtcc ccaacctgtt gtgatcttca gtagacaaac actcctggtg<br>tgtcacagga ttcaggccac taaacctcgg ccggctgtct cctggaatga agaaagcaaa<br>ggaagcctag agtggagaca aagaagcccg aggcactctg agagctgcca tctttttcctt<br>gtttgccgcc tgacacttct cagcaggatc cacataccct aagggagtgg agagaggcct<br>gggctgggcc aggttttctg gcttttttcc tgtgctccga gtaggtgggg tgtattttac<br>ccagtaggag tggaagactc cttggcgctt ggtgcttcaa ccggactgac ttcctgggcc<br>tggagttggc gattagaggt ctgacatggc tcacctgatg actgtgcagt tgttgctcct<br>ggtgatgtgg atggccgaat gtgctcagtc cagagctact cgggccagga ctgaacttct<br>caatgtctgc atggatgcca aacaccacaa agaaaaaccg ggccctgagg acaatttaca<br>cgaccagtgc agccctgga agacgaattc ctgctgttcc acgaacacaa gccaggaagc<br>acataaggac atttcctacc tgtaccggtt caactggaac cactgcggaa ctatgacatc<br>ggaatgcaaa cggcacttta tccaagacac ctgcctctat gagtgttccc cgaacttggg<br>accctggatc cagcaggtgg accagagctg gcgcaaagag cggatccttg atgttcccct<br>gtgcaaagag gactgtcagc agtggtggga ggactgccag agctcttta cctgcaagag<br>caattggcac aagggatgga actggtcctc ggggcataac gagtgtcctg tgggagcctc<br>ctgccatccc ttcaccttct acttcccac atctgctgct ctgtgtgagg aaatctggag<br>tcactcctac aagctcagca actacagtcg agggagcggc cgctgcattc agatgtggtt<br>cgaccagcc cagggcaacc ccaacgagga agtggcgagg ttcatgccg aggccatgag<br>tggagctggg tttcatggga cctggccact cttgtgcagc ctgtccttag tgctgctctg<br>ggtgatcagc tgagctcctg ttttaccttc agttgtctgg agcgccaccc tgcttggctc<br>agcctcccag ctcccagcct cctttgtggt ggggcctga cagcctcttt aataaaccag<br>acattccaca tgtgccttat gaattaaaaa aaaaaaaaaa aaa |
| AI663857<br>SEQ ID NO:160 | cccgttaaag gatttaaagt ggacctcatc caattacagg gccttgaaag aatcctgtat<br>tgttatattt |
| AI647841<br>SEQ ID NO:161 | ataaggcaca tgtggaatgt ctggttgatt aaagaggctg tcagagcccc accacaaagg<br>aggctgggag ctgggaggct gagccaagca gggtggcgct ccagacaact gaaggtaaaa<br>caggagctca gctgatcacc cagagcagca ctaaggacag gctgcacaag agtggccagg |

TABLE 6-continued

| Accessions/SEQ ID NOs | Sequence |
|---|---|
| | tcccatgaaa cccagctcca ctcatggcct cggcatagaa cctcgccact tcctcgttgg<br>ggttgccctg ggctgggtcg aaccacatct gaatgcagcg gccgctccct cgactgtagt<br>tgctgagctt gtaggagtga ctccagattt cctcacacag agcagcagat gtggggaagt<br>agaaggtgaa gggatggcag gaggctccca caggacactc gttatgcccc gaggaccagt<br>tccatccctt gtgccaattg ctcttgcagg taaaagagct ctggcagtcc tcccaccact<br>gctgacagtc ctctttgcac aggggaacat caaggatccg ctctttgcgc cagctctggt<br>ccacctgctg gatccagggt cccaagttcg gggaacactc atagaggcag gtgtcttgga<br>taaagtgccg tttgcattcc gatgtcatag tttcgcaggg ttccagttga accggtacag<br>gtaggaaatg tccctatgtg cttcctggct ttgtgtcgtg aacagcagga atcgtcttnc<br>aggggctgcc actgtcgtgt aaattgcctc aagggcccgt tttttctttg tgtggtgcat<br>ncatgcagac aatttgaaat cagtcctggc cgagtagctc tg |
| AI646950<br>SEQ ID NO:162 | aaggcctggt aattaaaaag gctgcaaagc cccacccaaa ggaggttggg agctgggagg<br>ttgacccaac cagggtggcc ctccaaacaa ctgaaggtaa aacaggagct cagttgatca<br>cccaaagcag cattaaggac aggcttgcca aaagtggcca ggtcccatga aacccagttc<br>cattc |
| AI607910<br>SEQ ID NO:163 | gtagttgctg agcttgtagg agtgactcca gatttcctca cacagagcag cagatgtggg<br>gaagtagaag gtgaagggat ggcaggaggc tcccacagga cactcgttat gccccgagga<br>ccagttccat cccttgtgcc aattgctctt gcaggtaaaa gagctctggc agtcctccca<br>ccactgctga cagtcctctt tgcacagggg aacatcaagg atccgctctt tgcgccagct<br>ctggtccacc tgctggatcc agggtcccaa gttcgggaa cactcataga ggcaggtgtc<br>ttggataaag tgccgtttgc attccgatgt catagttccg cagtggt |
| AI529173<br>SEQ ID NO:164 | taccacaacc aaagaaagca ttacacgcgc atattaccca ctg |
| AI509734<br>SEQ ID NO:165 | gagagttgaa cttgccaccc acttcaggga tctctggtac acaaggtct tgtttctctc<br>tctctcttgg aggcaggcta ctcaggtcta gctactggcg gctctccaca cctgtagctc<br>atagaagctg aaggctgata aaagggcagt gggtggagcg ccctcagccc gctcacctct<br>ttggcatcag gaggagcaac aggagggccc tgccttgaag gtcatggcac agtggtggca<br>gatcctcttg gggttgtggg cagtcctacc caccttggca ggggacaaac tgctcagcgt<br>ctgcatgaat tccaagcgcc acaagcaaga acctggccca gaagacgaac tctaccagga<br>gtgcaggcct tggaggaca atgcctgctg cacacgttcc acaagttggg aagcccacct<br>tgaggagccc ttgctcttta acttcagcat gatgcactgt ggactgctga ccccggcctg<br>tcgcaaagca ctcattccag nccatttgtt tccatgatgt tcccccaacc tggggccctg<br>gatcccaccc gtgtcc |
| AI506267<br>SEQ ID NO:166 | acacagagca gcagatgtgg ggaagtagaa ggtgaaggga tggcaggagg ctcccacagg<br>acactcgtta tgccccgagg accagttcca tcccttgtgc caattgctct tgcaggtaaa<br>agagctctgg cagtcctccc accactgctg acagtcctct ttgcacaggg gaacatcaag<br>gatccgctct tgcgccagc tctggtccac ctgctggatc cagggtccca agttcgggaa<br>acactcatag aggcaggtgt cttggataag tgccgttgca ttccgatgtc atagttccgc<br>agtggttcag ttgacccgta cggtaggaat gtcctatgtg cttctggctg tgt |
| AI498269<br>SEQ ID NO:167 | cccccggggc cggaagggg aaatttgccc cccggcgccc ttcctgggag ggggaacc |
| AI000444<br>SEQ ID NO:168 | cggcgaacac catcgaaagt taatagggca gacgttcaaa taggtcgtc |
| AA956337<br>SEQ ID NO:169 | cggccgctcc ctcggctgta gttgctgagc ttgtaggaat gactccagat tttctcacac<br>agaacagcag gtgtagggaa gtagaaagtg aagggatggc aggaggctcc cacagggcac<br>tcattatgcc ccgaggtcca gttccatccc ttgtgccagt tgctcttgca ggtaaaagag<br>ctcttgcagt cctcccacca cagcacacag tcttctttgc acagggaac atcaaggatc<br>cgctctttgc gccagctctg gtccacctgc tggatccagg gtcccaagtt cggggaacac<br>tcatagagcc aagtgtcttg gataaagtga cgtttgcact ccggggtcat agttccacag<br>tgattccagt tgaatcggta caggtangaa atgtccttat gtgcttggca tccatgcaga<br>cattgagaag ttcgcctcgt gccgaatt |
| AA955042<br>SEQ ID NO:170 | tttttttttt ttttttaga tgtgtcatag atttattgaa aatgattgtt gtagaaaccc<br>caagcccaa catggatcag gaactggatg gcagaggaga ggggtggaag caggctcaag<br>acttcctat tctttgaaga gttgaaccaa ccgagaccaa gggtagctag aggagaagac<br>tggcctcagt cagggagcca taatgacagc actgggggca ggctgggcac aagaagtatt<br>gctgcatggt acacagtccc agatgtcata aaggaagcat agaacttcac cacttcctca<br>ttgggattgc cctgggttga gtcaaaccac atctggatgc actggccact ccctctgcta<br>tagttgctga ccttgtanga gtgactccag agaccctcac aaaggctggc tggtgtcggg<br>aaatagtact gaaat |
| AA899838<br>SEQ ID NO:171 | cggccgctcc ctcggctgta gttgctgagc ttgtaggagt gactccagat tttctcacac<br>agaacagcag gtgtagggaa gtagaaagtg aagggatggc aggaggctcc cacagggcac<br>tcattatgcc ccgaggtcca gttccatccc ttgtgccagt tgctcttgca ggtaaaagag<br>ctcttgcagt cctcccacca cagcacacag tcttctttgc acagggaac atcaaggatc<br>cgctctttgc gccagctctg gtccacctgc tggatccagg gtcccaagtt cggggaacac<br>tcatagaggc aggtgtcttg gataaagtga cgtttgcact ccggggtcat agttccacag<br>tgattccagt tgaatcggta caggtangaa atgtccttat gtgcttcctg gcttgtgttg<br>gtggagcag |

TABLE 6-continued

| Accessions/SEQ ID NOs | Sequence |
| --- | --- |
| AA899718<br>SEQ ID NO:172 | cggccactcc ctcggctgta gttgctgagc ttgtaggagt gactccagat tttctcacac<br>agaacagcag gtgtagggaa gtagaaagtg aagggatggc aggaggctcc cacagggcac<br>tcattatgcc ccgaggtcca gttccatccc ttgtgccagt tgctcttgca ggtaaaagag<br>ctcttgcagt cctcccacca cagcacacag tcttctttgc acaggggaac atcaaggatc<br>cgctcttttgc gccagctctg gtccacctgc tggatccagg gtcccaagtt cggggaacac<br>tcatagaggc aggtgtcttg gataaagtga cgtttgcact ccggggtcat agttccacag<br>tgattccagt tgaatcggta caggtaggaa atgtccttat gtgcttcctg gcttgtgttg<br>gtggagc |
| AA858756<br>SEQ ID NO:173 | cggccgctcc ctcggctgta gttgctgagc ttgtaggagt gactccagat tttctcacac<br>agaacagcag gtgtagggaa gtagaaagtg aagggatggc aggaggctcc cacagggcac<br>tcattatgcc ccgaggtcca gttccatccc ttgtgccagt tgctcttgca ggtaaaagag<br>ctcttgcagt cctcccacca cagcacacag tcttctttgc acaggggaac atcaaggatc<br>cgctcttttgc gccagctctg gtccacctgc tggatccagg gtcccaagtt cggggaacac<br>tcatagaggc aggtgtcttg gataaagtga cgtttgcact ccggggtcat agttccacag<br>tgattccagt tgaatcggta ca |
| AI311561<br>SEQ ID NO:174 | aaggcccggg aactcccatc aaaagttgtt agggcaaact ttcaaatggg tc |
| AI385951<br>SEQ ID NO:175 | aattcggatc catgggctga tctggaagta taaacaagaa aggaggctga cggctctaga<br>agtcccccaac ctgttgtgat cttcagtata caaacactcc tggtgtgtca caggattcag<br>ctctgtttcc taggccacta aacctcggcc ggctgtctcc tggaatgaag aaagcaaagg<br>aagcctatag tggagacaaa gaagcccgag gcactctgag agctgccatc ttttccttgt<br>ttgccgcctg acacttctca gcaggatcca catacccctaa ggagtggaag actccttggc<br>gcttggtgct tcaaccggac tgacttcctg tgcctggagt tggcgattag actctgcctt<br>cagggtctga catggctcac ctgatgactg tgcagttgtt gctcctggtg atgtggatgg<br>ccgaatgtgc tcagtccata gctactcggg ccaggactga acttctcaat gtctgcatgg<br>atgcctaaca ccacaaagat aaaccgtccc tgaggacatn tacacgacca gtgcagcccc<br>tgcaagacaa ttactgctgt tccactaaca caagccagga agcacataat gacattttcct<br>acctgtaccg tttcactgga accactgctg aactatgaca tcggaatgca tacggcacta<br>tatccaagac acttgctcta tgagtgttcc cccgacttgt gacccctgtat tcagcangtg<br>gaacatgact tgcgcatata cggatcctg atgttcccct gtgcaaagag gactgtcagc<br>attgatgtga tgactgccat agctctttac ctgtcagaac atttgtccat ggtatgtaac<br>tgttcct |
| AI352406<br>SEQ ID NO:176 | gggtcatttc cacatgcttt attccagcaatcaaaataatt aaaaacatct caaattatt<br>atacacatac aaaataggta cagagtcttttgcttcctccc accctaggg ggaaaaact<br>gctttgtgct ttgggaagtt gtctctgaaacccggggacag aggacgcagg acagactag<br>gagggagccg ggaggatggg ctgcagctgtggaggagggtt tcaggagaga gaggtcgga<br>gagcagaggc ctgagaagcc tgattccccgtcaccgtggt caccatggta ggcacggca<br>actaccatcg aaagttgatg ggcaga |
| AF100161<br>SEQ ID NO:177 | actagttgtc tgttgctgca taacaaatca ttccataatt tgtggtgta ttgctgcaga<br>caatgttaaa ctaagtggat gaaaaggata ttcacatagt ctcagagtgt ctccctacaa<br>ggtaggatta ctaacaaagg gaaactaata attatatagt aaggaaatct ccttaaccca<br>ataatcacca gcaataagat gcagcaaccc tcatcatgta cctcttgata tgatgcactg<br>acaaaagcac ctctcttctc taattttctt gccaaaatcg ataagctcaa gctaattaca<br>ggaaaatata gacaaaccca aattgaggga cattctgcaa ataactgaa cagtaattct<br>ccaaaagtgt caaggtcata aaagacaaag acattgagga ctgtcacaga ttggagggag<br>actaagggga catgacaact acatgcaacc tggaatcatg gactgaatcc tgggccagag<br>aaggacattg ggggggaact ggtgtaaagg gcataaagct tgtagattag ttaacagtat<br>tgcctcaata ttaatttcct gattttttta agaactgggc tttggttaca taagatgcca<br>atatttgggg aagttgcata aaaacatacg ggaaatcttt tgacgatgtt ttgcagtttt<br>tctgcaaatc taaaattatt tcaaaacaaa aagtttaaaa atcaaataca catagttgct<br>tgaaatagta actattttat tatattccaa gatgttgtga gtcaggaatt tggccaaaac<br>tcaggtgggc gattcttctg caaagacccc cacaacacat tcaaagtcac aggcagaggt<br>tgttggggga gggcattgaa aagaagagaa gagtcatagg tgggtgcaat ggagggaggg<br>cagagggctg ctgactatgt gcaggactca tccataatgg agccctgggg aggcaaggc<br>ttcataacta gacactggtc ttgtcacctc agactcacct gtagcaggac cagatactga<br>ggtcagactg aaaacacagg ctctgcctca ggagaggctc tctactagct gagtaaatga<br>tgacagtatt ggaaatgttc caacatcat aatgggaaaa catcacttca cactacataa<br>gcaatacaca ggggcagtgc cggtcgtctt cccaggttag tagcagttct actgcctcca<br>agagtgttgg agaaataaca accaagcatt aggcacttt aacttgaaaa catgaagttc<br>tctttcctaa ctttctttgt ttccttattt cttcttcttc ttcttcttct tcttcttct<br>cttcttcttc ttcttcttct tcttcttctt cttcttcttc ttcctcttct tcttcttct<br>cttcttcttc ttcttcttcc ttctccttt cctttctttt ttttgctga gacaggggtct<br>cactctgaca gtacagtggt gccatcacag ctcactgcag cctcgacctc cagggctcaa<br>gcaatcctcc cagctcaccc tcccaaatgg ctgaaactac aagctcgcac caccatacgt<br>ggctaatttt tctatttttg tgtgcagatg aagttttcct atgttgccca agtggtctca<br>aactcctggg atcaagtgat ccatccacct caacctccca aaacgctggg attacaggtg<br>taagccacca cacccagccc actaactttt ttatatcggc taatgaaata gttttaagtt<br>tagacccctac gaggcataaa gaaataattt tagttatggc atcagatgta cagtaatact<br>caagtgtgca actgtggata acttgagttc atgaggtttt tgttttttg tcaaaagaat<br>aaatttatag tgaaactacc caaaaaagca aagtacagaa cagtatgcta ccatttgtgc<br>acagaaatgg gatatatatg gtgtaactgc atcgaattta ctggatgtat gtccagggac |

TABLE 6-continued

| Accessions/SEQ ID NOs | Sequence | |
|---|---|---|
| | cagaactctt ggtggcttca tgttcatact tttgcaagca catgtgtagt atccttaact | |
| | taaaggtact gttgtataca ttctagtgtt atcaaaattt acatacatat tatcaagtca | |
| | gagaggtcat tctgtgtctt agtattttca cttcatattt ggtatattta tgtatgtata | |
| | cacacatacc tatatgtatt taaataagat ttatagtcac atggtccaaa aatcaaaaca | |
| | atgtggaaag gtttacagag aaaagtctca agcctaatcc tgttctctac tgccaggtga | |
| | ccatgttatt aatttctttt cataccttgc cacagaattt tcacctgcaa acacagatat | |
| | tcttttcttt tttaatgaca gagtcacgtt ctgttatcca ggctggagtg cagtggcgtg | |
| | atcttggctc actgcaaact cctcccgggt tcaagtgatt ctcctgtctc agcctcctga | |
| | gtagctggga ttacaggcat gtgccaccac acccagctaa tttttgtatt tttagtacag | |
| | atggggtttt atcatattga ccaggctgat gtcgaactcc tgacctcaag tgatccgcct | |
| | gcctcggcct cccacagtgc tgggattaca ggcgtgagcc accacgccca gtcaacacag | |
| | acattcttac tccttttta cagagaattt attattatta tttttacat agcatttttc | |
| | tgcacctttc tttttccact taacaatgca cttgaagatt tttccatatt tgtacatcag | |
| | gagctttctc tttctttgtt accacattaa attccactgg gtagatgtac cataatttaa | |
| | ctgggtcctt attgaaagac aattgagctg tctcctagac aaagccttgt gcaccttccc | |
| | gaacagaggg tctaaccaag caggcaggat ggggttataa agtaggtggg gaggtgggag | |
| | agactccacc ttcccaggtg ggctgagaat ggaggtaagg ccctgcaaca ggacagaggg | |
| | aaaagtgggg atgagaggtg ggaggcgaga tagcgcccac tgttctcgct cagcccctc | |
| | ctccgtttgc cgctgacctg ttggcctccc ccaacctctg agcctgcctc tgcctaggta | |
| | atttcccaag acccagaagg ggtgaagggt gaggtgtgat tgcccccacc tccttgcctc | |
| | ccgcagcatc tgctccggga ccatgaacaa tagctgacag ctccatggcc cttgctgtcc | |
| | ccatctcagc ttccctgggc atctaaacct cagctgccat ggggtaggag gacaggctga | |
| | ggaagcagaa gcctgaggct gtctagagtc tcactcctgc atcagcaggc caccacctgt | |
| | ggttcctcct tgtgcaaatt tgaaaagaat tgcataaaac actggagaaa tccaagaggg 3420 | |
| | gaagtccaca agggcggtgg ctccctacaa ggtcacagag caagctggtg tcagagcctg 3480 | |
| | gacctacagc gctgttggtg gaggtcctgc ctccaggtag ggaagggcc cctctcacc 3540 | |
| | tctacacgca gcgcatttct tggctcagct gccctgtagg ggatgcaggg tggggacagc 3600 |
| AI326503<br>SEQ ID NO:178 | aattcggatc catgggctga tctggaagta taaacaagaa aggaggctga cggctctaga | |
| | agtcccccaac ctgttgtgat cttcagtaga caaacactcc tggtgtgtca caggattcag | |
| | ctctgttttc taggccacta aacctcggcc ggctgtctcc tggaatgaag aaagcaaagg | |
| | aagcctagag tggagacaaa aagcccgag gcactctgag agctgccatc tttcccttgt | |
| | ttgccgcctg acacttctca gcaggatcca catacccaa ggagtggaag actccttggc | |
| | gcttggtgct tcaaccggac tgacttcctg ggcctggagt tggcgattag actctgcctt | |
| | cagggtctga catggctcac ctgatgactg tgcagttgtt gctcctggtg atgtggatgg | |
| | ccgaatgtgc tcagtccaga gctactcggg cccagactga acctctcatg tctgatggat | |
| | gccaaacacc acatagaata accgggccct gaggacaatt tacacgacca gtgcagcccc | |
| | tggaagacga aatcctgctg ttccacgaac acaagccagg aagcacataa ggacatttcc | |
| | tacctgtacc ggttcaactg gaaccactgc ggaactatga catcngcaat gcanacggca | |
| | ctttatccaa gacacctgcc tctatgagtg ttccccgaac ttgggacact gnatccagca | |
| | ggtgggacca aagcttgcgc caaagagcgg atcccttgat gtttcccctg ggcaaagagg | |
| | actgtccagc agttgtgggg aggactgcca gaagctcttt tacctgccag agcaatttgc | |
| | accaggg | |
| AI325517<br>SEQ ID NO:179 | gtagttgctg agcttgtagg agtgactcca gatttcctca cacatagcag cagatgtggg | |
| | gaagtagaag gtgaagggat ggcaggaggc tcccacagga cactcgttat gccccgagga | |
| | ccagttccat cccttgtgcc aattgctctt gcaggtaaaa gagctctggc agtcctccca | |
| | ccactgctga cagtcctctt tgcacagggg aacatcaaga atccgctctt tgcgccagct | |
| | ctggtccacc tgctggatcc agggtcccaa gttcggggaa cactcataga ggcaggtgtc | |
| | ttggataaag tgccgtttgc attccgatgt catagttccg cagtggttcc agttgaaccg | |
| | gtacaggtag gaaatgtcct tatgtgcttc ctggcttgtg ttcgtggaac agcaggaatt | |
| | cgtcttccag gggctgcact ggtcgtgtaa attgtcctca gggcccggtt tttctttgtg | |
| | gtgtttggca tccatgcaga cattgagaag ttcagtcctg gcccgagtag ctctggactg | |
| | a | |
| AI325453<br>SEQ ID NO:180 | acacagtagt tttcagatgt ggggaagtag aaggtgaagg gagggcagga tgctcccaca | |
| | ggacactcgt tatgccccga ggaccagttc catcccttgt gccaattgct cttgcaggta | |
| | aaagagctct ggcagtcctc ccaccactgc tgacagtcct ctttgcacag gggaacatca | |
| | aggatccgct ctttgcgcca gctctggtcc acctgctgga tccagggtcc caagttcggg | |
| | gaacactcat agaggcaggt gtcttggata aagtgccgtt tgcattccga tgtcatagtt | |
| | ccgcagtggt tccagttgaa ccggtacagg taggaaatgt ccttatgtgc ttcctggctt | |
| | gtgttcgtgg aacagcagga attcgtcttc caggggctgc actggtcgtg taaattgtcc | |
| | tcagggcccg gttttctttt gtggtgtttg gcatccatgc agacattgag aagttcagtc | |
| | ctggcccgag tagctctgga ctgagcacat tcggccatcc acatc | |
| AI325382<br>SEQ ID NO:181 | gtggacgaag actgtagaga ctacccagag tctgacctag ggagaggcca actcggatac | |
| | ccctatgtgc gctcccagaa gctaaggaca ttgagacaga aagacatggc ctggaaacag | |
| | acaccactct tgcttttggt ctacatggtc acaacaggca gtggccggga cagaacagac | |
| | ctactcaacg tttgcatgga tgccaaacac cataagacaa agccgggccc cgaggacaag | |
| | ctgcatgacc agtgtagtcc atggaagaaa aatgcctgtt gctcagtcaa caccagccag | |
| | gagctacaca aggctagactc ccgtctgtac ttcaactggg atcactgtgg caagatggag | |
| | cctgcctgta agagtcactt catccaagac tcctgcctgt atgagtgctc cccaacctt | |
| | gggccttgga tccagcaagt ggaccaggagt tggcgtaaag agcgttttct ggatgtgcc | |
| | ctatgcaaag aggactgtca ccagtggtgg gaagcctgtc gtacctcctt taccntgcgc | |
| | agagactggc atanaggctg ggactggtcc tcaggcatta acaagtgccc anacacagca | |
| | ccctgtcaca cgtngtagta ctacttcccg acaccagcca gcctttgcga gggtctctgg | |
| | agtcactcct acaaggtcag caaactacag cagaggagtg gccgctgcat ccagatgtgg | |

TABLE 6-continued

| Accessions/SEQ ID NOs | Sequence |
|---|---|
| | ttgactcacc ccanngcann tcgaaatgag acgtggtgaa gtttatgctt ctttatacat ctgggatgtg cccatgcaca gtact |
| AI323700<br>SEQ ID NO:182 | acacagagca gcagatgtgg ggaagtagaa ggtgaaggga tggcaggagg ctcccacagg acactcgtta tgccccgagg accagttcca tcccttgtgc caattgctct tgcaggtaaa agagctctgg cagtcctccc accactgctg acagtcctct ttgcacaggg gaacatcaag gatccgctct ttgcgccagc tctggtccac ctgctggatc cagggtccca agttcgggga acactcatag aggcaggtgt cttggataaa gtgccgtttg cattccgatg tcatagttcc gcagtggttc cagttgaacc ggtacaggta ggaaatgtcc ttatgtgctt cctggcttgt gttcgtggaa cagcaagaat tcgtcttcca ggggctgcac tggtcgtgta aattgtgctc atggccctgg tcttctttag tgtgtttagc atccatgcag acatcgagaa gatcagtcct ggtccgagta gctctggact gagcacagtc agacattcac atcatccaga gcaacaactg cacagtcatc aggtgagcca tgtcagaccc tgatgcagag tctaa |
| AI323374<br>SEQ ID NO:183 | tgggtcataa attgattgaa aatgattgta gaaaccccaa cccccaacat ggatcaggaa ctggatgaca gaggagaggg gtggaagcag gctcaaaact tccttattct ttgaagagtt gaaccagacc aagggtagat agaggagaaa tctaaagagg aagactgacc tctcagccag ggagccataa tgacagcact ggggccaggc tgggcacaaa agtactgct gcatggggca cagtcccaga tgtcataaag gaagcataaa acttcaccac gtcctcattc ggattgccct gggttgagtc aaaccacatc tggatgcagc ggccactccc tctgctgtag ttgctgacct tgtaggagtg actccagaga ccctcgcaaa ggctggcttg tgtcgggaag tagtactcaa acgtgtgaca gggtgctgtt gttgggcacc ttgttaatgc ctgaggacca gtcccagcct tattgcaatc tttcttgcag gtaaaggagg acgacaggct tccaccactg gtgcagtcct ctttgataag ggacatncag aaacgctctt acgccactct ggtc |
| AI313973<br>SEQ ID NO:184<br>0 | ctatccattc gaacgtgtgc catatcatct tctgatgtac caacccgtgc ctaccatgtg gaccacgggt gactggcaat ccaga |
| AI196928<br>SEQ ID NO:185 | attccccgnc ccccggggtc accaggggag gcgcggggac taccattaaa agttgatagg gcaaactttt |
| AF091041<br>SEQ ID NO:186 | gaactagggc ggtatctaat cgccttcgaa cctctaactt tcgttcttga ttgatgaaaa cacctttggc aaatgctttc gctgatgttc gtcttgcgac gatccaagaa tttcacctct aacgtcgcaa tacgaatgcc cccagttatc cctattaatc attacctcgg agttctgaaa accaacaaaa tagaaccgag atcatattct attattccat gcacgaaata ttcaagcagc attttgagcc cgctttgagc actctaattt gttcaaagna aaattgtcgg cccatctcga cactcaccga agagcaccgc gataggattt tgatattgaa ccgacgtttg ttacaacgcc ggctcaccga cnatatgctc cgcagacgtg tcagtatcac cgcggatgcg gtgcaccgac agcncggcgc acaaatgcan ctacnagctt tttaaccgca acaattttag tatacgctat tggagctggg aattaccgcg gctgctggca ccagacttgc cctcaattgn cctcgttaaa atatttaaag tgtctcattc cgattacgaa gcctcg |
| AI156212<br>SEQ ID NO:187 | cagcgagcct ttgcggggt gtctggagtg actcctacga ggtgagcgac tacagcagag ggagtggccg ctgcgtccag atgtggtttg agtcagccca gggcgatccc aatgaggacg tggtggagtt ttatgcttcc tttatgacat ctgngactgt gccccatgca gcagtagttc ttgtgcccag cctnngccca gtgctgtcat tatagctccc tggctgagag gtcagtgttc ctctctagat ttcgtcctct atctacccct ggtgctggtt cagctcttca gagaa |
| AI120374<br>SEQ ID NO:188 | cagctcacct cctgttttac cttcacttct ctccacgccc caccctcgct tcgcgctcac gcctcccagc tcccacgcct ccttt |
| AI119000<br>SEQ ID NO:189 | cctcccggct cctgcccgag ggtcgggcgc ctgcggcttt ggtgacttta gattacctcg ggccgatcgc acgccccccg tggcggcg |
| Aa408670<br>SEQ ID NO:190 | gtctctctct ctcttctctt gcttcgctct cttgcttttc tctctctctt gcttttcgc tctcttgctt ctcgctctct cttgcttctt cgactctttt cctgaagatg taagaataaa gctttgccgc agaagattct ggtctgtggt gttcttcctg gccggtcgtg aaaacgcgtc taataacaat tggtgccgaa ttccgggaag aaaaaatccg ggacgagaaa aaaactccgg aatggcgcag gagggatact tcattccagg aaacagaact gcgaatcaag gttaaaaagg atcncgtaac acagattgat tgagaagnnn tccnactggc cgaattcnag aaactcatcg cttggggaa |
| AA408072<br>SEQ ID NO:191 | ggtttttcga gacagggttt ctctgtgtag ccctggctgt ccttgaactc actttgtaga ccaggctggc ctcgaactca gaaatccgcc tgcctctgcc tcccaagtgc tgggattaaa ggcattcgcc accaccaacc ggcgataaac aaattttata cgaaagaaaa gaagcaagta agattatgag aaacataagc tattttaaga gagtttagag aagatccttc aaatatttta aaagagatct gaataaatca gaaagcatta ttcctggata aataatgggg agagaaataa tagattaana tacaacctat caaaatttaa tc |
| AA407615<br>SEQ ID NO:192 | cgagacaggg tttctctgtg cagtcctgga actcactctg tagaccaggc tggccttgaa ctcagaaatc cacctgcctc tgcctcccaa gtgctgggat tgcaggcatg cgccaccact gcctggctgc ctggtttttt aattactggc tttagcctaa atggcaaatt ctataactag gttataagaa tagttttaaa agaaagagcc tcaggagagt gggaacagga acatggagaa gtaagaggac acctgggctt tagtcaagat cctgtctaaa acaaaacaga ggggncggna gagctngngc aatggctcag ttggttagag c |

TABLE 6-continued

| Accessions/SEQ ID NOs | Sequence |
|---|---|
| AA995272<br>SEQ ID NO:193 | ccgccacggg ggggtcgcga tcggtccgag gttatctaga gtcaccaaag ccgccggcgt<br>cgtccccc |
| C78593<br>SEQ ID NO:194 | ctctctccag gtattcctac ctaaccttaa cttttcctcg ggttcaagac ccttggaaag<br>gcctgtatac ttattttgtg aaccatattt tctctttgtt cctactcttt cttcccgctt<br>tacttctgat agcttgtcct gaatttcctc tagaattttc agccctatct taaccactat<br>ataacatgtg aaaaggaaca aaagggcttc taacactaga aaaaattcaa ggccaaacat<br>aacttgtaaa gccattttcc actttacttc tgatagactg tcttgaattt ccttagaaag<br>ttcaagatca gacttacctc gttccccagc tgaaaagttc tgaattcata cagttgaatc<br>ctcttaacag tctggcttta cgggaacctt atcaccgtcg ttccccagct ggatgagttc<br>tgaatcggca gttgaatcct tctcaacagt ctgtgttacg ggaaccttat aacctggatt<br>cgcagttcng ggttctggga aggaaagtaa tcccctcctg gcggccagtn ccgggagntt<br>ttttcctcgg tcccgggatt tttcctcggt ccccgggnaa ttcgggcacc caa |
| AA999910<br>SEQ ID NO:195 | tgggtccgtt cctaaaacaa aaaaaaaaaa acagcggtcc tattccaata ttcctagc |
| AA991491<br>SEQ ID NO:196 | tgggcagacg ttcgaatggg tc |
| X99994<br>SEQ ID NO:197 | gacatcgagc tcactcagtc tccagcttct ttggctgtgt ctctagggca gagggccatc<br>atctcctgca aggccagcca aagtgtcagt tttgctggta ctagtttaat gcactggtac<br>caccagaaac caggacagca acccaaactc ctcatctatc gtgcatccaa cctagaagct<br>ggggttccta ccaggtttag tggcagtggg tctaagacag acttcaccct caatatccat<br>cctgtggagg aggaggatgc tgcaacctat tactgtcagc aaagtaggga atatccgtac<br>acgttcggag ggggggacaaa gttg |
| X99993<br>SEQ ID NO:198 | caggtgcagc tgcagcagtc tggagctgag ctggtgaagc ctggggcttc agtgaagata<br>tcctgcaagg cttctggtta ctcatttact ggctacttta tgaactgggt gaagcagagc<br>catggaaaga gccttgagtg gattggacgt attcatcctt acgatggtga tactttctac<br>aaccagaact tcaaggacaa ggccacattg actgtagaca atcctctaa cacagcccac<br>atggagctcc tgagcctgac atctgaggac tttgcagtct attattgtac aagatacgac<br>ggtagtcggg ctatggacta ctggggccaa gggaccacgg tcaccgtctc c |
| X99992<br>SEQ ID NO:199 | caggtgcagc tggtggagtc tgggggaggc ttggtacagc cagggcggtc cctgagactc<br>tcctgcacaa cttctggatt cacttttggt gattatgcta tgatctgggc ccgccaggct<br>ccagggaagg gctggagtg ggtctcatcc attagtagta gtagtagtta catatactac<br>gcagactcag tgaagggccg attcaccatc tccagagaca acgccaagaa ctcactgtat<br>ctgcaaatga acagcctgag agccgaggac acggctgtgt attactgtgc agagaacga<br>tacgattttt ggagtggaat ggacgtctgg gcaaaggga ccacggtcac cgtgtcgagt |
| X99991<br>SEQ ID NO:200 | cagtctgccc tgactcagcc tgcctcagtg tccgggtctc ctggacagtc cgtctccatc<br>tcctgcactg gaaccatcaa tgatgttggt ggatataggt ttgtctcctg gtaccaacga<br>cgccccgca aagcccccaa actcatcatt tctgatgtca ttaggcggc atcaggggtc<br>cctgatcgct tctctagttc caagtctgac aacacggcct acctgaccat ctctgggctc<br>caggctgagg acgaggctga ttattactgc agctcatata aagcagcag cactctctat<br>gtcttcggaa ctgggaccaa ggtcaccgtc cta |
| X99990<br>SEQ ID NO:201 | cagtctgccc tgactcagcc tgcctccgtg tctgggtctc ctggacagtc gatcaccatc<br>tcctgcactg gaaccagcag tgatgttggg agttataacc ttgtctcctg gtaccaacag<br>cacccaggca aagcccccaa actcatgatt tatgaggca gtaagcggcc ctcagggggtt<br>tctaatcgct tctctggctc caagtctggc aacgcggcct ccctgacaat ctctgggctc<br>caggctgagg acgaggctga ttattactgc cagtcctatg acagcagcct gagtgtggta<br>ttcggcggag ggaccaagct gaccgtccta<br>cagtctgccc tgactcagcc tgcctccgtg tctgggtctc ctggacagtc gatcaccatc<br>tcctgcactg gaaccagcag tgatgttggg agttataacc ttgtctcctg gtaccaacag<br>cacccaggca aagcccccaa actcatgatt tatgaggca gtaagcggcc ctcagggggtt<br>tctaatcgct tctctggctc caagtctggc aacgcggcct ccctgacaat ctctgggctc<br>caggctgagg acgaggctga ttattactgc cagtcctatg acagcagcct gagtgtggta<br>ttcggcggag ggaccaagct gaccgtccta |
| AA958985<br>SEQ ID NO:202 | acacagagca gcagatgtgg ggaagtagaa ggtgaaggga tggcaggagg ctcccacagg<br>acactcgtta tgccccgagg accagttcca tcccttgtgc caattgctct tgcaggtaaa<br>agagctctgg cagtcctccc accactgctg acagtcctcc ttgcacaggg gaacatcaag<br>gatccgctt ttgcgccagc tctgtccgg ctgctggatc cagggtccca agttcgggga<br>acactcatag aggcaggtgt cttggataaa gtgccgtttg cattccgatg tcatagttcc<br>gcagtggttc cagttgaacc ggtacaggta ggaaatgtcc tcctcgtgc |
| AA873222<br>SEQ ID NO:203 | tttttttta aattcatgtt tttaattggc ttaatacaaa ggtcccccag gaggccctgg<br>gaggaggggg acagcctggg agaggcagag attcatggcc agcagcccac ccccacctgc<br>cacccactcc ccaacagggt tcccagactc tttcaataat cctaaaaaaa ccgacgagag<br>cgcaggcaga tgaagagccc cttcatcctc aaacggcgac taccatcgaa agttgatagg<br>gcagacgttc gaatgggtcg tcgccgccac gggggg |
| AA930051<br>SEQ ID NO:204 | gatccttcga ctccttggcg cttggtgctt caaccggact gacttcctgg gctggagtt<br>ggcgattaga ggtctgacat ggctcacctg atgactgtgc agttgttgct cctggtgatg<br>tggatggccg aatgtgctca gtcagagct actcgggcca ggactgaact tctcaatgtc |

TABLE 6-continued

| Accessions/SEQ ID NOs | Sequence |
|---|---|
| | tgcatggatg ccaaacacca caaagaaaaa ccgggccctg aggacaattt acacgaccag tgcagccctt ggaagacgaa ttcctgctgt tccacgaaca caagccagga agcacataag gacatttcct acctgtaccg gttcaactgg aaccactgcg gaactatgac atcggaatgc aaacggcact ttatccaaga cacctgcctc tatgagtgtt ccccgaactt gggaccttgg atccagcagg tggaccagag ctggcgcaaa gagcggatcc ttgattgttc ccctgtgcaa agaggactgt catcagtggt gggaggactt gcagagtcct tttccctgca agagcaattt ggacaaggga tggaacttgg tctcggggca taacgagtgt cctgtggggc ctccttgcaa tccttcacgt tttatttccc agattggttg gtcttgttgt gaggaatctg gggttcactc ttacagct |
| AA895334 SEQ ID NO:205 | ccagctccaa taacgtatat gagagttgca gcagataagg ggcaagtagt agagtatgga gagagggaga gcg |
| AA796142 SEQ ID NO:206 | ctgtcaccag tggtgggaag cctgtcgtac ctcctttacc tgcaagagag actggcataa aggctgggac tggtcctcag gcattaacaa gtgcccaaac acagcaccct gtcacacgtt tgagtactac ttcccgacac cagccagcct ttgcgagggt ctctggagtc actcctacaa ggtcagcaac tacagcagag ggagtggccg ctgcatccag atgtggtttg actcaaccca gggcaatccc aatgaggacg tggtgaagtt ttatgcttcc tttatgacat ctgggactgt gccccatgca gcagtacttc ttgtgcccag cctggccca gtgctgtcat tatggctccc tggctgagag gtcagtcttc ctctctagat ttctcctcta tctacccttg gtctggttca actcttcaaa gaataaggaa gtcttgagcc tggttccacc ctctcctct gtcatccagt tcctgatcca tgttggggga tggggtttct acatcatttc aataaactat gaacatctgg gc |
| AA798223 SEQ ID NO:207 | gacatttcct aactgtaacg ggtcaactgg aagcactgcg gaaatatgac atcggaatgc aaacgggact tttttcaaga cacctgcctc tatgagtgtt ccccgaattt ggaccttgat tcagcaggtg gagcaaaact tgcgcaagaa ggggttcctg aagttcccct gtgcaaaaag gactttcaca attggttgga ggatttccaa agctctttta cccgcaagag gaatttgcac aagggtttga acatgtcctc ggggaataa |
| AA734325 SEQ ID NO:208 | attcggatcc ttcaaacctc ggccggctgt ctcctggaat gaagaaagca aaggaagcct agagtggaga caaagaagcc cgaggactct gagagctgcc atctttcct tgtttgccgc ctgacacttc tcagcaggat ccacatacc aaggagtgg aagactcctt ggcgcttggt gcttcaaccg gactgacttc ctgggcctgg agttggcgat tagaggtctg acatggctca cctgatgact gtgcagttgt tgctcctggt gatgtgagtg gccgaatgtg ctcagtccag agctactcgg gccaggactg aacttctcaa tgtctgcatg gatgccaaac accacaaaga aaaacggggc cctgaggaca atttacacga ccagtgcagc ccctggaaga cgaattcctg ctgttccacg aacacaagcc aggaagcaca taaggacatt tcctacctgt accggttcaa ctggaaccac tgcggaacta tgacatcgga atgcaaacgg cactttatcc aagacacctg cctctatgag tgttccccga acttgggacc ctggatccag caggtggacc agagctggcg caaagagcgg atccttgatg ttcccctgtg caagaggact gtcagcagtg gtgggaggac tgccagagct cttttacccc tgcagagcaat tggcacaagg tggaatggt ccccccgggca taacgatttc ccgtggaggc ttctggaatc ccttaacctc taattcccaa tctgcggcct gtgtg |
| AA690871 SEQ ID NO:209 | attcggatcc ttcctggaag tataaacaag aaaggaggct gacggctcta gaagtcccaa cctgttgtga tcttcagtag acaaacactc ctggtgtgtc acaggattca ggccactaaa cctcggccgg ctgtctcctg gaatgaagaa agcctagagtg gagacaaaga gccccgaggc actctgagag ctgccatctt ttccttgttt gccgcctgac acttctcagc aggatccaca taccctaagg agtggaagac tccttggcgc ttggtgcttc aaccggactg acttcctggg cctggagttg gcgattagag gtctgacatg gctcacctga tgactgtgca gttgttgctc ctgctgatgt ggatgccga atgtgctcag tccagagcta ctcgggccag gactgaactt ctcaatgtct gcatggatgc caaacaccac aaagaaaaac cgggccctga ggacaattta cacgaccagt gcagcccctg gaagacgaat tcctgctgtt tcacgaacac aagccaggaa gcacataagg acagttccta cctgtaccgg ttcaactggg accactgcgg aactatgaca tcggaatgca aacggcactt tatccagaaa cctgcctcta ttagtgttcc cccacattgg gaccctggat tcaccagtgg gacaaagatg gcgcgaaaaa acgggtcc |
| AA674988 SEQ ID NO:210 | attcggatcc ttcggaacta tgacatcgga atgcaaacgg cactttatcc aagacacctg cctctatgag tgttccccga acttgggacc ctggatccag caggtggacc agagctggcg caaagagcgg atccttgatg ttcccctgtg caaaggggac tgtcagcagt ggtgggagga ctgccagagc tcttttacct gcaagagcaa ttggcacaag ggatggaact ggtcctcggg gcataacgag tgtcctgtgg gagcctcctg ccatcccttc accttctact ccccacatc tgctgctctg tgtgaggaaa tct |
| AA674863 SEQ ID NO:211 | attcggatcc ttcctggaag tataaaccag aaaggaggct gacggctcta gaagtccca acctgttgtg atcttcagta gacaaacact cctggtgtgt cacaggattc aggccactaa acctcggccg gctgtctcct ggaatgaaga aagcaaagga agcctagagt ggagacaaag aagcccgagg cactctgaga gctggcatct tttccttgtt tgccgcctga caattctcag cagggtccac atatcctaag taagagtggg agactccttt gcgcttggtg cttcaaccgg actgaattcc tgggcctgga attggcgatt agaggtccga catggctcaa ctgatgacct tgcaattgtt ggccccggtg atgtggatgg gcgaaagtgc ttcagttcaa gaagctactt cgggccaagg actgaaactt tctcaaatgt |
| AA674821 SEQ ID NO:212 | gaagactcct tggcgcttgg tgcttcaacc ggactgactt cctgggcctg gagttggcga ttagaggtct gacatggctc acctgatgac tgtgcagttg ttgctcctgg tgatgtggat ggccgaatgt gctcagtcca gagctactcg ggccaggact gaacttctca atgtctgcat |

TABLE 6-continued

| Accessions/SEQ ID NOs | Sequence |
|---|---|
| | ggatgccaaa caccacaaag aaaaaccggg ccctgaggac aatttacacg accagtgcag<br>ccctggaag acgaattcct gctgttccac gaacacaagc caggaagcac ataaggacat<br>ttcctacctg taccggttca actggaacca ctgcggaact atgacatcgg aatgcaaacg<br>gcactttatc aagacacct gcctctatga gtgttccccg aacttgggac cctggatcca<br>gcaggtggac cagagctggc gcaaagagcg gatccttgat gttcccctgt gcaagagga<br>ctgtcagcag tggtgggagg actgccagag ctcttttacc tgcaagagca attggcacaa<br>gggatgaac tggtcctcgg gcataacga gtgtcctgtg ggagcctcct gccatccctt<br>caccttccta cttcccaaca tctgctgctc tgtgtgagga aatctggagt cactcctcaa<br>gctcagcaac tacagttcga gg |
| AA674744<br>SEQ ID NO:213 | cgggccctga ggacaattta cacgaccagt gcagcccctg gaagacgaat tcctgctgtt<br>ccacgaacac aagccaggaa gcacataagg acatttccta cctgtaccgg ttcaactgga<br>accactgcgg aactatgaca tcggaatgca aacggcactt tatccaagac acctgcctct<br>atgagtgttc ccgaacttg ggaccctgga tccagcaggt ggaccagagc tggcgcaaag<br>agcggatcct tgatgttccc ctgtgcaaag gggactgtca gcagtggacg gaggactgcc<br>agagctcttt tacctgcaag agcaattggc acagggatg gaactggtcc tctgggcata<br>acgagtgtcc tgtgggagcc tcctgccatc ccttcacctt ctacttcccc a |
| AA671558<br>SEQ ID NO:214 | ctggagctga gcacacactt ggaggttcca cttaccttag ctctgccttc agggtctgac<br>atggctcacc tgatgactgt gcagttgtgg ctgctggtga tgtggatggc cgaatgtgct<br>cagtccagag ctactcgggc caggactgaa cttctcaatg tctgcatgga tgccaaacac<br>cacaaagaaa accgggccc tgaggacaat ttacacgacc agtgcagccc ctggaagacg<br>aattcctgct gttccacgaa cacaagccag gaagcacata aggacatttc ctacctgtac<br>cggttcaact ggaaccactg cggaactatg acatcggaat gcaaacggca cttttatccaa<br>gacacctggc tctatgagtg ttccccgaac ttgggaccct ggattcagca ggtggaccaa<br>agctggcgca agagagggat cctttatgtt cccctggtgc aaagaggact tgtcagcagt<br>tggtgggagg actgccagaa ctcgtgtacc tgccaggagc aattggcaca aggatggaa<br>ttggttcttc ggggcataac gaagtgctct gtgtggagcc tcctgcagtc ctgtaacgtc<br>taattccac atttggcggt ctgtgtaatg aatctcgggc actccacagg ctc |
| AF000381<br>SEQ ID NO:215 | acacctgcct ctacgagtgc tccccaact tggggccctg gatccagcag gtggatcaga<br>gctggcgcaa agagcgggta ctgaacgtgc ccctgtgcaa agaggactgt gagcaatggt<br>gggaagattg tcgcacctcc tacacctgca agagcaactg gcacaagggc tgcaactgga<br>cttcagggtt taacaagtgc gcagtgggag ctgcctgcca acctttccat ttctacttcc<br>ccacaccat tgcccg |
| AF000380<br>SEQ ID NO:216 | gtgtcccag aagtggcctt gaaccgaata tctccaatgg acagggctgg ggagcccaca<br>gggctggtgc ggcgggagtc agtggaggcg aagatgcaga gtgccagctg gaaggtcaga<br>atacgctcca ccaccatggc ctggccctgc gttgtgttgt tggtagagcg cgttgtctac<br>cctgtaccga agacagaggc tgtggggaca gcctagggc cctggatcta ttgcctactt<br>agagagaggc caactcagac acagccgtgt atgctcccag cagcaacgga ggttcagcac<br>cgcctgcagg gacagaaaga catggtctgg aaatggatgc cacttctgct gcttctggtc<br>tgtgtagcca ccatgtgcag tgcccaggac aggactgatc tcctcaatgt ctgtatggat<br>gccaagcacc acaagacaaa gccaggtcct gaggacaagc tgcatgacca atgcagtcc<br>tggaagaaga atgcctgctg cacagccagc accagccagg agctgcacaa ggacacctcc<br>cgcctgtaca actttaactg gaccactgc ggcaagatgg agcccgcctg cagcgccact<br>tcatccagga cacctgtctc tatgagtgct caccaacctg gggccctgga tccagcaggt<br>gaatcagagc tggcggcaaa gaacgcttcc tggatgtgcc cttatgcaaa ggacagtgtc<br>agcgctggtg ggaggattgt cacacctccc acacgtgcaa gagcaactgg cacagaggat<br>gggactggac ctcaggagtt aacaagtgcc cagctggggc tctctgccgc acctttgagt<br>cctacttccc cactccagct gccctttgtc aaggcctctg gagtcactca tacaaggtca<br>gcaactacag ccgagggagc ggccgctgca tccagatgtg gtttacttca gccccaggca<br>accccaacga ggaagtggcg aggttctatg ctgcagccat gcatgtgaat gctggtgaga<br>tgcttcatgg gactgggggt ctcctgctca gtctggccct gatgctgacc ctctggctcc<br>tcggctgcgt tcagtcctcc cagactacct gccctcagct tggataacca ggctgggctc<br>agctcagctc ccacaaatga cagccctta agcatgcttc tattagtcac ctaaccctct<br>gtcacccagt ctgttgctgc tccatggtgg ggccaagagt cacttctaat aaacagactg<br>ttttctaata aaaaaaaaa aa |
| AA637071<br>SEQ ID NO:217 | aggattctat gccgaggcca tgagtggagc tgggcttcat gggacctggc cactcttgtg<br>cagcctgtcc ttagtgctgc tctgggtgat cagctgagtt cctgttttac cttcagttgt<br>ctggagcgcc ccctgcttg gctcagcctc ccagctccca gctcctttg tggtggggct<br>ctgacagcct ctttaataaa ccagacattc c |
| AA616314<br>SEQ ID NO:218 | attaggatcc ttccttctca gcaggatcca catacccta ggagtggaag actccttggc<br>gcttggtgct tcaaccggac tgacttcctg ggcctggagt tggcgattag aggtctgaca<br>tggctcaact gatgactgtg cagttgttgc tcctggtgat gtggatggcc gaatgtgctc<br>agtccagagc tactcgggcc aggactgaac ttctcaatgt ctgcatggat gccaaacacc<br>acaaagaaaa accgggccct gaggacaatt tacacgacca gtgcagcccc tggaagacga<br>attcctgctg ttccacgaac acaagccagg aagcacataa ggacatttcc tacctgtacc<br>ggttcaactg gaaccactgc ggaaatatga atcggaatg caaacggcac tttatccaag<br>aaaccttgac tcaatgagtg ttacacgaaa cttgggacac tggataagca agtggaacag<br>agatggcga aaagagcgga tacattgatg taaccctgtg acaagaggac tgttcagcag<br>tggtgggagg actgccaga |
| AA109687<br>SEQ ID NO:219 | aattcggatc catgatctgg aagtataaac aagaaggag gctgacggct ctagaagtcc<br>ccaacctgtt gtgatcttca gtagacaaac actcctggtg tgtcacagga ttcaggccac |

TABLE 6-continued

| Accessions/SEQ ID NOs | Sequence |
|---|---|
| | taaacctcgg ccggctgtct cctggaatga agaaagcaaa ggaagcctag agtggagaca aagaagcccg aggcactctg agagctgcca tcttttcctt gtttgccgcc tgacacttct cagcaggatc cacatacact aaagcagggag tggagagagg cctgggctgg gccaggtttt ctgggctttt tcctgtgctc cgagtaggtg ggttgtattt tacccagtag gagtggaaga ctccttggcg cttggtgctt caaccggact gacttcctgg gcctggagtt ggcgattaga ggtctgacat ggctcacctg atgactgtgc agttgttgct cctggtgatg tggatggccg aatgtgctca gtccagagct actcgggcca ggactgaact tctcaatgtc tgcatggatg ccaaacacca caaagaaaaa ccgggccctg aggacaattt acacgaccag tgcagcccct ggaagacgaa ttcctgctgt tcaacgacac aagcaggaag cactaaggac ttttctactg t |
| AA608235 SEQ ID NO:220 | ttcggatcct tctctggaag tataaacaag aaaggaggct gacggctcta gaagtcccca acctgttgtg atcttcagta gacaaacact cctggtgtgt cacaggattc aggccactaa acctcggccg gctgtctcct ggaatgaaga aagcaaaga agcctagagt ggagacaaag aagcccgagg cactctgaga gctgccatct tttccttgtt tgccgcctga cacttctcag caggatccac atacactaag gagtggaaga ctccttggcg cttggtgctt caaccggact gacttcctgg gcctggagtt ggcgattaga ggtctgacat ggctcacctg atgactgtgc agttgttgct cctggtgatg tggatggccg aatgtgctca gtccagagct actcgggcc aggactgaac ttctcaatgt ctgcatggat gccaaacacc acaaagaaaa accgggccct gaggacaatt tacacgacca gtgcagcccc tggaagacga attcctgctg ttccacgaac acaagccagg aagcacataa ggacatttcc tacctgtacc ggttcaactg gaaccactgc ggaactatga catcggaatg caaacggcac tttatccaag acacctgcct ctatgagtgt tccccgaact gggactgga ttcagcaggt ggacc |
| AA589050 SEQ ID NO:221 | tggaagactc cttggcgctt ggtgcttcaa ccggactgac ttcctgggcc tggagttggc attagaggt ctgacatggc tcacctgatg actgtgcagt tgttgctcct ggtgatgtgg atggccgaat gtgctcagtc cagagctact cgggccagga ctgaactgct caatgtctgc atggatgcca agcaccacaa agaaaaaccg ggccctgagg acaatttaca cgaccagtgc agccctgga agacgaattc ctgctgttcc acgaacacaa gccaggaagc acataaggac atttcctacc tgtaccggtt caactggaac cactgcggaa ctatgacatc ggaatggcaa cggcactttt atcaaagaca cctgcctcta tgagttcc ccgaacttttg ggacctgga ttccagaagt tggacagagc ctgcgcaaaa gagcggattc ttgatggttc cctgtgcaaa gaggactgtc agcagtggtg ggagactgcc aagctcttta cctgcaagag cattggcaca aggatggaat ggtcctctgg caaacga |
| AA544782 SEQ ID NO:222 | atggctccct gatgactgtg cagttgttgc tcctgctgat gtggatggcc gaatgtgctc agtccagagc tactcgggcc aggactgaac ttctcagtgt ctgcatggat gccagacacc acaaagagaa accgggccct gaggacaatt tacacgacca gtgcagcccc tggaagacga attcctgctg ttccacgaac acaagccagt agcacataa ggacatttcc tacctgtacc ggttcaactg gaaccactgc ggaactatga catcggaatg caaacggcac tttatccaag acagctgcct ctatgagtgt tccccgaact gggagcctg tatgcagcag gtggacgaga gctgtcgcaa agagcggatc cttgatgtgc cctgtgcaaa gaggactgt cagcagtggt gcgagtgctg cggagctctt gtacctgcag agaggaattt gcacagggga tggaactggt tccctgggc ataacaagtg tcctgtgta gcctgccggc aggccgttag cgttgtagtt tcgcggatcg gctggtcggg tgaagaagtt gtgggcatg ccacatgtca gtagtttgtt |
| AA522095 SEQ ID NO:223 | aattcgcatc cttcataaac aagacaggag gctgacggct ctagaagtcc ccaacctgtt gtgatcttca gtagacaaac actcctggtg tgtcacagga ttcaggccac taaacctcgg ccggctgtct cctggaatga agaaagcaaa ggaagcctag agtggagaca aagaagcccg aggcactctg agagctgcca tcttttcctt gtttgccgcc tgacacttct cagcaggatc cacatacact aaggagtgga agactccttg gcgcttggtg cttcaaccgg actgacttcc tgggcctgga gttggcgatt agaggtctga catggctcac ctgatgactg tgcagttgtt gctcctggta tgttgatgg ccgaatgtgc tcagtccaga gctactcggg ccaggactga acttctcaat gtctgcatga tgccaaaca ccacaaagaa aaaccgggcc tgaggacaa tttacacgac cagtgcagcc cctggaagac gaatttctgc tgttccacga acacaagcca ggaagcacat aaggacattt cctaactgta acggttcaat gg |
| AA386821 SEQ ID NO:224 | tcccatttcc tacctgtacc ggttcaactg gaaccactgc ggaactatga catcggaatg caaacggcac tttatccaag acacctgcct ctatgagtgt tccccgaact gggaccctg gatccagcag gtggaccaga gctggcgcaa agagcggatc cttgatgtgc cctgtgcaa agaggactgt cagcagtggt gggaggactg ccagagctct tttacctgca agagcaattg gcacaaggga tggaactggt cctcggggca taacgagtgt cctgtgggag cctcctgcca tcccttcacc ttctacttcc ccacatctgc tgctctgtgt gaggaaatct ggagtcactc ctacgagctc ag |
| AA386818 SEQ ID NO:225 | ctatcccatt tcctacctgt accggttcaa ctggaaccac tgcggaacta tgacatcgga atgcaaacg cactttatcc aagacacctg cctctatgag tgttccccga acttgggacc ctggatccag caggtggacc agagctggcg caaagagcgg atccttgatg ttcccctgtg caaagaggac tgtcagcagt ggtggggga ctgccagagc tcttttacct gcaagagcaa ttggcacaag ggatggaact ggtcctcggg gcataacgag tgtcctgtgg gagcctcctg ccatcccttc accttctact tccccacatc tgctgctctg tgtgaggaaa tctggagtca ctcctacaag ctcag |
| AA386495 SEQ ID NO:226 | tatccctgag agctgccatc ttttccttgt tgccgcctg acacttctca gcaggatcca cataccctaa gagtggag agaggcctgg gctgggccag gttttctggg cttttcctg tgctccgagt cagtgggttg tattttaccc agtaggagtg aagactcct ggcgcttgg tgcttcaacc ggaactgact tcctgggcct ggagttggcg attagaggtc tacatggct |

TABLE 6-continued

| Accessions/SEQ ID NOs | Sequence |
|---|---|
| | cacctgatga ctgtgcaagt tgtgcccccg gtgatgttga atggcggatg tgctcagtcc<br>agaagtaatt tgggccaaga ctggacttct ccatggctgc attgatggca aacaccccaa<br>aggaaaacgg ggccttgggg caattatcac ggccctgtaa cccttggaaa ccaattcccg<br>ggttccgaaa cacagccgga |
| AA289278<br>SEQ ID NO:227 | aattcggatc catgggctga tctggaagta taaacaagaa aggaggctga cggctctaga<br>agtccccaac ctgttgtgat cttcagtaga caaacactcc tggtgtgtca caggattcag<br>gccactaaac ctcggccggc tgtctcctgg aatgaagaaa gcaaaggaag cctagagtgg<br>agacaaagaa gcccgaggac tctgagagct gccatctttt ccttgtttgc cgcctgacac<br>ttctcagcag gatccacata ccctaaggga gtggagagag gcctgggctg gcaggtttt<br>ctgggctttt tcctgtgctc cgagtaggtg ggttgtattt tacccagtag gagtggaaga<br>ctccttggcg cttggtgctt caaccggact gacttcctgg gcctggagtt ggcgattaga<br>ggtctgacat ggctcacctg atgactgtgc agttgttgct cctggtgatg tggatggccg<br>aatgtgctca gtccagagct actcgggcca ggactgaact tctcaatgtc tgcatggatg<br>ccaa |
| AA286342<br>SEQ ID NO:228 | ttggcatcca tgcagacatt gagaagttca gtcctggccc gagtagctct ggactgagca<br>cattcggcca tccacatcac caggagcaac aactgcacag tcatcaggtg agccatgtca<br>gacctctaat cgccaactcc aggcccagga agtcagtccg gttgaagcac caagcgccaa<br>ggagtcttcc actcctactg ggtaaaatac aacccaccta ctcggagcac aggaaaaagc<br>ccagaaaacc tggcccagcc caggcctctc tccactccct tagggtatgt ggatcctgct<br>gagaagtgtc aggcggcaaa caaggaaaag atggcagctc tcagagtgcc |
| AA276302<br>SEQ ID NO:229 | ttcggatcca tggtgctccg agtaggtggg ttgtatttta cccagtagga gtggaagact<br>ccttggcgct tggtgcttca accggactga cttcctgggc ctggagttgg cgattagagg<br>tctgacatgg ctcacctgat gactgtgcag ttgttgctcc tggtgatgtg gatggccgaa<br>tgtgctcagt ccagagctac tcgggccagg actgaacttc tcaatgtctg catggatgcc<br>aaacaccaca agaaaaaacc gggccctgag gacaatttac acgaccagtg cagcccctgg<br>aagacgaatt cctgctgttc cacgaacaca gccaggaag cacataagga catttcctac<br>ctgtaccggt tcaactggaa ccactgcgga actatgacat cggaatgcaa acggcacttt<br>atccaagaca cctgcctcta tgagtgttcc ccgaacttgg accctggat ccagcaagtg<br>gaccagagct ggcgcaagag cggatccttg aatgtccctg tgcaagagga ctgtcagcag<br>tggtgggaga ctgcagagct ctt |
| AA276123<br>SEQ ID NO:230 | aattcgggat ccatgggctg atctggaagt ataaacaaga aaggaggctg acggctctag<br>aagtccccaa cctgttgtga tcttcagtag acaaacactc tggtgtgtc acaggattca<br>gctctgtttc ctaggccact aaacctcggc cggctgtctc ctggaatgaa gaaagcaaag<br>gaagcctaga gtggagacaa agaagcccga ggcactctga gagctgccat ctttccttg<br>tttgccgcct gacacttctc agcaggatcc acatacccta aggagtggaa gactccttgg<br>cgcttggtgc ttcaaccgga ctgacttcct gggcctggag ttggcgatta gaggtctgac<br>atggctcacc tgatgactgt gcagttgttg ctcctggtga tgtggatggc cgaatgtgct<br>cagtccgag ctactcgggc caggactgaa cttctcaatg tctgcatgga tgccaaacac<br>cacaaagaaa aaccgggccc tgaggacaat ttacacgacc agtgcagccc ctggaagacg<br>aattcctgct gttccacgaa cacaagccag gaagcacata aggacat |
| AA277280<br>SEQ ID NO:231 | attcggatcc acgtataaac aagaaaggag gctgacggct ctagaagtcc ccaacctgtt<br>gtgatcttca gtagacaaac actcctggtg tgtcacagga ttcagctctg tttcctaggc<br>cactaaacct cggccggctg tctcctggaa tgaagaaagc aaaggaagcc tagagtggag<br>acaaagaagc ccgaggcact ctgagagctg ccatcttttc ccttgtttgc cgcctgacac<br>tctcagcagg atccacatac cctaagggag tggagagagg cctgggctgg caggttttc<br>tgggctttt cctgtgctcc gagtaggtgg gttgtatttt acccagtagg agtggaagac<br>tccttggcgc ttggtgcttc aaccggactg acttcctggg cctggagttg gcgattagag<br>gtctgacatg gctcacctga tgactgtgca gttgttgctc ctggtgatgt ggatggccga<br>attggctcat tccaaagcta ctcgggccgg aactgaactc ctcaaggtct gcatggatgc<br>aaacgccaca aagaaaa |
| AA273543<br>SEQ ID NO:232 | gttcggatcc atgggctgat ctggaagtat aaacaagaaa ggaggctgac ggctctagaa<br>gtccccaacc tgttgtgatc ttcagtagac aaacactcct ggtgtgtcac aggattcagc<br>tctgttcct aggccactaa acctcggccg gctgtctcct ggaatgaaga aagcaaagga<br>agcctagagt ggagacaaag agcccgagg cactctgaga gctgccatct tttccttgtt<br>tgccgcctga cacttctcag caggatccac ataccctaag ggagtggaga gaggcctggg<br>ctgggccagg ttttctgggc ttttcctgtg ctccgagtag gtggttgta ttttacccag<br>taggagtgga agactccttg gcgcttggtg cttcaaccgg actgacttcc tgggcctgga<br>gttggcgatt agaggtctga catggctcac ctgatgactg tgcagttgtt gctcctggtg<br>atgtggatgg cgaatgtgct cagtccagag ctactcgggc caagactgaa cttctcaatg<br>tctgcatgga tgccaacacc acaagaaaaa cggggcttga gacaatttca cgacagtgca<br>gccctggaaa aga |
| U89949<br>SEQ ID NO:233 | gaattcgcgg ccgctccggg aagggggaa gggcacaact ccctcgggaa gctcgccgct<br>gcctcctgga gcagaaggca gacaaagcca tgccctggaa gctgacagcc cttctgctct<br>ttctggccgg ggtggtctcc gtgtgccgcg cccggggccag gacggacctg ctcaacgtct<br>gcatggatgc caagcaccac aaggtagagc caggccctga ggacgagctg cacgaccagt<br>gcgtccctg gaagaagaac gcctgctgct cgccagagt cagccagagt ctgcaccggg<br>acaagtcctc cctgtataac ttttcctggg agcactgcgg caggatggaa ccggcctgca<br>agcgccactt cattcagaac aactgtctgt acgagtgctc gcccaacctg ggccctggt<br>tccaggaggt gaaccagaag tggcgcaaag gcggttcct gaacgtgccc ctctgcaaag<br>aggactgtct ggactggtgg gaagactgcc gcacctccta cacctgcaag agcagctggc |

TABLE 6-continued

| Accessions/SEQ ID NOs | Sequence |
|---|---|
| | acaagggctg gaactggagc tcaggatcta accagtgtcc cacggggacc acctgcgaca<br>catttgagtc cttcttcccc acacccgcag cgctgtgtga gggcatctgg aatcacgatt<br>ataagttcac caactacagc cggggcagcg gccgctgcat ccagatgtgg tttgacgcgg<br>ccgagggcaa ccccaacgag gaggtagcga ggttctacgc cttggccttg agtgcgggga<br>ccatgtccct tgggaccggg cctctcctgc tcagcgcagc cctgatgctg ccacttgggc<br>tccttgactg agtccggcgt ctccagacgg tccttctgcc tgtccccagc tttgatgacc<br>aggctggtct caactcagct cccaccaatg agggagccct aagcccgcct catctgttac<br>ccatccctct gtcatcaagt tcctgccgta gggtgggcct tggggtctct ctgacagcca<br>gttctaacag gcagattaac agcactgtgt ctgatgggct gttttggttg tgagctggtg<br>tgtggcagag gacagagccc atagcttttg gattccttca gcttagagaa atgagacctg<br>ggtttgaatt ccagctctgc cactcactat gtcaagtgaa gcagttgcgc gacggctcta<br>aaccataggc tcctcctcaa taaaatgaag |
| AA208306<br>SEQ ID NO:234 | aatctggagt cactcctaca agctcagcaa ctacagtcga gggagcggcc gctgcattca<br>gatgtggttc gacccagccc agggcaaccc caacgaggaa gtggcgaggt tctatgccga<br>ggccatgagt ggagctgggt tcatgggac ctggccactc ttgtgcagcc tgtccttagt<br>gctgctctgg gtgatcagct gagctcctgt tttaccttca gttgtctgga gcgccaccct<br>gcttggctca gcctcccagc tcccagcctc ctttgtggtg gggctctgac agcctcttta<br>ataaaccaga cattcca |
| AA208089<br>SEQ ID NO:235 | cacgaacaca agccaggaag cacataagga catttcctac ctgtaccggt tcaactggaa<br>ccactgcgga actatgacat cggaatgcaa acggcacttt atccaagaca catgcctcta<br>tgagtattcc ccgaacttgg gaccctggat ccgcaggtg gaccagagct gggcgcaaaga<br>gcggatcctt gatgttcccc tgtgcaaaga ggactgtcag cagtggtggg aggactgcca<br>gagctctttt acctgcaaga gcaattggca caagggatgg aactggtcct cggggcataa<br>cgagtgtcct gtgtgagcct cctgccatcg cttcaccttc tacttcccca catctgctgc<br>tctgtgtgaa gaaatctgga gtcactccta caagcttaac aactacagtc gagggaagcg<br>gccgctgcag tcagatgtgg ttcgacccag ccatggcaaa cccagcgagg aagttgcgag<br>gtctatgccg aggcaatagt gagctggtgt ctgggactgg gcactttgt |
| AA242285<br>SEQ ID NO:236 | aagactgtag agactaccca gagtctgacc tagggacagg ccaactcgga tacccctatg<br>tgcgctccca gaagctaagg acattgagac agaaagacat ggcctggaaa cagacaccac<br>tcttgctttt ggtctacatg gtcacaacag gcagtggcgg gacagaacag acctactcaa<br>cgtttgcatg gatgccaaac accataagac aaagccgggc cccgaggaca agctgcatga<br>ccagtgtagt ccatggaaga aaaatgcctg ttgctcagtc aacaccagcc aggagctaca<br>caaggctgac tcccgtctgt acttcaactg ggatcactgt ggcaagatgg agcctgcctg<br>taagagtcac ttcatccaag actcctgcct gtatgattgt tcccaaacc ttggcccttg<br>attcagtcaa gtggatcaag attgggctta aaaaggtttt cctgatgtgc ccctaatgca<br>agaagacctg tcaccagtgt tggaaagctt gtggtacctc ctttactggc agaagagact<br>ggcataaagc tcggact |
| AA139715<br>SEQ ID NO:237 | attcggatcc atgggctgat ctggaagtat aaacaagaaa ggaggctgac ggctctagaa<br>gtcccaacct gttgtgatct tcagtagaca aacactcctg gtgtgtcaca ggattcagct<br>ctgtttccta ggccactaaa cctcggccgg ctgtctcctg gaatgaagaa agcaagaa<br>gcctagagtg gagacaaaga agcccgaggc actctgagag ctgccatctt ttccttgttt<br>gccgcctgac acttctcagc aggatccaca taccctaagg agtggaagac tccttggcgc<br>ttggtgcttc aaccggactg acttcctggg cctggagttg gcgattagac tctgccttca<br>gggtctgaca tggctcacct gatgactgtg cagttgttgc tcctggtgat gtggatggcc<br>gaatgtgctc agtccagagc tactcgggcc aggactgaac ttctcaatgt ctgcatggat<br>gccaaacacc acagagaaag accgggccct gaggacaatt ttacacgaca gtgcagcccc<br>tggaagacga attcctgttg ttcacgaaca caagcaggat gacataggac atttctactg<br>taccgttcac tggaac |
| AA139709<br>SEQ ID NO:238 | aattcggatc catgggctga tctggaagta taaacaagaa aggaggctga cggctctaga<br>agtccccaac ctgttgtgat cttcagtaga caaacactcc tggtgtgtca caggattcag<br>ctctgttttcc taggccacta aacctcggcc ggctgtctcc tggaatgaag aaagcaaagg<br>aagcctagag tggagacaaa gaagcccgag gcactctgag agctgccatc ttttccttgt<br>ttgccgcctg acacttctca gcaggatcca catacccta ggagtggaag actccttggc<br>gcttggtgct tcaaccggac tgacttcctg ggcctggagt tggcgattag actctgcctt<br>cagggtctga catggctcac ctgatgactg tgcagttgtt gctcctggtg atgtggatgg<br>ccgaatgtgc tcagtccaga gctactcggg ccaggactga acttctcaat gtctgcatgg<br>atgccaaaca ccacaaagaa aaaccgggcg ctgaggacaa tttacacgac cagtgcagca<br>cctggaagac gaattcctgc tgttcacga gcacaagcta ggaagcacat aaggacattt<br>tctanctgta ccggttcaac tggacccact gcggactatg acatcgga |
| AA139675<br>SEQ ID NO:239 | attcggatcc atgcagctta aagggcctc cagctttagg ctttatagat acctggccca<br>cccttcccca gtcagcaggc tgatctggaa gtataaacaa gaaaggaggc tgacggctct<br>agaagtcccc aacctgttgt gatcttcagt agacaaacac tcctggtgtg tcacaggatt<br>caggccacta aacctcggcc ggctgtctcc tggaatgaag aaagcaaagg aagcctagag<br>tggagacaaa gaagcccgag gcactctgag agctgccatc ttttccttgt ttgccgcctg<br>acacttctca gcaggatcca catacccta gtaggagtgg aagactcctt ggcgcttggt<br>gcttcaaccg gactgacttc ctgggcctgg agttggcgat tagaggtctg acatggctca<br>cctgatgact gtgcagttgt tgctcctggt gatgtggatg gcgaatgtg ctcagtccag<br>agctactcgg gccaggactg aacttctcaa tgtctgcatg gatgtcaaac accacaaaga<br>aacaccgggc ctgaggacaa tttacacgac cagtgcagcc cctggaagac gaatcctgct<br>gttccagaaa caagcaggag cacataggcc attcct |

TABLE 6-continued

| Accessions/SEQ ID NOs | Sequence |
|---|---|
| AA139593<br>SEQ ID NO:240 | attcggatcc atgggctgat ctggaagtat aaacaagaaa ggaggctgac ggctctagaa<br>gtccccaacc tgttgtgatc ttcagtagac aaacactcct ggtgtgtcac aggattcagg<br>ccactaaacc tcggccggct gtctcctgga atgaagaaag caaaggaagc ctagagtgga<br>gacaaagaag cccgaggcac tctgagagct gccatctttt ccttgtttgc cgcctgacac<br>ttctcagcag gatccacata ccctaaggag tggaagactc cttggcgctt ggtgcttcaa<br>ccggactgac ttcctgggcc tggagttggc gattagaggt ctgacatggc tcacctgatg<br>actgtgcagt tgttgctcct ggtgatgtgg atggccgaat gtgctcagtc cagagctact<br>cgggccagga ctgaacttct caatgtctgc atggatgcca aacaccacaa agaaaaaccg<br>ggccctgagg acaatttaca cgaccagtgc atgccctgga agacgaattc ctgctgttcc<br>acgaacacaa gccaggaagc acatagagac attttcctgct gtaccggttc aactggacca<br>ctgcggaact atgacatcga atgcagacgc acttttgccag gacactggct ctatgagtgt |
| AA124010<br>SEQ ID NO:241 | aattcggatc catgggctct agaagtcccc aacctgttgt gatcttcagt agacaaacac<br>tccgtggtgt gtcacaggat tcaggccact aaacctcggc cggctgtctc ctggaatgaa<br>gaaagcaaag gaagcctaga gtggagacaa agaagcccga ggcactctga gagctgccat<br>cttttccttg tttgccgcct gacacttctc agcaggatcc atatccctaa aggagtggaa<br>gactccttgg cgcttggtgc ttcaaccgga ctgacttcct gggcctggag ttggcgatta<br>gaggtctgac atggctcacc tgatgactgt gcagttgttg ctcctggtga tgtggatggc<br>cgaatgtgct aagtccagag ctactcgggc caggactgaa cttctcaatg tctgcatgga<br>tgccaaacac acaaggaaa acgggcccc tgaggacaat tacacgacca gtgcaagccc<br>tggaagacga atttctgctg ttcaagacca aagccagta gcacataggg acattccaac<br>ctgtaccgtt caacttgaac actgcggaat atgactcg |
| AA108790<br>SEQ ID NO:242 | ccactaacca cataaggaca tttcctacct gtaccggttg acctgcaacg actgccgaac<br>tatgacatcg caatgcacac gccactttat cgaccacacc tgcctctatg agtgttaccc<br>gaacttcgca ccctccatcc accaggtgca cgacagctgg cccacagagc gcatccttca<br>tgttcccctg tccacagacg actgtcagca gtcgtcccag cactcccaca gctctcttac<br>ctgcaacacc aattcccaca acggatggaa ctcgtcctcg cggcatcacg agtgtcctgt<br>agcaccctcc tgccatccct tcaccttcta cttccgcaca tctcgtgctc tgtgtgatga<br>actctggagt cactcctaga cactcagcaa ctacagtcga cgg |
| AA108350<br>SEQ ID NO:243 | aattcggatc catgcatgga tccggatcca tggcccctgg aagacgaatt cctgctgttc<br>cacgaacaca agccaggaag cacataagga catttcctac ctgtaccggt tcaactggaa<br>ccactgcgga actatgacat cggaatgcaa acggcacttt atccaagaca cctgcctcta<br>tgagtgttcc ccgaacttgg gaccctggat ccagcaggtg gaccagagct ggcgcaaaga<br>gcggatcctt gatgttcccc tgtgcaaaga ggactgtcag cagtggtggg aggactgcca<br>gagctctttt acctgcaaga gcaattggca caagggatgg aactggtcct cggggcataa<br>cgagtgtcct gtgggagcct cctgccatcc cttcaccttc tacttcccac atctgctgct<br>ctgtgtgagg aatctggagt cactctacaa gctcagcact acagtcgagg agccgcc |
| AA028831<br>SEQ ID NO:244 | ctgagtctga ggccagctgg tcgacaaggg tctgacatgg ctcacctgat gactgtgcag<br>ttgttgctcc tggtgatgtg gatggccgaa tgtgctcagt ccagagctac tcgggccagg<br>actgaacttc tcaatgtctg catggatgcc aaacaccaca agaaaaaacc gggccctgag<br>gacaatttac acgaccagtg cagccctgg aagacgaatt cctgctgttc cacgaacaca<br>agccaggaag cacataagga catttcctac ctgtaccggt tcaactggaa ccactgcgga<br>actatgacat cggaatgcaa acggcacttt atccaagaca cctgcctcta tgagtgttcc<br>ccgaacttgg gaccctggat ccagcaggtg gaccagagct ggcgcaaaga gcggatcctt<br>gatgttcccc tgtgcaaaga ggactgtcag cagtggtggg aggactgcca gagctctttt<br>acctgcaaga gcaattggca caagggatgg aactggtcct cggggcataa cgagtgtcct<br>gtgggagcct cctgccatcc gttcacttct acttcgcaca tctgctgtct gtgtgaggaa<br>tctggagtca ctctacaagt ctagaataca gtcgaggacc ggc |
| AA061275<br>SEQ ID NO:245 | aaccactgcg gaactatgac atcggaatgc aaacggcact ttatccaaga cacctgcctc<br>tatgagtgtt ccccgaactt gggaccctgg atccagcagg tggaccagag ctggcgcaaa<br>gagcggatcc ttgatgttcc cctgtgcaaa gaggactgtc agcagtggtg ggaggactgc<br>cagagctctt ttacctgcaa gagcaattgg caagggat ggaactggtc ctcggggca<br>taacgagtgt cctgtgggag cctcctggca tcccttcagc ttctacttcc ccacatctgg<br>ctgctcctgt gttaggaaaa tcttggattc actcctacca agcttcagca a |
| W82933<br>SEQ ID NO:246 | aattcggcac taggggaggc tgacggctct agaagtcccc aacctgttgt gatcttcagt<br>agacaaacac tcctggtgtg tcacaggatt cagctctgtt tcctaggcca ctaaacctcg<br>gccggctgtc tcctggaatg aagaaagcaa aggaagccta gagtggagac aaagaagccc<br>gaggcactct gagagctgcc atcttttcct gtttgccgc ctgacacttc tcagcaggat<br>ccacataccc taaggagtgg aagactcctt ggcgcttagt gctgctctgg tgatcagct<br>gagctcctgt tttaccttca gttgtctgga gcgccaccct gcttggctca gcctcccagc<br>tcccagcctc ctttgtggtg gggctctgac agcctcttta ataaaccaga cattccaaaa<br>aag |
| AA015571<br>SEQ ID NO:247 | gtggacgaag actgtagaga ctacccagag tctgacctag gagaggcca actcggatac<br>ccctatgtgc gctcccagaa gctaaggaca ttgagacaga agacatggc ctggaaacag<br>acaccactct tgcttttggt ctacatggtc acaacaggca gtggccggga cagaacagac<br>ctactcaacg tttgcatgga tgccaaacac cataagacaa agccgggccc cgaggacaag<br>ctgcatgacc aatgtagtcc atggaagaaa aatttgctct gcagtcaa caccagccag<br>gagctacaca aggctgactc ccgtctgtac ttcaactggg atcactgtgg caagatggga<br>cctgcctgta agagtcactt catccaagac tcctgcctgt atgagtgctc cccaaacctt<br>gggccttgga tccagcaagt ggaccagagt tggcgtaaag agcgtttcct ggatgtgccc<br>ttatgcagag aggactgtca ccagtggtgg gaagcctgtc gtacctcctt tacctgcaag |

TABLE 6-continued

| Accessions/SEQ ID NOs | Sequence |
|---|---|
| | agagactggc ataaaggctg ggaatggtcg tcaggcatgt acaagtgcgc aacacagcac<br>ctgtacacgt gtgagtactc ttccgaacca gcagcttt |
| W71715<br>SEQ ID NO:248 | gggctgtgga cgaagactgt agagactacc cagagtctga cctagggaga ggccaactcg<br>gatacccta tgtgcgctcc cagaagctaa ggacattgag acagaaagac atggcctgga<br>aacagacacc actcttgctt ttggtctaca tggtcacaac aggcagtggc cgggacagaa<br>cagacctact caacgtttgc atggatgcca aacaccataa gacaaagccg ggccccgagg<br>acaagctgca tgaccagtgt agtccatgga agaaaaatgc ctgttgctca gtcaacacca<br>gccaggagct acacaaggct gactcccgtc tgtacttcaa ctgggatcac tgtggcaaga<br>tggagcctgc ctgtaagagt cacttcatcc aagactcctg cctgtatgag tgctccccca<br>accttgggcc ttggatccag caagtggacc agagttggcg taaagagcgt ttcctggatg<br>tgccttatgc aaagaggact gtcaccagtg gtgggaagcc tgtcgtacgt cctttacctg<br>caagagagac tggcataaag gctgggactg gtctcaggca ttaccagtgc caaacacagg<br>accctgtaaa cgttgagtac tattccgaaa cagcagcc |
| W59165<br>SEQ ID NO:249 | ttcggcacag ggggctgtgg acgaagactg tagagactac ccagagtctg acctagggag<br>aggccaactc ggatacccct atgtgcgctc ccagaagcta aggacattga cagaaagaa<br>catggcctgg aaacagacac cactcttgct tttggtctac atggtcacaa caggcagtgg<br>ccgggacaga acagacctac tcaacgtttg catggatgcc aaacaccata agacaaagcc<br>gggcccccgag acaagctgc atgaccagtg tagtccatgg aagaaaaatg cctgttgctc<br>agtcaacacc agccaggagc tacacaaggc tgactcccgt ctgtacttca actgggatca<br>ctgtggcaag atggagcctg cctgtaagag tcacttcatc caagactcct gcctgtatga<br>gtgctccccc aaccttgggc cttggatcca gcaagtggac cagagttggc gtaaagagcg<br>tttcctggat gtgcccttat gc |
| X62753<br>SEQ ID NO:250 | ggaaaggatt ttctcagccc ccatctccag cactgtgtgt tggccgcacc catgagagcc<br>tcagcactct gaaggtgcag ggggcaaagg ccaaaagagc tctggcctga acttgggtgg<br>tccctactgt gtgacttggg gcatggcctc atctgtgctg aaatgattcc acaaagatta<br>aactggctat catttgttga tttccccctt cttacattta atccttgcag gagaaagcta<br>agcctcaaga tagtttgctt ctctttcccc caaggccaag agaaggtgg agtgagggct<br>ggggtcggga caggttgaac gggaaccctg tgctctaaca gttagggccc gccgaggaac<br>tgaacccaaa ggatcacctg gtattccctg agagtacaga tttctccggc gtggccctca<br>agggacagac atggctcagc ggatgacaac acagctgctg ctccttctag tgtgggtggc<br>tgtagtaggg gaggctcaga caaggattgc atgggccagg actgagcttc tcaatgtctg<br>catgaacgcc aagcaccaca aggaaaagcc aggccccgag gacaagttgc atgagcagtg<br>tcgaccctgg aggaagaatg cctgctgttc taccaacacc agccaggaag cccataagga<br>tgtttcctac ctatatagat tcaactggaa ccactgtgga gagatggcac ctgcctgcaa<br>acggcatttc atccaggaca cctgcctcta cgagtgctcc cccaacttgg ggccctggat<br>ccagcaggtg gatcagagct ggcgcaaaga gcgggtactg aacgtgcccc tgtgcaaaga<br>ggactgtgag caatggtggg aagattgtcg caccctcctac acctgcaaga gcaactggca<br>caagggctgg aactggactt cagggtttaa caagtgcgca gtgggagctg cctgccaacc<br>tttccatttc tacttcccca caccccactgt tctgtgcaat gaaatctgga ctcactccta<br>caaggtcagc aactacagcc gagggagtgg ccgctgcatc cagatgtggt tcgacccagc<br>ccagggcaac cccaatgagg aggtggccga gttctatgct gcagccatga gtggggctgg<br>gccctgggca gcctggcctt tcctgcttag cctggcccta atgctgctgt ggctgctcag<br>ctgacctcct tttaccttct gatacctgaa aatccctgcc ctgttcagcc ccacagctcc<br>caactatttg gttcctgctc catggtcggg cctctgacag ccactttgaa taaaccagac<br>accgc |
| Z32564<br>SEQ ID NO:251 | cgcaggaata gatggacatg gcctggcaga tgatgcagct gctgcttctg gctttggtga<br>ctgctgcggg gagtgcccag cccaggagtg cgcgggccag gacggacctg ctcaatgtct<br>gcatgaacgc caagcaccac aagacacagc ccagcccga ggacgagctg tatggccagt<br>gcagtccctg gaagaagaat gcctgctgca cggccagcac cagccaggag ctgcacaagg<br>acacctcccg cctgtacaac tttaactggg atcactgtgg taagatggaa cccacctgca<br>agcgccactt tatccaggac agctgtctct atgagtgctc acccaacctg ggccctgga<br>tccggcaggt caaccagagc tggcgcaaag agcgcattct gaacgtgccc ctgtgcaaag<br>aggactgtga gcgctggtgg gaggactgtc gcacctccta cacctgcaaa agcaactggc<br>acaaaggctg gaattggacc tcaggattag atgagtgtcc ggccggggcc ctctgcagca<br>cctttgagtc ctacttcccc actccagccg cccttttgtga aggcctctgg agccactcct<br>tcaaggtcag caactatagt cgagggagcg gccgctgcat ccagatgtgg tttgactcag<br>cccagggcaa ccccaatgag gaggtggcca agttctatgc tgcggccatg aatgctgggg<br>ccccgtctcg tgggattatt gattcctgat ccaagaaggg tcctctgggg ttcttccaac<br>aacctattct aatagacaaa tccacatgaa aaaaaaaa |
| T29279<br>SEQ ID NO:252 | catgagcagt gtcgaccctg gaggaagaat gcctgctgtt ctaccaacac cagccaggaa<br>gcccataagg atgtttccta cctatataga ttcaactgga accactgtgg agagatggca<br>cctgcctgca aacggcattt catccaggac acctgcctct acgagtgctc cccaacttg<br>gggccctgga tccagcaggt ggatcagagc tggcgcaaag agcgggtact gaacgtgccc<br>ctgtgcaaag aggactgtna gcaaatggtg gggaagattg tcg |
| M25317<br>SEQ ID NO:253 | gaattccgga caaggattgc atgggccagg actgagcttc tcaatgtctg catgaacgcc<br>aagcaccaca aggaaaagcc aggccccgag acaagttgc atgagcagtg tcgaccctgg<br>aggaagaatg cctgctgttc taccaacacc agccaggaag cccataagga tgtttcttac<br>ctatatagat tcaactggaa ccactgtgga gagatggcac ctgcctgcaa acggcatttc<br>atccaggaca cctgcctcta cgagtgctcc cccaacttgg ggccctggat ccagcaggtg<br>gatcagagct ggcgcaaaga gcgggtactg aacgtgcccc tgtgcaaaga ggactgtgag<br>caatggtggg aagattgtcg caccctcctac acctgcaaga gcaactggca caagggctgg |

TABLE 6-continued

| Accessions/SEQ ID NOs | Sequence |
|---|---|
| | aactggactt cagggtttaa caagtgcgca gtgggagctg cctgccaacc tttccatttc |
| | tacttccct ctcccactgt tctgtgcaat gaaatctgca ctcactccta caaggtcagc |
| | aactacagcc gagggagtgg ccgctgcatc cagatgtggt tcgacccagc ccagggcaac |
| | cccaatgagg aggtggcgag gttctatgct gcagccatga gtggggctgg gccctgggca |
| | gcctggcctt tcctgcttag cctggcctaa tgctgctgtg gctgctcagc tgacctcctt |
| | ttaccttctg atacctggaa atccctgccc tgttcagcc cacagctccc aactatttgg |
| | ttcctgctcc atggtcgggc tctgacagc cattttgaat aaaccagaca ccgc |
| M86438 SEQ ID NO:254 | cctgtgtctt cccgcatcca gtgtagtctc tggagaaaga atgcctgagc tttaccagca ccacccagga agcccataag aatattccca tctatatgga ttcaactgga accactgtgg agagatggta cctgcctgca aacggcactt tatccaggac acctgccttt acgagtgacc ccccaacttg gggccctgga tccagcaggt atgcatggct tcctggcatc caagagctag cagaggagct gaattttcca ggcgtctctg caggcagcaa ccccagctcc acttctattc agggctgggt tcctgggatt cttgagcctg agcccttctt ttctaccaaa atctcccagg tggatcagag ctggtgcaaa gagtgggtgc tgaatgtgcc cctgtgcaaa gaggactgtg agcaatggtg ggaagattgt cgcacctcct acacctgcaa gagcaatggg cacaagggct ggaactggac ctcaggtgag ggctggggtg ggcaggaaag gagggatttg gaagtgaagg tgtgttgggt gtggaacagg tgtgtgacat tttgggggttg tagggctggc agaatcagag acctttgggg cccagtggct aaaggtcttc cctcttccta caggggtctaa caagtgccag gtggcagctg cctgactacc tttccatctc tacttctca cacccactgc tctgtgcagt gaaatctgga ctcactccta cagggtcagc aactacaacc gagggagcag ccgctgcatc cagatgtggt tcgacctggc ccagggcaac cccaatgagg aggtggcaag gttctatgct gcagctctga gtggggctgg gccctgggca cctggcccta atgctgctgt ggctgctcag ctgacctcct tttaccttct gatacttgga catccctgcc ctgtttagcc ccacagctcc caactatttg gttcctcttc tatggtcttg tctctgacag ccactttgaa taaaccacac accacacatg tatcttgaga attattt |
| J03922 SEQ ID NO:255 | gaattcctct agggagaagt ctcacccaga aggacagcaa aagaggaaaa gaagggaaca acaatgctga ggtttgccat caccctcttt gctgtcatca catcatctac ctgccagcag tatggatgtc tggaagggga cacccacaaa gcgaagccaa gtcctgagcc aaacatgcat gaatgcactc tgtattctga atcttcctgt tgctatgcaa acttcacaga gcaattggct cattccccaa taattaaagt aagcaacagc tactggaaca gatgtgggca gctcagtaaa tcctgtgaag atttcacaaa gaaatcgag tgcttttacc ggtgttctcc gcacgctgct cgctggatcg atcccagata tactgctgct attcagtctg ttccactgtg tcagagcttc tgtgatgact ggtatgaagc ctgcaaagat gattccattt gtgctcataa ctggctgacg gactgggaac gggatgaaag tggagaaaac cactgtaaga gtaaatgcgt accatacagt gagatgtatg caaatgggac cgacatgtgc cagagtatgt gggggggaatc ctttaaggtg agcgaatcct cctgcctctg cttgcaaatg aacaagaagg acatggtggc aatcaagcac ctcctctccg aaagctcaga ggaaagtcc agtatgagca gcagtgagga gcacgcctgc caaaagaaac tcctgaagtt tgaggcactg cagcaagagg aagggggaaga gagaagatga attttggtgg atgaatatca ggaggagagg aatcattgtg gaggttgtgc tcggggcatc acagcagcct gtcttatccc tcacttctga gaacacaata aatcaatggt tggctatatt |
| M64817 SEQ ID NO:256 | gctttagagg cagatcaggg tgtagttttc agctagcgcc gtgccttccc caccatgttc cttgccatga tgataatgta ctagacctct gaaactgtag cttcttgtt acagagtctc cgtgaatctg gaattcacca attcggcgag tctgaaagcc tcagtgatct ctcaggctcc atctgtctcc actcccagt ggaaggcttg cagctgtgtc accgctccag acttcacaca ggtgctggaa gactgaacta agacagaaag acatggcctg gaaacagaca ccactccttgc ttttggtcta catggtcaca acaggcagtg gccgggacga aacagaccta ctcaacgttt gcatggatgc caaacaccat aagacaaagc cgggcccga ggacaagctg catgaccagt gtagtccatg gaagaaaaat gcctgttgct cagtcaacac cagccaggag ctacacaagg ctgactcccg tctgtacttc aactgggatc actgtggcaa gatggagcct gcctgtaaga gtcacttcat ccaagactcc tgcctgtatg agtgctcccc caaccttggg ccttggatcc agcaagtgga ccagagttgg cgtaaagagc gtttcctgga tgtgccctta tgcaaagagg actgtcacca gtggtgggaa gcctgtcgta cctcctttac ctgcaagaga gactggcata aaggctggga ctggtcctca ggcattaaca agtgccaaa cacagcaccc tgtcacacgt ttgagtacta cttcccgaca ccagccagcc tttgcgaggg tctctggagt cactcctaca aggtcagcaa ctacagcaga gggagtggcc gctgcatcca gatgtggttt gactcaaccc agggcaatcc caatgaggac gtggtgaagt tttatgcttc ctttatgaca tctgggactg tgccccatgc agcagtactt cttgtgccca gcctggcccc agtgctgtca ttatgcctcc ctggctgaga ggtcagtctt cctctctaga tttctcctct atctaccctt ggtctggttc aactcttcaa agaataagga agtcttgagc ctgcttccac ccctctcctc tgtcatccag ttcctgatcc atgttggggg ttggggtttc tacaatcatt ttcaataaat ctatgacaca tctgggccta atgaaaaaaa aaa |
| L25338 SEQ ID NO:257 | ggatccaaga gattttatac tgtccttcag cactgtcctt cagttctttt tgtttttttg ttttttgttt tgttttgttt ttggttttc gagacagggt ttctctgtgt agccctggct gtcctggaac tcactctgta gaccaggctg gcctcgaact cagaaatcca cctgcctctg cctcccaagt gctgggttta aaggcatacg ccaccacgc ccggctcttc ggttctttag gtcattattt tttggggtag ggggacaaac aaattctcac tatgtatcac agattggcct agacccaca agccttcccc cttccgtcc tccatgtcct ggggttgcag gcgtgtctca ccaattgcag ctgggcttgt tttgtgtgtt tccttttgag aggtttcggt cgggtcgggt gcttttgctg cagatgccgc tgtcaggatg ggctgtcagg gcagaatggc ttttgggaga caggaaagga aaatactgag gaagcaaaac tttacaaagc agcactcttt cttgtgtacc ctctaaccac accatcctgt gggctgtcac ttggtcctcc tgccaatctg gagaacttgg cagggctggg tcaccacctc cctcagggct aacaggactt ctaggctgac atgatgaccc agctgataca gagtggaatg ccgagaacct cctgtgacag gatgaaggat ctgtgtgtcc |

TABLE 6-continued

| Accessions/SEQ ID NOs | Sequence |
|---|---|
| | ctggcccttg tcaaggtagc aagcagcagg aacctgaact atttaactat gtgtcataaa<br>gtctggaaat aagatgaaag catggggcat cccatcttct ctaggttgga aagctttgct<br>tcttttataa ccccctccc caatgccatg gggccatggg ataaaagagt ctccttgctg<br>acctctattc cagcttcagg gagcctgagg acatgaatgc tgaaggagaa gggactgatc<br>taatctttca ctatagggac agagagtctg agtcaggaa taaatgaagt ccctccccc<br>tctggtctag gtctccctaa ctttagctcc ctctgcacag acagaaagac atggcctgga<br>aacagacacc actcttgctt ttggtctaca tggtcacaac aggcagtggc cgggacagaa<br>cagacctact caacgtttgc atggatgcca acaccataa gacaaagccg ggccccgagg<br>acaagctgca tgaccaggtt ctgtgccagt gtggtcctga tgggagggtg atagagggca<br>gggtggggtt agtgagcagc cagacacacc cacaccctga gctcttgttg gcagagatgg<br>cttggtggaa agtagtgagg tgattttctg agggctgtcc ccagaagagg acacagtagt<br>ggcaatgaag cagttgatca ttagaagcct ctaattagag gccacgtgag gtcatgtgat<br>gataatctct atatctctca aataagggcc cgtggaagca cagggactca ctctcacagg<br>ttagacacac ctgattttt ttttttttgag agcattggtg ttttgcctac atatgtgttg<br>gatcc |
| M97701<br>SEQ ID NO:258 | tctagaattt tcagccctat cttaagcact atataacatg tgaaaaggaa caaaagggct<br>tctaacacta gaaaaaattt aaggccaaac ataacttgta aagccatttt ccactttact<br>tctgatagac tgtcttgaat ttccttagaa agttcaagat cagacttacc tcgttcccca<br>gctgaaaagt tctgaattca tacagttgaa tccttcttaa cagtctgctt tacgggaacc<br>tttatcaccg tcgttcccca gctgatgagt tctgaattcg cagttgaat ccttctcaac<br>agtctgtgtt acgggaacct tataaccttg attcgcagtt ctggttctgg aatgagggat<br>cttccttgcg cccagtcccga gtttttctc gtcccggatt ttctcgtccc ggaattcggc<br>accaattgtt attcgacgcg ttctcacgac cggccaggaa gaacaccaca gaccagaatc<br>ttctgcgaca aagctttatt cttacatctt caggaaaaga gagcaagaag caagagagag<br>caagaagcaa gagagggaag caagagagag caagaagcaa gagagggaag caagagagag<br>caaagcaaga gagagagaaa aacgaaaccc cttctatttt aaagagaaca accattgcct<br>agggcgcatc actccctgat tggctgcagc ccatggccga gctgacgttc acgggaaaaa<br>cagagtacaa gtagtcgtaa ataccttgg ctcatgcgca gattatttgt ttaccaactt<br>agaacacagg atgtcagcgc catcttgtga cggcgaatgt ggggcggct tcccacaagg<br>ctccacccac tggagctgag cacacacttg gaggttccac ttaccttagc tctgccttca<br>gggtctgaca tggctcacct gatgactgtg cagttgttgc tcctggtgat gtggatggcc<br>gaatgtgctc agtccagagc tactcgggcc aggactgaac |
| M97700<br>SEQ ID NO:259 | actagttgtg tctagatcct attgcactga tggtcatgaa gttgaaacat ggggggaaaat<br>gaactttata ccccttcttca tgacttctgt cctttgcct gcctcctttc tcatctccta<br>atattacagt cttggtttcc tctctaaatt tttagactt taacccacac ctaaacctgt<br>atcagctttt ataaaaatct tttcaaaact tcacactgaa gcatctgcct ccaaaggttt<br>tgaatgtgaa cgtgggtaaa ctctgttttt gcaaatggcc catctcttat tttttaattg<br>ccctgtgtga gtctcaggac cactaagtct aacaggctgt gaccagtgat tgtctctagg<br>gcatctgagc ctcacagagt ctgggaagac tgacaggagg aggtgaccca aggtctgtga<br>gtgcaggctc cacccactgg agctgagcac acacttggag gttccactta ccttagctct<br>gccttcaggg tctgacatgg ctcacctgat gactgtgcag ttgttgctcc tggtgatgtg<br>gatggccgaa tgtgctcagt ccagactac tcgggccagg actgaacttc tcaatgtctg<br>catggatgcc aagcaccaca aagaaaaacc gggccctgag gacaatttac acgaccaggt<br>aggacgaagg gtgatgtgtg gctgactaag ggctcgtggg tcaggagaaa gaagtatcta<br>gtcccagttt atggtggagg tggtcagacc tacctgagga gaccttcggt tctctctagt<br>gtgggtgact ttgacagtac atattggctg ccaactgcca gtgtgatatt atcagctcat<br>cttcctggta gctgaatttt gacgttgcat aagtaaggaa gtagattcaa ggaggaactt<br>gggaatgaaa caggcaaacc attgtgatgg ttttagattt aaactgattg ggggaggacgc<br>ctctgggagt ctcaggggag ggactgtatg ctgcccagtc acttttctgc cagcctttga<br>agacttgaga aggagactct catatctgag aagcctttgg aggcaggcat ctagcgaaca<br>cttggactgt ggtcctcagc ttgagggctg gagggcttga gggctctgtg ttataacagt<br>tgtttgccat agtgctttta gtatcccaaa gctcactaaa catttaataa aatcagtgtg<br>atgcaacaac tatgaagtca accagcagca ggtctgctat tgggaggta caatcagtgc<br>agacaacaaa gtgggagggg ggtctcaaaa aagccaagat gagggctgga gagttggctc<br>agtggttaaa agcacttgtt gagcttgcag aataccaagg tctgatccac aacatccaag<br>gtggtggatc c |
| M64782<br>SEQ ID NO:260 | tggagctgag cacacacttg gaggttccac ttaccttagc tctgccttca gggtctgaca<br>tggctcacct gatgactgtg cagttgttgc tcctggtgat gtggatggcc gaatgtgctc<br>agtccagagc tactcgggcc aggactgaac ttctcaatgt ctgcatggat gccaagcacc<br>acaaagaaaa accgggccct gaggacaatt tacacgacca gtgcagcccc tggaagacga<br>attcctgctg ttccacgaac acaagccagg agacattcc tacctgtacc<br>ggttcaactg gaaccactgc ggaactatga atcggaatg caaacggcac tttatccaag<br>acacctgcct ctatgagtgt tccccgaact tgggaccctg gatccagcag gtggaccaga<br>gctggcgcaa agagcggatc cttgatgttc ccctgtgcaa agaggactgt cagcagtggt<br>gggaggactg ccagagctct tttacctgca agagcaattg gcacaaggga tggaactggt<br>cctctgggca taacgagtgt cctgtgggag cctcctgcca tcccttcacc ttctacttcc<br>ccacatctgc tgctctgtgt gaggaaatct ggagtcactc ctacaagctc agcaactaca<br>gccgaggag cggccgctgc attcagatgt ggtttgaccc agcccagggc aaccccaacg<br>aggaagtggc gaggttctat gccgaggcca tgagtggagc tgggcttcat gggacctggc<br>cactcttgtg cagcctgtcc ttagtgctgc tctgggtgat cagctgagtt cctgttttac<br>cttcagttgt ctggagcgcc accctgcttg gtcagcctc ccagctccca gcctcctttg<br>tggtgggct ctgacagcct ctttaataaa ccagacattc cacatgtgcc ttatgaatta<br>aaaaaaaaaa aaaaaaaa |

TABLE 6-continued

| Accessions/SEQ ID NOs | Sequence |
|---|---|
| M35069<br>SEQ ID NO:261 | acaaggattg catgggccag gactgagctt ctcaatgtct gcatgaacgc caagcaccac<br>aaggaa |
| J05013<br>SEQ ID NO:262 | ctggaggcct ggctggtgct cacatacaat aattaactgc tgagtggcct tcgcccaatc<br>ccaggctcca ctcctgggct ccattcccac tccctgcctg tctcctaggc cactaaacca<br>cagctgtccc ctggaataag gcaaggggga gtgtagagca gagcagaagc ctgagccaga<br>cggagagcca cctcctctcc cagggacaga catggctcag cggatgacaa cacagctgct<br>gctccttcta gtgtgggtgg ctgtagtagg ggaggctcag acaaggattg catgggccag<br>gactgagctt ctcaatgtct gcatgaacgc caagcaccac aaggaaaagc caggccccga<br>ggacaagttg catgagcagt gtcgaccctg gaggaagaat gcctgctgtt ctaccaacac<br>cagccaggaa gcccataagg atgtttccta cctatataga ttcaactgga accactgtgg<br>agagatggca cctgcctgca aacggcattt catccaggac acctgcctct acgagtgctc<br>ccccaacttg gggccctgga tccagcaggt ggatcagagc tggcgcaaag agcgggtact<br>gaacgtgccc ctgtgcaaag aggactgtga gcaatggtgg gaagattgtc gcacctccta<br>cacctgcaag agcaactggc acaagggctg gaactggact tcagggttta acaagtgcgc<br>agtgggagct gcctgccaac ctttccattt ctacttcccc acacccactg ttctgtgcaa<br>tgaaatctgg actcactcct acaaggtcag caactacagc cgagggagtg gccgctgcat<br>ccagatgtgg ttcgacccag cccagggcaa cccaatgag gaggtggcga ggttctatgc<br>tgcagccatg agtgggggctg ggccctgggc agcctggcct ttcctgctta gcctggccct<br>aatgctgctg tggctgctca gctgacctcc ttttaccttc tgatacctgg aaatccctgc<br>cctgttcagc cccacagctc ccaactattt ggttcctgct ccatggtcgg gcctctgaca<br>gccactttga ataaaccaga caccgcac |
| M28099<br>SEQ ID NO:263 | ggagagccac ctcctctccc aggaactgaa cccaaaggat cacctggtat tccctgagag<br>tacagatttc tccggcgtgg ccctcaaggg acagacatgg ctcagcggat gacaacacag<br>ctgctgctcc ttctagtgtg ggtggctgta gtaggggagg ctcagacaag gattgcatgg<br>gccaggactg agcttctcaa tgtctgcatg aacgccaagc accacaagga aaagccaggc<br>cccgaggaca agttgcatga gcagtgtcga ccctggagga agaatgcctg ctgttctacc<br>aacaccagcc aggaagccca taaggatgtt tcctacctat atagattcaa ctggaaccac<br>tgtggagaga tggcacctgc ctgcaaacgg catttcatcc aggacacctg cctctacgag<br>tgctcccca acttgggggc ctggatccag caggtggatc agagctggcg caaagagcgg<br>gtactgaacg tgccctgtg caaagaggac tgtgagcaat ggtgggaaga ttgtcgcacc<br>tcctacacct gcaagagcaa ctggcacaag ggctggaact ggacttcagg gtttaacaag<br>tgcgcagtgg gagctgcctg ccaacctttc catttctact tccccacacc cactgttctg<br>tgcaatgaaa tctggactca ctcctacaag gtcagcaact acagccgagg gagtggccgc<br>tgcatccaga tgtggttcga cccagcccag ggcaacccca atgaggaggt ggcgaggttc<br>tatgctgcag ccatgagtgg ggctgggccc tgggcagcct ggccttcct gcttagcctg<br>gccctaatgc tgctgtggct gctcagctga cctccttta ccttctgata cctggaaatc<br>cctgccctgt tcagccccac agctcccaac tatttggttc ctgctccatg tcgggcctc<br>tgacagccac tttgaataaa ccagacaccg c |
| J02876<br>SEQ ID NO:264 | gaatcaattc ctccaaaccg caagaacagt aacatttatt attcaaaaaa acaaaaacca<br>gattatagga tatgacattt ggtataacaa taatgttatt gaaaaatgaa aaaatgatcc<br>attaatggct tgggctaaaa attcgggga cagcctaggg gcctgctagt attgcctact<br>tagagagagg ccaactcaga cacagccgtg tatgctccca gcagcaacgg aggttcacgt<br>ccgcctgcag ggacagaaag acatggtctg gaaatggatg ccacttctgc tgcttctggt<br>ctgtgtagcc accatgtgca gtgcccagga caggactgat ctcctcaatg tctgtatgga<br>tgccaagcac cacaagacaa agccaggtcc tgaggacaag ctgcatgacc aatgcagtcc<br>ctggaagaag aatgcctgct gcacagccag caccagccag gagctgcaca aggacacctc<br>ccgcctgtac aactttaact gggaccactg cggcaagatg gagcccgcct gcaagcgcca<br>cttcatccag gacacctgtc tctatgagtg ctcacccaac ctgggggccc ggatccagca<br>ggtgaatcag acgtggcgaa aagaacgctt cctggatgtg ccctatgca aagaggactg<br>tcagcgctgt gggaggatt gtcacacctc ccacacgtgc aagagcaact ggcacagagg<br>atgggactgg acctcaggag ttaacaagtg cccagctggg gctctctgcc gcacctttga<br>gtcctacttc cccactccag ctgcccttg tgaaggcctc tggagtcact catacaaggt<br>cagcaactac agccgaggga gcggccgctg catccagatg tggtttgatt cagcccaggg<br>caaccccaac gaggaagtgg cgaggttcta tgctgcagcc atgcatgtga atgctggtga<br>gatgcttcat gggactgggg gtcctcctgct cagtctggcc ctgatgctgc aactctggct<br>ccttggctga gttcagtcct cccagactac ctgccctcag cttggataac caggctgggc<br>tcagctcagc tcccacaaat gacagcccct taagcatgct tctattagtc acctaaccct<br>ctgtcaccca gtctgttgct gctccatggt ggggccaaga gtcacttcta ataaacagac<br>tgttttctaa taaaaaaaa aaaaaaaaaa |
| U08471<br>SEQ ID NO:265 | cgcaggaata gatggacatg gcctggcaga tgatgcagct gctgcttctg gctttggtga<br>ctgctgcggg gagtgcccag cccaggagtg cgcgggccag gacggacctg ctcaatgtct<br>gcatgaacgc caagcaccac aagacacagc ccagcccga ggacgagctg tatgccagt<br>gcagtccctg gaagaagaat gcctgctgca cggccagcac cagccaggct gcacaaggg<br>acacctcccg cctgtacaac tttaactggg atcactgtgg taagatggaa cccacctgca<br>agcgccactt tatccaggac agctgtctct atgagtgctc acccaacctg ggccctgga<br>tccggcaggt caaccagagc tggcgcaaag agcgcattct gaacgtgccc ctgtgcaaag<br>aggactgtga gcgctgtggt gaggactgtc gcacctccta cacctgcaaa agcaactggc<br>acaaaggctg gaattggacc tcagggatta atgagtgtcc ggccggggcc ctctgcagca<br>cctttgagtc ctacttcccc actccagccg ccctttgtga aggcctctgg agccactcct<br>tcaaggtcag caactatagt cgagggagcg gccgctgcat ccagatgtgg tttgactcag<br>cccagggcaa ccccaatgag gaggtggcca gttctatgc tgcggccatg aatgctgggg<br>ccccgtctcg tgggattatt gattcctgat ccaagaaggg tcctctgggg ttcttccaac<br>aacctattct aatagacaaa tccacatgaa aaaaaaaa |

TABLE 6-continued

| Accessions/SEQ ID NOs | Sequence |
|---|---|
| U02714<br>SEQ ID NO:266 | gaggagggta tggggaggca cttagttcct gtgtcttccc cacccagtgc agtccctgga<br>agaagaatgc ctgctgcaca gccagcacca gccaggagct gcacaaggac acctcccgcc<br>tgtacaactt taactgggac cactgcggca agatggagcc cgcctgcaag cgccacttca<br>tccaggacac ctgtctctat gagtgctcac ccaacctggg gccctggatc cagcaggtag<br>ggtgtctccc ccccacccac cccagcagac tgccatcccc ctcagtcact tcaaggcgat<br>ggctgccagc atccctggct gagaggagcc ctgcctcccc acctcccacc caggtgaatc<br>agacgtggcg caaagaacgc ttcctggatg tgcccttatg caaagaggac tgtcagcgct<br>ggtgggagga ttgtctcacc tcccacacgt gcaagagcaa ctggcacaga ggatgggact<br>ggacctcagg tgagggtgat tgagttgggg ttaggaaaaa ggagattgag gtagggtttg<br>gaaaatcctc aaggatttgg ggtggggtga agatttctgg gggtggccag aaatgagctt<br>tgggcccagg ggctgaaagt ctgtgtccac catgcctctc cctgcaggag ttaacaagtg<br>cccagctggg gctctctgcc gcacctttga gtcctacttc cccactccag ctgcccttg<br>tgaaggcctc tggagtcact catacaaggt cagcaactac agccgaggga gcggccgctg<br>catccagatg tggtttgatt cagcccaggg caacccaac gaggaagtgg cgaggttcta<br>tgctgcagcc atgcatgtga atgctggtga gatgcttcat gggactgggg gtctcctgct<br>caggctggcc ctgatgctgc aactctggct ccttggctga gttcagtcct cccagactac<br>ctgccctcag cttggataac caggctgggc tcagctcagc tcccacaaat gccagcccct<br>taagcatgct tctattagtc acctaaccct ctgtcaccca gtctgttgct gctccatggt<br>ggggccaaga gtcacttcta ataaacagac tgttttctaa taa |
| U02716<br>SEQ ID NO:267 | agcttcaggg ccccagcatc gaaggaacag ggtctgacct catttgccac cgtagggatg<br>gggagactga ggcaggaggt gaatggctcc cagcttggag cccttttcccc tcaggacttg<br>gtttccctac cctacgtccg cctgcaggga cagaaagaca tggtctggaa atggatgcca<br>cttctgctgc ttctggtctg tgtagccacc atgtgcagtg cccaggacag gactgatctc<br>ctcaatgtct gtatggatgc caagcaccac aagacaaagc caggtcctga ggacaagctg<br>catgaccaag tacggctgga gtgtgcctct gctaaggagg ggcttgttct aacagggagg<br>agaaagtcag gatg |
| SEQ ID NO:269<br>(E41) | L L S L A L M L L |

REFERENCES

The following references, to the extent that they provide exemplary procedural or other details supplementary to those set forth herein, are specifically incorporated herein by reference.

Patents

U.S. Pat. No. 3,826,364; issued Jul. 30, 1974.
U.S. Pat. No. 4,284,412; issued Aug. 18, 1981.
U.S. Pat. No. 4,498,766; issued Feb. 12, 1985.
U.S. Pat. No. 4,578,770; issued Mar. 25, 1986.
U.S. Pat. No. 4,596,792; issued Jun. 24, 1986.
U.S. Pat. No. 4,599,230; issued Jul. 8, 1986.
U.S. Pat. No. 4,599,231; issued Jul. 8, 1986.
U.S. Pat. No. 4,601,903; issued Jul. 22, 1986.
U.S. Pat. No. 4,608,251; issued Aug. 26, 1986.
U.S. Pat. No. 4,661,913; issued Apr. 28, 1987.
U.S. Pat. No. 4,714,682; issued Dec. 22, 1987.
U.S. Pat. No. 4,767,206; issued Aug. 30, 1988.
U.S. Pat. No. 4,774,189; issued Sep. 27, 1988.
U.S. Pat. No. 4,857,451; issued Aug. 15, 1989.
U.S. Pat. No. 4,989,977; issued Feb. 5, 1991.
U.S. Pat. No. 5,160,974; issued Nov. 3, 1992.
U.S. Pat. No. 5,478,722; issued Dec. 26, 1995.

Publications

Acres B., Hareuveni M., Balloul J. M. and Kieny M. P. (1993) VV-MUC1 immunisation of mice-immune response and protection against the growth of murine tumours bearing the MUC1 antigen J. Immunother. 14:136-143.

Acres B., Apostolopoulos V., Balloul J. M., Wreschner D. Xing P. X., Hadi D. A. et al. (1999) MUC1 specific cytotoxic T cell precursor analysis in human MUC1 transgenic mice immunised with human MUC1 vaccines. Cancer Immunol. Immunother. 2000 January; 48(10):588-94.

Almendro et al., "Cloning of the human platelet endothelial cell adhesion molecule-1 promoter and its tissue-specific expression. Structural and functional characterization," J. Immunol. 157(12):5411-5421, 1996.

Anichini, A. et al., (1993) et al., J. Exp. Med. 177:989-998.

Apostolopoulos V., Haurum J. S. and McKenzie I. F. C. (1997) MUCI peptide epitopes associated with 5 different H2 class I molecules. Eur. J. Immunol. 27:2579-2587.

Apostolopoulos V., Karanikas V., Haurum J. and McKenzie I. F. C. (1997) Induction of HLA-A2 restricted cytotoxic T lymphocytes to the MUCI human breast cancer antigen J. Immunol. 159:56211-5218.

Apostolopoulos V., Chelvanayagam G., Xing P.-X and McKenzie I. F. C. (1998) Anti-MUCI antibodies react directly with MUCI peptides presented by class I 142 and HLA molecules J. Immunol. 161:767-775.

Apostolopoulus V. Xing P.-X. and McKenzic I. F. C. (1994) Murine immuno response to cells transfected with human MUC1: Immunisation with cellular and synthetic antigens. Cancer Res. 54: 5186-5193.

Apostolopoulos V., Pietersz G. A., Loveland B. E., Sandrin M. S. and McKenzie I. F. C. (1995) Oxidative/reductive conjugation of mannan to antigen selects for T1 or T2 immune responses. Proc. Natl. Acad. Sci. USA 92: 10128-10132.

Apostolopoulos V., Popovski V. and McKenzie I. F. C. (1998) Cyclophosphamide enhances the CTL precursor frequency in mice immunized with MUC1-mannan fusion protein (M-FP). J. Immunother. 21:109-113.

Astori M. and Krachenbuhl J. P. (1996) Recombinant fusion peptices containing single or multiple repeats of a ubiquitous T-helper epitope are highly immunogenic. Mol. Immunol. 33: 1017-1024.

Barth, R. J., et al., (1991) J. Exp. Med. 173:647-658.

Bartnes K., Hannestad K., Guichard G. and Briand J. P. (1997) A retro-inverso analog mimics he cognate peptide epitope of a CD4+ T cell clone. Eur. J. Immunol. 27:1387-1391.

Beekman N.J., Schaaper W. M., Tesser G. I., Dalsgaard K., Kamstrup S., Langeveld J. P. et al. (1997) Synthetic peptide vaccines: palmitoylation of peptide antigens by a thioester bond increases immunogenicity. J. Pept. Res. 50: 357-364.

BenMohamed L., Gras-Masse H., Tarter A., Daubersies P., Bahimi K., Bossus M. et al. (1997) Lipopeptide immunization without adjuvant induces potent and long-lasting B. T. helper, and cytotoxic T lymphocyte resposes against a malaria liver stage antigen in mice and chimpanzees, Eur. J. Immunol. 27: 1242-1253.

Blaese, R. M., Pediatr. Res., 33 (1 Suppl):S49-S53 (1993).

Briand J. P., Benkirane N., Guichard G., Newman J. F. E., Van Regenmortel M. H., Brown F. et al. (1997) A retro-inverso peptide corresponding to the GH loop of foot-and-mouth disease virus elicits high levels of long-lasting protective neutralizing antibodies. Proc. Natl. Acad. Sci. USA 94: 12545-12550.

Chakraborty N. G., Sporn J. R., Tortora A. F., Kurtzman S. H., Yamase H., Ergin M. T. et al. (1998) Immunization with a tumor-cell-lysate-loaded autologous-antigen-presenting-cell-based vaccine in melanoma. Cancer Immunol. Immunother, 47: 58-64.

Chen T. T., Tao M. H. and Levy R. (1994) Idiotype-cytokine fusion proteins as cancer vaccines. Relative efficacy of IL-2, IL-4 and granulocyte-macrophage colony-stimulating factor. J. Immunol. 153:4775-4787.

Ciupitu A.M. Petersson M., O'Donnell C. L., Williams K., Jindal S., Kiessling R. et al. (1998) Immunization with a lymphocytic choriomeningitis virus peptide mixed with heat shock protein 70 results in protective antiviral immunity and specific cytotoxic T lymphocytes. J. Exp. Med. 187:685-691.

Creswell P. (1994) Assembly, transport and function of MHC class I molecules. Ann. Rev. Immunol. 12:259-293.

Culver, L., et al. Proc. Natl. Acad. Sci. USA, 88:3155-3159 (1991).

Dalgleish, A. G. Cancer vaccines. Br. J. Cancer 82(10): 1619-1624.

Darrow, T. L., et al., (1989) J. Immunol. 142:3329-3335.

DeLeo A. B. (1998) p53-based immunotherapy of cancer. Crit. Rev. Immunol. 18: 29-35.

Deprez B., Sauzet J. P., Boutillon C., Martinon F., Tartar A., Sergheraert C. et al. (1996) Comparative efficiency of simple lipopeptide constructs for in vivo induction of virus-specific CTL. Vaccine 14: 375-382.

Derossi D., Joliot G., Chassaing G. and Prochiantz A. (1994) The third helix of the Antennapedia homeodomain translocates through biological membranes. J. Biol. Chem. 269: 10444-10450.

Derossi D., Calvet S., Trembleau A., Brunissen A., Chassaing G. and Prochiantz A. (1996) Cell internalization of the helix of the Antennapedia homeodomain is receptor-independent. J. Biol. Chem. 271: 18188-18193.

Ding L., Lalani E. N. and Reddish M. (1993) Immunogenicity of synthetic peptides related to the core peptide sequence encoded by the human MUC1 gene: effect of immunisation on the growth of murine mammary adenocarcinoma cells transfected with the human MUC1 gene. Cancer Immunol. Immunother. 36:9-17.

Disis M. L., Bernhard H., Shiota F. M., Hand S. L., Gralow J. R., Huseby E. S. et al. (1996) Granulocyte macrophage colony-stimulating factor: an effective adjuvant for protein and peptide-based vaccines Blood 88:-202-210

Donnelly J. J., Ulmer J. B., Hawe L. A., Friedman A., Shi X. P., Leander K. R. et al. (1993) Targeted delivery of peptide epitopes to class I major histocompatibility molecules by a modified Pseudomanas exotoxin. Proc. Natl. Acad. Sci. USA 90: 3530-3534.

Elwood, P.C. Molecular cloning an dcharacterization of the human folate binding protein cDNA from placenta and malignant tissue culture (KB) cells. J. Biol. Chem. 264: 14893-14901, 1989.

Fayolle C., Sebo P., Ladant D., Ullmann A. and Leclerc C. (1996) In vivo induction of CTL responses by recombinant adenylate cyclase of Bordetella pertussis carrying viral CD8+T cell epitopes. J. Immunol. 156:4697-4706.

Fukasawa M., Shimizu Y., Shikata K., Nakata M., Sakakibara R., Yamamoto N. et al. (1998) Liposome oligomannase-coated with neoglycolipid, a new candidate for a safe adjuvant for induction of CD8+ cytotoxic T lymphocytes. FEBS Lett. 441: 353-356.

Garin-Chesa, P., Campbell, I. Suigo, P. E., Lewis, J. L., Old, L. J., and Rettig, W. J. Trophoblast and ovarian cancer antigen LK26. Sensitivity and specificity in immunopathology and molecular identification as a folate binding protein. Am. J. Pathol., 142: 557-567, 1993.

Gendler S. J., Papadimitriou J. T., Duhig T., Rothbard J. and Burchell J. (1998) A highly immunogenic region of human polymorphic epithelial mucin expressed by carcinomas is made up of tandem repeats, J. Biol. Chem. 263:12820-12823.

Goletz T. J., Klimpel K. R., Arora N., Leppla S. H., Keith J. M. and Berzofsky J. A. (1997) Targeting HIV proteins to the major histocompatibility complex class I processing pathway with a novel gp120-antrax toxin fusion protein, Proc. Natl. Acad. Sci. USA 94: 12059-12064.

Gong J., Chen D., Kashiwaba M. and Kufe D. (1997) Induction of antitumour activity by immunization with fusions of denddritic and carcinoma cells. Nature Med. 3: 558-561.

Gong J., Chen D., Kashiwaba M., Li Y., Chen L., Takeuchi H. et al. (1998) Reversal of tolerance to human MUC1 antigen in MUC1 transgenic mice immunized with fusions of dendritic and carcinoma cells. Proc. Natl. Acad. Sci. USA 95: 6279-6283.

Goydos J. S., Elder E., Whiteside T. L., Finn O. J. and Lotze M. T. (1996) A phase I trial of a synthetic mucin peptide vaccine. Induction of specific immune reactivity in patients with adenocarcinoma. J. Surg. Res. 63: 298-304.

Gras-Masse H., Boutillon C., Diesis E., Deprez B. and Tartar A. (1997) Confronting the degeneracy of convegent combinatorial immunogens or 'mixotopes', with the specificity of recognition of the target sequences. Vaccine 15:1568-1578.

Guan H. H., Budzynski W., Koganty R. R., Kantz M. J., Reddish M. A., Rogers J. A. et al (1998) Liposomal formulations of synthetic MUC1 peptides: effects of encapsulation versus surface display of peptides on immune responses. Bioconjug. Chem. 9:451-458.

Guichard G., Connan F., Graff R., Ostankovitch M., Muller S., Guillet J. G. et al. (1996) A partially modified retro-inverso pseudopeptide as a non-natural ligand for the human class I histocompatibility molecule HLA-A2. J. Med. Chem. 39: 2030-3039.

Hurpin C, Rotarioa C, Bisceglia H, Chevalier M, Tartaglia J, Erdile L. The mode of presentation and route of administration are critical for the induction of immune responses to p53 and antitumor immunity. Vaccine. 1998 January-February;16(2-3):208-15.

Heeg K., Kuon W. and Wagner H. (1991) Vaccination of class I major histocompatibility complex (MHC)-restricted murine CD8+ cytotoxic T lymphocytes towards soluble antigens: immunostimulating-ovalbumin complexes enter the class I MHC-restricted antigen pathway and allow sensitization against the immunodominant peptide. Eur. J. Immunol. 21: 1523-1527.

Heike M., Noll B. and Meyer zum Buschenfelde K. H. (1996) Heat shock protein-peptide completes for use in vaccines. J. Leukoc. Biol. 60: 153-158.

Henderson R. A., Konitsky W. M., Barratt-Boyes S. M., Soares M., Robbins P. D. and Finn O. J. (1998) Retroviral expression of MUC-1 human tumor antigen with intact repeat structure and capacity to elicit immunity in vivo. J. Immunother. 21:247-256.

Henderson R. A., Nimgaonkar M. T., Watkins S. C., Robbins P. D., Ball E. D. and Finn O. J. (1996) Human dendritic cells genetically engineered to express high levels of the human epithelial tumor antigen mucin (MUC-1). Cancer Res. 56:3763-3770.

Herve M., Maillere B., Mourier G., Texier C., Leroy S. and Menez A. (1997) On the immunogenic properties of retro-inverso peptides. Total retro-inversion of T-cell epitopes causes a loss of binding to MHC II molecules. Mol. Immunol. 34:157-163.

Hom, S. S., et al., (1991) J. Immunother. 10:153-164.

Hom, S. S., et al., (1993) J. Immunother. 13:18-30.

Hsu S.C., Schadeck E. B., Delmas A., Shaw M. and Stewart M. W., (1996) Linkage of a fusion peptide to a CTL epitope from the nucleoprotein of measles virus enables incorporation into ISCOMs and induction of CTL responses following intranasel immunization. Vaccine 14: 1159-1166.

Hwu, P., et al. J. Immunol, 150:4104-415 (1993).

Itoh, K. et al. (1986), Cancer Res. 46:3011-3017.

Jerome K. R., Domenech N. and Finn O. J. (1993) Rumor-specific CTL clones from patients with breast and pancreatic adenocarcinoma recognize EBV-immortalized B cells transfected with polymorphic epithelial mucin cDNA. J. Immunol. 151: 1654-1662.

Karanikas V., Hwang L., Pearson J., Ong C. S., Apostolopoulos V., Vaughan H. et al. (1997) Antibody and T cell responses of patients with adenocarcinoma immunized with mannan-MUC1 fusion protein. J. Clinical Invest. 100: 2783-2792.

Kawakami, Y., et al., (1992) J. Immunol. 148:638-643.

Kawakami, Y., et al, (1993) J. Immunother. 14:88-93.

Kawakami Y., Robbins P. F., Wanx X., Tupesis J. P., Parkhurst M. R., Kang X. et al. (1998) Identification of New melanoma epitopes on melanosomal proteins recognized by tumor infiltrating T lymphocytes restricted by HLA-A1, -A2, and -A3 alleles J. Immunology 161:6985-6992.

Kim, D., Lee, T. V., Castilleja, A., Anderson, B. W., Papler, G. E. Kudella, A. P., Murray, J. L., Sittisomwong, T., Wharton, J, T., Kim, J. Ioannides, C. G. Folate binding protein peptide 191-199 presented on dendritic cells can simulate CTL from ovarian and breast cancer patients. Anticancer Res., 18:2907-2916, 1999.

Kim D. T., Mitchell D. J., Brockstedt D. G., Fong L., Nolan G. P., Fathman C. G. et al. (1997) Introduction of soluble proteins into the MHC class I pathway by conjugation to an HIV tat peptide. J. Immunol: 159: 1666-1668.

Kraus et al., "Alternative promoter usage and tissue specific expression of the mouse somatostatin receptor 2 gene," FEBS Lett., 428(3):165-170, 1998.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," J. Biol. Chem., 274(12):8282-8290, 1999.

Lee et al., "Activation of beta3-adrenoceptors by exogenous dopamine to lower glucose uptake into rat adipocytes," J Auton Nerv Syst. 74(2-3):86-90, 1997.

Lee, T. V., Anderson, B. W., Peoples, G. E., Castilleja, A., Murray, J. L., Gershenson, D. M., and Ioannides, C. G. Identification of activated tumor-Ag-rective CD8+cells in healthy individuals, Oncology Reports, 7:455-466, 2000.

Lee R. S., Tartour E., van der Bruggen P., Vantomme V., Joyeaux l., Goud B. et al., (1998) Major histocompatibility complex class I presentation of exogenous soluble tumour antigen fused to the B-fragment of Shiga toxin. Eur. J. Immunol. 28:2726-2737.

Lees C. J. Apostolopoulos V., Acres B. A., Ong C.-S., and T2 cyokines on the cytotoxic T cell response to mannan-MUC1. Cancer Immuno. Immother. 2000 February;48(11): 644-52.

Li, P. Y., Del Vecchio, S., Fonti, R., Carrieto, M. V., Potena, M. T., Botti, G., Miotti, S., Lastoria, S., Menard, S., Colnaghi, M. I. and Salvatore, M. Local characterization of folate binding protein GP38 in sections of human ovarian carcinoma by in vitro quantitative autoradiography. J. Nucl. Med. 37:665-672, 1996.

Lofthouse S. A., Apostolopoulos V., Piertersz G. A. and McKenzie I. F. C. (1997) Induction of T1 (CTL) and/or T2 (antibody) response to a mucin 1 tumor antigen, Vaccine 25: 1586-1593.

Lustgarten J., Theobald M., Labadic C., LaFacc D., Peterson P., Disis M. L. et al. (1997) Identification of Her-2/NeuCTL epitopes using double transgenic mice expressing HLA-A2.1 and human CD*. Hum. Immunol. 52:109-118.

Malcherek G., Wirblich C., Willcox N., Rammensee H. G., Trowsdale J. and Melms A. (1998) MHC class II-associated invariant chain peptice replacement by T cell epitopes: engineered invariant chain as a vehicle for directed and enhanced MHC class II antigen processing and presentation. Eur. J. Immunol. 28:1524-1533.

Matco, L., Gardner J., Chen Q., Schmidt C., Down M., Elliott S. L. et al. (1999) An HLA-A2 polyepitope vaccine for melanoma immunotherapy. J. Immunol. 163:4058-4063.

McCarty T. M., Liu X., Sun J. Y., Peralta E. A., Diamond D. J. and Ellenhorn J. D. (1998) Targeting p53 for adoptive T-cell immunotherapy. Cancer Res. 58: 2601-2605.

Minev B. R., McFarland B. J., Spiess P. J., Rosenberg S. A. and Restifo N. P. (1994) Insertion signal sequence fused to minimal peptides elicits specific CD8+ T-cell responses and prolongs survival of thymoma-bearing mice. Cancer Res. 54:4155-4161.

Muul, L. M., et al. (1987), J. Immunol. 138:989-995.

Nakanishi T., Kunisawa J., Hayashi A., Tsutsumi Y., Kubo K., Nakagawa S. et al. (1997) Positively charged liposome functions as an efficient immunoadjuvant in inducing immune responses to soluble proteins. Biochem. Biophys. Res. Commun. 240:793-797.

Nakao M., Hazama M., Mayumi-Aono A., Hinuma S. and Fujisawa Y. (1994) Immunotherapy of acute and recurrent herpes simplex virus type 2 infection with an adjuvant-free form of recombinant glycoprotein D-interleukin-2 fusion protein. J. Infect Dis. 169:787-791.

Nestle F. O., Alijagic S., Gilliet M., Sun V., Grabbe S., Dumer R. et. al, (1998) Vaccination of melanoma patients with peptide- or tumor lysate-pursued dendritic cells, Nature Med. 4:328-332.

Noguchi Y., Noguchi T., Sata T., Yokoo Y., Itoh S., Yoshida M. et al. (1991) Priming for in vitro and in vivo anti-human T lymphotropic virus type I cellular immunity by virus-related protein reconstituted into liposome. J. Immunol. 146: 3599-3603.

Nomoto et al., "Cloning and characterization of the alternative promoter regions of the human LIMK2 gene responsible for alternative transcripts with tissue-specific expression," Gene, 236(2):259-271, 1999.

Obert M., Plkeuger H., Hanagarth H. G., Schulte-Monting J., Wiesmuller K. H., Braun D. G., et al. (1998) Protection of mice against SV40 tumors by Pam3Cys, MTP-PE and Pam3Cys conjugated with the SV40 T antigen-derived peptide K(698)-T(708). Vaccine 16: 161-169.

O'Neil, B. H., et al., (1993) J. Immunol. 151:1410-1418.

Pardoll, D. M. (2000) Clin. Immunol. 95 (1): S44-S62.

Parkhurst M. R., Fitzgerald E. B., Southwood S., Sette A., Rosenberg S. A. and Kawakami Y. (1998) Identification of a shared HLA-A*020-restricted T-cell epitope from the melanoma antigen tyrosinase related protein 2 (TRP2). Cancer Res. 58:4895-4901.

Partidos C. D., Vohra P. and Stewart M. W. (1996) Priming of measles virus-specific CTL responses after immunization with a CTL epitope linked to a fusogenic peptide. Virology 215: 107-110.

Peoples, G. E., Anderson, B. W., Fisk, B., Kudelka, A. P., Wharton, J. T., and Ioannides, C. G. Ovarian cancer-associated lymphocytes recognize folate binding protein (FBP) peptides. Ann. Surg Oncol., 5(8):743-750, 1998.

Peoples, G. E., Anderson, B. W., Murray, J. L., Kudelka, A. P., Eberlein, T. J., Wharton, J. T., and Ioannides, C. G. Vaccine implications of folate binding protein in epithelial cancers. Clin. Cancer Res., 5:4214-4223, 1999.

Piete0rsz, G. A. et al. (2000) Generation of cellular immune responses to antigenic tumor peptides. Cell. Mol. Life Sci. 57:290-310.

Pietersz G. A., Wenjun L., Popovski V., Caruana J. A. Apostolopoulos V. and McKenzie I. F. C. (1998) Parameters in using mannan-fusion protein (M-FP) to induce cellular immunity. Cancer Immunol. Immunother. 45: 321-326.

Rammensee H. G. (1995) Chemistry of peptides associated with MHC class I and class I molecules. Curr. Opin. Immunol. 7:85-96.

Rammensee H. G., Friede T. and Stevanovic S. (1995) MHC ligands and peptide motifs: first listing. Immunogenetics 41:178-228.

Reddish M., MacLean G. D., Koganty R. R., Kan-Mitchell J., Jones V., Mitchell M. S. et al. (1998) Anti-MUC1 class I restricted CTLs in metastatic breast cancer patients immunized with a synthetic MUC1 peptide. Int. J. Cancer 76: 817-823.

Remington's Pharmaceutical Sciences, 18th Ed. Mack Printing Company, 1990.

Retrig, W. J., Cordon-Cardo, C., Koulos, J. P., Lewis, J. L., Oertgen, H. F., and Old, L. J. Cell surface antigens of human trophoblast and choriocarcinoma defined by monoclonal antibodies. Int. J. Cancer 35: 469-475, 1985.

Reynolds S. R., Celis E., Sette A., Oratz R., Shapiro R. L., Johnston D. et al, (1998) HLA-independent heterogeneity of CDS+ T cell responses to MAGE-3, Melan-A/MART-1, gp 100, tyronsinase, MCIR and TRP-2 in vaccine-treated melanoma patients, J. Immunol. 161:6970-6976.

Rimmelzwaan G. F., Baars M., van Beek R., van Amerongen G., Lovgren-Bengtsson K., Claas E. C. et al. (1997) Induction of protective immunity against influenza virus in a macaque model: comparison of conventional and iscom vaccines. J. Gen. Virol. 78:757-765.

Rivoltini L., Squarcina P., Loftus D. J., Castelli C., Tarsini P., Mazzocchi A. et al. (1999) A superagonist variant of peptide-MARTi/Melan A27-35 elicits anti-melanoma CD8+ T cells with enhanced functional characteristics: implication for more effective immunotherapy. Cancer Res. 59:301-306.

Rosenberg, S. A., et al., (1986) Science 3233:1318-1321.

Rosenberg, S. A., et al., (1988) N Engl J Med 319:1676-1680.

Rosenberg S. A. (1992) J. Clin. Oncol. 10:180-199.

Rosenberg, S. A. (2000) Cancer J. 6, Supp. 2: S142-S149.

Rosenberg S. A., Yang J. C., Schwartzentruber D. J., Hwu P., Marincola F. M., Topalian S. L. et al. (1998) Immunologic and therapeutic evaluation of a synthetic peptide vaccine for the treatment of patients with metastatic melanoma, Nature Med. 4: 321-327.

Rowell J. F., Ruff A. L., Guarnieri G. G., Stavely-O'Carroll K., Lin X., Tang J. et al. (1995) Lysosome-associated membrane protein-1-mediated targeting of the HIV-1 envelope protein to an endosomal/lysosomal compartment enhances its presentation to MHC class II-restricted T cells. J. Immunol. 155: 1818-1828.

Rowse G. J., Tempero R. M., VanLith M. L., Hillingsworth M. A. and Gendler S. J. (1998) Tolerance and immunity to MUC1 in a human MUC1 transgenic murine model. Cancer Res. 58: 315-321.

Samuel J., Budynski W. A., Reddish M. A., Ding L., Zimmermann G. I., Krantz M. I. et al. (1998) Immunogenicity and antitumour activity of a liposomal MUC1 peptide-based vaccine. Int. J. Cancer 75: 295-302.

Schutze-Redelmeier M. P., Gournier H., Garcia-Pons F., Moussa M., Joliot A. H., Volovitch M. et al. (1996) Introduction of exogenous antigens into the MHC class I processing and presentation pathway by Drosophila antennapedia homeodomain primes cytotoxic T. cells in vivo. J. Immunol. 157:650-655.

Sensi, M., et al., (1993) J. Exp. Med. 178:1231-1246.

Sjolander A., van't Land B. and Lovgren Bengtsson K., (1997) Iscoms containing purified Quillaja saponins upregulate both Th1-like and Th2-like immune responses. Cell Immunol. 10:69-76.

Speir J. A., Abdel-Motal U. M., Jondal M. and Wilson I. A. (1999) Crystal structure of an MHC class I presented glycopeptide that generates carbohydrates-specific CTL. Immunity 10:51-61.

Stenmark H., Moskaug J. O., Madshus I. H., Sandvig K. and Olsnes S. (1991) Peptices fused on the amino-terminal end of diphtheria toxin are translocated to the cytosol. J. Cell Biol. 113: 1025-1032.

Suzue K., Zhou X., Eisen H. N. and Young R. A. (1997) Heat shock fusion proteins as vehicles for antigen delivery into the major histocompatibility complex class I presentation pathway. Proc. Nal. Acad. Sci. USA 94: 13146-13151.

Tao M. H. and Levy R. (1993) Idiotype/granulocyte-macrophage colony-stimulating factor fusion protein as a vaccine: for B-cell lymphoma. Nature 362:755-758.

Tarpey I., Stacey S. N., McIndoe A. and Davies D. H. (1996) Priming in vivo and quantification in vitro of class I MHC-restricted cytotoxic T cells to human papilloma virus type 11 early proteins (E6 and E7) using immunostimulating complexes (ISCOMs). Vaccine 14: 230-236.

Theobald M., Biggs J., Dittmer D., Levine A. J. and Sherman L. A. (1995) Targeting p53 as a general tumor antigen. Proc. Natl. Acad. Sci. USA 92: 11993-11997.

Topalian, S. L., et al., (1989) J. Immunol. 142:3714-3725.

Tsumaki et al., "Modular arrangement of cartilage- and neural tissue-specific cis-elements in the mouse alpha2(XI) collagen promoter," J. Biol. Chem. 273(36):22861-22864, 1998.

Udono H. and Srivastava P. K. (1993) Heat shock protein 70 associated peptides elicit specific cancer immunity. J. Exp. Med. 178: 1391-1396.

Van Der Burg S. H., Vissern M. J., Brandt R. M., Kast W. M. and Melief C. J. (1996) Immunogenicity of peptices bound to MHC class I molecules depends on the MHC peptide complex stability. J. Immunol. 156:3308-3314.

Villacres-Eriksson M. (1995) Antigen presentation by naïve macrophages, dendritic cells and B cells primed T lymphocytes and their cytokine production following exposure to immunostimulating complexes. Clin. Exp. Immunol. 102:46-52.

Vogel F. R. and Powell M. F. (1995) A compendium of vaccine adjuvants and excipients. In: Vaccine Deign: The Subunit and Adjuvant Approach. Pharmaceutical Biotechnology, vol. 6, pp. 141-228, Powell M. F. and Newman M. J. (eds), Plenum Press, New York.

Weitman, S. D., Lark, R. H., Coney, L. R., Fort, D. W., Frasca, V., Zurawski, V. R., and Kamen, B. A. Distribution of the folate receptor GP38 in normal and malignant cell lines and tissues. Cancer Res. 52: 3396-3401, 1992.

Wu et al., "Promoter-dependent tissue-specific expressive nature of imprinting gene, insulin-like growth factor II, in human tissues," Biochem Biophys Res Commun. 233(1): 221-226, 1997.

Wu T. C., Guarnieri F. G., Staveley-O'Carroll K. F., Viscidi R. P., Levitsky H. I., Hedrick I., et al. (1995) Engineering an intracellular pathway for major histocompatibility complex class II presentation of antigens. Proc. Natl. Acad. Sci. USA 92:11671-11675.

Xing P.-X., Tjandra J. J., Stacker S. A., T. J. G., Thompson C. H., McLaughlin P. J. et al, (1989) Monoclonal antibodies reactive with mucin expressed in breast cancer. Immunol. Cell. Biol. 67: 183-195.

Xing P.-X., Apostolopoulos V., Michaels M., Prenzoska J., Bishop J. and McKenzie I. F. C. (1995) Phase I study of synthetic MUC1 peptides in cancer. Int:J. Oncol. 6:1283-1289.

Xing P.-X, Reynolds K., Tjandra J. J., Tang X. L. and McKenzie I. F. C. (1990) Synthetic peptides reactive with anti-human milk fat globule membrane monoclonal antibodies. Cancer Res. 50:89-96.

Zeng Z. H., Castano A. R., Segelke B. W., Stura E. A. Peterson P. A. and Wilson I. A. (1997) Crystal structure of mouse CD1: an MHC-like fold with a large hydrophobic binding groove. Science 277: 339-345.

Zhang S., Graeber L. A., Helling F., Ragupathi G., Adluri S., Lloyd K. O. et al. (1996) Augmenting the immunogenicity of synthetic MUC1 peptide vaccines in mice. Cancer Res. 56: 3315-3319.

Zhao-Emonet et al., "The equine herpes virus 4 thymidine kinase is a better suicide gene than the human herpes virus I thymidine kinase," Gene Ther. 6(9):1638-1642, 1999.

Zhu X., Zhao X., Burkholder W. F., Gragerov A., Ogata C. M., Gottesman M. E. et al. (1996) Structural analysis of substrate binding by the molecular chaperone DnaK. Science 272: 1606-1614.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as described herein.

The invention claimed is:

1. A peptide comprising the amino acid sequence of a variant of a peptide fragment of the polypeptide of SEQ ID NO:10, wherein said peptide is of at least 10 amino acids or up to about 30 amino acids, comprises SEQ ID NO:268 but for substitution therein of the amino acids at positions 1 and 7 thereof by phenylalanine and threonine, respectively, and further comprises from 1 to 21 additional contiguous amino acids of the amino acid sequences of SEQ ID NO:10 that flank SEQ ID NO:268 as contained therein.

2. A peptide comprising the amino acid sequence of the peptide of claim 1 and the amino acid sequence of at least one additional peptide, wherein said additional peptide is of at least 9 amino acids or up to about 30 amino acids and comprises an amino acid sequence selected from the group consisting of:

(a) the amino acid sequence of SEQ ID NO:268 but for substitution therein of the amino acid at position 5 thereof by phenylalanine;
(b) the amino acid sequence of SEQ ID NO:268 but for substitution therein of the amino acids at positions 6 and 7 thereof by alanine and threonine, respectively;
(c) the amino acid sequence of SEQ ID NO:268 but for substitution therein of the amino acids at positions 5 and 7 thereof by phenylalanine and threonine, respectively;
(d) the amino acid sequence of SEQ ID NO:268 but for substitution therein of the amino acids at positions 1, 5, and 7 thereof by phenylalanine, phenylalanine, and threonine, respectively; and
(e) the amino acid sequence of SEQ ID NO:268 but for substitution therein of the amino acids at positions 1 and 7 thereof by glycine and threonine, respectively.

* * * * *

SEQUENCE LISTING

```
<160> NUMBER OF SEQ ID NOS: 271

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Glu Ile Trp Thr His Ser Thr Lys Val
  1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Glu Ile Trp Thr Phe Ser Tyr Lys Val
  1               5
```

```
<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Phe Ile Trp Thr Phe Ala Thr Lys Val
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Glu Ile Trp Thr His Ala Thr Lys Val
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Glu Ile Trp Thr Phe Ser Thr Lys Val
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Glu Ile Trp Thr Phe Ser Tyr Lys Val
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Gly Ile Trp Thr His Ser Thr Lys Val
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide
```

-continued

<400> SEQUENCE: 8

Phe Ile Trp Thr His Ser Thr Lys Val
1               5

<210> SEQ ID NO 9
<211> LENGTH: 255
<212> TYPE: PRT
<213> ORGANISM: Homo sapiens

<400> SEQUENCE: 9

Met Val Trp Lys Trp Met Pro Leu Leu Leu Leu Val Cys Val Ala
1               5                   10                  15

Thr Met Cys Ser Ala Gln Asp Arg Thr Asp Leu Leu Asn Val Cys Met
            20                  25                  30

Asp Ala Lys His His Lys Thr Lys Pro Gly Pro Glu Asp Lys Leu His
        35                  40                  45

Asp Gln Cys Ser Pro Trp Lys Lys Asn Ala Cys Cys Thr Ala Ser Thr
    50                  55                  60

Ser Gln Glu Leu His Lys Asp Thr Ser Arg Leu Tyr Asn Phe Asn Trp
65                  70                  75                  80

Asp His Cys Gly Lys Met Glu Pro Ala Cys Lys Arg His Phe Ile Gln
                85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
        115                 120                 125

Cys Lys Glu Asp Cys Gln Arg Trp Trp Glu Asp Cys His Thr Ser His
    130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 10
<211> LENGTH: 257
<212> TYPE: PRT
<213> ORGANISM: Homo sapiens

<400> SEQUENCE: 10

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

```
Pro Glu Asp Lys Leu His Glu Gln Cys Arg Pro Trp Arg Lys Asn Ala
 50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 11
<211> LENGTH: 293
<212> TYPE: PRT
<213> ORGANISM: RAT

<400> SEQUENCE: 11

Met Val Asp Ser Val Tyr Arg Thr Arg Ser Leu Gly Val Ala Ala Glu
 1               5                  10                  15

Gly Ile Pro Asp Gln Tyr Ala Asp Gly Glu Ala Ala Arg Val Trp Gln
                 20                  25                  30

Leu Tyr Ile Gly Asp Thr Arg Ser Arg Thr Ala Glu Tyr Lys Ala Trp
             35                  40                  45

Leu Leu Gly Leu Leu Arg Gln His Gly Cys His Arg Val Leu Asp Val
 50                  55                  60

Ala Cys Gly Thr Gly Val Asp Ser Ile Met Leu Val Glu Glu Gly Phe
 65                  70                  75                  80

Ser Val Thr Ser Val Asp Ala Ser Asp Lys Met Leu Lys Tyr Ala Leu
                 85                  90                  95

Lys Glu Arg Trp Asn Arg Arg Lys Glu Pro Ala Phe Asp Lys Trp Val
                100                 105                 110

Ile Glu Glu Ala Asn Trp Leu Thr Leu Asp Lys Asp Val Pro Ala Gly
            115                 120                 125

Asp Gly Phe Asp Ala Val Ile Cys Leu Gly Asn Ser Phe Ala His Leu
130                 135                 140

Pro Asp Ser Lys Gly Asp Gln Ser Glu His Arg Leu Ala Leu Lys Asn
145                 150                 155                 160
```

```
Ile Ala Ser Met Val Arg Pro Gly Gly Leu Val Ile Asp His Arg
                165                 170                 175

Asn Tyr Asp Tyr Ile Leu Ser Thr Gly Cys Ala Pro Gly Lys Asn
            180                 185                 190

Ile Tyr Tyr Lys Ser Asp Leu Thr Lys Asp Ile Thr Thr Ser Val Leu
        195                 200                 205

Thr Val Asn Asn Lys Ala His Met Val Thr Leu Asp Tyr Thr Val Gln
    210                 215                 220

Val Pro Gly Ala Gly Arg Asp Gly Ala Pro Gly Phe Ser Lys Phe Arg
225                 230                 235                 240

Leu Ser Tyr Tyr Pro His Cys Leu Ala Ser Phe Thr Glu Leu Val Gln
                245                 250                 255

Glu Ala Phe Gly Gly Arg Cys Gln His Ser Val Leu Gly Asp Phe Lys
                260                 265                 270

Pro Tyr Arg Pro Gly Gln Ala Tyr Val Pro Cys Tyr Phe Ile His Val
                275                 280                 285

Leu Lys Lys Thr Gly
            290

<210> SEQ ID NO 12
<211> LENGTH: 257
<212> TYPE: PRT
<213> ORGANISM: Homo sapiens

<400> SEQUENCE: 12

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240
```

```
Ala Trp Pro Phe Leu Leu Ser Leu Ala Leu Met Leu Leu Trp Leu Leu
                245                 250                 255

Ser

<210> SEQ ID NO 13
<211> LENGTH: 257
<212> TYPE: PRT
<213> ORGANISM: Homo sapiens

<400> SEQUENCE: 13

Met Ala Gln Arg Met Thr Thr Gln Leu Leu Leu Leu Val Trp Val
  1               5                  10                  15

Ala Val Val Gly Glu Ala Gln Thr Arg Ile Ala Trp Ala Arg Thr Glu
                 20                  25                  30

Leu Leu Asn Val Cys Met Asn Ala Lys His His Lys Glu Lys Pro Gly
                 35                  40                  45

Pro Glu Asp Lys Leu His Glu Gln Cys Arg Pro Trp Arg Lys Asn Ala
             50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
    210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 14
<211> LENGTH: 244
<212> TYPE: PRT
<213> ORGANISM: Mus musculus

<400> SEQUENCE: 14

Met Ala Gln Trp Trp Gln Ile Leu Leu Gly Leu Trp Ala Val Leu Pro
  1               5                  10                  15

Thr Leu Ala Gly Asp Lys Leu Leu Ser Val Cys Met Asn Ser Lys Arg
                 20                  25                  30

His Lys Gln Glu Pro Gly Pro Glu Asp Glu Leu Tyr Gln Glu Cys Arg
```

```
                35                  40                  45
Pro Trp Glu Asp Asn Ala Cys Cys Thr Arg Ser Thr Ser Trp Glu Ala
 50                  55                  60

His Leu Glu Glu Pro Leu Leu Phe Asn Phe Ser Met Met His Cys Gly
 65                  70                  75                  80

Leu Leu Thr Pro Ala Cys Arg Lys His Phe Ile Gln Ala Ile Cys Phe
                 85                  90                  95

His Glu Cys Ser Pro Asn Leu Gly Pro Trp Ile Gln Pro Val Val Pro
                100                 105                 110

Asn Gly Gln Glu Glu Gln Arg Val Trp Gly Val Pro Leu Cys Gln Glu
                115                 120                 125

Asp Cys Glu Asp Trp Trp Arg Ala Cys His Ser Ser Leu Thr Cys Lys
130                 135                 140

Ser Asn Trp Leu His Gly Trp Asp Trp Ser Glu Glu Lys Lys His Cys
145                 150                 155                 160

Pro Ala His Glu Pro Cys Leu Pro Phe Ser Tyr His Phe Pro Thr Pro
                165                 170                 175

Asp Asp Leu Cys Glu Lys Ile Trp Asn Asn Thr Phe Lys Ala Ser Pro
                180                 185                 190

Glu Arg Arg Asn Ser Gly Arg Cys Leu Gln Lys Trp Phe Glu Pro Thr
                195                 200                 205

Leu Ser Asn Pro Asn Val Glu Val Ala Leu His Phe Ala Gly Ser Ala
210                 215                 220

Leu Ala Pro Gln Leu Ser Tyr Thr Leu Pro Ala Phe Ser Leu Cys Leu
225                 230                 235                 240

Leu Phe His Pro

<210> SEQ ID NO 15
<211> LENGTH: 295
<212> TYPE: PRT
<213> ORGANISM: Homo sapiens

<400> SEQUENCE: 15

Met Val Asp Ser Val Tyr Arg Thr Arg Ser Leu Gly Val Ala Ala Glu
 1               5                  10                  15

Gly Leu Pro Asp Gln Tyr Ala Glu Gly Ala Ala Arg Val Trp Gln
                 20                  25                  30

Leu Tyr Ile Gly Asp Thr Arg Ser Arg Thr Ala Glu Tyr Lys Ala Trp
             35                  40                  45

Leu Leu Gly Leu Leu Arg Gln His Gly Cys Gln Arg Val Leu Asp Val
 50                  55                  60

Ala Cys Gly Thr Gly Val Asp Ser Ile Met Leu Val Glu Glu Gly Phe
 65                  70                  75                  80

Ser Val Thr Ser Val Asp Ala Ser Asp Lys Met Leu Lys Tyr Ala Leu
                 85                  90                  95

Lys Glu Arg Trp Asn Arg Arg His Glu Pro Ala Phe Asp Lys Trp Val
                100                 105                 110

Ile Glu Glu Ala Asn Trp Met Thr Leu Asp Lys Asp Val Pro Gln Ser
                115                 120                 125

Ala Glu Gly Gly Phe Asp Ala Val Ile Cys Leu Gly Asn Ser Phe Ala
130                 135                 140

His Leu Pro Asp Cys Lys Gly Asp Gln Ser Glu His Arg Leu Ala Leu
145                 150                 155                 160

Lys Asn Ile Ala Ser Met Val Arg Ala Gly Gly Leu Leu Val Ile Asp
```

```
            165                 170                 175
His Arg Asn Tyr Asp His Ile Leu Ser Thr Gly Cys Ala Pro Pro Gly
                180                 185                 190

Lys Asn Ile Tyr Tyr Lys Ser Asp Leu Thr Lys Asp Val Thr Thr Ser
            195                 200                 205

Val Leu Ile Val Asn Asn Lys Ala His Met Val Thr Leu Asp Tyr Thr
        210                 215                 220

Val Gln Val Pro Gly Ala Gly Gln Asp Gly Ser Pro Gly Leu Ser Lys
225                 230                 235                 240

Phe Arg Leu Ser Tyr Tyr Pro His Cys Leu Ala Ser Phe Thr Glu Leu
                245                 250                 255

Leu Gln Ala Ala Phe Gly Gly Lys Cys Gln His Ser Val Leu Gly Asp
            260                 265                 270

Phe Lys Pro Tyr Lys Pro Gly Gln Thr Tyr Ile Pro Cys Tyr Phe Ile
        275                 280                 285

His Val Leu Lys Arg Thr Asp
290                 295

<210> SEQ ID NO 16
<211> LENGTH: 293
<212> TYPE: PRT
<213> ORGANISM: RAT

<400> SEQUENCE: 16

Met Val Asp Ser Val Tyr Arg Thr Arg Ser Leu Gly Val Ala Ala Glu
1               5                   10                  15

Gly Ile Pro Asp Gln Tyr Ala Asp Gly Glu Ala Ala Arg Val Trp Gln
            20                  25                  30

Leu Tyr Ile Gly Asp Thr Arg Ser Arg Thr Ala Glu Tyr Lys Ala Trp
        35                  40                  45

Leu Leu Gly Leu Leu Arg Gln His Gly Cys His Arg Val Leu Asp Val
    50                  55                  60

Ala Cys Gly Thr Gly Val Asp Ser Ile Met Leu Val Glu Glu Gly Phe
65                  70                  75                  80

Ser Val Thr Ser Val Asp Ala Ser Asp Lys Met Leu Lys Tyr Ala Leu
                85                  90                  95

Lys Glu Arg Trp Asn Arg Arg Lys Glu Pro Ala Phe Asp Lys Trp Val
            100                 105                 110

Ile Glu Glu Ala Asn Trp Leu Thr Leu Asp Lys Asp Val Pro Ala Gly
        115                 120                 125

Asp Gly Phe Asp Ala Val Ile Cys Leu Gly Asn Ser Phe Ala His Leu
    130                 135                 140

Pro Asp Ser Lys Gly Asp Gln Ser Glu His Arg Leu Ala Leu Lys Asn
145                 150                 155                 160

Ile Ala Ser Met Val Arg Pro Gly Gly Leu Leu Val Ile Asp His Arg
                165                 170                 175

Asn Tyr Asp Tyr Ile Leu Ser Thr Gly Cys Ala Pro Pro Gly Lys Asn
            180                 185                 190

Ile Tyr Tyr Lys Ser Asp Leu Thr Lys Asp Ile Thr Thr Ser Val Leu
        195                 200                 205

Thr Val Asn Asn Lys Ala His Met Val Thr Leu Asp Tyr Thr Val Gln
    210                 215                 220

Val Pro Gly Ala Gly Arg Asp Gly Ala Pro Gly Phe Ser Lys Phe Arg
225                 230                 235                 240
```

```
Leu Ser Tyr Tyr Pro His Cys Leu Ala Ser Phe Thr Glu Leu Val Gln
                245                 250                 255

Glu Ala Phe Gly Gly Arg Cys Gln His Ser Val Leu Gly Asp Phe Lys
            260                 265                 270

Pro Tyr Arg Pro Gly Gln Ala Tyr Val Pro Cys Tyr Phe Ile His Val
        275                 280                 285

Leu Lys Lys Thr Gly
        290

<210> SEQ ID NO 17
<211> LENGTH: 222
<212> TYPE: PRT
<213> ORGANISM: bovidae
<220> FEATURE:
<221> NAME/KEY: MOD_RES
<222> LOCATION: (55)
<223> OTHER INFORMATION: Xaa = anything

<400> SEQUENCE: 17

Ala Gln Ala Pro Arg Thr Pro Arg Ala Arg Thr Asp Leu Leu Asn Val
1               5                   10                  15

Cys Met Asp Ala Lys His His Lys Ala Glu Pro Gly Pro Glu Asp Ser
            20                  25                  30

Leu His Glu Gln Cys Ser Pro Trp Arg Lys Asn Ala Cys Cys Ser Val
        35                  40                  45

Asn Thr Ser Ile Glu Ala Xaa Lys Asp Ile Ser Tyr Leu Tyr Arg Phe
    50                  55                  60

Asn Trp Asp His Cys Gly Lys Met Glu Pro Ala Cys Lys Arg His Phe
65                  70                  75                  80

Ile Gln Asp Thr Cys Leu Tyr Glu Cys Ser Pro Asn Leu Gly Pro Trp
                85                  90                  95

Ile Arg Glu Val Asn Gln Arg Trp Arg Lys Glu Arg Val Leu Gly Val
            100                 105                 110

Pro Leu Cys Lys Glu Asp Cys Gln Ser Trp Trp Glu Asp Cys Arg Thr
        115                 120                 125

Ser Tyr Thr Cys Lys Ser Asn Trp His Lys Gly Trp Asn Trp Thr Ser
    130                 135                 140

Gly Tyr Asn Gln Cys Pro Val Lys Ala Ala His Cys Arg Phe Asp Phe
145                 150                 155                 160

Tyr Phe Pro Thr Pro Ala Ala Leu Cys Asn Glu Ile Trp Ser His Ser
                165                 170                 175

Tyr Lys Val Ser Asn Tyr Ser Arg Gly Ser Gly Arg Cys Ile Gln Met
            180                 185                 190

Trp Phe Asp Pro Phe Gln Gly Asn Pro Asn Glu Glu Val Ala Arg Phe
        195                 200                 205

Tyr Ala Glu Asn Pro Thr Ser Gly Ser Thr Pro Gln Gly Ile
    210                 215                 220

<210> SEQ ID NO 18
<211> LENGTH: 22
<212> TYPE: PRT
<213> ORGANISM: RAT

<400> SEQUENCE: 18

Gln Ala Thr Arg Ala Arg Thr Glu Leu Leu Asn Val Phe Ala Asp Ala
1               5                   10                  15

Lys Arg Glu Lys Pro Lys
            20
```

<210> SEQ ID NO 19
<211> LENGTH: 22
<212> TYPE: PRT
<213> ORGANISM: RAT

<400> SEQUENCE: 19

```
Gln Ala Thr Arg Ala Glu Thr Glu Asn Leu Asn Val Asp Met Asp Ala
  1               5                  10                  15

Lys His His Lys Glu Lys
             20
```

<210> SEQ ID NO 20
<211> LENGTH: 589
<212> TYPE: PRT
<213> ORGANISM: Homo sapiens

<400> SEQUENCE: 20

```
Met Val Pro Ser Ser Pro Ala Val Glu Lys Gln Val Pro Val Glu Pro
  1               5                  10                  15

Gly Pro Asp Pro Glu Leu Arg Ser Trp Arg His Leu Val Cys Tyr Leu
             20                  25                  30

Cys Phe Tyr Gly Phe Met Ala Gln Ile Arg Pro Gly Glu Ser Phe Ile
         35                  40                  45

Thr Pro Tyr Leu Leu Gly Pro Asp Lys Asn Phe Thr Arg Glu Gln Val
     50                  55                  60

Thr Asn Glu Ile Thr Pro Val Leu Ser Tyr Ser Tyr Leu Ala Val Leu
 65                  70                  75                  80

Val Pro Val Phe Leu Leu Thr Asp Tyr Leu Arg Tyr Thr Pro Val Leu
                 85                  90                  95

Leu Leu Gln Gly Leu Ser Phe Val Ser Val Trp Leu Leu Leu Leu Leu
            100                 105                 110

Gly His Ser Val Ala His Met Gln Leu Met Glu Leu Phe Tyr Ser Val
        115                 120                 125

Thr Met Ala Ala Arg Ile Ala Tyr Ser Ser Tyr Ile Phe Ser Leu Val
    130                 135                 140

Arg Pro Ala Arg Tyr Gln Arg Val Ala Gly Tyr Ser Arg Ala Ala Val
145                 150                 155                 160

Leu Leu Gly Val Phe Thr Ser Ser Val Leu Gly Gln Leu Leu Val Thr
                165                 170                 175

Val Gly Arg Val Ser Phe Ser Thr Leu Asn Tyr Ile Ser Leu Ala Phe
            180                 185                 190

Leu Thr Phe Ser Val Val Leu Ala Leu Phe Leu Lys Arg Pro Lys Arg
        195                 200                 205

Ser Leu Phe Phe Asn Arg Asp Asp Arg Gly Arg Cys Glu Thr Ser Ala
    210                 215                 220

Ser Glu Leu Glu Arg Met Asn Pro Gly Pro Gly Gly Lys Leu Gly His
225                 230                 235                 240

Ala Leu Arg Val Ala Cys Gly Asp Ser Val Leu Ala Arg Met Leu Arg
                245                 250                 255

Glu Leu Gly Asp Ser Leu Arg Arg Pro Gln Leu Arg Leu Trp Ser Leu
            260                 265                 270

Trp Trp Val Phe Asn Ser Ala Gly Tyr Tyr Leu Val Val Tyr Tyr Val
        275                 280                 285

His Ile Leu Trp Asn Glu Val Asp Pro Thr Thr Asn Ser Ala Arg Val
    290                 295                 300
```

-continued

Tyr Asn Gly Ala Ala Asp Ala Ala Ser Thr Leu Leu Gly Ala Ile Thr
305                 310                 315                 320

Ser Phe Ala Ala Gly Phe Val Lys Ile Arg Trp Ala Arg Trp Ser Lys
            325                 330                 335

Leu Leu Ile Ala Gly Val Thr Ala Thr Gln Ala Gly Leu Val Phe Leu
        340                 345                 350

Leu Ala His Thr Arg His Pro Ser Ser Ile Trp Leu Cys Tyr Ala Ala
    355                 360                 365

Phe Val Leu Phe Arg Gly Ser Tyr Gln Phe Leu Val Pro Ile Ala Thr
370                 375                 380

Phe Gln Ile Ala Ser Ser Leu Ser Lys Glu Leu Cys Ala Leu Val Phe
385                 390                 395                 400

Gly Val Asn Thr Phe Phe Ala Thr Ile Val Lys Thr Ile Ile Thr Phe
            405                 410                 415

Ile Val Ser Asp Val Arg Gly Leu Gly Leu Pro Val Arg Lys Pro Val
        420                 425                 430

Ile Leu Arg Val Leu Pro Asp Pro Val His His Leu Leu Gly Leu Gly
    435                 440                 445

His Ala Gly Trp Pro Ala Ala Leu Pro Ala Gly Pro Pro Ala Ala
450                 455                 460

Ala Pro Gly Pro Gly Pro Glu Glu Cys Arg Gly Gly Glu Gly Ser Thr
465                 470                 475                 480

Gly Thr Glu Arg Ala Gly Gln Gly Pro Arg Arg Leu Gln Pro Ala Gln
            485                 490                 495

Ser Pro Pro Leu Ser Pro Glu Asp Ser Leu Gly Ala Val Gly Pro Ala
        500                 505                 510

Ser Leu Glu Gln Arg Gln Ser Asp Pro Tyr Leu Ala Gln Ala Pro Ala
    515                 520                 525

Pro Gln Ala Ala Glu Phe Leu Ser Pro Val Thr Thr Pro Ser Pro Cys
530                 535                 540

Thr Leu Ser Ser Ala Gln Ala Ser Gly Pro Glu Ala Ala Asp Glu Thr
545                 550                 555                 560

Cys Pro Gln Leu Ala Val His Pro Pro Gly Val Ser Lys Leu Gly Leu
            565                 570                 575

Gln Cys Leu Pro Ser Asp Gly Val Gln Asn Val Asn Gln
        580                 585

<210> SEQ ID NO 21
<211> LENGTH: 257
<212> TYPE: PRT
<213> ORGANISM: Homo sapiens

<400> SEQUENCE: 21

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys

```
                         85                  90                  95
Lys Arg His Phe Ile Gln Asp Thr Cys Leu Tyr Glu Cys Ser Pro Asn
                100                 105                 110
Leu Gly Pro Trp Ile Gln Gln Val Asp Gln Ser Trp Arg Lys Glu Arg
            115                 120                 125
Val Leu Asn Val Pro Leu Cys Lys Glu Asp Cys Glu Gln Trp Trp Glu
130                 135                 140
Asp Cys Arg Thr Ser Tyr Thr Cys Lys Ser Asn Trp His Lys Gly Trp
145                 150                 155                 160
Asn Trp Thr Ser Gly Phe Asn Lys Cys Ala Val Gly Ala Ala Cys Gln
                165                 170                 175
Pro Phe His Phe Tyr Phe Pro Thr Pro Thr Val Leu Cys Asn Glu Ile
            180                 185                 190
Trp Thr His Ser Tyr Lys Val Ser Asn Tyr Ser Arg Gly Ser Gly Arg
        195                 200                 205
Cys Ile Gln Met Trp Phe Asp Pro Ala Gln Gly Asn Pro Asn Glu Glu
210                 215                 220
Val Ala Arg Phe Tyr Ala Ala Met Ser Gly Ala Gly Pro Trp Ala
225                 230                 235                 240
Ala Trp Pro Phe Leu Leu Ser Leu Ala Leu Met Leu Leu Trp Leu Leu
                245                 250                 255
Ser
```

<210> SEQ ID NO 22
<211> LENGTH: 255
<212> TYPE: PRT
<213> ORGANISM: Homo sapiens

<400> SEQUENCE: 22

```
Met Val Trp Lys Trp Met Pro Leu Leu Leu Leu Val Cys Val Ala
1               5                   10                  15
Thr Met Cys Ser Ala Gln Asp Arg Thr Asp Leu Leu Asn Val Cys Met
                20                  25                  30
Asp Ala Lys His His Lys Thr Lys Pro Gly Pro Glu Asp Lys Leu His
            35                  40                  45
Asp Gln Cys Ser Pro Trp Lys Lys Asn Ala Cys Cys Thr Ala Ser Thr
        50                  55                  60
Ser Gln Glu Leu His Lys Asp Thr Ser Arg Leu Tyr Asn Phe Asn Trp
65                  70                  75                  80
Asp His Cys Gly Lys Met Glu Pro Ala Cys Lys Arg His Phe Ile Gln
                85                  90                  95
Asp Thr Cys Leu Tyr Glu Cys Ser Pro Asn Leu Gly Pro Trp Ile Gln
                100                 105                 110
Gln Val Asn Gln Thr Trp Arg Lys Glu Arg Phe Leu Asp Val Pro Leu
            115                 120                 125
Cys Lys Glu Asp Cys Gln Arg Trp Trp Glu Asp Cys His Thr Ser His
        130                 135                 140
Thr Cys Lys Ser Asn Trp His Arg Gly Trp Asp Trp Thr Ser Gly Val
145                 150                 155                 160
Asn Lys Cys Pro Ala Gly Ala Leu Cys Arg Thr Phe Glu Ser Tyr Phe
                165                 170                 175
Pro Thr Pro Ala Ala Leu Cys Glu Gly Leu Trp Ser His Ser Tyr Lys
            180                 185                 190
Val Ser Asn Tyr Ser Arg Gly Ser Gly Arg Cys Ile Gln Met Trp Phe
```

```
                195                 200                 205
Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 23
<211> LENGTH: 251
<212> TYPE: PRT
<213> ORGANISM: Mus musculus

<400> SEQUENCE: 23

Met Ala Trp Lys Gln Thr Pro Leu Leu Leu Val Tyr Met Val Thr
  1               5                  10                  15

Thr Gly Ser Gly Arg Asp Arg Thr Asp Leu Leu Asn Val Cys Met Asp
                20                  25                  30

Ala Lys His His Lys Thr Lys Pro Gly Pro Glu Asp Lys Leu His Asp
            35                  40                  45

Gln Cys Ser Pro Trp Lys Lys Asn Ala Cys Cys Ser Val Asn Thr Ser
        50                  55                  60

Gln Glu Leu His Lys Ala Asp Ser Arg Leu Tyr Phe Asn Trp Asp His
 65                  70                  75                  80

Cys Gly Lys Met Glu Pro Ala Cys Lys Ser His Phe Ile Gln Asp Ser
                85                  90                  95

Cys Leu Tyr Glu Cys Ser Pro Asn Leu Gly Pro Trp Ile Gln Gln Val
            100                 105                 110

Asp Gln Ser Trp Arg Lys Glu Arg Phe Leu Asp Val Pro Leu Cys Lys
        115                 120                 125

Glu Asp Cys His Gln Trp Trp Glu Ala Cys Arg Thr Ser Phe Thr Cys
130                 135                 140

Lys Arg Asp Trp His Lys Gly Trp Asp Trp Ser Ser Gly Ile Asn Lys
145                 150                 155                 160

Cys Pro Asn Thr Ala Pro Cys His Thr Phe Glu Tyr Tyr Phe Pro Thr
                165                 170                 175

Pro Ala Ser Leu Cys Glu Gly Leu Trp Ser His Ser Tyr Lys Val Ser
            180                 185                 190

Asn Tyr Ser Arg Gly Ser Gly Arg Cys Ile Gln Met Trp Phe Asp Ser
        195                 200                 205

Thr Gln Gly Asn Pro Asn Glu Asp Val Val Lys Phe Tyr Ala Ser Phe
    210                 215                 220

Met Thr Ser Gly Thr Val Pro His Ala Ala Val Leu Leu Val Pro Ser
225                 230                 235                 240

Leu Ala Pro Val Leu Ser Leu Trp Leu Pro Gly
                245                 250

<210> SEQ ID NO 24
<211> LENGTH: 255
<212> TYPE: PRT
<213> ORGANISM: Mus musculus

<400> SEQUENCE: 24

Met Ala His Leu Met Thr Val Gln Leu Leu Leu Val Met Trp Met
  1               5                  10                  15

Ala Glu Cys Ala Gln Ser Arg Ala Thr Arg Ala Arg Thr Glu Leu Leu
```

```
                    20                  25                  30
Asn Val Cys Met Asp Ala Lys His His Lys Glu Lys Pro Gly Pro Glu
                35                  40                  45
Asp Asn Leu His Asp Gln Cys Ser Pro Trp Lys Thr Asn Ser Cys Cys
            50                  55                  60
Ser Thr Asn Thr Ser Gln Glu Ala His Lys Asp Ile Ser Tyr Leu Tyr
 65                  70                  75                  80
Arg Phe Asn Trp Asn His Cys Gly Thr Met Thr Ser Glu Cys Lys Arg
                85                  90                  95
His Phe Ile Gln Asp Thr Cys Leu Tyr Glu Cys Ser Pro Asn Leu Gly
            100                 105                 110
Pro Trp Ile Gln Gln Val Asp Gln Ser Trp Arg Lys Glu Arg Ile Leu
        115                 120                 125
Asp Val Pro Leu Cys Lys Glu Asp Cys Gln Gln Trp Trp Glu Asp Cys
    130                 135                 140
Gln Ser Ser Phe Thr Cys Lys Ser Asn Trp His Lys Gly Trp Asn Trp
145                 150                 155                 160
Ser Ser Gly His Asn Glu Cys Pro Val Gly Ala Ser Cys His Pro Phe
                165                 170                 175
Thr Phe Tyr Phe Pro Thr Ser Ala Ala Leu Cys Glu Glu Ile Trp Ser
            180                 185                 190
His Ser Tyr Lys Leu Ser Asn Tyr Ser Arg Gly Ser Gly Arg Cys Ile
        195                 200                 205
Gln Met Trp Phe Asp Pro Ala Gln Gly Asn Pro Asn Glu Glu Val Ala
    210                 215                 220
Arg Phe Tyr Ala Glu Ala Met Ser Gly Ala Gly Leu His Gly Thr Trp
225                 230                 235                 240
Pro Leu Leu Cys Ser Leu Ser Leu Val Leu Leu Trp Val Ile Ser
                245                 250                 255

<210> SEQ ID NO 25
<211> LENGTH: 257
<212> TYPE: PRT
<213> ORGANISM: Homo sapiens

<400> SEQUENCE: 25

Met Ala Gln Arg Met Thr Thr Gln Leu Leu Leu Leu Leu Val Trp Val
  1               5                  10                  15
Ala Val Val Gly Glu Ala Gln Thr Arg Ile Ala Trp Ala Arg Thr Glu
                20                  25                  30
Leu Leu Asn Val Cys Met Asn Ala Lys His His Lys Glu Lys Pro Gly
            35                  40                  45
Pro Glu Asp Lys Leu His Glu Gln Cys Arg Pro Trp Arg Lys Asn Ala
        50                  55                  60
Cys Cys Ser Thr Asn Thr Ser Gln Glu Ala His Lys Asp Val Ser Tyr
 65                  70                  75                  80
Leu Tyr Arg Phe Asn Trp Asn His Cys Gly Glu Met Ala Pro Ala Cys
                85                  90                  95
Lys Arg His Phe Ile Gln Asp Thr Cys Leu Tyr Glu Cys Ser Pro Asn
            100                 105                 110
Leu Gly Pro Trp Ile Gln Gln Val Asp Gln Ser Trp Arg Lys Glu Arg
        115                 120                 125
Val Leu Asn Val Pro Leu Cys Lys Glu Asp Cys Glu Gln Trp Trp Glu
    130                 135                 140
```

```
Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser
```

<210> SEQ ID NO 26
<211> LENGTH: 257
<212> TYPE: PRT
<213> ORGANISM: Homo sapiens

<400> SEQUENCE: 26

```
Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Arg Lys Asn Ala
        50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255
```

Ser

<210> SEQ ID NO 27
<211> LENGTH: 257
<212> TYPE: PRT
<213> ORGANISM: Homo sapiens

<400> SEQUENCE: 27

```
Met Ala Gln Arg Met Thr Thr Gln Leu Leu Leu Leu Val Trp Val
 1               5                  10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Arg Lys Asn Ala
        50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser
```

<210> SEQ ID NO 28
<211> LENGTH: 257
<212> TYPE: PRT
<213> ORGANISM: Homo sapiens

<400> SEQUENCE: 28

```
Met Ala Gln Arg Met Thr Thr Gln Leu Leu Leu Leu Val Trp Val
 1               5                  10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Arg Lys Asn Ala
        50                  55                  60
```

```
Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
                115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
                180                 185                 190

Trp Thr His Ser Tyr Lys Val Ser Asn Tyr Ser Arg Gly Ser Gly Arg
                195                 200                 205

Cys Ile Gln Met Trp Phe Asp Pro Ala Gln Gly Asn Pro Asn Glu Glu
210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 29
<211> LENGTH: 257
<212> TYPE: PRT
<213> ORGANISM: Homo sapiens

<400> SEQUENCE: 29

Met Ala Gln Arg Met Thr Thr Gln Leu Leu Leu Leu Leu Val Trp Val
  1               5                  10                  15

Ala Val Val Gly Glu Ala Gln Thr Arg Ile Ala Trp Ala Arg Thr Glu
                 20                  25                  30

Leu Leu Asn Val Cys Met Asn Ala Lys His His Lys Glu Lys Pro Gly
                 35                  40                  45

Pro Glu Asp Lys Leu His Glu Gln Cys Arg Pro Trp Arg Lys Asn Ala
                 50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
                115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175
```

-continued

```
Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                    245                 250                 255

Ser
```

<210> SEQ ID NO 30
<211> LENGTH: 254
<212> TYPE: PRT
<213> ORGANISM: Homo sapiens

<400> SEQUENCE: 30

```
Met Ala Ser Val Pro Lys Thr Asn Lys Ile Glu Pro Arg Ser Tyr Ser
1               5                   10                  15

Ile Ile Pro Ser Cys Ser Ile Arg Arg Leu Gly Pro Ala Leu Asn Thr
                20                  25                  30

Pro Ile Phe Gln Ser Lys Arg Asn Gly Pro Arg Gly His Ser Ala Tyr
            35                  40                  45

Ser Ile Glu Gly Arg Gln Arg Gln Gly Ala Gly Arg Ala Val Val Pro
        50                  55                  60

Arg Ala Asp Arg Pro Pro Ala Pro Lys Ile Gln Leu Arg Ala Phe Tyr
65                  70                  75                  80

Leu Gln Gln Leu Tyr Tyr Thr Leu Leu Glu Leu Glu Leu Pro Arg Leu
                85                  90                  95

Leu Ala Pro Asp Leu Pro Ser Asn Gly Ser Ser Leu Lys Asp Leu Lys
            100                 105                 110

Trp Thr His Ser Asn Tyr Arg Ala Ser Lys Glu Ser Cys Ile Val Ile
        115                 120                 125

Phe Val Thr Thr Ser Pro Gly Arg Glu Trp Val Ile Cys Ala Pro Ala
130                 135                 140

Ala Phe Leu Gly Cys Gly Ser Leu Gln Ala Pro Ser Pro Glu Ser Glu
145                 150                 155                 160

Pro Ser Phe Pro Val Thr Arg Gly His His Gly Arg His Gly Asp Tyr
                165                 170                 175

His Arg Lys Leu Ile Gly Gln Thr Phe Glu Trp Val Val Arg Arg
            180                 185                 190

His Gly Gly Arg Ala Ile Gly Pro Arg Leu Ser Arg Val Thr Lys Ala
        195                 200                 205

Ala Gly Ala Arg Pro Pro Ala Gly Ala Gly Glu Gly Leu Arg Val Gly
210                 215                 220

Phe Asp Leu Ile Asn Ala Pro Ile Pro Pro Ala Lys Gly Val Ser Ala
225                 230                 235                 240

Arg Arg His Val Leu Ala Leu Glu Leu Pro Gln Leu Ser Lys
                245                 250
```

<210> SEQ ID NO 31
<211> LENGTH: 251
<212> TYPE: PRT
<213> ORGANISM: Mus musculus

<400> SEQUENCE: 31

```
Met Ala Trp Lys Gln Thr Pro Leu Leu Leu Val Tyr Met Val Thr
  1               5                  10                  15

Thr Gly Ser Gly Arg Asp Arg Thr Asp Leu Leu Asn Val Cys Met Asp
             20                  25                  30

Ala Lys His His Lys Thr Lys Pro Gly Pro Glu Asp Lys Leu His Asp
         35                  40                  45

Gln Cys Ser Pro Trp Lys Lys Asn Ala Cys Cys Ser Val Asn Thr Ser
     50                  55                  60

Gln Glu Leu His Lys Ala Asp Ser Arg Leu Tyr Phe Asn Trp Asp His
 65                  70                  75                  80

Cys Gly Lys Met Glu Pro Ala Cys Lys Ser His Phe Ile Gln Asp Ser
                 85                  90                  95

Cys Leu Tyr Glu Cys Ser Pro Asn Leu Gly Pro Trp Ile Gln Gln Val
            100                 105                 110

Asp Gln Ser Trp Arg Lys Glu Arg Phe Leu Asp Val Pro Leu Cys Lys
        115                 120                 125

Glu Asp Cys His Gln Trp Trp Glu Ala Cys Arg Thr Ser Phe Thr Cys
130                 135                 140

Lys Arg Asp Trp His Lys Gly Trp Asp Trp Ser Ser Gly Ile Asn Lys
145                 150                 155                 160

Cys Pro Asn Thr Ala Pro Cys His Thr Phe Glu Tyr Tyr Phe Pro Thr
                165                 170                 175

Pro Ala Ser Leu Cys Glu Gly Leu Trp Ser His Ser Tyr Lys Val Ser
            180                 185                 190

Asn Tyr Ser Arg Gly Ser Gly Arg Cys Ile Gln Met Trp Phe Asp Ser
        195                 200                 205

Thr Gln Gly Asn Pro Asn Glu Asp Val Val Lys Phe Tyr Ala Ser Phe
    210                 215                 220

Met Thr Ser Gly Thr Val Pro His Ala Ala Val Leu Leu Val Pro Ser
225                 230                 235                 240

Leu Ala Pro Val Leu Ser Leu Trp Leu Pro Gly
                245                 250
```

<210> SEQ ID NO 32
<211> LENGTH: 255
<212> TYPE: PRT
<213> ORGANISM: Mus musculus

<400> SEQUENCE: 32

```
Met Ala His Leu Met Thr Val Gln Leu Leu Leu Val Met Trp Met
  1               5                  10                  15

Ala Glu Cys Ala Gln Ser Arg Ala Thr Arg Ala Arg Thr Glu Leu Leu
             20                  25                  30

Asn Val Cys Met Asp Ala Lys His His Lys Glu Lys Pro Gly Pro Glu
         35                  40                  45

Asp Asn Leu His Asp Gln Cys Ser Pro Trp Lys Thr Asn Ser Cys Cys
     50                  55                  60

Ser Thr Asn Thr Ser Gln Glu Ala His Lys Asp Ile Ser Tyr Leu Tyr
 65                  70                  75                  80

Arg Phe Asn Trp Asn His Cys Gly Thr Met Thr Ser Glu Cys Lys Arg
                 85                  90                  95

His Phe Ile Gln Asp Thr Cys Leu Tyr Glu Cys Ser Pro Asn Leu Gly
            100                 105                 110
```

```
Pro Trp Ile Gln Gln Val Asp Gln Ser Trp Arg Lys Glu Arg Ile Leu
        115                 120                 125

Asp Val Pro Leu Cys Lys Glu Asp Cys Gln Gln Trp Glu Asp Cys
    130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
            180                 185                 190

His Ser Tyr Lys Leu Ser Asn Tyr Ser Arg Gly Ser Gly Arg Cys Ile
        195                 200                 205

Gln Met Trp Phe Asp Pro Ala Gln Gly Asn Pro Asn Glu Glu Val Ala
    210                 215                 220

Arg Phe Tyr Ala Glu Ala Met Ser Gly Ala Gly Leu His Gly Thr Trp
225                 230                 235                 240

Pro Leu Leu Cys Ser Leu Ser Leu Val Leu Leu Trp Val Ile Ser
                245                 250                 255

<210> SEQ ID NO 33
<211> LENGTH: 243
<212> TYPE: PRT
<213> ORGANISM: Homo sapiens

<400> SEQUENCE: 33

Met Ala Trp Gln Met Met Gln Leu Leu Leu Ala Leu Val Thr Ala
1               5                   10                  15

Ala Gly Ser Ala Gln Pro Arg Ser Ala Arg Ala Arg Thr Asp Leu Leu
            20                  25                  30

Asn Val Cys Met Asn Ala Lys His His Lys Thr Gln Pro Ser Pro Glu
        35                  40                  45

Asp Glu Leu Tyr Gly Gln Cys Ser Pro Trp Lys Lys Asn Ala Cys Cys
    50                  55                  60

Thr Ala Ser Thr Ser Gln Glu Leu His Lys Asp Thr Ser Arg Leu Tyr
65                  70                  75                  80

Asn Phe Asn Trp Asp His Cys Gly Lys Met Glu Pro Thr Cys Lys Arg
                85                  90                  95

His Phe Ile Gln Asp Ser Cys Leu Tyr Glu Cys Ser Pro Asn Leu Gly
            100                 105                 110

Pro Trp Ile Arg Gln Val Asn Gln Ser Trp Arg Lys Glu Arg Ile Leu
        115                 120                 125

Asn Val Pro Leu Cys Lys Glu Asp Cys Glu Arg Trp Trp Glu Asp Cys
    130                 135                 140

Arg Thr Ser Tyr Thr Cys Lys Ser Asn Trp His Lys Gly Trp Asn Trp
145                 150                 155                 160

Thr Ser Gly Ile Asn Glu Cys Pro Ala Gly Ala Leu Cys Ser Thr Phe
                165                 170                 175

Glu Ser Tyr Phe Pro Thr Pro Ala Ala Leu Cys Glu Gly Leu Trp Ser
            180                 185                 190

His Ser Phe Lys Val Ser Asn Tyr Ser Arg Gly Ser Gly Arg Cys Ile
        195                 200                 205

Gln Met Trp Phe Asp Ser Ala Gln Gly Asn Pro Asn Glu Glu Val Ala
    210                 215                 220

Lys Phe Tyr Ala Ala Ala Met Asn Ala Gly Ala Pro Ser Arg Gly Ile
```

```
                225                 230                 235                 240

Ile Asp Ser

<210> SEQ ID NO 34
<211> LENGTH: 255
<212> TYPE: PRT
<213> ORGANISM: Homo sapiens

<400> SEQUENCE: 34

Met Val Trp Lys Trp Met Pro Leu Leu Leu Leu Val Cys Val Ala
  1               5                  10                  15

Thr Met Cys Ser Ala Gln Asp Arg Thr Asp Leu Leu Asn Val Cys Met
                 20                  25                  30

Asp Ala Lys His His Lys Thr Lys Pro Gly Pro Glu Asp Lys Leu His
             35                  40                  45

Asp Gln Cys Ser Pro Trp Lys Lys Asn Ala Cys Cys Thr Ala Ser Thr
         50                  55                  60

Ser Gln Glu Leu His Lys Asp Thr Ser Arg Leu Tyr Asn Phe Asn Trp
 65                  70                  75                  80

Asp His Cys Gly Lys Met Glu Pro Ala Cys Lys Arg His Phe Ile Gln
                 85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
        115                 120                 125

Cys Lys Glu Asp Cys Gln Arg Trp Trp Glu Asp Cys His Thr Ser His
130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 35
<211> LENGTH: 255
<212> TYPE: PRT
<213> ORGANISM: RAT

<400> SEQUENCE: 35

Met Ala His Leu Met Ala Gly Gln Trp Leu Leu Leu Met Trp Met
  1               5                  10                  15

Ala Glu Cys Ala Gln Ser Arg Ala Thr Arg Ala Arg Thr Glu Leu Leu
                 20                  25                  30

Asn Val Cys Met Asp Ala Lys His His Lys Glu Lys Pro Gly Pro Glu
             35                  40                  45

Asp Lys Leu His Asp Gln Cys Ser Pro Trp Lys Thr Asn Ala Cys Cys
         50                  55                  60
```

-continued

```
Ser Thr Asn Thr Ser Gln Glu Asp Thr Lys Asp Ile Ser Tyr Leu Tyr
 65                  70                  75                  80

Arg Phe Asn Trp Asn His Cys Gly Thr Met Thr Pro Glu Cys Lys Arg
                 85                  90                  95

His Phe Ile Gln Asp Thr Cys Leu Tyr Glu Cys Ser Pro Asn Leu Gly
            100                 105                 110

Pro Trp Ile Gln Gln Val Asp Gln Ser Trp Arg Lys Glu Arg Ile Leu
        115                 120                 125

Asp Val Pro Leu Cys Lys Glu Asp Cys Val Leu Trp Trp Glu Asp Cys
130                 135                 140

Lys Ser Ser Phe Thr Cys Lys Ser Asn Trp Leu Lys Gly Trp Asn Trp
145                 150                 155                 160

Thr Ser Gly His Asn Glu Cys Pro Val Gly Ala Ser Cys His Pro Phe
                165                 170                 175

Thr Phe Tyr Phe Pro Thr Pro Ala Val Leu Cys Glu Lys Ile Trp Ser
            180                 185                 190

His Ser Tyr Lys Leu Ser Asn Tyr Ser Arg Gly Ser Gly Arg Cys Ile
        195                 200                 205

Gln Met Trp Phe Asp Pro Ala Gln Gly Asn Pro Asn Glu Glu Val Ala
210                 215                 220

Arg Phe Tyr Ala Glu Val Met Ser Gly Ala Gly Leu Arg Glu Ala Trp
225                 230                 235                 240

Leu Leu Val Cys Ser Leu Ser Leu Val Leu Phe Cys Val Val Ser
                245                 250                 255

<210> SEQ ID NO 36
<211> LENGTH: 46
<212> TYPE: PRT
<213> ORGANISM: chicken

<400> SEQUENCE: 36

Met Leu Arg Phe Ala Ile Thr Leu Phe Ala Val Ile Thr Ser Ser Thr
 1               5                  10                  15

Cys Gln Gln Tyr Gly Cys Leu Glu Gly Asp Thr His Lys Ala Asn Pro
             20                  25                  30

Ser Pro Glu Pro Asn Met His Glu Cys Thr Leu Tyr Ser Glu
         35                  40                  45

<210> SEQ ID NO 37
<211> LENGTH: 238
<212> TYPE: PRT
<213> ORGANISM: chicken

<400> SEQUENCE: 37

Met Leu Arg Phe Ala Ile Thr Leu Phe Ala Val Ile Thr Ser Ser Thr
 1               5                  10                  15

Cys Gln Gln Tyr Gly Cys Leu Glu Gly Asp Thr His Lys Ala Asn Pro
             20                  25                  30

Ser Pro Glu Pro Asn Met His Glu Cys Thr Leu Tyr Ser Glu Ser Ser
         35                  40                  45

Cys Cys Tyr Ala Asn Phe Thr Glu Gln Leu Ala His Ser Pro Ile Ile
 50                  55                  60

Lys Val Ser Asn Ser Tyr Trp Asn Arg Cys Gly Gln Leu Ser Lys Ser
 65                  70                  75                  80

Cys Glu Asp Phe Thr Lys Lys Ile Glu Cys Phe Tyr Arg Cys Ser Pro
                 85                  90                  95
```

His Ala Ala Arg Trp Ile Asp Pro Arg Tyr Thr Ala Ala Ile Gln Ser
            100                 105                 110

Val Pro Leu Cys Gln Ser Phe Cys Asp Asp Trp Tyr Glu Ala Cys Lys
        115                 120                 125

Asp Asp Ser Ile Cys Ala His Asn Trp Leu Thr Asp Trp Glu Arg Asp
    130                 135                 140

Glu Ser Gly Glu Asn His Cys Lys Ser Lys Cys Val Pro Tyr Ser Glu
145                 150                 155                 160

Met Tyr Ala Asn Gly Thr Asp Met Cys Gln Ser Met Trp Gly Glu Ser
                165                 170                 175

Phe Lys Val Ser Glu Ser Ser Cys Leu Cys Leu Gln Met Asn Lys Lys
            180                 185                 190

Asp Met Val Ala Ile Lys His Leu Leu Ser Glu Ser Ser Glu Glu Ser
        195                 200                 205

Ser Ser Met Ser Ser Ser Glu Glu His Ala Cys Gln Lys Lys Leu Leu
    210                 215                 220

Lys Phe Glu Ala Leu Gln Gln Glu Gly Glu Arg Arg
225                 230                 235

<210> SEQ ID NO 38
<211> LENGTH: 251
<212> TYPE: PRT
<213> ORGANISM: Mus musculus

<400> SEQUENCE: 38

Met Ala Trp Lys Gln Thr Pro Leu Leu Leu Val Tyr Met Val Thr
1               5                   10                  15

Thr Gly Ser Gly Arg Asp Arg Thr Asp Leu Leu Asn Val Cys Met Asp
                20                  25                  30

Ala Lys His His Lys Thr Lys Pro Gly Pro Glu Asp Lys Leu His Asp
            35                  40                  45

Gln Cys Ser Pro Trp Lys Lys Asn Ala Cys Cys Ser Val Asn Thr Ser
        50                  55                  60

Gln Glu Leu His Lys Ala Asp Ser Arg Leu Tyr Phe Asn Trp Asp His
65                  70                  75                  80

Cys Gly Lys Met Glu Pro Ala Cys Lys Ser His Phe Ile Gln Asp Ser
                85                  90                  95

Cys Leu Tyr Glu Cys Ser Pro Asn Leu Gly Pro Trp Ile Gln Gln Val
            100                 105                 110

Asp Gln Ser Trp Arg Lys Glu Arg Phe Leu Asp Val Pro Leu Cys Lys
        115                 120                 125

Glu Asp Cys His Gln Trp Trp Glu Ala Cys Arg Thr Ser Phe Thr Cys
    130                 135                 140

Lys Arg Asp Trp His Lys Gly Trp Asp Trp Ser Ser Gly Ile Asn Lys
145                 150                 155                 160

Cys Pro Asn Thr Ala Pro Cys His Thr Phe Glu Tyr Tyr Phe Pro Thr
                165                 170                 175

Pro Ala Ser Leu Cys Glu Gly Leu Trp Ser His Ser Tyr Lys Val Ser
            180                 185                 190

Asn Tyr Ser Arg Gly Ser Gly Arg Cys Ile Gln Met Trp Phe Asp Ser
        195                 200                 205

Thr Gln Gly Asn Pro Asn Glu Asp Val Val Lys Phe Tyr Ala Ser Phe
    210                 215                 220

Met Thr Ser Gly Thr Val Pro His Ala Ala Val Leu Leu Val Pro Ser

```
                225                 230                 235                 240
Leu Ala Pro Val Leu Ser Leu Trp Leu Pro Gly
                245                 250

<210> SEQ ID NO 39
<211> LENGTH: 255
<212> TYPE: PRT
<213> ORGANISM: Mus musculus

<400> SEQUENCE: 39

Met Ala His Leu Met Thr Val Gln Leu Leu Leu Val Met Trp Met
  1               5                  10                  15

Ala Glu Cys Ala Gln Ser Arg Ala Thr Arg Ala Arg Thr Glu Leu Leu
                 20                  25                  30

Asn Val Cys Met Asp Ala Lys His His Lys Glu Lys Pro Gly Pro Glu
                 35                  40                  45

Asp Asn Leu His Asp Gln Cys Ser Pro Trp Lys Thr Asn Ser Cys Cys
             50                  55                  60

Ser Thr Asn Thr Ser Gln Glu Ala His Lys Asp Ile Ser Tyr Leu Tyr
 65                  70                  75                  80

Arg Phe Asn Trp Asn His Cys Gly Thr Met Thr Ser Glu Cys Lys Arg
                     85                  90                  95

His Phe Ile Gln Asp Thr Cys Leu Tyr Glu Cys Ser Pro Asn Leu Gly
                100                 105                 110

Pro Trp Ile Gln Gln Val Asp Gln Ser Trp Arg Lys Glu Arg Ile Leu
             115                 120                 125

Asp Val Pro Leu Cys Lys Glu Asp Cys Gln Gln Trp Trp Glu Asp Cys
130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                    165                 170                 175

Thr Phe Tyr Phe Pro Thr Ser Ala Ala Leu Cys Glu Glu Ile Trp Ser
                180                 185                 190

His Ser Tyr Lys Leu Ser Asn Tyr Ser Arg Gly Ser Gly Arg Cys Ile
            195                 200                 205

Gln Met Trp Phe Asp Pro Ala Gln Gly Asn Pro Asn Glu Glu Val Ala
210                 215                 220

Arg Phe Tyr Ala Glu Ala Met Ser Gly Ala Gly Leu His Gly Thr Trp
225                 230                 235                 240

Pro Leu Leu Cys Ser Leu Ser Leu Val Leu Leu Trp Val Ile Ser
                    245                 250                 255

<210> SEQ ID NO 40
<211> LENGTH: 222
<212> TYPE: PRT
<213> ORGANISM: Cow
<220> FEATURE:
<221> NAME/KEY: MOD_RES
<222> LOCATION: (55)
<223> OTHER INFORMATION: Xaa = anything

<400> SEQUENCE: 40

Ala Gln Ala Pro Arg Thr Pro Arg Ala Arg Thr Asp Leu Leu Asn Val
  1               5                  10                  15

Cys Met Asp Ala Lys His His Lys Ala Glu Pro Gly Pro Glu Asp Ser
                 20                  25                  30
```

Leu His Glu Gln Cys Ser Pro Trp Arg Lys Asn Ala Cys Cys Ser Val
           35                  40                  45

Asn Thr Ser Ile Glu Ala Xaa Lys Asp Ile Ser Tyr Leu Tyr Arg Phe
 50                  55                  60

Asn Trp Asp His Cys Gly Lys Met Glu Pro Ala Cys Lys Arg His Phe
 65                  70                  75                  80

Ile Gln Asp Thr Cys Leu Tyr Glu Cys Ser Pro Asn Leu Gly Pro Trp
                 85                  90                  95

Ile Arg Glu Val Asn Gln Arg Trp Arg Lys Glu Arg Val Leu Gly Val
                100                 105                 110

Pro Leu Cys Lys Glu Asp Cys Gln Ser Trp Trp Glu Asp Cys Arg Thr
            115                 120                 125

Ser Tyr Thr Cys Lys Ser Asn Trp His Lys Gly Trp Asn Trp Thr Ser
        130                 135                 140

Gly Tyr Asn Gln Cys Pro Val Lys Ala Ala His Cys Arg Phe Asp Phe
145                 150                 155                 160

Tyr Phe Pro Thr Pro Ala Ala Leu Cys Asn Glu Ile Trp Ser His Ser
                165                 170                 175

Tyr Lys Val Ser Asn Tyr Ser Arg Gly Ser Gly Arg Cys Ile Gln Met
                180                 185                 190

Trp Phe Asp Pro Phe Gln Gly Asn Pro Asn Glu Glu Val Ala Arg Phe
            195                 200                 205

Tyr Ala Glu Asn Pro Thr Ser Gly Ser Thr Pro Gln Gly Ile
        210                 215                 220

<210> SEQ ID NO 41
<211> LENGTH: 261
<212> TYPE: PRT
<213> ORGANISM: Hamster sp.

<400> SEQUENCE: 41

Met Ala His Leu Met Thr Met Gln Leu Leu Leu Leu Ile Trp Val
  1               5                  10                  15

Ser Glu Cys Ala Gln Ser Arg Ala Thr Arg Ala Arg Thr Glu Leu Leu
                 20                  25                  30

Asn Val Cys Met Asp Ala Lys His His Lys Glu Lys Pro Gly Pro Glu
            35                  40                  45

Asp Asn Leu His Asn Gln Cys Ser Pro Trp Lys Lys Asn Ser Cys Cys
 50                  55                  60

Ser Thr Asn Thr Ser Gln Glu Ala His Glu Asp Ile Ser Tyr Leu Tyr
 65                  70                  75                  80

Arg Phe Asn Trp Asp His Cys Gly Lys Met Thr Leu Glu Cys Lys Arg
                 85                  90                  95

His Phe Ile Gln Asp Thr Cys Leu Tyr Glu Cys Ser Pro Asn Leu Gly
            100                 105                 110

Pro Trp Ile Gln Gln Val Asp Gln Ser Trp Arg Lys Glu Arg Ile Leu
        115                 120                 125

Asp Val Pro Leu Cys Lys Glu Asp Cys Gln Arg Trp Trp Glu Asp Cys
130                 135                 140

Arg Thr Ser Phe Thr Cys Lys Ser Asn Trp His Lys Gly Trp Asn Trp
145                 150                 155                 160

Thr Ser Gly Tyr Asn Gln Cys Pro Val Gly Ala Ser Cys Arg His Phe
                165                 170                 175

Asp Phe Tyr Phe Pro Thr Pro Ala Ala Leu Cys Glu Glu Ile Trp Ser
                180                 185                 190

```
His Ser Tyr Lys Leu Ser Asn Tyr Ser Arg Gly Ser Gly Arg Cys Ile
            195                 200                 205

Gln Met Trp Phe Asp Pro Ala Gln Gly Asn Pro Asn Glu Glu Val Ala
        210                 215                 220

Arg Phe Tyr Ala Glu Ala Met Ser Gly Ala Gly Leu His Gly Ala Trp
225                 230                 235                 240

Pro Leu Met Cys Ser Leu Ser Leu Val Leu Leu Trp Val Phe Ser Arg
                245                 250                 255

Val Pro Leu Thr Phe
            260

<210> SEQ ID NO 42
<211> LENGTH: 249
<212> TYPE: PRT
<213> ORGANISM: Pig

<400> SEQUENCE: 42

Met Ala Leu Gly Arg Ala Arg Leu Leu Leu Leu Val Cys Val Ala
  1               5                  10                  15

Val Thr Trp Ala Ala Arg Pro Asp Leu Leu Asn Ile Cys Met Asp Ala
            20                  25                  30

Lys His His Lys Thr Lys Pro Gly Pro Glu Asp Gly Leu His Glu Gln
        35                  40                  45

Cys Ser Pro Trp Glu Met Asn Ala Cys Cys Ser Val Asn Thr Ser Gln
    50                  55                  60

Glu Ala His Asn Asp Ile Ser Tyr Leu Tyr Lys Phe Asn Trp Glu His
65                  70                  75                  80

Cys Gly Lys Met Lys Pro Ala Cys Lys Arg His Phe Ile Gln Asp Thr
                85                  90                  95

Cys Leu Tyr Glu Cys Ser Pro Asn Leu Gly Pro Trp Ile Gln Glu Val
            100                 105                 110

Asn Gln Lys Trp Arg Arg Glu Arg Ile Leu Asn Val Pro Leu Cys Lys
        115                 120                 125

Glu Asp Cys Gln Asn Trp Trp Glu Asp Cys Arg Thr Ser Tyr Thr Cys
    130                 135                 140

Lys Ser Asn Trp His Glu Gly Trp Asn Trp Ser Ser Gly Tyr Asn Arg
145                 150                 155                 160

Cys Pro Ala Asn Ala Ala Cys His Pro Phe Asp Phe Tyr Phe Pro Thr
                165                 170                 175

Pro Ala Ala Leu Cys Ser Gln Ile Trp Ser Asn Ser Tyr Lys Gln Ser
            180                 185                 190

Asn Tyr Ser Arg Gly Ser Gly Arg Cys Ile Gln Met Trp Phe Asp Pro
        195                 200                 205

Glu Gln Gly Asn Pro Asn Glu Val Val Ala Arg Tyr Tyr Ala Gln Ile
    210                 215                 220

Met Ser Gly Ala Gly Leu Ser Glu Ala Trp Pro Leu Gln Phe Gly Leu
225                 230                 235                 240

Ala Leu Thr Leu Leu Trp Leu Leu Ser
                245

<210> SEQ ID NO 43
<211> LENGTH: 252
<212> TYPE: PRT
<213> ORGANISM: Pig

<400> SEQUENCE: 43
```

Met Ala Trp Arg Leu Thr Leu Phe Val Leu Leu Gly Leu Val Ala Ala
1               5                   10                  15

Val Gly Gly Ala Arg Ala Lys Ser Asp Met Leu Asn Val Cys Met Asp
            20                  25                  30

Ala Lys His His Lys Pro Lys Pro Ser Pro Glu Asp Lys Leu His Asp
        35                  40                  45

Gln Cys Ser Pro Trp Arg Lys Asn Ser Cys Cys Ser Val Asn Thr Ser
50                  55                  60

Leu Glu Ala His Lys Asp Ile Ser Tyr Leu Tyr Arg Phe Asn Trp Asp
65                  70                  75                  80

His Cys Gly Lys Met Glu Pro Ala Cys Lys Arg His Phe Ile Gln Asp
                85                  90                  95

Thr Cys Leu Tyr Glu Cys Ser Pro Asn Leu Gly Pro Trp Ile Gln Glu
            100                 105                 110

Val Asn Gln Lys Trp Arg Arg Glu Arg Ile Leu Asn Val Pro Leu Cys
        115                 120                 125

Lys Glu Asp Cys Gln Ile Trp Trp Glu Asp Cys Arg Thr Ser Tyr Thr
130                 135                 140

Cys Lys Ser Asn Trp His Lys Gly Trp Asn Trp Thr Ser Gly Tyr Asn
145                 150                 155                 160

Gln Cys Pro Val Ser Ala Ala Cys His Arg Phe Asp Phe Tyr Phe Pro
                165                 170                 175

Thr Pro Ala Ala Leu Cys Asn Glu Ile Trp Ser His Ser Phe Glu Val
            180                 185                 190

Ser Ser Tyr Ser Arg Gly Ser Gly Arg Cys Ile Gln Met Trp Phe Asp
        195                 200                 205

Pro Ala Gln Gly Asn Pro Asn Glu Ala Val Ala Arg Tyr Tyr Ala Glu
210                 215                 220

Asn Gly Asp Ala Gly Ala Val Ala Gln Gly Ile Gly Pro Leu Leu Thr
225                 230                 235                 240

Asn Leu Thr Glu Met Val Lys His Trp Val Thr Gly
                245                 250

<210> SEQ ID NO 44
<211> LENGTH: 42
<212> TYPE: PRT
<213> ORGANISM: Mus musculus

<400> SEQUENCE: 44

Met Ala His Leu Met Thr Val Gln Leu Leu Leu Val Met Trp Met
1               5                   10                  15

Ala Glu Cys Ala Gln Ser Arg Ala Thr Arg Ala Arg Thr Glu Leu Leu
            20                  25                  30

Asn Val Cys Met Asp Ala Lys His His Lys
        35                  40

<210> SEQ ID NO 45
<211> LENGTH: 255
<212> TYPE: PRT
<213> ORGANISM: Mus musculus

<400> SEQUENCE: 45

Met Ala His Leu Met Thr Val Gln Leu Leu Leu Val Met Trp Met
1               5                   10                  15

Ala Glu Cys Ala Gln Ser Arg Ala Thr Arg Ala Arg Thr Glu Leu Leu
            20                  25                  30

```
Asn Val Cys Met Asp Ala Lys His His Lys Glu Lys Pro Gly Pro Glu
         35                  40                  45

Asp Asn Leu His Asp Gln Cys Ser Pro Trp Lys Thr Asn Ser Cys Cys
 50                  55                  60

Ser Thr Asn Thr Ser Gln Glu Ala His Lys Asp Ile Ser Tyr Leu Tyr
 65                  70                  75                  80

Arg Phe Asn Trp Asn His Cys Gly Thr Met Thr Ser Glu Cys Lys Arg
                 85                  90                  95

His Phe Ile Gln Asp Thr Cys Leu Tyr Glu Cys Ser Pro Asn Leu Gly
            100                 105                 110

Pro Trp Ile Gln Gln Val Asp Gln Ser Trp Arg Lys Glu Arg Ile Leu
        115                 120                 125

Asp Val Pro Leu Cys Lys Glu Asp Cys Gln Gln Trp Trp Glu Asp Cys
    130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
            180                 185                 190

His Ser Tyr Lys Leu Ser Asn Tyr Ser Arg Gly Ser Gly Arg Cys Ile
        195                 200                 205

Gln Met Trp Phe Asp Pro Ala Gln Gly Asn Pro Asn Glu Glu Val Ala
    210                 215                 220

Arg Phe Tyr Ala Glu Ala Met Ser Gly Ala Gly Phe His Gly Thr Trp
225                 230                 235                 240

Pro Leu Leu Cys Ser Leu Ser Leu Val Leu Leu Trp Val Ile Ser
                245                 250                 255

<210> SEQ ID NO 46
<211> LENGTH: 54
<212> TYPE: PRT
<213> ORGANISM: Homo sapiens

<400> SEQUENCE: 46

Met Ala Trp Gln Met Met Gln Leu Leu Leu Leu Ala Leu Val Thr Ala
 1               5                  10                  15

Ala Gly Ser Ala Gln Pro Arg Ser Ala Arg Ala Arg Thr Asp Leu Leu
                 20                  25                  30

Asn Val Cys Met Asn Ala Lys His His Lys Thr Gln Pro Ser Pro Glu
         35                  40                  45

Asp Glu Leu Tyr Gly Gln
 50

<210> SEQ ID NO 47
<211> LENGTH: 85
<212> TYPE: PRT
<213> ORGANISM: Homo sapiens

<400> SEQUENCE: 47

Thr Cys Leu Tyr Glu Cys Ser Pro Asn Leu Gly Pro Trp Ile Gln Gln
 1               5                  10                  15

Val Asp Gln Ser Trp Arg Lys Glu Arg Val Leu Asn Val Pro Leu Cys
                 20                  25                  30

Lys Glu Asp Cys Glu Gln Trp Trp Glu Asp Cys Arg Thr Ser Tyr Thr
         35                  40                  45
```

-continued

```
Cys Lys Ser Asn Trp His Lys Gly Cys Asn Trp Thr Ser Gly Phe Asn
     50                  55                  60

Lys Cys Ala Val Gly Ala Ala Cys Gln Pro Phe His Phe Tyr Phe Pro
 65                  70                  75                  80

Thr Pro Ile Ala Arg
             85

<210> SEQ ID NO 48
<211> LENGTH: 245
<212> TYPE: PRT
<213> ORGANISM: Homo sapiens

<400> SEQUENCE: 48

Met Leu Pro Ala Ala Thr Glu Val Gln His Arg Leu Gln Gly Gln Lys
 1               5                  10                  15

Asp Met Val Trp Lys Trp Met Pro Leu Leu Leu Leu Val Cys Val
             20                  25                  30

Ala Thr Met Cys Ser Ala Gln Asp Arg Thr Asp Leu Leu Asn Val Cys
             35                  40                  45

Met Asp Ala Lys His His Lys Thr Lys Pro Gly Pro Glu Asp Lys Leu
 50                  55                  60

His Asp Gln Cys Ser Pro Trp Lys Lys Asn Ala Cys Cys Thr Ala Ser
 65                  70                  75                  80

Thr Ser Gln Glu Leu His Lys Asp Thr Ser Arg Leu Tyr Asn Phe Asn
                 85                  90                  95

Trp Asp His Cys Gly Lys Met Glu Pro Ala Cys Ser Ala Thr Ser Ser
             100                 105                 110

Arg Thr Pro Val Ser Met Ser Ala His Gln Pro Gly Ala Leu Asp Pro
         115                 120                 125

Ala Gly Glu Ser Glu Leu Ala Ala Lys Asn Ala Ser Trp Met Cys Pro
     130                 135                 140

Tyr Ala Lys Ser Thr Val Ser Ala Gly Gly Arg Ile Val Thr Pro Pro
145                 150                 155                 160

Thr Arg Ala Arg Ala Thr Gly Thr Glu Asp Gly Thr Gly Pro Gln Glu
                165                 170                 175

Leu Thr Ser Ala Gln Leu Gly Leu Ser Ala Ala Pro Leu Ser Pro Thr
            180                 185                 190

Ser Pro Leu Gln Leu Pro Phe Val Lys Ala Ser Gly Val Thr His Thr
        195                 200                 205

Arg Ser Ala Thr Thr Ala Glu Gly Ala Ala Ala Ser Arg Cys Gly
    210                 215                 220

Leu Leu Gln Pro Arg Ala Thr Pro Thr Arg Lys Trp Arg Gly Ser Met
225                 230                 235                 240

Leu Gln Pro Cys Met
                245

<210> SEQ ID NO 49
<211> LENGTH: 253
<212> TYPE: PRT
<213> ORGANISM: Pig

<400> SEQUENCE: 49

Met Pro Trp Lys Leu Thr Ala Leu Leu Leu Phe Leu Ala Gly Val Val
 1               5                  10                  15

Ser Val Cys Arg Ala Arg Ala Arg Thr Asp Leu Leu Asn Val Cys Met
             20                  25                  30
```

```
Asp Ala Lys His His Lys Val Glu Pro Gly Pro Glu Asp Glu Leu His
         35                  40                  45

Asp Gln Cys Val Pro Trp Lys Lys Asn Ala Cys Cys Ser Ala Arg Val
     50                  55                  60

Ser His Glu Leu His Arg Asp Lys Ser Ser Leu Tyr Asn Phe Ser Trp
 65                  70                  75                  80

Glu His Cys Gly Arg Met Glu Pro Ala Cys Lys Arg His Phe Ile Gln
                 85                  90                  95

Asn Asn Cys Leu Tyr Glu Cys Ser Pro Asn Leu Gly Pro Trp Phe Gln
                100                 105                 110

Glu Val Asn Gln Lys Trp Arg Lys Glu Arg Phe Leu Asn Val Pro Leu
            115                 120                 125

Cys Lys Glu Asp Cys Leu Asp Trp Trp Glu Asp Cys Arg Thr Ser Tyr
        130                 135                 140

Thr Cys Lys Ser Ser Trp His Lys Gly Trp Asn Trp Ser Ser Gly Ser
145                 150                 155                 160

Asn Gln Cys Pro Thr Gly Thr Thr Cys Asp Thr Phe Glu Ser Phe Phe
                165                 170                 175

Pro Thr Pro Ala Ala Leu Cys Glu Gly Ile Trp Asn His Asp Tyr Lys
            180                 185                 190

Phe Thr Asn Tyr Ser Arg Gly Ser Gly Arg Cys Ile Gln Met Trp Phe
        195                 200                 205

Asp Ala Ala Glu Gly Asn Pro Asn Glu Glu Val Ala Arg Phe Tyr Ala
    210                 215                 220

Leu Ala Leu Ser Ala Gly Thr Met Ser Leu Gly Thr Gly Pro Leu Leu
225                 230                 235                 240

Leu Ser Ala Ala Leu Met Leu Pro Leu Gly Leu Leu Asp
                245                 250

<210> SEQ ID NO 50
<211> LENGTH: 22
<212> TYPE: PRT
<213> ORGANISM: RAT

<400> SEQUENCE: 50

Gln Ala Thr Arg Ala Glu Thr Glu Asn Leu Asn Val Asp Met Asp Ala
 1               5                  10                  15

Lys His His Lys Glu Lys
            20

<210> SEQ ID NO 51
<211> LENGTH: 222
<212> TYPE: PRT
<213> ORGANISM: Cow
<220> FEATURE:
<221> NAME/KEY: MOD_RES
<222> LOCATION: (55)
<223> OTHER INFORMATION: Xaa = anything

<400> SEQUENCE: 51

Ala Gln Ala Pro Arg Thr Pro Arg Ala Arg Thr Asp Leu Leu Asn Val
 1               5                  10                  15

Cys Met Asp Ala Lys His His Lys Ala Glu Pro Gly Pro Glu Asp Ser
            20                  25                  30

Leu His Glu Gln Cys Ser Pro Trp Arg Lys Asn Ala Cys Cys Ser Val
        35                  40                  45

Asn Thr Ser Ile Glu Ala Xaa Lys Asp Ile Ser Tyr Leu Tyr Arg Phe
```

```
                50                  55                  60
Asn Trp Asp His Cys Gly Lys Met Glu Pro Ala Cys Lys Arg His Phe
 65                  70                  75                  80

Ile Gln Asp Thr Cys Leu Tyr Glu Cys Ser Pro Asn Leu Gly Pro Trp
                 85                  90                  95

Ile Arg Glu Val Asn Gln Arg Trp Lys Glu Arg Val Leu Gly Val
                100                 105                 110

Pro Leu Cys Lys Glu Asp Cys Gln Ser Trp Trp Glu Asp Cys Arg Thr
                115                 120                 125

Ser Tyr Thr Cys Lys Ser Asn Trp His Lys Gly Trp Asn Trp Thr Ser
                130                 135                 140

Gly Tyr Asn Gln Cys Pro Val Lys Ala Ala His Cys Arg Phe Asp Phe
145                 150                 155                 160

Tyr Phe Pro Thr Pro Ala Ala Leu Cys Asn Glu Ile Trp Ser His Ser
                165                 170                 175

Tyr Lys Val Ser Asn Tyr Ser Arg Gly Ser Gly Arg Cys Ile Gln Met
                180                 185                 190

Trp Phe Asp Pro Phe Gln Gly Asn Pro Asn Glu Glu Val Ala Arg Phe
                195                 200                 205

Tyr Ala Glu Asn Pro Thr Ser Gly Ser Thr Pro Gln Gly Ile
                210                 215                 220

<210> SEQ ID NO 52
<211> LENGTH: 114
<212> TYPE: PRT
<213> ORGANISM: Homo Sapiens
<220> FEATURE:
<221> NAME/KEY: MOD_RES
<222> LOCATION: (12)..(92)
<223> OTHER INFORMATION: X = anything

<400> SEQUENCE: 52

Ile Ala Trp Ala Arg Thr Glu Leu Leu Asn Val Xaa Met Asn Ala Lys
 1               5                  10                  15

His His Lys Glu Lys Pro Gly Pro Glu Asp Lys Leu His Glu Gln Xaa
                 20                  25                  30

Xaa Pro Trp Arg Lys Asn Ala Xaa Xaa Ser Thr Xaa Thr Xaa Gln Glu
                 35                  40                  45

Ala Xaa Lys Asp Val Ser Tyr Leu Tyr Arg Phe Asn Ala Pro Ala Cys
             50                  55                  60

Lys Arg His Phe Ile Gln Asp Thr Cys Leu Tyr Glu Xaa Ser Pro Asn
 65                  70                  75                  80

Leu Gly Pro Xaa Ile Gln Gln Val Asp Gln Ser Xaa Arg Lys Glu Arg
                 85                  90                  95

Val Leu Asn Val Trp Phe Asp Pro Ala Gln Gly Asn Pro Asn Glu Gln
                100                 105                 110

Val Ala

<210> SEQ ID NO 53
<211> LENGTH: 257
<212> TYPE: PRT
<213> ORGANISM: Homo Sapiens

<400> SEQUENCE: 53

Met Ala Gln Arg Met Thr Thr Gln Leu Leu Leu Leu Leu Val Trp Val
 1               5                  10                  15

Ala Val Val Gly Glu Ala Gln Thr Arg Ile Ala Trp Ala Arg Thr Glu
```

-continued

```
                20                  25                  30
Leu Leu Asn Val Cys Met Asn Ala Lys His His Lys Glu Lys Pro Gly
                35                  40                  45

Pro Glu Asp Lys Leu His Glu Gln Cys Arg Pro Trp Arg Lys Asn Ala
         50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
        130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
                180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
        210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 54
<211> LENGTH: 243
<212> TYPE: PRT
<213> ORGANISM: Homo Sapiens

<400> SEQUENCE: 54

Met Ala Trp Gln Met Met Gln Leu Leu Leu Leu Ala Leu Val Thr Ala
 1               5                  10                  15

Ala Gly Ser Ala Gln Pro Arg Ser Ala Arg Ala Arg Thr Asp Leu Leu
                20                  25                  30

Asn Val Cys Met Asn Ala Lys His His Lys Thr Gln Pro Ser Pro Glu
                35                  40                  45

Asp Glu Leu Tyr Gly Gln Cys Ser Pro Trp Lys Lys Asn Ala Cys Cys
         50                  55                  60

Thr Ala Ser Thr Ser Gln Glu Leu His Lys Asp Thr Ser Arg Leu Tyr
 65                  70                  75                  80

Asn Phe Asn Trp Asp His Cys Gly Lys Met Glu Pro Thr Cys Lys Arg
                 85                  90                  95

His Phe Ile Gln Asp Ser Cys Leu Tyr Glu Cys Ser Pro Asn Leu Gly
                100                 105                 110

Pro Trp Ile Arg Gln Val Asn Gln Ser Trp Arg Lys Glu Arg Ile Leu
            115                 120                 125

Asn Val Pro Leu Cys Lys Glu Asp Cys Glu Arg Trp Trp Glu Asp Cys
```

```
                130             135             140
Arg Thr Ser Tyr Thr Cys Lys Ser Asn Trp His Lys Gly Trp Asn Trp
145                 150                 155                 160

Thr Ser Gly Ile Asn Glu Cys Pro Ala Gly Ala Leu Cys Ser Thr Phe
                165                 170                 175

Glu Ser Tyr Phe Pro Thr Pro Ala Ala Leu Cys Glu Gly Leu Trp Ser
            180                 185                 190

His Ser Phe Lys Val Ser Asn Tyr Ser Arg Gly Ser Gly Arg Cys Ile
            195                 200                 205

Gln Met Trp Phe Asp Ser Ala Gln Gly Asn Pro Asn Glu Glu Val Ala
            210                 215                 220

Lys Phe Tyr Ala Ala Ala Met Asn Ala Gly Ala Pro Ser Arg Gly Ile
225                 230                 235                 240

Ile Asp Ser

<210> SEQ ID NO 55
<211> LENGTH: 226
<212> TYPE: PRT
<213> ORGANISM: Homo Sapiens

<400> SEQUENCE: 55

Thr Arg Ile Ala Trp Ala Arg Thr Glu Leu Leu Asn Val Cys Met Asn
1               5                   10                  15

Ala Lys His His Lys Glu Lys Pro Gly Pro Glu Asp Lys Leu His Glu
                20                  25                  30

Gln Cys Arg Pro Trp Arg Lys Asn Ala Cys Cys Ser Thr Asn Thr Ser
            35                  40                  45

Gln Glu Ala His Lys Asp Val Ser Tyr Leu Tyr Arg Phe Asn Trp Asn
    50                  55                  60

His Cys Gly Glu Met Ala Pro Ala Cys Lys Arg His Phe Ile Gln Asp
65                  70                  75                  80

Thr Cys Leu Tyr Glu Cys Ser Pro Asn Leu Gly Pro Trp Ile Gln Gln
                85                  90                  95

Val Asp Gln Ser Trp Arg Lys Glu Arg Val Leu Asn Val Pro Leu Cys
            100                 105                 110

Lys Glu Asp Cys Glu Gln Trp Trp Glu Asp Cys Arg Thr Ser Tyr Thr
            115                 120                 125

Cys Lys Ser Asn Trp His Lys Gly Trp Asn Trp Thr Ser Gly Phe Asn
            130                 135                 140

Lys Cys Ala Val Gly Ala Ala Cys Gln Pro Phe His Phe Tyr Phe Pro
145                 150                 155                 160

Ser Pro Thr Val Leu Cys Asn Glu Ile Trp Thr His Ser Tyr Lys Val
                165                 170                 175

Ser Asn Tyr Ser Arg Gly Ser Gly Arg Cys Ile Gln Met Trp Phe Asp
            180                 185                 190

Pro Ala Gln Gly Asn Pro Asn Glu Glu Val Ala Arg Phe Tyr Ala Ala
            195                 200                 205

Ala Met Ser Gly Ala Gly Pro Trp Ala Ala Trp Pro Phe Leu Leu Ser
            210                 215                 220

Leu Ala
225

<210> SEQ ID NO 56
<211> LENGTH: 238
<212> TYPE: PRT
```

<213> ORGANISM: Chicken

<400> SEQUENCE: 56

```
Met Leu Arg Phe Ala Ile Thr Leu Phe Ala Val Ile Thr Ser Ser Thr
 1               5                  10                  15

Cys Gln Gln Tyr Gly Cys Leu Glu Gly Asp Thr His Lys Ala Lys Pro
                20                  25                  30

Ser Pro Glu Pro Asn Met His Glu Cys Thr Leu Tyr Ser Glu Ser Ser
            35                  40                  45

Cys Cys Tyr Ala Asn Phe Thr Glu Gln Leu Ala His Ser Pro Ile Ile
50                  55                  60

Lys Val Ser Asn Ser Tyr Trp Asn Arg Cys Gly Gln Leu Ser Lys Ser
65                  70                  75                  80

Cys Glu Asp Phe Thr Lys Lys Ile Glu Cys Phe Tyr Arg Cys Ser Pro
                85                  90                  95

His Ala Ala Arg Trp Ile Asp Pro Arg Tyr Thr Ala Ala Ile Gln Ser
            100                 105                 110

Val Pro Leu Cys Gln Ser Phe Cys Asp Asp Trp Tyr Glu Ala Cys Lys
        115                 120                 125

Asp Asp Ser Ile Cys Ala His Asn Trp Leu Thr Asp Trp Glu Arg Asp
130                 135                 140

Glu Ser Gly Glu Asn His Cys Lys Ser Lys Cys Val Pro Tyr Ser Glu
145                 150                 155                 160

Met Tyr Ala Asn Gly Thr Asp Met Cys Gln Ser Met Trp Gly Glu Ser
                165                 170                 175

Phe Lys Val Ser Glu Ser Ser Cys Leu Cys Leu Gln Met Asn Lys Lys
            180                 185                 190

Asp Met Val Ala Ile Lys His Leu Leu Ser Glu Ser Ser Glu Glu Ser
        195                 200                 205

Ser Ser Met Ser Ser Ser Glu Glu His Ala Cys Gln Lys Lys Leu Leu
210                 215                 220

Lys Phe Glu Ala Leu Gln Gln Glu Gly Glu Arg Arg
225                 230                 235
```

<210> SEQ ID NO 57
<211> LENGTH: 251
<212> TYPE: PRT
<213> ORGANISM: Mus musculus

<400> SEQUENCE: 57

```
Met Ala Trp Lys Gln Thr Pro Leu Leu Leu Val Tyr Met Val Thr
 1               5                  10                  15

Thr Gly Ser Gly Arg Asp Arg Thr Asp Leu Leu Asn Val Cys Met Asp
                20                  25                  30

Ala Lys His His Lys Thr Lys Pro Gly Pro Glu Asp Lys Leu His Asp
            35                  40                  45

Gln Cys Ser Pro Trp Lys Lys Asn Ala Cys Cys Ser Val Asn Thr Ser
        50                  55                  60

Gln Glu Leu His Lys Ala Asp Ser Arg Leu Tyr Phe Asn Trp Asp His
65                  70                  75                  80

Cys Gly Lys Met Glu Pro Ala Cys Lys Ser His Phe Ile Gln Asp Ser
                85                  90                  95

Cys Leu Tyr Glu Cys Ser Pro Asn Leu Gly Pro Trp Ile Gln Gln Val
            100                 105                 110

Asp Gln Ser Trp Arg Lys Glu Arg Phe Leu Asp Val Pro Leu Cys Lys
```

```
            115                 120                 125
Glu Asp Cys His Gln Trp Trp Glu Ala Cys Arg Thr Ser Phe Thr Cys
    130                 135                 140

Lys Arg Asp Trp His Lys Gly Trp Asp Trp Ser Ser Gly Ile Asn Lys
145                 150                 155                 160

Cys Pro Asn Thr Ala Pro Cys His Thr Phe Glu Tyr Tyr Phe Pro Thr
                165                 170                 175

Pro Ala Ser Leu Cys Glu Gly Leu Trp Ser His Ser Tyr Lys Val Ser
            180                 185                 190

Asn Tyr Ser Arg Gly Ser Gly Arg Cys Ile Gln Met Trp Phe Asp Ser
        195                 200                 205

Thr Gln Gly Asn Pro Asn Glu Asp Val Val Lys Phe Tyr Ala Ser Phe
    210                 215                 220

Met Thr Ser Gly Thr Val Pro His Ala Ala Val Leu Leu Val Pro Ser
225                 230                 235                 240

Leu Ala Pro Val Leu Ser Leu Trp Leu Pro Gly
                245                 250

<210> SEQ ID NO 58
<211> LENGTH: 30
<212> TYPE: PRT
<213> ORGANISM: Mus musculus

<400> SEQUENCE: 58

Met Ala His Leu Met Thr Val Gln Leu Leu Leu Val Met Trp Met
1               5                  10                  15

Ala Glu Cys Ala Gln Ser Arg Ala Thr Arg Ala Arg Thr Glu
            20                  25                  30

<210> SEQ ID NO 59
<211> LENGTH: 30
<212> TYPE: PRT
<213> ORGANISM: Mus musculus

<400> SEQUENCE: 59

Met Phe Gly Leu Lys Phe Phe Leu Val Leu Glu Ala Leu Leu Phe Leu
1               5                  10                  15

Phe Thr Cys Tyr Ile Val Leu Lys Ile Gly Leu Lys Ile Leu
            20                  25                  30

<210> SEQ ID NO 60
<211> LENGTH: 49
<212> TYPE: PRT
<213> ORGANISM: Mus musculus

<400> SEQUENCE: 60

Met Ala Trp Lys Gln Thr Pro Leu Leu Leu Val Tyr Met Val Thr
1               5                  10                  15

Thr Gly Ser Gly Arg Asp Arg Thr Asp Leu Leu Asn Val Cys Met Asp
            20                  25                  30

Ala Lys His His Lys Thr Lys Pro Gly Pro Glu Asp Lys Leu His Asp
        35                  40                  45

Gln

<210> SEQ ID NO 61
<211> LENGTH: 54
<212> TYPE: PRT
<213> ORGANISM: Mus musculus
```

<400> SEQUENCE: 61

Met Ala His Leu Met Thr Val Gln Leu Leu Leu Val Met Trp Met
1               5                   10                  15

Ala Glu Cys Ala Gln Ser Arg Ala Thr Arg Ala Arg Thr Glu Leu Leu
            20                  25                  30

Asn Val Cys Met Asp Ala Lys His His Lys Glu Lys Pro Gly Pro Glu
        35                  40                  45

Asp Asn Leu His Asp Gln
        50

<210> SEQ ID NO 62
<211> LENGTH: 255
<212> TYPE: PRT
<213> ORGANISM: Mus musculus

<400> SEQUENCE: 62

Met Ala His Leu Met Thr Val Gln Leu Leu Leu Val Met Trp Met
1               5                   10                  15

Ala Glu Cys Ala Gln Ser Arg Ala Thr Arg Ala Arg Thr Glu Leu Leu
            20                  25                  30

Asn Val Cys Met Asp Ala Lys His His Lys Glu Lys Pro Gly Pro Glu
        35                  40                  45

Asp Asn Leu His Asp Gln Cys Ser Pro Trp Lys Thr Asn Ser Cys Cys
        50                  55                  60

Ser Thr Asn Thr Ser Gln Glu Ala His Lys Asp Ile Ser Tyr Leu Tyr
65              70                  75                  80

Arg Phe Asn Trp Asn His Cys Gly Thr Met Thr Ser Glu Cys Lys Arg
            85                  90                  95

His Phe Ile Gln Asp Thr Cys Leu Tyr Glu Cys Ser Pro Asn Leu Gly
        100                 105                 110

Pro Trp Ile Gln Gln Val Asp Gln Ser Trp Arg Lys Glu Arg Ile Leu
        115                 120                 125

Asp Val Pro Leu Cys Lys Glu Asp Cys Gln Gln Trp Trp Glu Asp Cys
        130                 135                 140

Gln Ser Ser Phe Thr Cys Lys Ser Asn Trp His Lys Gly Trp Asn Trp
145             150                 155                 160

Ser Ser Gly His Asn Glu Cys Pro Val Gly Ala Ser Cys His Pro Phe
            165                 170                 175

Thr Phe Tyr Phe Pro Thr Ser Ala Ala Leu Cys Glu Glu Ile Trp Ser
        180                 185                 190

His Ser Tyr Lys Leu Ser Asn Tyr Ser Arg Gly Ser Gly Arg Cys Ile
        195                 200                 205

Gln Met Trp Phe Asp Pro Ala Gln Gly Asn Pro Asn Glu Glu Val Ala
        210                 215                 220

Arg Phe Tyr Ala Glu Ala Met Ser Gly Ala Gly Leu His Gly Thr Trp
225             230                 235                 240

Pro Leu Leu Cys Ser Leu Ser Leu Val Leu Leu Trp Val Ile Ser
            245                 250                 255

<210> SEQ ID NO 63
<211> LENGTH: 22
<212> TYPE: PRT
<213> ORGANISM: Homo Sapiens

<400> SEQUENCE: 63

Thr Arg Ile Ala Trp Ala Arg Thr Glu Leu Leu Asn Val Cys Met Asn

Ala Lys His His Lys Glu
            20

<210> SEQ ID NO 64
<211> LENGTH: 257
<212> TYPE: PRT
<213> ORGANISM: Homo Sapiens

<400> SEQUENCE: 64

Met Ala Gln Arg Met Thr Thr Gln Leu Leu Leu Leu Val Trp Val
 1               5                  10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
                35                  40                  45

Pro Glu Asp Lys Leu His Glu Gln Cys Arg Pro Trp Arg Lys Asn Ala
            50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
                180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
    210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 65
<211> LENGTH: 257
<212> TYPE: PRT
<213> ORGANISM: Homo sapiens

<400> SEQUENCE: 65

Met Ala Gln Arg Met Thr Thr Gln Leu Leu Leu Leu Val Trp Val
 1               5                  10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
                35                  40                  45

```
Pro Glu Asp Lys Leu His Glu Gln Cys Arg Pro Trp Arg Lys Asn Ala
 50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
             85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 66
<211> LENGTH: 255
<212> TYPE: PRT
<213> ORGANISM: Homo sapiens

<400> SEQUENCE: 66

Met Val Trp Lys Trp Met Pro Leu Leu Leu Leu Val Cys Val Ala
  1               5                  10                  15

Thr Met Cys Ser Ala Gln Asp Arg Thr Asp Leu Leu Asn Val Cys Met
             20                  25                  30

Asp Ala Lys His His Lys Thr Lys Pro Gly Pro Glu Asp Lys Leu His
         35                  40                  45

Asp Gln Cys Ser Pro Trp Lys Lys Asn Ala Cys Cys Thr Ala Ser Thr
 50                  55                  60

Ser Gln Glu Leu His Lys Asp Thr Ser Arg Leu Tyr Asn Phe Asn Trp
 65                  70                  75                  80

Asp His Cys Gly Lys Met Glu Pro Ala Cys Lys Arg His Phe Ile Gln
             85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
        115                 120                 125

Cys Lys Glu Asp Cys Gln Arg Trp Trp Glu Asp Cys His Thr Ser His
130                 135                 140

Thr Cys Lys Ser Asn Trp His Arg Gly Trp Asp Trp Thr Ser Gly Val
145                 150                 155                 160
```

```
Asn Lys Cys Pro Ala Gly Ala Leu Cys Arg Thr Phe Glu Ser Tyr Phe
            165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
            195                 200                 205

Asp Ser Ala Gln Gly Asn Pro Asn Glu Glu Val Ala Arg Phe Tyr Ala
            210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255
```

<210> SEQ ID NO 67
<211> LENGTH: 243
<212> TYPE: PRT
<213> ORGANISM: Homo sapiens

<400> SEQUENCE: 67

```
Met Ala Trp Gln Met Met Gln Leu Leu Leu Leu Ala Leu Val Thr Ala
  1               5                  10                  15

Ala Gly Ser Ala Gln Pro Arg Ser Ala Arg Ala Arg Thr Asp Leu Leu
                 20                  25                  30

Asn Val Cys Met Asn Ala Lys His His Lys Thr Gln Pro Ser Pro Glu
             35                  40                  45

Asp Glu Leu Tyr Gly Gln Cys Ser Pro Trp Lys Lys Asn Ala Cys Cys
 50                  55                  60

Thr Ala Ser Thr Ser Gln Glu Leu His Lys Asp Thr Ser Arg Leu Tyr
 65                  70                  75                  80

Asn Phe Asn Trp Asp His Cys Gly Lys Met Glu Pro Thr Cys Lys Arg
                 85                  90                  95

His Phe Ile Gln Asp Ser Cys Leu Tyr Glu Cys Ser Pro Asn Leu Gly
            100                 105                 110

Pro Trp Ile Arg Gln Val Asn Gln Ser Trp Arg Lys Glu Arg Ile Leu
        115                 120                 125

Asn Val Pro Leu Cys Lys Glu Asp Cys Glu Arg Trp Trp Glu Asp Cys
130                 135                 140

Arg Thr Ser Tyr Thr Cys Lys Ser Asn Trp His Lys Gly Trp Asn Trp
145                 150                 155                 160

Thr Ser Gly Ile Asn Glu Cys Pro Ala Gly Ala Leu Cys Ser Thr Phe
                165                 170                 175

Glu Ser Tyr Phe Pro Thr Pro Ala Ala Leu Cys Glu Gly Leu Trp Ser
            180                 185                 190

His Ser Phe Lys Val Ser Asn Tyr Ser Arg Gly Ser Gly Arg Cys Ile
        195                 200                 205

Gln Met Trp Phe Asp Ser Ala Gln Gly Asn Pro Asn Glu Glu Val Ala
    210                 215                 220

Lys Phe Tyr Ala Ala Ala Met Asn Ala Gly Ala Pro Ser Arg Gly Ile
225                 230                 235                 240

Ile Asp Ser
```

<210> SEQ ID NO 68
<211> LENGTH: 255
<212> TYPE: PRT
<213> ORGANISM: Homo sapiens

<400> SEQUENCE: 68

| | | | | | | | | | | | | | | |
|---|---|---|---|---|---|---|---|---|---|---|---|---|---|---|
|Met|Val|Trp|Lys|Trp|Met|Pro|Leu|Leu|Leu|Leu|Val|Cys|Val|Ala|
|1| | | |5| | | | |10| | | | |15|
|Thr|Met|Cys|Ser|Ala|Gln|Asp|Arg|Thr|Asp|Leu|Leu|Asn|Val|Cys|Met|
| | | | |20| | | | |25| | | | |30|
|Asp|Ala|Lys|His|His|Lys|Thr|Lys|Pro|Gly|Pro|Glu|Asp|Lys|Leu|His|
| | | | |35| | | | |40| | | | |45|
|Asp|Gln|Cys|Ser|Pro|Trp|Lys|Lys|Asn|Ala|Cys|Cys|Thr|Ala|Ser|Thr|
| | | | |50| | | | |55| | | | |60|
|Ser|Gln|Glu|Leu|His|Lys|Asp|Thr|Ser|Arg|Leu|Tyr|Asn|Phe|Asn|Trp|
|65| | | | |70| | | | |75| | | | |80|
|Asp|His|Cys|Gly|Lys|Met|Glu|Pro|Ala|Cys|Lys|Arg|His|Phe|Ile|Gln|
| | | | |85| | | | |90| | | | |95|
|Asp|Thr|Cys|Leu|Tyr|Glu|Cys|Ser|Pro|Asn|Leu|Gly|Pro|Trp|Ile|Gln|
| | | | |100| | | | |105| | | | |110|
|Gln|Val|Asn|Gln|Thr|Trp|Arg|Lys|Glu|Arg|Phe|Leu|Asp|Val|Pro|Leu|
| | | | |115| | | | |120| | | | |125|
|Cys|Lys|Glu|Asp|Cys|Gln|Arg|Trp|Trp|Glu|Asp|Cys|Leu|Thr|Ser|His|
| | | |130| | | | |135| | | | |140|
|Thr|Cys|Lys|Ser|Asn|Trp|His|Arg|Gly|Trp|Asp|Trp|Thr|Ser|Gly|Val|
|145| | | | |150| | | | |155| | | | |160|
|Asn|Lys|Cys|Pro|Ala|Gly|Ala|Leu|Cys|Arg|Thr|Phe|Glu|Ser|Tyr|Phe|
| | | | |165| | | | |170| | | | |175|
|Pro|Thr|Pro|Ala|Ala|Leu|Cys|Glu|Gly|Leu|Trp|Ser|His|Ser|Tyr|Lys|
| | | |180| | | | |185| | | | |190|
|Val|Ser|Asn|Tyr|Ser|Arg|Gly|Ser|Gly|Arg|Cys|Ile|Gln|Met|Trp|Phe|
| | | |195| | | | |200| | | | |205|
|Asp|Ser|Ala|Gln|Gly|Asn|Pro|Asn|Glu|Glu|Val|Ala|Arg|Phe|Tyr|Ala|
| | | |210| | | | |215| | | | |220|
|Ala|Ala|Met|His|Val|Asn|Ala|Gly|Glu|Met|Leu|His|Gly|Thr|Gly|Gly|
|225| | | | |230| | | | |235| | | | |240|
|Leu|Leu|Leu|Arg|Leu|Ala|Leu|Met|Leu|Gln|Leu|Trp|Leu|Leu|Gly| |
| | | | |245| | | | |250| | | | |255| |

<210> SEQ ID NO 69
<211> LENGTH: 478
<212> TYPE: DNA
<213> ORGANISM: Homo sapiens

<400> SEQUENCE: 69

```
tctcattggg tcccattggc ctgaccctaa agcctgggtt cttttccacc agacctaatc      60
tccatcgagc tggccttatc ctaagaacca cttggggtat ctataaaatc cagatgcccc     120
ctggtgatga gcaattctct agattttgat gaaagttgaa tgtgtggatg ctggaatgag     180
taaattaaca agtaaggaga tgaatgcaag caggaatgac taaatggaca gactcaggga     240
gccttgaaga gggtggggtc tggaagggaa ggaagagagg aaggagaata gctaagtagg     300
gagatttcac tcagtgctta ccagagcgcg ttgtctaccc tgtaccgaag acagaggctg     360
tggggacagc ctaggggcct ggatctattg cctacttaga gagaggccaa ctcagacaca     420
gccgtgtatg ctcccagcag caacggaggt tcaggcaaga tgcccgaaga gggaaggg      478
```

<210> SEQ ID NO 70
<211> LENGTH: 701
<212> TYPE: DNA

<213> ORGANISM: Salmon

<400> SEQUENCE: 70

```
gggggctggg acaggcggta gctcgcctcg cggcggaccg ccagctcgat cccgagatcc      60
aactacgagc tttttaactg cagcaacttt aagatacgct attggagctg gaattaccgc     120
ggctgctggc accagacttg ccctccaatg gatcctcgtt aaaggattta aagtgtactc     180
attccaatta cagggcctcg aaagagtcct gtattgttat ttttcgtcac tacctccccg     240
agtcgggagt gggtaatttg cgcgcctgct gccttccttg gatgtggtag ccgttctctca    300
ggctccctct ccggaatcga accctgattc cccgttaccc gtggtcacca tggtaggcac     360
agaaagtacc atcgaaagtt gatagggcag acattcgaat gagacgtcac cgccacaaag     420
ggcgcgcgat cggctcgagg ttatctagag tcaccaaagc ggccggggca accgagattg     480
gcccgcatgg gttttgggtc tgataaatgc acgcatcccc ggaggtcagc gctcgtctgc     540
atgtattagc tctagaattg ccacagttat ccaagtaacg ttggagcgat caaaggaacc     600
ataactgatt taatgagcca ttcgcagttt cactgtaccg gccgtgtgta cttagacttg     660
catggcttaa tctttgagac aagcatatgc tactggcagg a                         701
```

<210> SEQ ID NO 71
<211> LENGTH: 356
<212> TYPE: DNA
<213> ORGANISM: Homo sapiens

<400> SEQUENCE: 71

```
gcggccgcct actactacta ctactgctcg aattcaagct tctaacgatg tacggggaca      60
tgccgacggg cgctgacccc cttcgcgggg gggatgcgtg catttatcag atcaaaacca     120
acccggtcag cccctctccg gccccggccg ggggcgggc gccggcggct ttggtgactc      180
tagataacct cgggccgatc gcacgccccc cgtggcggcg acgacccatt cgaacgtctg     240
ccctctccct taccaggacc acagctctgt tccttcggcc tctggtcctc tctggtcccc     300
tcctgggttt cttacgtagt tgattttttcc tctttagtct ccccgacct gcgccc         356
```

<210> SEQ ID NO 72
<211> LENGTH: 155
<212> TYPE: DNA
<213> ORGANISM: Frog

<400> SEQUENCE: 72

```
ttttttttt tttcaaagta aacgcttcgg gccccggga cactcagtca agagcatcgg        60
ggaggcgccg agaggcaggg gctgggacag gcggtagctc gcctcgcggc ggaccgccag     120
ctcgatccca agatccaact acgagctttt taact                                155
```

<210> SEQ ID NO 73
<211> LENGTH: 944
<212> TYPE: DNA
<213> ORGANISM: Homo sapiens

<400> SEQUENCE: 73

```
tcaagattaa acgacaagga cagacatggc tcagcggatg acaacacagc tgctgctcct      60
tctagtgtgg gtggctgtag taggggaggc tcagacaagg attgcatggg ccaggactga     120
gcttctcaat gtctgcatga acgccaagca ccacaaggaa aagccaggcc ccgaggacaa     180
gttgcatgag cagtgtcgac cctggaggaa gaatgcctgc tgttctacca acaccagcca     240
ggaagcccat aaggatgttt cctacctata tagattcaac tggaaccact gtggagagat     300
```

```
ggcacctgcc tgcaaacggc atttcatcca ggacacctgc ctctacgagt gctccccccaa    360 cttggggccc tggatccagc aggtggatca gagctggcgc aaagagcggg tactgaacgt    420 gccccctgtgc aaagaggact gtgagcaatg gtgggaagat tgtcgcacct cctacacctg    480
caagagcaac tggcacaagg gctggaactg gacttcaggg tttaacaagt gcgcagtggg    540
agctgcctgc caacctttcc atttctactt ccccacaccc actgttctgt gcaatgaaat    600
ctggactcac tcctacaagg tcagcaacta cagccgaggg agtggccgct gcatccagat    660
gtggttcgac ccagcccagg caaccccaa tgaggaggtg gcgaggttct atgctgcagc     720
catgagtggg gctgggccct gggcagcctg gcctttcctg cttagcctgg ccctaatgct    780
gctgtggctg ctcagctgac ctccttttac cttctgatac ctggaaatcc ctgccctgtt    840
cagccccaca gctcccaact atttggttcc tgctccatgg tcgggcctct gacagccact    900
ttgaataaac cagacaccgc acatgtgtct tgagaattat ttgg                     944

<210> SEQ ID NO 74
<211> LENGTH: 7720
<212> TYPE: DNA
<213> ORGANISM: Homo sapiens

<400> SEQUENCE: 74
taagttgaca cttctcaggt tgtcacaaga ttcaggtatg gctcactgtt gcaggacata     60
agctgggatc tcctgggaat tggtctgctt gcaggcccta gagagccttc cttcttggtt    120
gattttcctc tagagatcca actgtcttct caggctcccc tgcctgcctc ctccttgggt    180
cctttcttgt ggcattgcca gattactggg ccccattttt ccctacactt actgccactc    240
atagtctgat ggttcccaca tctgcatcca acctggactc ttcccctgag ctttcccctc    300
tacaaccacc ttccccgggc caagggcaca caggcacctc gacaaaacag tgttctatgt    360
ttcttcctgc ccaaacctgc ccctcccctct ccttttccc atctgtggta ccaccatggg    420
ctcagagaat aaaaaaaatg aaggcttctg tcattgactg gggtggagat ggagggaaga    480
gttagcccag aatcacaggt gctgtagaaa ggatacctga gttgccggga gaggggggtcc    540 atgagttggg gatggaagga gagcttggcc cttcaaacaa ttgaagatct gatcaaaaga    600
ttcagaacat ctgtgatttt gtggctggtg atgggtgaca cctgggctaa tggggttggg    660
ggagttggtg gctctacaat ttatggcctt gggagatcct tgctctctat agctgactgg    720
gaggttggaa gcctgggctc tagcccttgc cttgatcctc cggatctcat tttcctcatc    780
tgcctaacag gacagagggg ttggaaactg atgagattag ctcaaaggat cctggcagct    840
caggctgcaa gattttttc agacctcagt gtttgggaaa aaattgggta ggtggagctt    900
agggactggc cttaggcctg cactgttaat tcacccccctc ccactacccc atggaggcct    960
ggctggtgct cacatacaat aattaactgc tgagtggcct tcgcccaatc ccaggctcca   1020
ctcctgggct ccattcccac tccctgcctg tctcctaggc cactaaacca cagctgtccc   1080
ctggaataag gcaaggggga gtgtagagca gagcagaagc ctgagccaga cggagagcca   1140
cctcctctcc caggtatgtg acactccccca tcccccttca gaggccacac accctatggc   1200
attcccacca tgtgttaagg attttctgaa ctggaagggc cctctgtttg cctgaaggcc   1260
agagaatctt gaagtggaga ctgaggccca gaccagagtg tggcctgctc aagattaaac   1320
gacaagttag tgttcatccc cctgaactag tacctgggct ctagcccttc agtccagagc   1380
tgagttctca gctcttctag tctggggccc caaggttggg tgtgggggtc atgattgttg   1440
```

```
gtggggaggg gtcacagctg gactaagacc tgaaggtgag actaggcagg tgggaaagga    1500
gcttgcagag tgatgctgct caaaaggaca ggaagagagc ctggcttcag aagcagccac    1560
agcaagagag actactgact gaacaggtgg gctccactgg gggctccgga aaggattttc    1620
tcagccccca tccccagcac tgtgtgttgg ccgcacccat gagagcctca gcactctgaa    1680
ggtgcagggg gcaaaggcca aaagagctct ggcctgaact tgggtggtcc ctactgtgtg    1740 acttgggca tggccctcat ctgtgctgaa atgattccac aaagattaaa ctggctatca     1800
tttgttgatt tccccttct tacatttaat ccttgcagga gaaagctaag cctcaagata     1860
gtttgcttct ctttccccca aggccaagga gaaggtggag tgagggctgg ggtcgggaca    1920
ggttgaacgg gaaccctgtg ctctaaacag ttagggtttg ttcccgcagg aactgaaccc    1980
aaaggatcac ctggtattcc ctgagagtac agatttctcc ggcgtggccc tcaaggttag    2040
tgagtgagca ggtccacagg ggcatgattg gatcctggaa tgaatgaatc aaccatgaga    2100
gagtgaatga acactggaat caatagagta gcagagtaat ggattgtgga gcaggaaaga    2160
gagctgctgg gtgggaattc aattccaggc ttatatgagc cctgctgtgc agtcggcctg    2220
gagacagccc agctcaggcc ctgcctagac ccctgtcaag gaggccctgt caagaggaga    2280
ggaggggcag cacgggggca aggcaagctt gtgagcggga aaggcatgtc cactttagcg    2340
actggtatgt ggaagatgag ttagaggaga cagatggaga gaagtcatag gaaataaatt    2400
ctgagcattt taggagggcc cagacacctg gtgtccagtg gagtgaagga aacagtcgcc    2460
tcccaaaatt cagtgtctga ggtcaaagga ttgaagttct gtgatgacca aggagaagcc    2520
agctctgtgg taggggcac aggagctccc caaggcccca gggctgtcca gctggctgtc      2580
ccctgccagc acccatgtcc tgtgacccca ccccaccaag atcccatggt tccgggaag      2640 ggcctactaa actagcttga gtgatgaggc tagaaagggg ctgggaccaa ggtttaaaaa    2700 gcaaacaaa ctaacaaaaa ccacactgca gccccccaa ctaaaacatt tttataaact      2760 ttttttttt ttttgagatg gagtctcgct ctgtcaccca ggctagagtg caatggcaca     2820
atcttggctc actgtaacct ccacctcctg gattcaagtg attctcctgc ctcagcctcc    2880
cacgtagctg ggactacagg cacacgacac cgcacccagc tcattttgta tttttagtag    2940
agacagggtt tcactatgtt ggccaggctg gtctcaaact tctgacctca ggtgatccac    3000
ccacctcagc cttccaaagt gctgggatta caggcatgag ccaccgcgcc cagcccattt    3060
ttgtaaactt ttacaatgaa gtaatttggt gtcaaaatct gacctgaaaa ttaatgtgag    3120
tttatgtata gttttaattt atcccactag tgtaactgtt tcaccccaga atatacactt    3180
gattattggg tatatgaaaa aaatattttc tttgaatcac ctttgatgaa atcctaaaaa    3240
attttaaccc tgaaacattt gaataaggca ttgtggacct atggcaaact cctggctatt    3300
tctgcatttt gcccaaatcc atccttgaat tatatcacct gaacctcgtg accacctgga    3360
gaaggcaatg aggctcaagc cagggagggg tggtgtctaa tcctacccttt cattggatct   3420 gggaaaactg agggagatgg gggcagggct ctatctgccc caggcttccg tccaggcccc    3480
accctcctgg agccctgcac acaacttaag gccccacctc cgcattcctt ggtgccactg    3540
accacagctc tttcttcagg gacagacatg gctcagcgga tgacaacaca gctgctgctc    3600
cttctagtgt gggtggctgt agtaggggag gctcagacaa ggattgcatg ggccaggact    3660
gagcttctca atgtctgcat gaacgccaag caccacaagg aaaagccagg ccccgaggac    3720
aagttgcatg agcaggtggg ccagggggtg atctggggtg gtgagggact ggctcaggaa    3780
gaggaaacga ggacatggaa atgccaaacc ccattggcac tggtgaactg aagtggagga    3840
```

```
gcccttcagt ttgcattaat atgggtgact tatttcagag acactgtgcc aaatgtcggt    3900
acaatgccaa cagttcacct tcttggttgt tgagtttccg cattacagaa ataaggaagc    3960
aggcccaaag gagagcctgg gaaatgaagt tggagtgacc catcctgggg ttgcttgatt    4020
tagggattta gactgggaat gactcctcca aagatctgag ggaagaaact gcacactgtg    4080
catagtggcc tcttttctgc cagccctaaa cagctcaaga agggagagtc tctcacatta    4140
tgaggctgtg tgcaaagcat tcttttttttt ttttcctgag acaaagtctc catatgttgc    4200
ccaggctggt ctcaaattcc tggactcaag tgatcctccc acctcagccc tcccaaagtg    4260
tgggattaca gaaatgagcc gtacgccctc ctgaagcatc ttggttcatg catctcgcaa    4320
aactttgggc tgtgtctctc gaccacattg gacctgaggt ctccctataa catttatttt    4380
gctaccaccc ctttaatatc ctgaacatga tgatataact aaagaaaaag cagaggaaaa    4440
gtaatttgta ggccaggtgt tacggctcac gcctgtaatc ccaacactgt gggatgtcga    4500
gatgggcaga tcacttgagc tcaggagttc gagaccagcc tggcaagat ggcaaaaccc    4560 catctctact aaaaaataaa aaaattagt caggtgtggt ggcacatgcc tgcagtccca    4620
gctactcagg aggctgaggt gggcaggtca gttgagccca ggaggcagag attgtagatc    4680
gtgccactgc actccagcct gggcaacaga gtgagacctt gtcaaaagaa agaaagaacg    4740
aaaaaaagaa agaaaggaag gaaggaaggg gaggaaggaa agggagggag gaaagggagg    4800
gaggaaaggg agggaggcaa gggagagaaa cttgtaatac gcatttctttt ttttttttct    4860 tgagatagag ttttgctctt gttgcccagg gtggatggca gtggcacaat ctcagctcac    4920
tgcaacctcc acctcccagg ttcaagtgat tctcctgcct cagcctcctg agtaggcaca    4980
cgccaccaca cccagctaat ttttttgtttg tttgtttgtt ttgtttgttg gtattttttag    5040 tagagatggg ggtttcacca tgttggccag gctggtctcg aactcctcac ctcataatcc    5100
gcccctcttg gcctcccaaa gtgctgagat tacaggtgtg agccactgcg cccggcctta    5160
agtgcacatt ttatttattt atttatttat ttatttattg agatggagtc ttgctctgtt    5220
gcccaggctg gagtgcagtg gcacaatctc agctcactgc aacctccacc tcccaggttc    5280
aagcaattct tctgccttgg cctccagagt agctgggact ataggcacct gccaccatgc    5340
ctagctaatt tttgtatttt tagtagaaat ggggttttgc catgttggcc aggctggtct    5400
ccattcttga cctaagtga tctgtccacc tccacctccc aaagtgctgg gattacaggc    5460
actatgtgag ccactgtgcc ggcccacatt ttaatattta gcttgtcagc cttaagtaat    5520
gagattcagg aagcttgagg ataggcacac aggagcatag tttcaagttg tcctgaattt    5580
tgcagccatc acaagttagt ttttaaggaa aaagattagt tcctaagttg tttctcaata    5640
acttataata aaataacatc cacaattgat tggctataca ttgtttttt gtatcacaaa    5700 ttccacaaac agataatggg tgaggcagct agtcagggac aaaacacttc ccaagtagct    5760
gggattacag gtgtccgcca ccacacttgg ctagtttttt gtttgtttat tttttgagat    5820
ggagtcttgc tctgtcgccc aggctggagt gcagtggcat gatctcggct cactgcaagc    5880
tccacctgcc gggttcacac cattctcctg cctcagcctc caagtagct gggactacag    5940 gtgccagcca ccacgcccgg ctaattttt gtattttag tagagacggg gtttcaccat    6000
gttggccagg atggtcttga tctcttagcc tcgtgatcca cccgcctcgg cctcccaaaa    6060
tgctgggatt acaggcgtga gccaccgcac ccggcctaat ttttatattt ttagtagaga    6120
cggggtttca ccatgttggc caggctggtc tcaaactctt gatctcaggt gatccacctg    6180
```

```
ccttggcctc ccaaagtgct gggattacac aagtaagcca ctgcacccag cctggggtta    6240
caatttaaat tgcttttta ccttcaaatc tttgacacct cagtgaggct taatctgacc     6300
gcactattac actacaagtc cccatccgtc tctgcttaat ttttgtccaa agcaaaaatc    6360
aggtgatgtg ttcattgttg taaccccagt ttctacaaaa gtacctgggt gagagtaagt    6420
aggatctcaa taaggttga attaacaaat tttgtaatga ctgcaactcc agcaggagct     6480
cccttttggg ctcccactgt ctctgacggc cctctcccct aaagaggtcc caatagcaag    6540
tattttcctg ggtgacttcc agtgggctgg ggaatcaagg actaagaggg gagacactgc    6600
atgtggaata ttctggctgt gctggctgtg ctggctgtgg actgagtcct ctgtcttccc    6660
ccatccagtg tcgaccctgg aggaagaatg cctgctgttc taccaacacc agccaggaag    6720
cccataagga tgtttcctac ctatatagat tcaactggaa ccactgtgga gagatggcac    6780
ctgcctgcaa acggcatttc atccaggaca cctgcctcta cgagtgctcc cccaacttgg    6840
ggccctggat ccagcaggta tgcatggctt cctgcaggta caagacctag cggagcagct    6900
gagctttcca ggcatctctg caggctgcaa ccccagctcc agttctattc ggggctgagt    6960
tgctgggatt cttgaacctg agcccttctt ttgtatcaaa atcacccagg tggatcagag    7020
ctggcgcaaa gagcgggtac tgaacgtgcc cctgtgcaaa gaggactgtg agcaatggtg    7080
ggaagattgt cgcacctcct acacctgcaa gagcaactgg cacaagggct ggaactggac    7140
ttcaggtgag ggctggggtg ggcaggaatg gagggatttg gaagtggagg tgtgtgggtg    7200
tggaacaggt atgtgacaat ttggagttgt agggctggca gacctcaaga tagttccggg    7260
cccagtggct aaaggtcttc cctcctctct acagggttta acaagtgcgc agtgggagct    7320
gcctgccaac ctttccattt ctacttcccc acacccactg ttctgtgcaa tgaaatctgg    7380
actcactcct acaaggtcag caactacagc cgagggagtg gccgctgcat ccagatgtgg    7440
ttcgacccag cccagggcaa ccccaatgag gaggtggcga ggttctatgc tgcagccatg    7500
agtggggctg ggccctgggc agcctggcct ttcctgctta gcctggccct aatgctgctg    7560
tggctgctca gctgacctcc ttttaccttc tgatacctgg aaatccctgc cctgttcagc    7620
cccacagctc ccaactattt ggttcctgct ccatggtcgg gcctctgaca gccactttga    7680
ataaaccaga caccgcacat gtgtcttgag aattatttgg                          7720
```

<210> SEQ ID NO 75
<211> LENGTH: 929
<212> TYPE: DNA
<213> ORGANISM: Homo sapiens

<400> SEQUENCE: 75

```
agggacagac atggctcagc ggatgacaac acagctgctg ctccttctag tgtgggtggc      60
tgtagtaggg gaggctcaga caaggattgc atgggccagg actgagcttc tcaatgtctg     120
catgaacgcc aagcaccaca aggaaaagcc aggccccgag acaagttgc atgagcagtg      180 tcgaccctgg aggaagaatg cctgctgttc taccaacacc agccaggaag cccataagga     240
tgtttcctac ctatatagat tcaactggaa ccactgtgga gagatggcac ctgcctgcaa     300
acggcatttc atccaggaca cctgcctcta cgagtgctcc cccaacttgg ggccctggat     360
ccagcaggtg gatcagagct ggcgcaaaga gcgggtactg aacgtgcccc tgtgcaaaga     420
ggactgtgag caatggtggg aagattgtcg cacctcctac acctgcaaga gcaactggca     480
caagggctga aactggactt cagggtttaa caagtgcgca gtgggagctg cctgccaacc     540
tttccatttc tacttcccca cacccactgt tctgtgcaat gaaatctgga ctcactccta    600
```

```
caaggtcagc aactacagcc gagggagtgg ccgctgcatc cagatgtggt tcgacccagc    660
ccagggcaac cccaatgagg aggtggcgag gttctatgct gcagccatga gtggggctgg    720
gccctgggca gcctggcctt tcctgcttag cctggcccta atgctgctgt ggctgctcag    780
ctgacctcct tttaccttct gatacctgga aatccctgcc ctgttcagcc ccacagctcc    840
caactatttg gttcctgctc catggtcggg cctctgacag ccactttgaa taaaccagac    900
accgcacatg tgtcttgaga attatttgg                                      929

<210> SEQ ID NO 76
<211> LENGTH: 1331
<212> TYPE: DNA
<213> ORGANISM: Homo sapiens

<400> SEQUENCE: 76
ggaaaggatt ttctcagccc ccatccccag cactgtgtgt tggccgcacc catgagagcc     60
tcagcactct gaaggtgcag ggggcaaagg ccaaaagagc tctggcctga acttgggtgg    120
tccctactgt gtgacttggg gcatggccct catctgtgct gaaatgattc cacaaagatt    180
aaactggcta tcatttgttg atttcccccct tcttacattt aatccttgca ggagaaagct    240
aagcctcaag atagtttgct tctctttccc ccaaggccaa ggagaaggtg gagtgagggc    300
tggggtcggg acaggttgaa cgggaaccct gtgctctaaa cagttagggt tgttcccgc    360 aggaactgaa cccaaaggat cacctggtat tccctgagag tacagatttc tccggcgtgg    420
ccctcaaggg acagacatgg ctcagcggat gacaacacag ctgctgctcc ttctagtgtg    480
ggtggctgta gtaggggagg ctcagacaag gattgcatgg gccaggactg agcttctcaa    540
tgtctgcatg aacgccaagc accacaagga aaagccaggc cccgaggaca gttgcatga    600 gcagtgtcga ccctggagga agaatgcctg ctgttctacc aacaccagcc aggaagccca    660
taaggatgtt tcctacctat atagattcaa ctggaaccac tgtggagaga tggcacctgc    720
ctgcaaacgg catttcatcc aggacacctg cctctacgag tgctcccca acttggggcc    780 ctggatccag caggtggatc agagctggcg caaagagcgg gtactgaacg tgcccctgtg    840
caaagaggac tgtgagcaat ggtgggaaga ttgtcgcacc tcctacacct gcaagagcaa    900
ctggcacaag ggctggaact ggacttcagg gtttaacaag tgcgcagtgg agctgcctg    960 ccaacctttc catttctact tccccacacc cactgttctg tgcaatgaaa tctggactca   1020
ctcctacaag gtcagcaact acagccgagg gagtggccgc tgcatccaga tgtggttcga   1080
cccagcccag ggcaacccca atgaggaggt ggcgaggttc tatgctgcag ccatgagtgg   1140
ggctgggccc tgggcagcct ggcctttcct gcttagcctg ccctaatgc tgctgtggct   1200 gctcagctga cctccttta ccttctgata cctggaaatc cctgccctgt tcagccccac   1260
agctcccaac tatttggttc ctgctccatg gtcgggcctc tgacagccac tttgaataaa   1320
ccagacaccg c                                                        1331

<210> SEQ ID NO 77
<211> LENGTH: 939
<212> TYPE: DNA
<213> ORGANISM: Homo sapiens

<400> SEQUENCE: 77
cattccttgg tgccactgac cacagctctt tcttcaggga cagacatggc tcagcggatg     60
acaacacagc tgctgctcct tctagtgtgg gtggctgtag taggggaggc tcagacaagg    120
```

```
attgcatggg ccaggactga gcttctcaat gtctgcatga acgccaagca ccacaaggaa      180
aagccaggcc ccgaggacaa gttgcatgag cagtgtcgac cctggaggaa gaatgcctgc      240
tgttctacca acaccagcca ggaagcccat aaggatgttt cctacctata tagattcaac      300
tggaaccact gtggagagat ggacctgcc tgcaaacggc atttcatcca ggacacctgc       360
ctctacgagt gctcccccaa cttggggccc tggatccagc aggtggatca gagctggcgc      420
aaagagcggg tactgaacgt gcccctgtgc aaagaggact gtgagcaatg gtgggaagat      480
tgtcgcacct cctacacctg caagagcaac tggcacaagg gctggaactg gacttcaggg      540
tttaacaagt gcgcagtggg agctgcctgc caacctttcc atttctactt ccccacaccc      600
actgttctgt gcaatgaaat ctggactcac tcctacaagg tcagcaacta cagccgaggg      660
agtggccgct gcatccagat gtggttcgac ccagcccagg caacccccaa tgaggaggtg      720
gcgaggttct atgctgcagc catgagtggg gctgggccct gggcagcctg gcctttcctg      780
cttagcctgg ccctaatgct gctgtggctg ctcagctgac ctccttttac cttctgatac      840
ctggaaatcc ctgccctgtt cagccccaca gctcccaact atttggttcc tgctccatgg      900
tcgggcctct gacagccact ttgaataaac cagacaccg                             939

<210> SEQ ID NO 78
<211> LENGTH: 1104
<212> TYPE: DNA
<213> ORGANISM: Homo sapiens

<400> SEQUENCE: 78
tggaggcctg gctggtgctc acatacaata attaactgct gagtggcctt cgcccaatcc       60
caggctccac tcctgggctc cattcccact ccctgcctgt ctcctaggcc actaaaccac      120
agctgtcccc tggaataagg caaggggggag tgtagagcag agcagaagcc tgagccagac    180
ggagagccac ctcctctccc agggacagac atggctcagc ggatgacaac acagctgctg      240
ctccttctag tgtgggtggc tgtagtaggg gaggctcaga caaggattgc atgggccagg      300
actgagcttc tcaatgtctg catgaacgcc aagcaccaca aggaaaagcc aggccccgag      360
gacaagttgc atgagcagtg tcgaccctgg aggaagaatg cctgctgttc taccaacacc      420
agccaggaag cccataagga tgtttcctac ctatatagat tcaactggaa ccactgtgga      480
gagatggcac ctgcctgcaa acggcatttc atccaggaca cctgcctcta cgagtgctcc      540
cccaacttgg ggcctggat ccagcaggtg gatcagagct ggcgcaaaga gcgggtactg       600
aacgtgcccc tgtgcaaaga ggactgtgag caatggtggg aagattgtcg cacctcctac      660
acctgcaaga gcaactggca caagggctgg aactggactt caggtttaa caagtgcgca      720 gtgggagctg cctgccaacc tttccatttc tacttcccca cacccactgt tctgtgcaat      780
gaaatctgga ctcactccta caaggtcagc aactacagcc gagggagtgg ccgctgcatc      840
cagatgtggt tcgacccagc ccagggcaac cccaatgagg aggtggcgag gttctatgct      900
gcagccatga gtgggctgg gccctgggca gcctggcctt tcctgcttag cctggcccta      960
atgctgctgt ggctgctcag ctgacctcct tttaccttct gatacctgga aatccctgcc     1020
ctgttcagcc ccacagctcc caactatttg gttcctgctc catggtcggg cctctgacag     1080
ccactttgaa taaaccagac accg                                            1104

<210> SEQ ID NO 79
<211> LENGTH: 1032
<212> TYPE: DNA
<213> ORGANISM: Homo sapiens
```

<400> SEQUENCE: 79

```
ggcaaggggg agtgtagagc agagcagaag cctgagccag acggagagcc acctcctctc      60
ccaggaactg aacccaaagg atcacctggt attccctgag agtacagatt tctccggcgt     120
ggccctcaag ggacagacat ggctcagcgg atgacaacac agctgctgct ccttctagtg     180
tgggtggctg tagtagggga ggctcagaca aggattgcat gggccaggac tgagcttctc     240
aatgtctgca tgaacgccaa gcaccacaag gaaaagccag ccccgagga caagttgcat      300
gagcagtgtc gaccctggag gaagaatgcc tgctgttcta ccaacaccag ccaggaagcc     360
cataaggatg tttcctacct atatagattc aactggaacc actgtggaga gatggcacct     420
gcctgcaaac ggcatttcat ccaggacacc tgcctctacg agtgctcccc caacttgggg     480
ccctggatcc agcaggtgga tcagagctgg cgcaaagagc gggtactgaa cgtgcccctg     540
tgcaaagagg actgtgagca atggtgggaa gattgtcgca cctcctacac ctgcaagagc     600
aactggcaca agggctggaa ctggacttca gggtttaaca agtgcgcagt gggagctgcc     660
tgccaacctt ccatttcta cttccccaca cccactgttc tgtgcaatga aatctggact      720
cactcctaca aggtcagcaa ctacagccga gggagtggcc gctgcatcca gatgtggttc     780
gacccagccc agggcaaccc caatgaggag gtggcgaggt tctatgctgc agccatgagt     840
ggggctgggc cctgggcagc ctggcctttc ctgcttagcc tggccctaat gctgctgtgg     900
ctgctcagct gacctccttt taccttctga tacctggaaa tccctgccct gttcagcccc     960
acagctccca actatttggt tcctgctcca tggtcgggcc tctgacagcc actttgaata    1020
aaccagacac cg                                                        1032
```

<210> SEQ ID NO 80
<211> LENGTH: 765
<212> TYPE: DNA
<213> ORGANISM: Homo sapiens

<400> SEQUENCE: 80

```
atggcctcag ttccgaaaac caacaaaata gaaccgcggt cctattccat tattcctagc      60
tgcagtatca ggcggctcgg gcctgctttg aacactccaa tttttcaaag taaacgcaac     120
gggcccccgcg gacactcagc ttacagcatc gaggggcgcc agaggcaagg ggcgggacgg     180
gcggtggtcc ctcgcgcgga ccgcccgccc gctcccaaga tccaactacg agctttttac     240
ctgcagcaac tttactatac gctattggag ctggaattac gcggctgct ggcaccagac     300
ttgccctcca atggctcctc gttaaaggat ttaaagtgga ctcattccaa ttacagggcc     360
tcgaaagagt cctgtattgt tattttcgtc actacctccc cgggtcggga gtgggtaatt     420
tgcgcgcctc ctgccttcct tggatgtggt agcctccagg ctccctctcc ggaatctgaa     480
ccctcattcc ccgtcacccg tggtcaccat ggtcggcacg gcgactacca tcgaaagttg     540
atagggcaga cgttcgaatg ggtcgtcgtc cgccgccacg gggggcgtgc gatcggcccg     600
aggttatcta gagtcaccaa agccgccggc gcccgccccc cggccggggc cggagagggg     660
ctgagggttg gttttgatct gataaatgca ccgatccccc ccgcgaaggg ggtcagcgcc     720
cgtcggcatg tattagctct agaattacca cagttatcca agtag                     765
```

<210> SEQ ID NO 81
<211> LENGTH: 1223
<212> TYPE: DNA
<213> ORGANISM: Mus musculus

<400> SEQUENCE: 81

| | | | | | |
|---|---|---|---|---|---|
| gctttagagg | cagatcaggg | tgtagttttc | agctagcgcc | gtgccttccc | caccatgttc | 60 |
| cttgccatga | tgataatgta | ctagacctct | gaaactgtag | cttctttgtt | acagagtctc | 120 |
| cgtgaatctg | gaattcacca | attcggcgag | tctgaaagcc | tcagtgatct | ctcaggctcc | 180 |
| atctgtctcc | actccccagt | ggaaggcttg | cagctgtgtc | accgctccag | acttcacaca | 240 |
| ggtgctggaa | gactgaacta | agacagaaag | acatggcctg | gaaacagaca | ccactcttgc | 300 |
| ttttggtcta | catggtcaca | acaggcagtg | gccgggacag | aacagaccta | ctcaacgttt | 360 |
| gcatggatgc | caaacaccat | aagacaaagc | cgggccccga | ggacaagctg | catgaccagt | 420 |
| gtagtccatg | gaagaaaaat | gcctgttgct | cagtcaacac | cagccaggag | ctacacaagg | 480 |
| ctgactcccg | tctgtacttc | aactgggatc | actgtggcaa | gatggagcct | gcctgtaaga | 540 |
| gtcacttcat | ccaagactcc | tgcctgtatg | agtgctcccc | caaccttggg | ccttggatcc | 600 |
| agcaagtgga | ccagagttgg | cgtaaagagc | gtttcctgga | tgtgcccta | tgcaaagagg | 660 |
| actgtcacca | gtggtgggaa | gcctgtcgta | cctcctttac | ctgcaagaga | gactggcata | 720 |
| aaggctggga | ctggtcctca | ggcattaaca | agtgcccaaa | cacagcaccc | tgtcacacgt | 780 |
| ttgagtacta | cttcccgaca | ccagccagcc | tttgcgaggg | tctctggagt | cactcctaca | 840 |
| aggtcagcaa | ctacagcaga | gggagtggcc | gctgcatcca | gatgtggttt | gactcaaccc | 900 |
| agggcaatcc | caatgaggac | gtggtgaagt | tttatgcttc | ctttatgaca | tctgggactg | 960 |
| tgccccatgc | agcagtactt | cttgtgccca | gcctggcccc | agtgctgtca | ttatggctcc | 1020 |
| ctggctgaga | ggtcagtctt | cctctctaga | tttctcctct | atctaccctt | ggtctggttc | 1080 |
| aactcttcaa | agaataagga | agtcttgagc | ctgcttccac | ccctctcctc | tgtcatccag | 1140 |
| ttcctgatcc | atgttggggg | ttggggtttc | tacaatcatt | tcaataaat | ctatgacaca | 1200 |
| tctgggccta | atgaaaaaaa | aaa | | | | 1223 |

<210> SEQ ID NO 82
<211> LENGTH: 979
<212> TYPE: DNA
<213> ORGANISM: Mus musculus

<400> SEQUENCE: 82

| | | | | | |
|---|---|---|---|---|---|
| tggagctgag | cacacacttg | gaggttccac | ttaccttagc | tctgccttca | gggtctgaca | 60 |
| tggctcacct | gatgactgtg | cagttgttgc | tcctggtgat | gtggatggcc | gaatgtgctc | 120 |
| agtccagagc | tactcgggcc | aggactgaac | ttctcaatgt | ctgcatggat | gccaagcacc | 180 |
| acaaagaaaa | accgggccct | gaggacaatt | tacacgacca | gtgcagcccc | tggaagacga | 240 |
| attcctgctg | ttccacgaac | acaagccagg | aagcacataa | ggacatttcc | tacctgtacc | 300 |
| ggttcaactg | gaaccactgc | ggaactatga | catcggaatg | caaacggcac | tttatccaag | 360 |
| acacctgcct | ctatgagtgt | tccccgaact | tgggaccctg | gatccagcag | gtggaccaga | 420 |
| gctggcgcaa | agagcggatc | cttgatgttc | ccctgtgcaa | agaggactgt | cagcagtggt | 480 |
| gggaggactg | ccagagctct | tttacctgca | agagcaattg | gcacaaggga | tggaactggt | 540 |
| cctctgggca | taacgagtgt | cctgtgggag | cctcctgcca | tcccttcacc | ttctacttcc | 600 |
| ccacatctgc | tgctctgtgt | gaggaaatct | ggagtcactc | ctacaagctc | agcaactaca | 660 |
| gccgagggag | cggccgctgc | attcagatgt | ggtttgaccc | agcccagggc | aaccccaacg | 720 |
| aggaagtggc | gaggttctat | gccgaggcca | tgagtggagc | tgggcttcat | gggacctggc | 780 |
| cactcttgtg | cagcctgtcc | ttagtgctgc | tctgggtgat | cagctgagtt | cctgttttac | 840 |

```
cttcagttgt ctggagcgcc accctgcttg gctcagcctc ccagctccca gcctcctttg    900
tggtggggct ctgacagcct ctttaataaa ccagacattc cacatgtgcc ttatgaatta    960
aaaaaaaaaa aaaaaaaaa                                                 979

<210> SEQ ID NO 83
<211> LENGTH: 647
<212> TYPE: DNA
<213> ORGANISM: Solanum tuberosum

<400> SEQUENCE: 83
ctccgatccc gaaggccaac gtaataggac cgaaatccta taatgttatc ccatgctaat     60
gtatacagag cgtaggcttg ctttgagcac tctaatttct tcaaagtaac agcgccggag    120
gcacgacccg gccaattaag gccaggagcg catcgccgac agaagggacg agacgaccgg    180
tgcacaccta gggcggaccg gccggcccat cccaaagtcc aactacgagc tttttaactg    240
caacaactta aatatacgct attggagctg gaattaccgc ggctgctggc accagacttg    300
ccctccaatg gatcctcgtt aagggattta gattgtactc attccaatta ccagactcat    360
agagcccggt attgttattt attgtcacta cctccccgtg tcaggattgg gtaatttgcg    420
cgcctgctgc cttccttgga tgtggtagcc gtttctcagg ctccctctcc ggaatcgaac    480
cctaattctc cgtcacccgt caccaccatg gtaggccact atcctaccat cgaaagttga    540
tagggcagaa atttgaatga tgcgtcgccg gcacgatggc cgtgcgatcc gtcgagttat    600
catgaatcat cgcagcaacg ggcagagccc gcgtcgacct tttatct                  647

<210> SEQ ID NO 84
<211> LENGTH: 280
<212> TYPE: DNA
<213> ORGANISM: Suaeda maritima supsb. salsa

<400> SEQUENCE: 84
cgacgcatca ttcaaatttc tgccctatca actttcgatg gtaggatagt ggcctaccat     60
ggtggtgacg ggtgacggag aattagggtt cgattccgga gagggagcct gagaaacggc    120
taccacatcc aaggaaggca gtaggcgcgc aaattaccca atcctgacac ggggaggtag    180
tgacaataaa taacaatacc gggctcttcg agtctggtaa ttggaatgag tacaatctaa    240
atcccttaac gaggatccat tggagggcaa gtctggtgcc                          280

<210> SEQ ID NO 85
<211> LENGTH: 300
<212> TYPE: DNA
<213> ORGANISM: Avicennia marina

<400> SEQUENCE: 85
gcacggccct cgtgccggcg acgcatcatt caaatttctg ccctatcaac tttcgatggt     60
aggatagtgg cctactatgg tggtgacggg tgacggagaa ttagggttcg attccggaga    120
gggagcctga gaaacggcta ccacatccaa ggaaggcagc aggcgcgcaa attacccaat    180
cctgatacgg ggaggtagtg acaataaata acaataccgg gctctcagag tctggtaatt    240
ggatgagtac aatctaatcc ttaacgagga tccattggag ggcaagtctg gtgcacgagc    300

<210> SEQ ID NO 86
<211> LENGTH: 453
<212> TYPE: DNA
<213> ORGANISM: Homo sapiens
```

<400> SEQUENCE: 86

```
gaagacacac gtttagtatt ttattatgaa tcattatttc aaagtcccat actgcatatt      60
catataaggc aacacggcac aatttcaggc ttcatcacaa aggatgaaaa agactgtttc     120
taactccctc ctaatttgca gacatgcttg aacacttaat ggaaggtgaa gtttattttg     180
tggcccctca gttctctttc aagtcctcta gtagaaagtc tccatggtgt gatcttctga     240
ctgggtagaa cccgcaattc tctgctgttt ttagtctttg ttccagatga ctaattacat     300
gacttggctg catttgtgag gggccgacac caacacaatt aaatcagtgc accattcagg     360
gccatagggt aggaggcacc agtggtcacc atggtaggca cggcgactac catcgaaagt     420
tgatagggca gacgttcgaa tgggtcgtcg ccg                                   453
```

<210> SEQ ID NO 87
<211> LENGTH: 70
<212> TYPE: DNA
<213> ORGANISM: RAT

<400> SEQUENCE: 87

```
gttgaagagt cacctggtgc ttcaacggga ctgatttcct gggcctggag ttggagatca      60
gaggtctgac                                                             70
```

<210> SEQ ID NO 88
<211> LENGTH: 381
<212> TYPE: DNA
<213> ORGANISM: RAT

<400> SEQUENCE: 88

```
cgctgatctg gaagcataaa caagaactga agctgaaggc tctaggggtt cccaacctgt      60
gatctccagc agacactcct ggtgtgtcac cggattcagg ctcctgggat aaagaaagca     120
aaggaagtct ggagtggaga cgaagaaacc ccaggcactc tgagagctgc tacctttttcc    180
atgtgtgctg ccagacactt ctcgtcaggg accaaatacc caagggagt ggagagaggc     240
ctgggctggg ccagacttcc tgggctttaa cctgtgctcc aagtaggtgg gtcacatttt     300
ccccagcggg agttgaagag tcacctggtg cttcaacggg actgatttcc tgggcctgga     360
gttggagatc agaggtctga c                                               381
```

<210> SEQ ID NO 89
<211> LENGTH: 916
<212> TYPE: DNA
<213> ORGANISM: RAT

<400> SEQUENCE: 89

```
ggggctggag ttggagatca gaggtctgac atggctcacc tgatggctgg gcagtggttg      60
ctcctgctga tgtggatggc cgaatgtgcc cagtccagag ctactcgggc caggaccgaa     120
cttctcaatg tctgcatgga tgccaagcac cacaaagaaa agccaggccc agaggacaag     180
ttacacgacc agtgcagccc ctggaagacg aatgcctgct gctccaccaa cacaagccag     240
gaagacacta aggacatttc ctacctgtac cgattcaact ggaatcactg tggaactatg     300
accccggagt gcaaacgtca ctttatccaa gacacctgcc tctatgagtg ttccccgaac     360
ttgggaccct ggatccagca ggtggaccag agctggcgca agagcggat ccttgatgtt      420
cccctgtgca aagaagactg tgtgctgtgg tgggaggact gcaagagctc ttttacctgc     480
aagagcaact ggctcaaggg atggaactgg acctcggggc ataatgagtg ccctgtggga     540
gcctcctgcc atcccttcac tttctacttc cctacacctg ctgtgctgtg tgagaaaatc     600
```

```
tggagtcact cctacaagct cagcaactac agccgaggga gcggccgctg catccagatg      660
tggttcgacc cagcccaagg caaccccaac gaggaagtgg cgaggttcta tgccgaggtc      720
atgagtggag ctgggcttcg cgaggcctgg ctgctggtgt gcagcctgtc cttagtgctg      780
ttctgcgtcg tcagctgagt tcctgttact ccttgtctgg agctccaccc tgcccggctt      840
agcctcccag ctccagcctc ctttgtggtg gggctctgac agcctgttta gtaaaccaga      900
cattctaaaa aaaaaa                                                      916

<210> SEQ ID NO 90
<211> LENGTH: 478
<212> TYPE: DNA
<213> ORGANISM: Mus musculus

<400> SEQUENCE: 90
acccggtgag ctccctcccg gctccggccg ggggtcgggc gccggcggct ttggtgactc       60
tagataacct cgggccgatc gcacgccccc aggtcaagtt tgtttatgaa ggtattttgg      120
tattgttttc ctttgcttaa ttgcctcaca ttttgttctg aaaaacatgg gtccactgtt      180
aaaaccgaat gtatgtgtag ctttattctg tttcacaggc gcatgtgatt ggaaaactca      240
ttgtctcctc cagcctcagg agacttctaa aaagttttgc gtagctcaag ttgtgcatga      300
attaccgaat atattatttt tcagcttttc ttcatgaacg atatttgaca tgtgctttgg      360 taccttctc tgaaagttga aaacctacct acttagtccc ttctgtgcct tttttatttt      420
gccaaccatg ttttatggaa aagacattag caattacatt ttgcaaatgg aattatgt       478

<210> SEQ ID NO 91
<211> LENGTH: 821
<212> TYPE: DNA
<213> ORGANISM: Mastigamoeba balamuthi
<220> FEATURE:
<221> NAME/KEY: modified_base
<222> LOCATION: (560)
<223> OTHER INFORMATION: N = A, C, G, or T/U

<400> SEQUENCE: 91
ggcaccagag tagtcatatg cttgtgttaa agattaagcc atgcatgcct aagtacaaac       60
tattcttatg gtaaaactgc ggacggctcc atagatcagt aatagttcgt tcagtgattt      120
gaaaaagtac ttgataacc ctgttaattg tagagctaat acatgcaccg acggcctgat      180
cgggtgaccg agagggtcgc acttgtctta attcacagtg ccccggaact gaggctgttc      240
gacgtggtag gggaggacgc tgaatggggc tggtagaaac aactgggggt ataaaaccaa      300
ggaggaagca aaaaagccat aacccggcga tggccttggt ggaaacctct gggctcaagg      360
ttgttattat gttcattgtg gcctctcggg gttattttga atgtggtaat aaaccgaaag      420
caactctatc agtttggttt ggatgtccgt taatcctgcg tggccagcgg ctttggggac      480 tccagggac agggcgaaac gaggcaattc aaagctgatc gctttctaac gagggcgaca      540
cactgttcga attcctgacn tatcaactcg atggtaggat agtggcctac catggttata      600
acgggtaacg gggaatcagg gctcgattcc ggagagggag cctgagaaac ggctaccact      660
tccaaggaag gcagcaggcg cgtaaattac tccctgccga cacggcgagg tagtgacgac      720
aaataccaag gaaaaccgcc tttggtggtt ttccattgga atgagcagaa ttcaaacccc      780
tctgcaagta acaattggag ggcaagtctg gtgccagcag c                          821

<210> SEQ ID NO 92
```

```
<211> LENGTH: 110
<212> TYPE: DNA
<213> ORGANISM: Mus musculus

<400> SEQUENCE: 92
tccctcgact gtagttgctg agcttgtagg agtgactcca gatttcctca cacagagcag      60
cagatgtggg gaagtagaag gtgaagggat ggcaggaggc tcccacagga               110

<210> SEQ ID NO 93
<211> LENGTH: 334
<212> TYPE: DNA
<213> ORGANISM: Frog

<400> SEQUENCE: 93
ctatcgatat ccgatggtac ttgttgtgcc taccatggtg accccagttc atagcgaatg      60
agggtgcgat ggcagagagg gaggatgtga tgcagctatc gcatgcggtg gatgctggag     120
gcgcgcatgt tgcaccctcc cgacggcgag aggtggtgac tacccatatc gtgcaggact     180 cttttcgacgc gctgtagtct gaatgagtac actttaagtc cgtgagcgcg gatctatcgg    240
ttggcgagtt tagtgccagc agcgcgaggc tttacagcct caatgtcgtg tatgacagtt     300
gcgtgtcctt atggagcgtg agttggatca tggg                                 334

<210> SEQ ID NO 94
<211> LENGTH: 220
<212> TYPE: DNA
<213> ORGANISM: Homo sapiens
<220> FEATURE:
<221> NAME/KEY: modified_base
<222> LOCATION: (54)  (77)
<223> OTHER INFORMATION: N = A, C, G, or T/U

<400> SEQUENCE: 94
gcggccgcct actactacta aattcgcggc cgcgtcgacc gacgacccat tcgntcgtct      60
gccctatcaa ctttcgntgg ttgtcgccgt gcctaccatg gtgaccacgg gtgacgggga    120
ttctgggttc gtttccggtg agggtgcctg tggggcggtt gcctcttctc tggttggctg    180
caggcgcgct ttttcctcc tcccggcccg gggtggttgt                           220

<210> SEQ ID NO 95
<211> LENGTH: 630
<212> TYPE: DNA
<213> ORGANISM: Haemonchus contortus

<400> SEQUENCE: 95
ctggctgcag gaattcgcac gaggctatat gctcagttta aagattaagc catgcatgtc      60
gagttcatct ttgaagagaa actgcgaacg gctcattaga gcagatgtca tttattcgga     120
acgtcctttt ggataactgc ggtaattctg gagctaatac atgcaaataa accctgactt    180
ttgaaagggt gcaattatta gagcaaatca atcactttcg ggtgcagttt gctgactctg    240
aataacgcag catatcggcg gcttgttcgc cgatattccg aaaaagtgtc tgccctatca    300
acctgatggt agtctattag tctaccatgg ttattacggg taacggagaa taagggttcg    360
actccggaga gggagcctta gaaacggcta ccacatccaa ggaaggcagc aggcgcgaaa    420
cttatccaat cttgaacaga tgagatagtg actaaaaata aaaagaccat tcctatggaa    480
cggtcatttc aatgagttga tcataaacct tttttcgagg atcaagtgga gggcaagtct    540
ggtgccagca gccgcggtaa ttccagctcc actagtgtaa atcgtcattg ctgcggttaa    600
aaagctcgta gttggatctg agttacatgc                                     630
```

<210> SEQ ID NO 96
<211> LENGTH: 340
<212> TYPE: DNA
<213> ORGANISM: Mus musculus

<400> SEQUENCE: 96

| | | | | | |
|---|---|---|---|---|---|
| atcatccaga | tttcgtttga | tttcacccccg | ggccttccgg | aggaggacct | cctgaaattt | 60 |
| tctccttcct | atatgacatt | agggactgtg | ccccaagcag | cagtactttt | tgtccccagc | 120 |
| ctgcccccag | tgccgtcatt | atggctcccc | gctgagaggt | cagttttcct | ctctagattt | 180 |
| ttcctctatt | tacccttggt | ctggttcaac | ttttcaaaga | ataaggaagt | cttgaccctg | 240 |
| cttccacccc | tttcctctgt | catccagttc | ctgatccatg | tggggggttg | gggtttctac | 300 |
| aatcattttc | aataaattta | tgacacatct | gggcctaatg | | | 340 |

<210> SEQ ID NO 97
<211> LENGTH: 284
<212> TYPE: DNA
<213> ORGANISM: Mus musculus

<400> SEQUENCE: 97

| | | | | | |
|---|---|---|---|---|---|
| aggacgtttg | atgtcttatg | cttcctttat | gaaatccggg | attgtgcccc | atccagcagt | 60 |
| attcttgtgc | ccagcctggc | cccactgcag | tcattatgcc | tccctggctg | agaggtcatt | 120 |
| cttcctcttt | agatttctcc | tcaatctacc | cttgttctgg | ttcaactctt | caagaataa | 180 |
| ggaagtcttg | accctgcttc | cacccctttc | ctctttcatc | cagttcctga | tccatgttgg | 240 |
| gggttggggt | ttctacattc | attttcaata | aatctatgac | acac | | 284 |

<210> SEQ ID NO 98
<211> LENGTH: 263
<212> TYPE: DNA
<213> ORGANISM: Mus musculus

<400> SEQUENCE: 98

| | | | | | |
|---|---|---|---|---|---|
| tccgggcctt | tcccccccaca | caccaaaaac | ttttctgcct | actctggccc | cagcgctttc | 60 |
| cttatgcctc | cctggctgag | aggtcatttt | cttctataga | tttctcctct | atttaccctc | 120 |
| gctctggttc | aactcttcaa | agaataagga | acttttgagc | ctgcttccac | ccttttcctc | 180 |
| tgtcatccag | ttcctgatcc | atgttggggg | ttggggtttc | tacaatcatt | ttcaataaat | 240 |
| ctatgacaca | tctgggccta | atg | | | | 263 |

<210> SEQ ID NO 99
<211> LENGTH: 489
<212> TYPE: DNA
<213> ORGANISM: Homo sapiens

<400> SEQUENCE: 99

| | | | | | |
|---|---|---|---|---|---|
| tttttgtgcg | gtgtctggtt | tattcaaagt | ggctgtcaga | ggcccgacca | tggagcagga | 60 |
| accaaatagt | tgggagctgt | ggggctgaac | agggcaggga | tttccaggta | tcagaaggta | 120 |
| aaaggaggtc | agctgagcag | ccacagcagc | attagggcca | ggctaagcag | gaaaggccag | 180 |
| gctgcccagg | gccagccccc | actcatggct | gcagcataga | acctcgccac | ctcctcattg | 240 |
| gggttgccct | gggctgggtc | gaaccacatc | tggatgcagc | ggccactccc | tcggctgtag | 300 |
| ttgctgacct | tgtaggagtg | agtccagatt | tcattgcaca | gaacagtggg | tgtgggaag | 360 |
| tagaaatgga | aaggttggca | ggcagctccc | actgcgcact | tgttaaaccc | tgaagtccag | 420 |

```
tttcagccct tgtgccagtt gctcttgcag gtgtaggagg tgcgacaatc ttcccaccat    480
tgctcacag                                                            489

<210> SEQ ID NO 100
<211> LENGTH: 102
<212> TYPE: DNA
<213> ORGANISM: Mus musculus

<400> SEQUENCE: 100
ggatggaact ggtcctcggg gcataacgag tgtcctgtgg gagcctcctg ccatcccttc     60
accttctact tccccacatc tgctgctctg tgtgaggaaa tc                       102

<210> SEQ ID NO 101
<211> LENGTH: 583
<212> TYPE: DNA
<213> ORGANISM: Homo sapiens

<400> SEQUENCE: 101
tagtgtgggt ggctgtagta ggggaggctc agacaaggat tgcatgggcc aggactgagc     60
ttctcaatgt ctgcatgaac gccaagcacc acaaggaaaa gccaggcccc gaggacaagt    120
tgcttgtagc agtgtcgacc ctggaggaag aatgcctggg gttctaccaa caccagccag    180
gaagcccata aggatgtttc ctacctatat agattcaact ggaaccactg tggagagatg    240
gcacctgcct gcaaacggca tttcatccag gacacctgcc tctacgagtg ctcccccaac    300
ttggggccct ggatccagca ggtggatcag agctggcgca aagagcgggt actgaacgtg    360
cccctgtgca aagaggactg tgagcaatgg tgggaagatt gtcgcacctc ctacacctgc    420
aagagcaact ggcacaaggg ctggaactgg acttcagggt ttaacaagtg cgcagtggga    480
gctgcctgcc aaccttttcca tttctacttc cccacaccca ctgttctgtg caatgaaatc    540
tggactcact cctacaggtc agcaactaca gccgagggag tgg                      583

<210> SEQ ID NO 102
<211> LENGTH: 514
<212> TYPE: DNA
<213> ORGANISM: Homo sapiens
<220> FEATURE:
<221> NAME/KEY: modified_base
<222> LOCATION: (122) (131)
<223> OTHER INFORMATION: N = A, C, G, or T/U

<400> SEQUENCE: 102
tgcggtgtct ggtttattca aagtggctgt cagaggcccg accatggagc aggaaccaaa     60
tagttgggag ctgtggggct gaacagggca ttttatttcc aggtatcata ttgtttgttg    120
tnggagctga ncagccacag cagcattagg gccaggctaa gcaggaaagg ccaggctgcc    180
cagggcccag ccccactcat ggctgcagca tagaacctcg ccacctcctc attggggttg    240
ccctgggctg ggtcgaacca catctggatg cagcggccac tccctcggct gtagttgctg    300
accttgtagg agtgagtcca gatttcattg cacagaacag tgggtgtggg gaagtagaaa    360
tggaaaggtt ggcaggcagc tcccactgcg cacttgttaa accctgaaga ccagttccag    420
cccttgtgcc agttgctctt ggaggtgtag gaggtgccac aatcttccca ccattgctca    480
cagtccttct tgcacagggg cacgttcaga accc                                514

<210> SEQ ID NO 103
<211> LENGTH: 321
<212> TYPE: DNA
<213> ORGANISM: Suaeda maritima supsb. salsa
```

<400> SEQUENCE: 103

```
cgacgcatca ttcaaatttc tgccctatca actttcgatg gtaggatagt ggcctaccat    60
ggtggtgacg ggtgacggag aattagggtt cgattccgga gagggagcct gagaaacggc   120
taccacatcc aaggaaggca gtaggcgcgc aaattaccca atcctgacac ggggaggtag   180
tgacaataaa taacaatacc gggctcttcg agtctggtaa ttggaatgag tacaatctaa   240
atcccttaac gaggatccat tggagggcaa gtctggtgcc agcagccgcg gtaattccag   300
ctccaatagc gtatatttaa g                                             321
```

<210> SEQ ID NO 104
<211> LENGTH: 504
<212> TYPE: DNA
<213> ORGANISM: Haemonchus contortus

<400> SEQUENCE: 104

```
tatatgctca gtttaaagat taagccatgc atgtcgagtt catctttgaa gagaaactgc    60
gaacggctca ttagagcaga tgtcatttat tcggaacgtc cttttggata actgcggtca   120
ttctggagct aatacatgca aataaaccct gacttttgaa agggtgcaat tattagagca   180
aatcaatcac tttcgggtgc agtttgctga ctctgaataa cgcagcatat cggcggcttg   240
ttcgccgata ttccgaaaaa gtgtctgccc tatcaacctg atggtagtct attagtctac   300
catggttatt acgggtaacg gagaataagg gttcgactcc ggagagggag ccttagaaac   360
ggctaccaca tccaaggaag gcagcaggcg cgaaacttat ccaatcttga acagatgaga   420
tagtgactaa aaataaaaag accattccta tggaacggtc atttcaatga gttgatcata   480
aacctttttt ccagttaatt ctac                                          504
```

<210> SEQ ID NO 105
<211> LENGTH: 600
<212> TYPE: DNA
<213> ORGANISM: Meloidogyne incognita

<400> SEQUENCE: 105

```
tggccgggat tagaacaaaa ccacgcggct tcggctgctt cttgttgact cagaataact    60
aagctgaccg catggccttg tgccggcggc gtgtctttca agcgtccact ttatcaactt   120
gacgggagca taatcgactc ccgtggtggt gacggataac ggaggatcag ggttcgactc   180
cggagaaggg gcctgagaaa tggccactac gtctaaggat ggcagcaggc gcgcaaatta   240
cccactctcg gctcgaggag gtagtgacga gaaataacga gatcgttctc tttgaggccg   300
gtcatcggaa tgagtacaat ttaaacccctt aacgagtat caagcagagg gcaagtctgg   360
tgccagcagc cgcggtaatt ccagctctgc taatacatag aattattgct gcggttaaaa   420
agctcgtagt tggattcgta tcggtaccct ggaaccctcc gggtgtttct gggtgttatc   480
gatttatcgt aatgttcggt tttgagtcct taacaggatt cttaacaggc attgcaagtt   540
tactttgaac aaatcagagt gcttcaaaca ggcgtttgcg ctgaatgatc gtgcatggat   600
```

<210> SEQ ID NO 106
<211> LENGTH: 634
<212> TYPE: DNA
<213> ORGANISM: Meloidogyne incognita

<400> SEQUENCE: 106

```
tgcctaatgt gccaccgctg agtgtgatga tattgacaat cggtagcatt atggccgggt    60
```

```
gtgtctattt caaagattaa gccatgcatg tataagttta aatcgttttg acgagaaacc    120
gcgaacggct cattacaatg gccatgattt acttgatctt gattatctaa atggattaac    180
tgtggaaaag ctagagctaa tacatgcacc aaaacttgtt cctctcggaa aagcgcattt    240
attagaacaa aaccacgcgg cttcggctgc ttcttgtgac tcagaataac taagctgacc    300
gcatggcctt gtgccggcgg cgtgtctttc aagcgtccac tttatcaact tgacgggagc    360
ataatcgact cccgtggtgg tgacggataa cggaggatca gggttcgact ccggagaagg    420
ggcctgagaa atggccacta cgtctaagga tggcagcagg cgcgcaaatt acccactctc    480
ggctcgagga ggtagtgacg agaaataacg agatcgttct ctttgaggcc ggtcatcgga    540
atgggtacaa tttaaaccct ttaacgagta tcaagcagag ggcaagtctg gtgccagcag    600
ccgggtattc cagctctgct aatacataga atta    634
```

<210> SEQ ID NO 107
<211> LENGTH: 222
<212> TYPE: DNA
<213> ORGANISM: Mus musculus
<220> FEATURE:
<221> NAME/KEY: modified_base
<222> LOCATION: (40)
<223> OTHER INFORMATION: N = A, C, G, or T/U

<400> SEQUENCE: 107

```
tccccaccct gccccagtg ctgtcattat ggatccctgn ctgagaggtc aatcttcctt    60
tctagatttt tcctctatct acccttggtc tggttcaaat tttcaaagaa taaggaagtc    120
ttgagcctgc ttccacccct ctcctctttc atccagttcc taatccatgt tgggggttgg    180
ggtttctaca atcattttca ataaatttat gacacatctg gg    222
```

<210> SEQ ID NO 108
<211> LENGTH: 311
<212> TYPE: DNA
<213> ORGANISM: Mus musculus

<400> SEQUENCE: 108

```
gtagttgctg agcttgtagg agtgactcca gatttcctca cacagagcag cagatgtggg    60
gaagtagaag gtgaagggat ggcaggaggc tcccacagga cactcgttat gccccgagga    120
ccagttccat cccttgtgcc aattgctctt gcaggtaaaa gagctctggc agtcctccca    180
ccactgctga cagtcctctt tgcacagggg aacatcaagg atccgctctt gcgccagct    240 ctggtccacc tgctggatcc agggtcccaa gttcggggaa cactcataga ggcaggtgtc    300
ttggataaag t    311
```

<210> SEQ ID NO 109
<211> LENGTH: 272
<212> TYPE: DNA
<213> ORGANISM: Mus musculus

<400> SEQUENCE: 109

```
acacagagca gcagatgtgg ggaagtagaa ggtgaaggga tggcaggagg ctcccacagg    60
acactcgtta tgccccgagg accagttcca tcccttgtgc caattgctct tgcaggtaaa    120
agagctctgg cagtcctccc accactgctg acagtcctct tgcacaggg gaacatcaag    180 gatccgctct tgcgccagc tctggtccac ctgctggatc cagggtccca agttcgggga    240
acactcatag aggcaggtgt cttggataaa gt    272
```

```
<210> SEQ ID NO 110
<211> LENGTH: 315
<212> TYPE: DNA
<213> ORGANISM: Mus musculus
<220> FEATURE:
<221> NAME/KEY: modified_base
<222> LOCATION: (196)
<223> OTHER INFORMATION: N = A, C, G, or T/U

<400> SEQUENCE: 110
actgcggaac tatgacatcg gaatgcaaac ggcactttat ccaagacacc tgcctctatg     60
agtgttcccc gaacttggga ccctggatcc agcaggtgga ccagagctgg cgcaaagagc    120
ggatccttga tgttcccctg tgcaaagagg actgtcagca gtggtgggag gactgccaga    180
gctcttttac ctgcangagc aattggcaca agggatggaa ctggtcctcg ggcataacg     240 agtgtcctgt gggagcctcc tgccatccct tcaccttcta cttccccaca tctgctgctc    300
tgtgtgagga aatct                                                     315

<210> SEQ ID NO 111
<211> LENGTH: 315
<212> TYPE: DNA
<213> ORGANISM: Mus musculus

<400> SEQUENCE: 111
actgcggaac tatgacatcg gaatgcaaac ggcactttat ccaagacacc tgcctctatg     60
agtgttcccc gaacttggga ccctggatcc agcaggtgga ccagagctgg cgcaaagagc    120
ggatccttga tgttcccctg tgcaaagagg actgtcagca gtggtgggag gactgccaga    180
gctcttttac ctgcaagagc aattggcaca agggatggaa ctggtcctcg ggcataacg     240 agtgtcctgt gggagcctcc tgccatccct tcaccttcta cttccccaca tctgctgctc    300
tgtgtgagga aatct                                                     315

<210> SEQ ID NO 112
<211> LENGTH: 685
<212> TYPE: DNA
<213> ORGANISM: Cladosporium fulvum
<220> FEATURE:
<221> NAME/KEY: modified_base
<222> LOCATION: (197)..(683)
<223> OTHER INFORMATION: N = A, C, G, or T/U

<400> SEQUENCE: 112
gaggccagta gtcatatgct tgtctcaaag attaagccat gcatgtctaa gtataagcaa     60
ctatacggtg aaactgcgaa tggctcatta aatcagttat cgtttatttg atagtacctt    120
actacatgga taaccgtggt aattctagag ctaatacatg ctaaaaaccc gacttcgga    180 aggggtgtat ttattanata aaaaccaac gccctcggg gctccttggt gaatcataat      240
aacttcacga atcgcatggc cttgcgccgg cgatggttca ttcaaatttc tgccctatca    300
actttcgatg gtaggataga ggcctaccat ggtttcaacg ggtaacgggg aattagggtt    360
cgactccgga gagggagcct gagaaacggc taccacatcc aaggaaggca gcaggcgcgc    420
aaattaccca atcccgaccg gggagggagn gacaataaat actgatncng gctntttggg    480
gtcttgnaat tggaatgagt ncaattaaat cccttaccag gaacaattgg aggcaanttg    540
gngcccccan cncggnattc cactccatag cgttntaaag tttgcaatta aaagttgaat    600
taacttggcc tggtggcggc ccctacgggt ctggccggcg gcnttnttttg gggccgnncc   660 tttatgnggg gggaacngct ttntt                                          685
```

<210> SEQ ID NO 113
<211> LENGTH: 440
<212> TYPE: DNA
<213> ORGANISM: Cladosporium fulvum
<220> FEATURE:
<221> NAME/KEY: modified_base
<222> LOCATION: (72)..(433)
<223> OTHER INFORMATION: N = A, C, G, or T/U

<400> SEQUENCE: 113

| | | | | | |
|---|---|---|---|---|---|
| tgacaattga | atacggatgc | ccccgactat | ccctattaat | cattacgggg | gtcctagaaa | 60 |
| ccaacaaaat | anaaccacnc | gtcctattct | attattccat | gctaatgtat | tcgagcaaag | 120 |
| gcctgctttg | aacactntaa | ttttttcaaa | gnaaaagtcc | tggttccccg | acncnccccag | 180 |
| ngaagggcat | gcggctcccc | aaaaggaaag | gcccggccgg | accagtacac | gcggngaggn | 240 |
| ggaccggcca | gccaggccca | aggttcaact | acgagctttt | taactgcaac | aactttaata | 300 |
| tacgctattg | gagctggaat | taccgnggnt | gctggcacca | aacttgccct | ccaattgttc | 360 |
| ctcgttaagg | ggatttaaat | tgtactcatt | ccaattacaa | gacccaaaag | agccctgtat | 420 |
| cagtatttat | tgncactact | | | | | 440 |

<210> SEQ ID NO 114
<211> LENGTH: 246
<212> TYPE: DNA
<213> ORGANISM: Mus musculus

<400> SEQUENCE: 114

| | | | | | |
|---|---|---|---|---|---|
| tgtgcccccat | gcaacagtaa | ttttgagcc | caccctggcc | ccagtgctgt | cattatggct | 60 |
| ccctggctga | gaggtcagtt | ttcctatcta | gattttttcct | gtatctaccc | ttggtctggt | 120 |
| tcaaattttc | aaagaataag | gaagtcttga | gcctgcttcc | accccttttcc | tctgtcatcc | 180 |
| agttcctgat | ccatgttggg | ggttggggtt | tctacaatca | ttttcaataa | atctatgaca | 240 |
| catctg | | | | | | 246 |

<210> SEQ ID NO 115
<211> LENGTH: 694
<212> TYPE: DNA
<213> ORGANISM: Mesembryanthemum crystallinum
<220> FEATURE:
<221> NAME/KEY: modified_base
<222> LOCATION: (23) (609)
<223> OTHER INFORMATION: N = A, C, G, or T/U

<400> SEQUENCE: 115

| | | | | | |
|---|---|---|---|---|---|
| cccctagat | gctagtagca | gtngncacga | ggtcatatgc | ttgtctcaaa | gattaagcca | 60 |
| tgcatgtgta | agtatgaact | aattcagact | gtgaaactgc | gaatggctca | ttaaatcagt | 120 |
| tatagtttgt | ttgatggtac | ctgctactcg | gataaccgta | gtaattctag | agctaatacg | 180 |
| tgcaacaaac | cccgacttct | ggaagggatg | catttattag | ataaaaggtc | gacgcgggct | 240 |
| ttgcccgttg | ctctgatgat | tcatgataac | tcgacggatc | gcacggncttt | tgcgccggcg | 300 |
| acgcatcatt | caaatttctg | ccctatcaac | tttcgatggt | aggatagtgg | cctaccatgg | 360 |
| tggtgacggg | tgacggagaa | ttaggggttcg | attccggaga | gggagcctga | gaaacggcta | 420 |
| ccacatccaa | ggaaggcagc | aggcgcgcaa | attacccaat | cctgcacggg | gaggtaggga | 480 |
| caataaataa | caataccggg | ctcttcgagt | ctggtaattg | gaatgagtac | aatctaaatc | 540 |
| ccttaacgag | gatacattgg | agggccaagt | ctgttgccag | cagccgcggt | atattccagc | 600 |
| ttcaatagnc | gtatatttaa | agttgttggc | agttaaaaag | cttgtatttg | gactctgggg | 660 |

```
tgggcgaccc ggtcgtctag cggtgtgcac cggc                              694
```

<210> SEQ ID NO 116
<211> LENGTH: 1266
<212> TYPE: DNA
<213> ORGANISM: Mesembryanthemum crystallinum
<220> FEATURE:
<221> NAME/KEY: modified_base
<222> LOCATION: (16)..(1230)
<223> OTHER INFORMATION: N = A, C, G or T/U

<400> SEQUENCE: 116

```
gactactcat cagtgncagg ctagctgcac gaggtcatat gctcgtctca tagattaagc    60
catgcatgtg taagtatgaa ctaattcaga ctgtgaaact gcgaatggct cattaaatca   120
gttatagttt gtttgatggt acctgctact aggataaccg tagtaattct agagctaata   180
cgtgcaacaa accccgactt ctggaaggga tgcatttatt agataaaagg tcgacgcggg   240
cttttgcccgt tgctctgatg attcatgata actcgacgga tcgcacggcc tttgcgccgg  300
cgacgcatca ttcaaatttc tgccctatca actttcgatg gtaggatagt ggcctaccat   360
ggtggtgacg ggtgacggag aattagggtt cgattccgga gagggagcct gagaaacggc   420
taccacatcc aaggaaggca tcaggcgcgc atattaccca atcctgacac ggcgaggtag   480
tgacaataaa taacaatacc gggctcttcg agtctcggta atcggaatga gttcaatcta   540
tatcccttta cgaggatcca ttggagggca agtcctgctg ccagcagcct gctgtccttt   600
cagctccaat agcgtatatt taagttgttg cagtttaaca agctcttatt cgaccttgtc   660
gtgcgaccgt tctcattacg ctatatgcct catcatatgt ccatatctat tctcgacttc   720
tcgctcccct cgtcttctct agtacttctg cctcttctat tatattcact atgatctatt   780
ctctacgcct cttcctctgc actcttatat tcatcgcact cttcactcta ctctctctta   840
tcgtctgcta gtcttttcgct tcttcctctt tctactttct catgtctctc atcttatctt   900
accctctctc actctttctg ttcgtctcct ctcactctgc gatttctcca ctgtatcacg   960
cttcgttctc tctactcttc tacttgttct ctctctatct cgtcctcatc tcctccgtct  1020
cgtctctatc gtcgtctacc gatactcttt ccttctctgt catcttcctc tctcttcctc  1080
tcttgcttac ttctcgtctc tcttcacgat tatcntctag cacgtcatct ctttactctc  1140
tctatcttca tgtctactca ctctctcctg tgcgtactac tcttggctat catcatctcc  1200
tagagtggct cgatgaggcg aatgtgcncn tctatctctc tacgttctct tactgatact  1260
tctttg                                                            1266
```

<210> SEQ ID NO 117
<211> LENGTH: 1162
<212> TYPE: DNA
<213> ORGANISM: Mesembryanthemum crystallinum
<220> FEATURE:
<221> NAME/KEY: modified_base
<222> LOCATION: (34)..(960)
<223> OTHER INFORMATION: N = A, C, G or T/U

<400> SEQUENCE: 117

```
gtcgacgcac tagtgctata gtagcgttca tgcnagcngc acgaggagag agagagagag    60
agagagagag agagagagag agagagagag agagagagag agagagagag agagagagag   120
agagagagag agagagcggc acgagcttgt ctcaaagatt aagccatgca tgtgtaagta   180
tgaactaatt cagactgtga aactgcgaat ggctcattaa atcagttata gtttgtttga   240
```

| | |
|---|---|
| tggtacctgc tactaggata accgtagtaa ttctagagct aatacgtgca acaaaccccg | 300 |
| acttctggaa gggatgcatt tattagataa aaggtcgacg cgggctttgc ccgttgctct | 360 |
| gatgattcat gataactcga cggatcgcac ggccttttgcg ccggcgacgc atcattcaaa | 420 |
| tttctgccct atcaactttc gatggtagga tagtggccta ccatggtggt gacgggtgac | 480 |
| agagaattag ggttcgattc cggagaggga gcctgagaaa cggctaccac atccaaggaa | 540 |
| ggcagcatgc gcgcaaatta cccaatcctg acacggagag gtagtgacaa tatataacaa | 600 |
| taccgcgctc ttcgagtctg gtaattggaa tgagtacaat ctatatccct aacgaggat | 660 |
| ccattgtagg gcatgtctgg tgccagcagt cgcggtaatt tcagttccaa ttagcgatat | 720 |
| ttaattcgtt gcagtaaaaa gctcgtattt gaactttgcg tgggcccacc taccgtctag | 780 |
| cggtgtgcac tgtcttctct gcttttttcg catagcctc tgccttaaag cttgtctcgc | 840 |
| actgctctta cttcgatatt tgatcttcat gcgctctctt ggatctcatc atggataccct | 900 |
| aatgatctgc ctttctttgc ttggattcgc atcatcattg tacctggtct ttcgttctan | 960 |
| ttagtatttc tcgattttat catcctgcta ccctactcga tttattttaa actatttgtc | 1020 |
| ttaacctatt tctttctctt cttacttcac tcttcctcgt aatctgtctt attatcactc | 1080 |
| ttcctcattt ctttattact gttcatttac ttatttactt tatttccttc tacatctttt | 1140 |
| ctctcatctt ctactcacgt cg | 1162 |

<210> SEQ ID NO 118
<211> LENGTH: 537
<212> TYPE: DNA
<213> ORGANISM: Mesembryanthemum crystallinum
<220> FEATURE:
<221> NAME/KEY: modified_base
<222> LOCATION: (460)
<223> OTHER INFORMATION: N = A, C, G, or T/U

<400> SEQUENCE: 118

| | |
|---|---|
| cccacactag ttctagagga ttcggcacga ggtctcaaag attaagccat gcatgtgtaa | 60 |
| gtatgaacta attcagactg tgaaactgcg aatggctcat taaatcagtt atagtttgtt | 120 |
| tgatggtacc tgctactagg ataaccgtag taattctaga gctaatacgt gcaacaaacc | 180 |
| ccgacttctg gaagggatgc atttattaga taaaaggtcg acgcgggctt tgcccgttgc | 240 |
| tctgatgatt catgataact cgacggatcg cacggccttt gcgccggcga cgcatcattc | 300 |
| aaatttctgc cctatcaact ttcgatggta ggatagtggc ctaccatggt ggtgacgggt | 360 |
| gacggagaat tagggttcga ttccggagag ggagcctgag aaacggctac acatccaag | 420 |
| gaaggcagca ggcgcgcaaa ttacccaatc ctgacacggn gaggtagtga acaataataa | 480 |
| caataccggg ctcttcgagt ctggtaatgg gaatgagtac aatctaaatt ccttaac | 537 |

<210> SEQ ID NO 119
<211> LENGTH: 968
<212> TYPE: DNA
<213> ORGANISM: Mesembryanthemum crystallinum
<220> FEATURE:
<221> NAME/KEY: modified_base
<222> LOCATION: (635) (658)
<223> OTHER INFORMATION: N = A, C, G, or T/U

<400> SEQUENCE: 119

| | |
|---|---|
| gcacgagcga cgcgggcttt gcccgttgct ctgatgattc atgataactc gacggatcgc | 60 |
| acggcctttg cgccggcgac gcatcattca aatttctgcc ctatcaactt tcgatggtag | 120 |
| gatagtggcc taccatggtg gtgacgggtg acggagaat agggttcgat tccggagagg | 180 |

```
gagcctgaga acggctacc acatccaagg aaggcagcag gcgcgctaat tacccaatcc    240
tgacacgggg aggtagtgac aataaataac aataccgggc tcttcgagtc tggtaattgg    300
aatgagtaca atctaaatcc cttaacgagg atccattgga gggcaagtct ggtgccagca    360
gccgcggtaa ttccagctcc aatagcgtat atttaagttg ttgcagttaa aaagctcgta    420
gttggacctt ggggtgggcc gaccggtccg cctagcggtg tgcaccggtc gtcctgcctc    480
ttctgccggc gatgcgctcc tggccttaac tgggccggtc gtgccaccgg gcgctgtact    540
ttgaagaaat agagtgctca agcaggccta cgctctggat acattagcat gggataacat    600
cataggaatt ccgtcctatt ctgttgccct tcggnattcg agtaattgat aacaggnnac    660
agcgggggca ttcgtatttc atagtcagag gtgaaaatct tggattattg aagaccaaca    720
actgccaaag catttggcca ggatgttttc attattcaag accgaaagtt ggggcttcga    780
agaccaacag attcccgtct aatcttaaac cttaaacata tcccaccagg ggatcgggga    840
tgtaactttt aggaccccgc cggccccta tgagaaatta agttttggg gtcccggggg    900 gagtttggtg ccaaggcttt aacttaaggg aattgcgcgg aggggcccc cccgggaatg    960 ggccctgt                                                            968
```

<210> SEQ ID NO 120
<211> LENGTH: 893
<212> TYPE: DNA
<213> ORGANISM: Mesembryanthemum crystallinum
<220> FEATURE:
<221> NAME/KEY: modified_base
<222> LOCATION: (660)
<223> OTHER INFORMATION: N = A, C, G, or T/U

<400> SEQUENCE: 120

```
gcacgaggtc tcaaagatta agccatgcat gtgtaagtat gaactaattc agactgtgaa     60
actgcgaatg gctcattaaa tcagttatag tttgtttgat ggtacctgct actaggataa    120
ccgtagtaat tctagagcta atacgtgcaa caaaccccga cttctggaag ggatgcattt    180
attagataaa aggtcgacgc gggctttgcc cgttgctctg atgattcatg ataactcgac    240
ggatcgcacg gccttcgcgc cggcgacgca tcattcaaat ttctgcccta tcaactttcg    300
atggtaggat agtggcctac catggtggtg acgggtgacg gagaattagg gttcgattcc    360
ggagagggag cctgagaaac ggctaccaca tccaaggaag gcagcaggcg cgcaaattac    420
ccaatcctga cacggggagg tagtgacaat aaataacaat accgggctct tcgagtctgg    480
taattggaat gagtacaatc taaatccctt aacgaggatc cattggaggg caagtctggt    540
gccagcagcc gcggtaattc cagctccaat agcgtatatt taagttgttg cagttaaaaa    600
gctcgtagtt ggaccttggg gtgggccgac cggtccgcct agcggtgtgc accggtcggn    660
cttgcctctt ttgtcggcga tgcgctcctg gcctttaact ggccggggttg tgccaccggc    720 gctgttactt ttgaagaaat aagagtgctc aaagcaagcc ctacgctctg gttacattag    780
catgggataa caatatagga tttccggtcc tatttgttg gcctttggga tcggagttat    840
gaataacagg gaccgtccgg gggcatttct tttttaatat tcaaaggtga aat           893
```

<210> SEQ ID NO 121
<211> LENGTH: 996
<212> TYPE: DNA
<213> ORGANISM: Mesembryanthemum crystallinum
<220> FEATURE:
<221> NAME/KEY: modified_base
<222> LOCATION: (676) (854)

<223> OTHER INFORMATION: N = A, C, G, or T/U

<400> SEQUENCE: 121

```
agctggtacg cctgcggtac cggtccggaa ttcccgggtc gacccacgcg tccgcggacg    60
cgtgggcgga cgcgtggggc taatacatgc aactcggtct ctaccggaaa tggtagggac   120
gcttttatta gaccaaaacc aatcgggcgt tctcgtccgt tttgccttgg tgactctgaa   180
taaattgtgt gcagatcgca cggtcctcgt accggcgacg catctttcaa atgtctgcct   240
tatcaacttt cgatggtagg tcctgcgcct accatggttg taacgggtaa cggggaatca   300
gggttcgatt ccggagaggg agcctgagaa acggctgcta catccaagga aggcagcagg   360
cgcgcaaatt acccactccc ggcacgggga ggtagtgacg acaaataacg atacgggact   420
catccgaggc cccgtaatcg gaatgaacac actttaaatc ctttaatgag tatccattgg   480
agggcaagtc tggtgccagc agccgcggta attccagctc caatagcgta tattaaagtt   540
gttgcggtta aaaagctcgt agtcggactt gtgtcacacg ctgccggttc accgcccgtc   600
ggtgctaact ggcatgcacg tgttgacgtc ctgctggtgg ccgtagccgg tccgggtgtt   660
ctgggatccc ttcggngttt cccggacccc ggtgcttggt gaaggcctac ttgacctacc   720
cgtcgcggtg ctcttaaccg agtgtctcga tgggccggca ctttctactttt gaacaattag   780
agtgcttaaa gcaggcagta tcagccctga tactgagtgc atggaataat ggaataggaa   840
cctcggtcta tttntgtggt tttcggaatg ccctagatcg cgagcggccg ctctagaaga   900
tccaagctta cgtacgcctg cattgccaag tataagcttt tttatatggg gaaccctaaa   960
ttcaatcaac tggcgcgcgg tttaacacac gcggag                             996
```

<210> SEQ ID NO 122
<211> LENGTH: 607
<212> TYPE: DNA
<213> ORGANISM: Mus musculus
<220> FEATURE:
<221> NAME/KEY: modified_base
<222> LOCATION: (106)
<223> OTHER INFORMATION: N = A, C, G, or T/U

<400> SEQUENCE: 122

```
tgctgctcct tctagtgtgg gtggctgtag taggggaggc tcagacaagg attgcatggg    60
ccaggactga gcttctcaat gtctgcatga acgccaagca ccacanagga aaattctttc   120
cccgaggaca agttgcatgt tctgtggggg ccctggagga agaatgcctg ctgttctacc   180
aacaccagcc aggaagccca taaggatgtt tcctacctat atagattcaa ctggaaccac   240
tgtggagaga tggcacctgc ctgcaaacgg catttcatcc aggacacctg cctctacgag   300
tgctccccca acttggggcc ctggatccag caggtggatc agagctggcg caaagagcgg   360
gtactgaacg tgcccctgtg caaagaggac tgtgagcaat ggtgggaaga ttgtcgcacc   420
tcctacacct gcaagagcaa ctggcacaag ggcctggaac ctggacttca gggttttaac   480
aaggtgcgca ggtgggaggc tgccctgccc acctttttcca ttttctactt ctctcacacc   540
cactgttgct gttgcattgc aaatcttgtc ctcacttctt acaaggtaca gcaactacca   600
agaaaaa                                                             607
```

<210> SEQ ID NO 123
<211> LENGTH: 351
<212> TYPE: DNA
<213> ORGANISM: Mus musculus

<400> SEQUENCE: 123

```
aggacatttc ctacctgtac cggttcaact ggaaccactg cggaactatg acatcggaat    60
gcaaacggca ctttatccaa gacacctgcc tctatgagtg ttccccgaac ttgggaccct   120
ggatccagca ggtggaccag agctggcgca aagagcggat ccttgatgtt ccctgtgca   180 aagaggactg tcagcagtgg tgggaggact gccagagctc ttttacctgc aagagcaatt   240
ggcacaaggg atggaactgg tcctcggggc ataacgagtg tcctgtggga gcctcctgcc   300
atcccttcac cttctacttc cccacatctg ctgctctgtg tgaggaaatc t            351

<210> SEQ ID NO 124
<211> LENGTH: 365
<212> TYPE: DNA
<213> ORGANISM: Mus musculus

<400> SEQUENCE: 124
gcggccgctc cctcgactgt agttgctgag cttgtaggag tgactccaga tttcctcaca    60
cagagcagca gatgtgggga agtagaaggt gaagggatgg caggaggctc ccacaggaca   120
ctcgttatgc cccgaggacc agttccatcc cttgtgccaa ttgctcttgc aggtaaaaga   180
gctctggcag tcctcccacc actgctgaca gtcctctttg cacaggggaa catcaaggat   240
ccgctctttg cgccagctct ggtccacctg ctggatccag ggtcccaagt tcggggaaca   300
ctcatagagg caggtgtctt ggataaagtg ccgtttgcat tccgatgtca tagttccgca   360
gtggt                                                               365

<210> SEQ ID NO 125
<211> LENGTH: 653
<212> TYPE: DNA
<213> ORGANISM: Mus musculus
<220> FEATURE:
<221> NAME/KEY: modified_base
<222> LOCATION: (532)
<223> OTHER INFORMATION: N = A, C, G, or T/U

<400> SEQUENCE: 125
gggctgtgga cgaagactgt agagactacc cagagtctga cctagggaga ggccaactcg    60
gataccccta tgtgcgctcc cagaagctaa ggacattgag acagaaagac atggcctgga   120
aacagacacc actcttgctt ttggtctaca tggtcacaac aggcagtggc cgggacagaa   180
cagacctact caacgtttgc atggatgcca acaccataa gacaaagccg ggccccgagg    240
acaagctgca tgaccagtgt agtccatgga agaaaaatgc ctgttgctca gtcaacacca   300
gccaggagct acacaaggct gactcccgtc tgtacttcaa ctgggatcac tgtggcaaga   360
tggagcctgc ctgtaagagt cacttcatcc aagactcctg cctgtatgag tgctccccca   420
accttgggcc ttggatccag caagtggacc agagttggcg taaagagcgt gtcctggatg   480
tgcccttatg caaagaggac tgtcaccagt ggtgggaagc ctgtcgtacc tnctttacct   540
gcaagagaga ctggcataaa ggctgggact ggtcctcagg catttacaag tgcccaaaca   600
cagcaccctg tcacacgttt gagtactact cccgacacc agccagccct tgc            653

<210> SEQ ID NO 126
<211> LENGTH: 649
<212> TYPE: DNA
<213> ORGANISM: Mus musculus

<400> SEQUENCE: 126
tttttttttt ttcccaaatg tgtcatagat ttattgaaaa tgattgtaga aaccccaacc    60
```

```
cccaacatgg atcaggaact ggatgacaga ggaaaggggt ggaagcaggc tcaagacttc        120
cttattcttt gaagagttga accaaaccaa gggtagatag aggagaaatc tagagaggaa        180
gactgacctc tcagccaggg agccataatg acagcactgg gccaggctg  gcacaaaaa        240
gtactgctgc atggggcaca gtcccagatg tcataaagga agcataaaac ttcaccacgt        300
cctcattcgg attgccctgg gttgagtcaa accacatttg gatgcagcgg ccactccctc        360
tgctgtagtt gctgacctttg taggagtgac tccagagacc ctcgcaaagg ctggctggtg       420
tcgggaagta gtactcaaac gtgtgacagg gtgctgtgtt gggcacttg  ttaatgcctg        480
aggaccagtc ccagcctttta tgccagtctc tcttgcaggt aaaggaggta cgacaggctt       540
cccaccactg gtgacagtcc ttttttgcata agggcaccat ccagaaaacg ctctttacgc       600
caactcttgt tccacttgct gatccaaagg ccaaagttgg gggagcact                    649
```

<210> SEQ ID NO 127
<211> LENGTH: 668
<212> TYPE: DNA
<213> ORGANISM: chicken

<400> SEQUENCE: 127

```
cagcctcttg cacacagctt tactctgtca gccccagggt ggaaacaaag ggctggctgt         60
tcatcacact gcactttgtg taatcactcg ctctcacaac tggcaaatct cttttgccag        120
tggtgggact gaataacatt ttaaagggat gaagtacagc acagagctgt acaagatagt        180
ggatgactgc agacttttttc ataatttttgt accatttcta aaaagtgat  gtttctcaaa     240
ttactacaag ttgattttaa ctccattctt tttaaaatgt gattgatgtg tgtttctcat        300
tttacacaca gatgtatgca aatgggaccg acatgtgcca gagtatgtgg ggggaatcct       360
ttaaggtgag cgaatcctcc tgcctctgct tgcaaatgaa caagaaggac atggtggcaa       420
tcaagcacct cctctccgaa agctcagagg aaagctccag tatgagcagc agtgaggagc      480
acgcctgcca aagaaaactc ctgaagtttg aggcactgca gcaagaggaa ggggaagaga      540
gaagatgaat tttggtggat gaatatcagg aggagaggaa tcattgtgga ggttgtgctc      600
ggggcatcac agcagcctgt cttatcccttc acttctgaga acacaataaa tcaatggttg     660
gctatatt                                                                668
```

<210> SEQ ID NO 128
<211> LENGTH: 3632
<212> TYPE: DNA
<213> ORGANISM: chicken

<400> SEQUENCE: 128

```
acaagcagat taatttcatt agcacgcatc accatatata ataaagctgt aataggccaa         60
atgctccaat ttacacttgt gaaactccgt ctcactccag ccacactgtt gttacacttt        120
catgatgcca aggagggaaa cagatctggc agctgtcaca agttggaagt acaaacaatt        180
tttcccttca ccactacagc tttgcagagt taacaaaaat ataaaccag  aaaagcttac       240
ttcagtcatt agagagatct gcctcactaa aaagggatca ctgtgttgag ttaggagatg        300
tcagtttgac atagatacta actcaatggc cagaagctgt gaagttagca actagctgga        360
gttcttgtat ctcttttgca ttttttttccc tcattaccca atggtagctc ttgcagaagg      420
aattcatgca ggcaggtagc ggctcctgag agctcaaata gctgcgtctg tgatttcgga      480
ataaatacat ccttctgcta acatcgctgg ccattatcag atagtcagat gataatgtaa      540
taataataat gtacccgtgc cagaattact gtctgtggca atatctgtaa catcatgcat      600
```

-continued

```
gctttaacgc tgtataaaaa ctttgagaag atgaatataa gttcataggg caatgatatt      660
aatgttaaaa ataaatgata acaggagttt tatcagtaca aaaatatgag cgagtacttg      720
caaataaatt cagcattaac aaatgaggtt aacaacccat tcaagtattg aaagcaataa      780
gaaacattct ttaataaatt tctcaatata agacttacgg tcttatactg agactttttct    840
tactcagaat aagaaaaaga agactcaaga tgatgaagat gtgtggctga aatctctaga     900
agctcctgtg cttgagcctg cctacatcta ttgttaacca aagccaagtc tgagaaatca     960
caaacatatg acaatttttcc ttcctgctgt tagaaattct gcctaatctc ccagcaagtg   1020
gtcccatttg gctcatattc aaagcttgaa aaagatccca gtctcctata gcttaatata    1080
atttgtatgt caattccata acaaaggca ttacatgaaa cctcctggct cctaacacct    1140
ttacaagagt gaatacattt catacaaacc aagcagtaag gaacagaaca cgtgctttttt  1200
caccaggctg gctagcacag ccactcatcc tcagattgaa aggggatgtt tatgtggcac    1260
agtggtctttt actttgtatg aatacactga tcttagtacc aagcaatatg cacaagtcct   1320
ttacactaca aatcagcaag aagctccatt aatttcagcc agcacaaaat caagccacat    1380
gaagtgaagg cacaggcaat aaggtcttac atttacttca gtttctccta tacttatatt    1440
atgtctcttt gtatttgttt taattaaatt cactctggaa agcagaaaac actagggttt    1500
caaatgatct gaaaatggtc ttgtaaaggc agcagcactt ttgcctcaag gaaggcttca    1560
gccagagcag gaattggtgc ttacagctca gcagagatca ttatcatact gtgagtttgc    1620
tcagtgagat tcattccaca cttccactgt gccagtgttt gttttattca agcaaaaaag    1680
ttttgtaaat actgacccac agttactatt tgacaaacca ctgttgtgtt ttaaaataga    1740
aacaagagat gctatttttcc atttgcatct gaataattgc aaagtagtca gtggcgtgtt   1800
gctagttagg gagctcactg ggatttgacc tatggaagta agtgcaccta tttgtaatga    1860
ccacgtctgc tttctgtgat ggtccatgtt cagatgtgga atcccctctg cagaaagcac   1920
acctggtaag gaaatccagt cagcaactgc tgtcagtggt actcgcaaca gtttctccta    1980
gtgtttgtga cacccttgga aagcacaaac atggcaggta gagaaagaag gacaaacatc   2040
agcaggttaa aaaagaatc ttctgggcaa agagcaaagg cctgagaatc aggagaccaa    2100
ttctcccttca ggggctgcag taaaattact gagtaaccca aagcaaactg atatgtttac   2160
ggtcaaaatt aagccagaca ggttgaaata tgaagagttg tttgaaatgt ctataattca    2220
gtgaagttgg tgataagaac ccaattaagc tgttgtagaa atgaatctaa taattataac    2280
aaaaggaatc attgcaaaat caggcagggg gtgggaggta gttgtattgg gtacactgga    2340
gagctgttgt ttttctaatt ctagtctatg tttgtacttt cctgtttatt atgtccacat    2400
ttgcaagcaa taaagggca ttatgtgctg gtcattccat ctgcttttga gataaatcta    2460
tgttagcatt tcaaagggtc aaggaactct ccagggcaaa caaattctgg agcgctgctg    2520
ccagatggcg cgtatataaa gtggaaagcg agaaaagcaa tttgctgtgt ttctgttcca    2580
gggagaagtc tcacccagaa ggacagcaaa agaggtgaga aactaccgag aaattgtaca    2640
ggcggttttc ttctgtaaca tgttgctttc tttgcatctg aaaagtttag gtacggagag    2700
aagctcagtt cttgttcagg caaagctctt ccaaaaggt atcaggaata tttaaccaaa     2760
gaattgaagg ttaagttaat aacacctata agaattatg cacttcttta tgtgggaggt    2820
tctagattta tctgtataac tcactaatat gtagtctgta cttacagaaa ctctatgctc    2880
gcagaccaaa tggtggttat cttgcatatt tgactgaact ctacaaaagc agacacaaaa    2940
```

-continued

| | |
|---|---|
| ccattgatca gattattagg ttcaaataag cgtgaccctca acaaaggcaa gttatctgca | 3000 |
| taatttatcc agctcaattg ccaccttatg ctctgctatt agcttgtcaa ttctgtaaac | 3060 |
| agaagcactg caattaaatg ggtaatttcc cagcacacaa aagaactctg taagtttcgg | 3120 |
| agctgatcaa tcttgccttc aaatctagtg tagcagtggg atgggaaatc catatctgca | 3180 |
| tgagaaattt aaaaaccttt tgttaaatac tgaaaaccat aacatatagc cttcattctt | 3240 |
| catatagcct gtattcttca taggtcacca gaaactgaaa atatgtagca gaagcattaa | 3300 |
| gtgtttggac atgagcaaag gaaagggaga atgagtgacc caatatttat atgcgtacct | 3360 |
| ctcttgagca tatttaattg tatatatatg tagctttttt acagcagccc ttcttttttac | 3420 |
| tatcaggact tttcctacaa ataaaggata tcagtaaaga cttctctccg cacaggaaaa | 3480 |
| gaagggaaca acaatgctga ggtttgccat caccctcttt gctgtcatca catcatctac | 3540 |
| ctgccagcag tatggatgtc tggaagggga cacccacaaa gcgaatccaa gtcctgagcc | 3600 |
| aaacatgcat gaatgcactc tgtattctga at | 3632 |

<210> SEQ ID NO 129
<211> LENGTH: 713
<212> TYPE: DNA
<213> ORGANISM: Mus musculus

<400> SEQUENCE: 129

| | |
|---|---|
| tttccccagt cagctggctg atctggaagt ataaacaaga aaggaggctg acggctctag | 60 |
| aagtccccaa cctgttgtga tcttcagtag acaaacactc ctggtgtgtc acaggattca | 120 |
| ggccactaaa cctcggccgg ctgtctcctg gaatgaagaa agcaaaggaa gcctagagtg | 180 |
| gagacaaaga aacccgaggc actctgagag ctgccatctt atccttgttt gccgcctgac | 240 |
| acttctcagc aggatccaca taccctaagg agtggaagac tccttggcgc ttggtgcttc | 300 |
| aaccggactg acttcctggg cctggagttg gcgattagag gtctgacatg gctcacctga | 360 |
| tgactgtgca gttgttgctc ctggtgatgt ggatggccga atgtgctcag tccagagcta | 420 |
| ctcgggccag gactgaactt ctcaatgtct gcatggatgc catacaccac agagaaaaac | 480 |
| cgggccctga tgacaattta cacgaccagt gcagcctctg gaaacgaatt cctgctgttc | 540 |
| cacgaacact agccatgaag cacataagga catgtcctac ctgttccaga tcaactggaa | 600 |
| ccactgcggg actatgacat cggaatgcag actgcactgt atgcaagaca cctgcctcta | 660 |
| tgagtgtaca cagaacttgg gacgctggat tcatctagtg aaccaaagct ggc | 713 |

<210> SEQ ID NO 130
<211> LENGTH: 444
<212> TYPE: DNA
<213> ORGANISM: Mus musculus

<400> SEQUENCE: 130

| | |
|---|---|
| cacctgatga ctgtgcagtt gttgctcctg gtgatgtgga tggccgaatg tgctcagtcc | 60 |
| agagctactc gggccaggac tgaacttctc aatgtctgca tggatgccaa acaccacaaa | 120 |
| gaaaaaccgg gccctgagga caatttacac gaccagtgca gcccctggaa gacgaattcc | 180 |
| tgctgttcca cgaacacaag ccaggaagca cataaggaca tttcctacct gtaccggttc | 240 |
| aactggaacc actgcggaac tatgacatcg gaatgcaaac ggcactttat ccaagacacc | 300 |
| tgcctctatg agtgttcccc gaacttggga ccctggatcc agcaggtgga ccagagctgg | 360 |
| cgcaaagagc ggatccttga tgttcccctg tgcaaagagg actgtcagca gtggtgggag | 420 |
| gactgccaga gctcttttac ctgc | 444 |

<210> SEQ ID NO 131
<211> LENGTH: 286
<212> TYPE: DNA
<213> ORGANISM: Mus musculus
<220> FEATURE:
<221> NAME/KEY: modified_base
<222> LOCATION: (263)
<223> OTHER INFORMATION: N = A, C, G, or T/U

<400> SEQUENCE: 131

```
caacaaccca ttcaaacatc taccctatca actttcaata atagtcacca tacctaccat      60
aataaccacg aataacaaaa aatcataatt caattccaaa taagaatcct aagaaactac     120
taccacatcc aaataataca gcatacactc aaattaccca ctcccgaccc aagaaaattt     180
aacgaaaaat aacaatacaa tactctttcg aagccctata attaaaataa atccacttta     240
aatcctttaa cgaagatcca ttngagaaca attctgctga tatcac                    286
```

<210> SEQ ID NO 132
<211> LENGTH: 590
<212> TYPE: DNA
<213> ORGANISM: Homo sapiens
<220> FEATURE:
<221> NAME/KEY: modified_base
<222> LOCATION: (18)..(577)
<223> OTHER INFORMATION: N = A, C, G, or T/U

<400> SEQUENCE: 132

```
aagattatgc ctcccccnaa ttcggcacga ngcggggagc gagcggnccc cctccctgtc      60
cgtctcctgg tcggggtcct tttttaataa cgcgtaaacc tatccaangg tacacaacga     120
agaagcttgg acaaaaggcg gaaaagcgtc ttgccaaaag ggggactgga ngtnaactgg     180
aaaaaaacta attttccaag agaagaactt ggnagaaagg ggaattgngt ttcngggggtg    240
nccttctcgn tctccggggn cgnanttctg natncgcaac aagcaaggac caatccaatc     300
ccgggnacgc gggcggnccc anccgcgaag nttttcannc ccganaatcc aaacaatcct     360
ggccnaagaa atatgccctt gngtaacaaa ccntcccaat ttttttaata tatcccaaan    420
tnttattatt aaaacaaatg ctnaaanccc tccactcccn nanggttaaa naaatggggt     480
ccnnttggca ccaactttaa tgggangttt gggnttanaa anaaacaccc cttccntttt     540
cccggggngc gttatttggg gnngcacccc ccccgcnctt taattttgtt                590
```

<210> SEQ ID NO 133
<211> LENGTH: 247
<212> TYPE: DNA
<213> ORGANISM: Mus musculus

<400> SEQUENCE: 133

```
atgggaatat cccccataca atagtacttc ttgtgcccaa tctggcccca gtgccgtcat      60
tatgggtccc tgcgtgagag gtcattttct tctttagatt tttcctctat ttacccttgg    120
tctggttcaa ttcttcaaag aataaggaag ttttgagcct gcttccaccc ctttcttctt    180
tcatccagtt cctgatccat gttgggggtt ggggtttcta caatcatttt caataaatct    240
atgacac                                                              247
```

<210> SEQ ID NO 134
<211> LENGTH: 665
<212> TYPE: DNA
<213> ORGANISM: Pseudopleuronectes americanus
<220> FEATURE:

<221> NAME/KEY: modified_base
<222> LOCATION: (40)  (596)
<223> OTHER INFORMATION: N = A, C, G, or T/U

<400> SEQUENCE: 134

| gaattcggca cgagccagta gcatatgctt gtctcaaagn ttaagccatg caagtctaag | 60 |
| tacacacggc cggtacagtg aaactgcgaa tggctcatta atcagttat ggttcctttg | 120 |
| atcgctctca cgttacttgg ataactgtgg caattccaga gctaatacat gccaacgggc | 180 |
| gctgacctcc ggggacgcgt gcatttatca gacccaaaac ccatgcgggg tgctcctcac | 240 |
| ggggtgcccc ggccgctttg gtgactctag ataacctcga gctgatcgct ggccctcgtg | 300 |
| gcggcgacgt ctcattcgaa tgtctgccct atcaactttc gatggtactt tttgtgccta | 360 |
| ccatggtgac cacgggtaac ggggaatcag ggttcgattc cggagaggga gcctgagaaa | 420 |
| cggctaccac atccaaggaa ggcagcaggc gcgcaaatta cccactcccg actcggggag | 480 |
| gtagtgacga aaaataacaa tacaggactc tttcgaggcc ctgtaattgg aatgagtaca | 540 |
| ctttaaatcc tttaacgaag atccattgga gggcaagtct ggtgccagca gccgcnggta | 600 |
| attcagctcc aatagcgtat cttaaagttg ctgcaattaa aaagctccgt attggacctc | 660 |
| ggatc | 665 |

<210> SEQ ID NO 135
<211> LENGTH: 666
<212> TYPE: DNA
<213> ORGANISM: Pseudopleuronectes americanus

<400> SEQUENCE: 135

| gaattcggca cgagcagtag catatgcttg tctcaaagat taagccatgc aagtctaagt | 60 |
| acacacggcc ggtacagtga aactgcgaat ggctcattaa atcagttatg gttcctttga | 120 |
| tcgctctcac gttacttgga taactgtggc aattccagag ctaatacatg ccaacgggcg | 180 |
| ctgacctccg gggacgcgtg catttatcag acccaaaacc catgcggggt gctcctcacg | 240 |
| ggtgccccg gccgctttgg tgactctaga taacctcgag ctgatcgctg ccctcgtgg | 300 |
| cggcgacgtc tcattcgaat gtctgcccta tcaactttcg atggtactttttgtgcctac | 360 |
| catggtgacc acgggtaacg gggaatcagg gttcgattcc ggagagggag cctgagaaac | 420 |
| ggctaccaca tccaaggaag gcagcaggcg cgcaaattac ccactcccga ctcggggagg | 480 |
| tagtgacgaa aaataacaat acaggactct ttcgaggccc tgtaattgga atgagtacac | 540 |
| tttaaatcct taacgagga tccattggaa ggcaagtctg gtgccagcag ccgcggtaat | 600 |
| tccagctcca atagcgtatc ttaaagttgc tgcagttcaa caagcctcgt attggacctc | 660 |
| ggattc | 666 |

<210> SEQ ID NO 136
<211> LENGTH: 645
<212> TYPE: DNA
<213> ORGANISM: Pseudopleuronectes americanus
<220> FEATURE:
<221> NAME/KEY: modified_base
<222> LOCATION: (508)..(569)
<223> OTHER INFORMATION: N = A, C, G or T/U

<400> SEQUENCE: 136

| gaattcggca cgaggcggta ttcaggcgac cgggcctgct ttgaacactc taattttttc | 60 |
| aaagtaaacg cttcggaccc cgcgggacac tcagctaaga gcatcgaggg ggcgccgaga | 120 |
| ggcaggggct gggacagacg gtagctcgcc tcgcggcgga ccgtcagctc gatcccgagg | 180 |

```
tccaactacg agcttttta  ctgcagcaac tttaagatac gctattggag ctggaattac    240
cgcggctgct ggcaccagac ttgccctcca atggatcctc gttaaggat  ttaaagtgta    300 ctcattccaa ttacagggcc tcgaaagagt cctgtattgt tattttcgt  cactacctcc    360 ccgagtcggg agtgggtaat ttgcgcgcct gctgccttcc ttggatgtgg tagccgtttc    420
tcaggctccc tctccggaat cgaaccctga ttccccgtta cccgtggtca ccatggtagg    480
cacaaaaagt accatcgaaa gttgatangg cagacattcg aatgagacgt cccgccacga    540
aggccagcga tcagctcgag gttatctana gtcaccacag cggccggggc acccgttga     600 ggaaccaccg ccgcattggg ggttttgggt ctgaataaat tgcac                    645
```

<210> SEQ ID NO 137
<211> LENGTH: 542
<212> TYPE: DNA
<213> ORGANISM: Pseudopleuronectes americanus
<220> FEATURE:
<221> NAME/KEY: modified_base
<222> LOCATION: (18)..(504)
<223> OTHER INFORMATION: N = A, C, G, or T/U

<400> SEQUENCE: 137

```
gaattcggca cgaggctnga cctccgggga cgcgtgcatt tatcagaccc aaaacccatg     60
cggggtgctc ctcacggggt gccccggccg ctttggtgac tctagataac ctcgagctga    120
tcgctggccc tcgtggcggc gacgtctcat tcgaatgtct gccctatcaa ctttcgatgg    180 tacttttgt  gcctaccatg gtgaccacgg gtaacgggga atcagggttc gattccggag    240
agggagcctg agaaacggct accacatcca aggaaggcag caggcgcgca aattacccac    300
tcccgactcg ggggaggtagt gacgaaaaat aacaatacag gactctttcg aggccctgta    360
attggaatga gtacactta  aatccttta  cnaggatcca ttggagggca agtctggtgc    420
catcagccgc ggtaattcca gctccaatan cgtatcttaa agttggctgc acttaaaaag    480
ctcntanttg gacctcggga tccnagctga cggtccgccg ctaagcgaac ttaccgtctg    540
tc                                                                   542
```

<210> SEQ ID NO 138
<211> LENGTH: 650
<212> TYPE: DNA
<213> ORGANISM: Pseudopleuronectes americanus
<220> FEATURE:
<221> NAME/KEY: modified_base
<222> LOCATION: (626)
<223> OTHER INFORMATION: N = A, C, G or T/U

<400> SEQUENCE: 138

```
gaattcggca cgagcagtag catatgcttg tctcaaagat taagccatgc aagtctaagt     60
acacacggcc ggtacagtga aactgcgaat ggctcattaa atcagttatg gttcctttga    120
tcgctctcac gttacttgga taactgtggc aattccagag ctaatacatg ccaacgggcg    180
ctgacctccg gggacgcgtg catttatcag acccaaaacc catgcggggt gctcctcacg    240
gggtgccccg ccgctttggg tgactctaga taacctcgag ctgatcgctg gccctcgtgg    300
cggcgacgtc tcattcgaat gtctgcccta tcaactttcg atggtacttt ttgtgcctac    360
catggtgacc acgggtaacg gggaatcagg gttcgattcc ggagagggag cctgagaaac    420
ggctaccaca tccaaggaag gcagcaggcg cgcaaattac ccactcccga ctcggggagg    480
tagtgacgaa aaataacaat acaggactct ttcgaggccc tgtaattgga atgagtacac    540
```

```
tttaaatcct ttaacgagga tccattggag ggcaagtctg gtgccagcag ccgccggtaa    600
ttccagctcc atagcgtatc ttaaanttgc ctgccagtta aataagcctc              650
```

<210> SEQ ID NO 139
<211> LENGTH: 709
<212> TYPE: DNA
<213> ORGANISM: Pseudopleuronectes americanus

<400> SEQUENCE: 139

```
gaattcggca cgagtggccg tccctcttaa tcatggcccc agttcagaga agaaaaccca     60
caaaatagaa ccggagtcct attccattat tcctagctgc ggtattcagg cgaccgggcc    120
tgctttgaac actctaattt tttcaaagta aacgcttcgg accccgcggg acactcagct    180
aagagcatcg agggggcgcc gagaggcagg ggctgggaca gacggtagct cgcctcgcgg    240
cggaccgtca gctcgatccc gaggtccaac tacgagcttt ttaactgcag caactttaag    300
atacgctatt ggagctggaa ttaccgcggc tgctggcacc agacttgccc tccaatggat    360
cctcgttaaa ggatttaaag tgtactcatt ccaattacag ggcctcgaaa gagtcctgta    420
ttgttatttt tcgtcactac ctccccgagt cgggagtggg taatttgcgc gcctgctgcc    480
ttccttggat gtggtagccg tttctcaggc tccctctccg gaatcgaacc ctgattcccc    540
gttacccgtg gtcaccatgg taggcacaaa aagtaccatc gaaagttgat agggcagaca    600
ttccgaatga gacgtcgccg ccaccgaggg ccagcggatc tagctcgagg ttatctagag    660
tcaccaaaag ccggccgggg caccccgtga ggaacacccc gccattggg               709
```

<210> SEQ ID NO 140
<211> LENGTH: 679
<212> TYPE: DNA
<213> ORGANISM: Pseudopleuronectes americanus

<400> SEQUENCE: 140

```
gaattcggca cgaggtcagc tcgatcccga ggtccaacta cgagcttttt aactgcagca     60
actttaagat acgctattgg agctggaatt accgcggctg ctggcaccag acttgccctc    120
caatggatcc tcgttaaagg atttaaagtg tactcattcc aattacaggg cctcgaaaga    180
gtcctgtatt gttattttc gtcactacct ccccgagtcg ggagtgggta atttgcgcgc    240
ctgctgcctt ccttggatgt ggtagccgtt tctcaggctc cctctccgga atcgaaccct    300
gattccccgt tacccgtggt caccatggta ggcacaaaaa gtaccatcga aagttgatag    360
ggcagacatt cgaatgagac gtcgccgcca cgagggccag cgatcagctc gaggttatct    420
agagtcacca aagcggccgg ggcaccccgt gaggagcacc ccgcatgggt tttgggtctg    480
ataaatgcac gcgtccccgg aggtcagcgc ccgttggcat gtattagctc tggaattgcc    540
acagttatcc aagtaacgtg agagcgatca aggaaccat aactgattta atgagccatt    600
cgcagtttca ctgtaccggc cgtgtgtatt agacttgcat ggcttaatct ttgagacaag    660
catatctcgt gccgaattc                                                 679
```

<210> SEQ ID NO 141
<211> LENGTH: 611
<212> TYPE: DNA
<213> ORGANISM: Pseudopleuronectes americanus

<400> SEQUENCE: 141

```
gaattcggca cgaggcccta tcaactttcg atggtacttt ttgtgcctac catggtgacc     60
acgggtaacg gggaatcagg gttcgattcc ggagagggag cctgagaaac ggctaccaca    120
```

```
tccaaggaag gcagcaggcg cgcaaattac ccactcccga ctcggggagg tagtgacgaa      180
aaataacaat acaggactct ttcgaggccc tgtaattgga atgagtacac tttaaatcct      240
ttaacgagga tccattggag ggcaagtctg gtgccagcag ccgcggtaat tccagctcca      300
atagcgtatc ttaaagttgc tgcagttaaa aagctcgtag ttggacctcg ggatcgagct      360
gacggtccgc cgcgaggcga gctaccgtct gtcccagccc ctgcctctcg gcgccccctc      420
gatgctctta gctgagtgtc ccgcggggtc cgaaacgttt actttgaaaa aattagagtg      480
ttcaaagcag gcccggtcgc ctgaataccg catctaggaa taatggaata ggactccggt      540
tctattttgt gggttttctt ctctgaactg gggccatgat taagaaggac ggccgggctc      600
gtgccgaatt c                                                          611

<210> SEQ ID NO 142
<211> LENGTH: 476
<212> TYPE: DNA
<213> ORGANISM: Pseudopleuronectes americanus
<220> FEATURE:
<221> NAME/KEY: modified_base
<222> LOCATION: (335)
<223> OTHER INFORMATION: N = A, C, G, or T/U

<400> SEQUENCE: 142
gaattcggca cgaggtgccc ttccgtcaat tcctttaagt ttcagctttg caaccatact       60 cccccggaa cccaaagact ttggtttccc ggacgctgcc cggcgggtca tgggaataac      120
gccgccggat cgctagttgg catcgtttac ggtcggaact acgacggtat ctgatcgtct      180
tcgaacctcc gactttcgtt cttgattaat gaaaacattc ttggcaaatg ctttcgcttt      240
cgtccgtctt gcgccggtcc aagaatttca cctctagcgg cacaatacga atgcccccgg      300
ccgtccctct taatcatggc cccagttcag agaanaaaac ccacaaaata gaaccggagt      360
cctattccat tattcctagc tgcggtattc aggcgaccgg gcctgctttg aacactctaa      420
ttttttcaaa gtaaacgctt cggaccccgc gggacactca gcctcgtgcc gaattc         476

<210> SEQ ID NO 143
<211> LENGTH: 740
<212> TYPE: DNA
<213> ORGANISM: Pseudopleuronectes americanus
<220> FEATURE:
<221> NAME/KEY: modified_base
<222> LOCATION: (526)
<223> OTHER INFORMATION: N = A, C, G or T/U

<400> SEQUENCE: 143
gaattcggca cgaggctgcg gtattcaggc gaccgggcct gctttgaaca ctctaatttt       60
ttcaaagtaa acgcttcgga ccccgcggga cactcagcta agagcatcga gggggcggaa      120
ttcggcacga gctgggacag acggtagctc gcctcgcggc ggaccgtcag ctcgatcccg      180
aggtccaact acgagctttt taactgcagc aactttaaga tacgctattg gagctggaat      240
taccgcggct gctggcacca gacttgccct ccaatggatc ctcgttaaag gatttaaagt      300
gtactcattc caattacagg gcctcgaaag agtcctgtat tgttattttt cgtcactacc      360
tccccgagtc gggagtgggt aatttgcgcg cctgctgcct tccttggatg tggtagccgt      420
ttctcaggct ccctctccgg aatcgaaccc tgattccccg ttacccgtgg tcaccatggt      480
aggcacaaaa agtaccatcg aaagttgata gggcagacat tcgaangaga cgtcgccgcc      540
acgagggcca gcgatcagct cgaggttatc tagagtcacc aaagcggccg gggcaccccg      600
```

```
tgaggagcac cccgcatggg ttttgggtct gataaatgca cgcgctctct ctctctctct    660
ctctctctct ctctctctct ctctctctct ctctctctct ctctctctct ctctctctct    720
ctctccctcg tgccgaattc                                                 740

<210> SEQ ID NO 144
<211> LENGTH: 334
<212> TYPE: DNA
<213> ORGANISM: Pseudopleuronectes americanus

<400> SEQUENCE: 144
gaattcggca cgaggctgcg gtattcaggc gaccgggcct gctttgaaca ctctaatttt     60
ttcaaagtaa acgcttcgga ccccgcggga cactcagcta agagcatcga ggggcgccg    120 agaggcaggg gctgggacag acggtagctc gcctcgcggc ggaccgtcag ctcgatcccg    180
aggtccaact acgagctttt taactgcagc aactttaaga tacgctattg gagctggaat    240
taccgcggct gctggcacca gacttgccct ccaatggatc ctcgttaaag gatttaaagt    300
gtactcattc caattacagg gcctcgaaag agtc                                334

<210> SEQ ID NO 145
<211> LENGTH: 542
<212> TYPE: DNA
<213> ORGANISM: Pseudopleuronectes americanus
<220> FEATURE:
<221> NAME/KEY: modified_base
<222> LOCATION: (516)..(521)
<223> OTHER INFORMATION: N = A, C, G, or T/U

<400> SEQUENCE: 145
gaattcggca cgagtacttg gataactgtg gcaattccag agctaataca tgccaacggg     60
cgctgacctc cggggacgcg tgcatttatc agacccaaaa cccatgcggg gtgctcctca    120
cggggtgccc cggccgcttt ggtgactcta gataacctcg agctgatcgc tggccctcgt    180
ggcggcgacg tctcattcga atgtctgccc tatcaacttt cgatggtact ttttgtgcct    240
accatggtga ccacgggtaa cggggaatca gggttcgatt ccggagaggg agcctgagaa    300
acggctacca catccaagga aggcagcagg cgcgcaaatt ccccactccc gactcgggga    360
ggtagtgacg aaaaataaca atacaggact cttttcgagg cctgtaattg gaatgagtac    420
actttaaatc ctttaacgag gatccattgg agggcaagtc tggtgccagc agccgcggta    480
attccagctc caatagcgta tcttaaagtt gcctcntgcc naatcctgca gccggggat    540 cc                                                                    542

<210> SEQ ID NO 146
<211> LENGTH: 532
<212> TYPE: DNA
<213> ORGANISM: Pseudopleuronectes americanus

<400> SEQUENCE: 146
cgtccgtctt gggccggtcc aagaatttca cctctagcgg cacaatacga atgccccgg      60 ccgtccctct taatcatggc cccagttcag agaagaaaac ccacaaaata gaaccggagt    120
cctattccat tattcctagc tgcggtattc aggcgaccgg gctgctttg aacactctaa    180 ttttttcaaa gtaaacgctt cggaccccgc gggacactca gctaagagca tcgagggggc    240
gccgagaggc aggggctggg acagacggta gctcgcctcg cggcggaccg tcagctcgat    300
cccgaggtcc aactacgagc tttttaactg cagcaacttt aagatacgct attggagctg    360
gaattaccgc ggctgctggc accagacttg ccctccaatg gatcctcgtt aaaggattta    420
```

```
aagtgtactc attccaatta cagggcctcg aaagagtcct gtattgttat ttttcgtcac    480
tacctccccg agtcgggagt gggtaatttg cgcgcctgct gccttccttg ga            532

<210> SEQ ID NO 147
<211> LENGTH: 1135
<212> TYPE: DNA
<213> ORGANISM: Cricetulus griseus

<400> SEQUENCE: 147
gggcggcgac ggtttcctgg tggccgcgcg ctgctctgtg agcggcgggt ggcagacgga     60
cctgggccct cacccagac gcaccgcgga tctggcatgg ctcacctgat gacaatgcag    120
ttgctgctcc tgctgatatg ggtatctgag tgtgcccaat caagagctac tcgggccaga    180
actgaactgc tcaatgtttg catggatgca aagcaccaca agaaaaagcc aggccctgag    240
gacaatttac acaaccagtg cagtccctgg aagaagaatt cctgctgttc caccaacaca    300
agccaggaag cccacgagga catttcctac ctgtaccgat caactgggac ccactgtgga    360
aagatgacat tggaatgcaa gcgacacttt atccaggata cctgtctcta tgagtgttct    420
cctaacttgg gaccctggat tcagcaggtg gaccagagct ggcgaaaaga gcgaatcctt    480
gatgttcctc tgtgcaaaga ggactgtcag cgatggtggg aggactgccg cacctctttc    540
acctgcaaga gcaactggca aaggggtgg aactggacct cggggtataa ccagtgccct    600
gtgggagcct cctgtcgcca cttcgacttc tatttcccta cacctgctgc tctgtgtgag    660
gaaatctgga gtcactccta caaactcagt aactacagcc gagggagtgg ccgctgtatc    720
cagatgtggt tcgacccagc ccaaggcaac cccaacgagg aagtggcaag gttctatgct    780
gaggccatga gtggagctgg gcttcacggg gcctggccac taatgtgcag cctgtctttc    840
gtgctgctct gggtgttcag ccgagttcct ttaaccttct gatccccagg aactccctgc    900
cgggcttaga ctcccagctc ccaacctcct ttgtggtggg gcctctgaca ggcattcaat    960
atctctctta tgaattattt gggtgtgaat gggaatataa ttattttgca tcctacttac   1020
cactgattga agttgtttaa acttggttag ttccctgctc taacacttac tgtgggcaag   1080
ttaaataaac ttaattttcc tgtgctgttc cacaaaaaaa aaaaaaaaaa aaaaa         1135

<210> SEQ ID NO 148
<211> LENGTH: 70
<212> TYPE: DNA
<213> ORGANISM: Mus musculus

<400> SEQUENCE: 148
atcggacgcc cccgtgtcg gtgacgaccc attcgaacgt ctgccctatc aactttcgat     60
ggtagtcgct                                                            70

<210> SEQ ID NO 149
<211> LENGTH: 470
<212> TYPE: DNA
<213> ORGANISM: Mus musculus

<400> SEQUENCE: 149
gtggacgaag actgtagaga ctacccagag tctgacctag ggagaggcca actcggatac     60
ccctatgtgc gctcccagaa gctaaggaca ttgagacaga aagacatggc ctggaaacag    120
acaccactct tgcttttggt ctacatggtc acaacaggca gtggcgggac agaacagacc    180
tactcaacgt ttgcatggat gccaaacacc ataagacaaa gccgggcccc gaggacaagc    240
```

```
tgcatgacca gtgtagtcca tggaagaaaa atgcctgttg ctcagtcaac accagccagg      300
agctacacaa ggctgactcc cgtctgtact tcaactggga tcactgtggc aagatggagc      360
ctgcctgtaa gagtcacttc atccaagact cctgcctgta tgagtgctcc ccaaccttgg      420
ccttggatca gcaagtggac agagttggcg taagagcgtt ctggatgtgc                 470

<210> SEQ ID NO 150
<211> LENGTH: 387
<212> TYPE: DNA
<213> ORGANISM: Mus musculus

<400> SEQUENCE: 150
gagaattagg gttcgattcc ggagagggag cctgagaaac ggctaccaca tccaaggaag      60
gcagcaggcg cgcaaattac ccaatcctga cacggggagg tagtgacaat aaataacaat     120
accgggctct tcgagtctgg taattggaat gagtacaatc taaatccctt aacgaggatc     180
cattggaggg caagtctggt gccagcagcc gcggtaattc cagctccaat agcgtatatt     240
taagttgttg cagttaaaaa gctcgtagtt gctgtcttta ggggactctc actctcctgc     300
ttgtcgttgt gttcttaagg tcttgtcttt attgccggtt gatgtactgc tagtcgtaat     360
tgctctcatt tgccctgtcg tttccgt                                         387

<210> SEQ ID NO 151
<211> LENGTH: 22
<212> TYPE: DNA
<213> ORGANISM: Mus musculus

<400> SEQUENCE: 151
cgccgtgcct accatggtga cc                                              22

<210> SEQ ID NO 152
<211> LENGTH: 46
<212> TYPE: DNA
<213> ORGANISM: Homo sapiens

<400> SEQUENCE: 152
gggccccgcg ggacactcag ctaaaagcat cgagggggcg ccgaga                    46

<210> SEQ ID NO 153
<211> LENGTH: 635
<212> TYPE: DNA
<213> ORGANISM: Gossypium hirsutum
<220> FEATURE:
<221> NAME/KEY: modified_base
<222> LOCATION: (565)
<223> OTHER INFORMATION: N = A, C, G, or T/U

<400> SEQUENCE: 153
ctaaatccct taacgaggat ccattggagg gcaagtctgg tgccagcagc cgcggtaatt      60
ccagctccaa tagcgtatat ttaagttgtt gcagttaaaa agctcgtagt tggacttagg     120
ggtgggtcgg ccggtccgcc tcacggtgag caccggtctg ctcgtcccta ctgccggcga     180
tgcgctcctg gccttaattg gccgggtcgt tcctccggcg ctgttacttt gaagaaatta     240
gagtgctcaa agcaggccta cgcttgtata cattagcatg gataacatc ataggatttc      300 gatcctattg tgttggcctt cgggatcgga gtaatgatta acagggacag tcggggcat      360 tcgtatttca tagtcagagg tgaaattctt ggatttatga agacgaaca actgcgatag      420 catttgccaa ggatgttttc attaatcaag aacgaaagtt gggggctcga aaacgatcag     480
ataccgtcct agtctcaacc ataaatctcc tccagttccg gaaccacatc ctccgccagt     540
```

```
tccagtctat aagaaaacac atccnactcc agttccagta tacaagatac catgtcctcc    600
ccagttccag tctataaatc tcctccggtt ccatt                                635

<210> SEQ ID NO 154
<211> LENGTH: 584
<212> TYPE: DNA
<213> ORGANISM: Gossypium hirsutum
<220> FEATURE:
<221> NAME/KEY: modified_base
<222> LOCATION: (389)..(513)
<223> OTHER INFORMATION: N = A, C, G, or T/U

<400> SEQUENCE: 154
ggataaccgt agtaattcta gagctaatac gtgcaacaaa ccccgacttc tggaagggat    60
gcatttatta aataaaaggt cgacgcgggc tttgcccgtt gctctgatga ttcatgataa    120
ctcgacggat cgcacggcct tgtgccggc gacgcatcat tcaaatttct gccctatcaa    180
ctttcgatgg taggatagtg gcctactatg gtggtgacgg gtgacggaga attagggttc    240
gattccggag agggagcctg agaaacggct accacatcca aggaaggcag caggcgcgca    300
aattacccaa tcctgacacg gggaggtatt gacaataaat aacaataccg ggctctatga    360
gtctggtaat tggaatgagt acaatctana tcccttaacg aagatccatt ggagggcaat    420
tctggtgcca ncanccgcgg taattccact cccatancgt atatttaagt gtttgcagtc    480
aaaaagctcg taattggact taggggtggg tcngccggtc cccctcacgg tgagcacggg    540
tctgctcttc cctactgcgg gcgatgccct cctggcctta attg                     584

<210> SEQ ID NO 155
<211> LENGTH: 65
<212> TYPE: DNA
<213> ORGANISM: Pig

<400> SEQUENCE: 155
ggattcctgc tgcttttgac cacagttctt tctgcaggac aagcatggcc cttgggagag    60
cacgg                                                                65

<210> SEQ ID NO 156
<211> LENGTH: 959
<212> TYPE: DNA
<213> ORGANISM: Pig

<400> SEQUENCE: 156
gatgagggag tccaggagtt ccagcaagct cgacctgctt aacactccca gacggtcaca    60
ggattcagga caagcatggc ccttgggaga gcacggctgc tgctgctctt ggtgtgtgtg    120
gctgtcacat gggcggcccg gcctgatctc ctcaacatct gcatggacgc caagcaccac    180
aagaccaagc ccggcccgga agatggcctg catgagcagt gcagcccctg ggagatgaac    240
gcctgctgct ccgtcaacac cagccaagaa gcccataacg acatctccta cctgtacaaa    300
ttcaactggg agcactgcgg caagatgaag ccggcctgca gcgccactt cattcaagac    360 acctgtctct atgagtgctc gcccaacctg gggcctgga tccaggaggt gaaccagaag    420
tggcgcagag agcggatcct gaacgtgccc ctctgcaaag aggactgtca gaactggtgg    480
gaagactgcc gcacctccta cacctgcaag agcaactggc acgagggctg gaactggagc    540
tcagggtata accggtgccc cgcgaacgcc gcctgccacc ccttcgactt ctacttcccc    600
acgcctgctg ccctgtgcag ccagatctgg agcaactcct acaaacaaag caactacagc    660
```

```
cggggcagcg gccgctgcat ccagatgtgg ttcgacccgg aacagggcaa ccccaacgag      720
gtggtggcga gatactacgc ccagatcatg agtggcgctg ggctctccga ggcctggcct      780
ctccagttcg gcctggccct gacgctgctc tggctgctga gctgagcttc tgtcttcgga      840
gagctggaca gccctcccct gttcggcccc acagcaccca gctcgtcagt gcctcagtgg      900
tggtggtagt ggtggtggtg gtggcggcgg ggggactctg aataaaccag tcaccccac       959
```

```
<210> SEQ ID NO 157
<211> LENGTH: 1218
<212> TYPE: DNA
<213> ORGANISM: Pig

<400> SEQUENCE: 157
gacactgctt ccgggtgggc ctccaggagg gccgaggcag aggagcctct gcctgtgggt       60
gaagcactgg ctggcgaact ccggaagggg aggtccggag aggtggtgcc tcccccgca      120 gcaaagctca gactgcactg tcctcaggtg gcagtggtgt cctaccactt ggcacagacc     180
tccacgggcc cttcatcgct tggctccact gtgctgtggg gtaagcggcg cggggaggga     240
cgacgatctg ggcttggaag ggaaacagga atctggcca agaagcttac ggcagctttc      300
tggcagaagt ggatcaacat ggcctggcgg ctgacgctct tcgtgctcct gggtttggtg     360
gctgctgtgg ggggcgcccg ggccaagtcg acatgctca atgtctgcat ggatgccaag      420
caccacaagc caaagccaag cccggaggac aagctgcacg accagtgcag ccctggagg     480 aagaactcct gctgctcagt caacaccagc ctagaagccc ataaagacat ctcctacctg     540
tacagattca actgggacca ctgcggcaag atggagccgg cctgcaagcg ccacttcatt     600
caagacacct gtctctatga gtgctcgccc aacctggggc cctggatcca ggaggtgaac     660
cagaagtggc gcagagagcg gatcctgaac gtgcccctct gcaaagagga ctgtcagatc     720
tggtgggaag actgccgtac ctcctacacc tgcaagagca actggcacaa gggctggaac     780
tggacctcag ggtataacca gtgcccagtg agcgccgcct gccaccgctt cgacttctac     840
ttccccacgc ccgctgccct gtgcaacgag atctggagcc actcctttga agtcagcagc     900
tacagccggg gcagcggccg ctgcatccag atgtggttcg acccggccca gggcaaccccc   960 aacgaggcgg tggcgagata ctatgcagag aatgggatg ctggggccgt ggcccagggg    1020
atcgggcctc tcctgaccaa cttgacggag atggtgaaac actgggtcac cggctaagct    1080 gttccccgc cgaccctgc tttccgccca caccccctgg gttactctcc gggtggcctc      1140
agcaccccgg tcattggctc ctgatctaag atccgatggg gagcctctga tggcctcttc   1200
caatacaata tccacgtg                                                  1218
```

```
<210> SEQ ID NO 158
<211> LENGTH: 406
<212> TYPE: DNA
<213> ORGANISM: Mus musculus

<400> SEQUENCE: 158
ctcagtcgca catagataaa attggccttt atttggagac gggtttgttc ttctatgttt      60
aatcctcggg tgaaatgacc tgaagatatt tgtgtctgtt ttccgcatgg tcaagcaggg     120
agtggagaga ggcctgggct gggccaggtt ttctgggctt tttcctgtgc tccgagtagg     180
tgggttgtat tttacccagt aggagtggaa gactccttgg cgcttggtgc ttcaaccgga     240
ctgacttcct gggcctggag ttggcgatta gaggtctgac atggctcacc tgatgactgt     300
gcagttgttg ctcctggtga tgtggatggc cgaatgtgct cagtccagag ctactcgggc    360
```
caggactgaa cttctcaatg tctgcatgga tgccaaacac cacaaa 406

<210> SEQ ID NO 159
<211> LENGTH: 1303
<212> TYPE: DNA
<213> ORGANISM: Mus musculus

<400> SEQUENCE: 159
gctgacggct ctagaagtcc ccaacctgtt gtgatcttca gtagacaaac actcctggtg 60
tgtcacagga ttcaggccac taaacctcgg ccggctgtct cctggaatga agaaagcaaa 120
ggaagcctag agtggagaca agaagcccg aggcactctg agagctgcca tcttttcctt 180
gtttgccgcc tgacacttct cagcaggatc cacataccct aagggagtgg agagaggcct 240
gggctgggcc aggttttctg gcttttttcc tgtgctccga gtaggtgggt tgtattttac 300
ccagtaggag tggaagactc cttggcgctt ggtgcttcaa ccggactgac ttcctgggcc 360
tggagttggc gattagaggt ctgacatggc tcacctgatg actgtgcagt tgttgctcct 420
ggtgatgtgg atggccgaat gtgctcagtc cagagctact cgggccagga ctgaacttct 480
caatgtctgc atggatgcca aacaccacaa agaaaaaccg ggccctgagg acaatttaca 540
cgaccagtgc agcccctgga agacgaattc ctgctgttcc acgaacacaa gccaggaagc 600
acataaggac atttcctacc tgtaccggtt caactggaac cactgcggaa ctatgacatc 660
ggaatgcaaa cggcactttta tccaagacac ctgcctctat gagtgttccc cgaacttggg 720
accctggatc cagcaggtgg accagagctg gcgcaaagag cggatccttg atgttcccct 780
gtgcaaagag gactgtcagc agtggtggga ggactgccag agctctttta cctgcaagag 840
caattggcac aagggatgga actggtcctc ggggcataac gagtgtcctg tgggagcctc 900
ctgccatccc ttcaccttct acttccccac atctgctgct ctgtgtgagg aaatctggag 960
tcactcctac aagctcagca actacagtcg agggagcggc cgctgcattc agatgtggtt 1020
cgacccagcc cagggcaacc ccaacgagga agtggcgagg ttctatgccg aggccatgag 1080
tggagctggg tttcatggga cctggccact cttgtgcagc ctgtccttag tgctgctctg 1140
ggtgatcagc tgagctcctg ttttaccttc agttgtctgg agcgccaccc tgcttggctc 1200
agcctcccag ctcccagcct cctttgtggt ggggctctga cagcctcttt aataaaccag 1260
acattccaca tgtgccttat gaattaaaaa aaaaaaaaa aaa 1303

<210> SEQ ID NO 160
<211> LENGTH: 70
<212> TYPE: DNA
<213> ORGANISM: Mus musculus

<400> SEQUENCE: 160
cccgttaaag gatttaaagt ggacctcatc caattacagg gccttgaaag aatcctgtat 60
tgttatattt 70

<210> SEQ ID NO 161
<211> LENGTH: 822
<212> TYPE: DNA
<213> ORGANISM: Mus musculus
<220> FEATURE:
<221> NAME/KEY: modified_base
<222> LOCATION: (719)  (781)
<223> OTHER INFORMATION: N = A, C, G, or T/U

<400> SEQUENCE: 161

```
ataaggcaca tgtggaatgt ctggttgatt aaagaggctg tcagagcccc accacaaagg      60
aggctgggag ctgggaggct gagccaagca gggtggcgct ccagacaact gaaggtaaaa     120
caggagctca gctgatcacc cagagcagca ctaaggacag gctgcacaag agtggccagg     180
tcccatgaaa cccagctcca ctcatggcct cggcatagaa cctcgccact tcctcgttgg     240
ggttgccctg ggctgggtcg aaccacatct gaatgcagcg gccgctccct cgactgtagt     300
tgctgagctt gtaggagtga ctccagattt cctcacacag agcagcagat gtggggaagt     360
agaaggtgaa gggatggcag gaggctccca caggacactc gttatgcccc gaggaccagt     420
tccatccctt gtgccaattg ctcttgcagg taaaagagct ctggcagtcc tcccaccact     480
gctgacagtc ctctttgcac aggggaacat caaggatccg ctctttgcgc cagctctggt     540
ccacctgctg gatccagggt cccaagttcg ggaacactc atagaggcag gtgtcttgga     600
taaagtgccg tttgcattcc gatgtcatag tttcgcaggg ttccagttga accggtacag     660
gtaggaaatg tccctatgtg cttcctggct ttgtgtcgtg aacagcagga atcgtcttnc     720
aggggctgcc actgtcgtgt aaattgcctc angggcccgt ttttctttg tgtggtgcat      780 ncatgcagac aatttgaaat cagtcctggc cgagtagctc tg                        822

<210> SEQ ID NO 162
<211> LENGTH: 185
<212> TYPE: DNA
<213> ORGANISM: Mus musculus

<400> SEQUENCE: 162
aaggcctggt aattaaaaag gctgcaaagc cccacccaaa ggaggttggg agctgggagg     60
ttgacccaac cagggtggcc ctccaaacaa ctgaaggtaa acaggagct cagttgatca     120 cccaaagcag cattaaggac aggcttgcca aaagtggcca ggtcccatga aacccagttc     180
cattc                                                                 185

<210> SEQ ID NO 163
<211> LENGTH: 347
<212> TYPE: DNA
<213> ORGANISM: Mus musculus

<400> SEQUENCE: 163
gtagttgctg agcttgtagg agtgactcca gatttcctca cacagagcag cagatgtggg     60
gaagtagaag gtgaagggat ggcaggaggc tcccacagga cactcgttat gccccgagga    120
ccagttccat cccttgtgcc aattgctctt gcaggtaaaa gagctctggc agtcctccca    180
ccactgctga cagtcctctt tgcacagggg aacatcaagg atccgctctt tgcgccagct    240
ctggtccacc tgctggatcc agggtcccaa gttcggggaa cactcataga ggcaggtgtc    300
ttggataaag tgccgtttgc attccgatgt catagttccg cagtggt                   347

<210> SEQ ID NO 164
<211> LENGTH: 43
<212> TYPE: DNA
<213> ORGANISM: Mus musculus

<400> SEQUENCE: 164
taccacaacc aaagaaagca ttacacgcgc atattaccca ctg                        43

<210> SEQ ID NO 165
<211> LENGTH: 556
<212> TYPE: DNA
<213> ORGANISM: Mus musculus
```

```
<220> FEATURE:
<221> NAME/KEY: modified_base
<222> LOCATION: (501)
<223> OTHER INFORMATION: N = A, C, G or T/U

<400> SEQUENCE: 165
gagagttgaa cttgccaccc acttcaggga tctctggtac cacaaggtct tgtttctctc      60
tctctcttgg aggcaggcta ctcaggtcta gctactggcg gctctccaca cctgtagctc     120
atagaagctg aaggctgata aagggcagt gggtggagcg ccctcagccc gctcacctct      180
ttggcatcag gaggagcaac aggagggccc tgccttgaag gtcatggcac agtggtggca     240
gatcctcttg gggttgtggg cagtcctacc caccttggca ggggacaaac tgctcagcgt     300
ctgcatgaat tccaagcgcc acaagcaaga acctggccca gaagacgaac tctaccagga     360
gtgcaggcct tgggaggaca atgcctgctg cacacgttcc acaagttggg aagcccacct     420
tgaggagccc ttgctcttta acttcagcat gatgcactgt ggactgctga ccccggcctg     480
tcgcaaagca ctcattccag nccatttgtt tccatgatgt tcccccaacc tggggccctg     540
gatcccaccc gtgtcc                                                      556

<210> SEQ ID NO 166
<211> LENGTH: 353
<212> TYPE: DNA
<213> ORGANISM: Mus musculus

<400> SEQUENCE: 166
acacagagca gcagatgtgg ggaagtagaa ggtgaaggga tggcaggagg ctcccacagg      60
acactcgtta tgccccgagg accagttcca tcccttgtgc caattgctct tgcaggtaaa     120
agagctctgg cagtcctccc accactgctg acagtcctct ttgcacaggg gaacatcaag     180
gatccgctct ttgcgccagc tctggtccac ctgctggatc cagggtccca aagttcggga     240
acactcatag aggcaggtgt cttggataag tgccgttgca ttccgatgtc atagttccgc     300
agtggttcag ttgacccgta cggtaggaat gtcctatgtg cttctggctg tgt           353

<210> SEQ ID NO 167
<211> LENGTH: 58
<212> TYPE: DNA
<213> ORGANISM: Mus musculus

<400> SEQUENCE: 167
cccccggggc cggaaggggg aaatttgccc cccggcgccc ttcctgggag ggggaacc        58

<210> SEQ ID NO 168
<211> LENGTH: 49
<212> TYPE: DNA
<213> ORGANISM: Homo sapiens

<400> SEQUENCE: 168
cggcgaacac catcgaaagt taatagggca gacgttcaaa taggtcgtc                  49

<210> SEQ ID NO 169
<211> LENGTH: 448
<212> TYPE: DNA
<213> ORGANISM: RAT
<220> FEATURE:
<221> NAME/KEY: modified_base
<222> LOCATION: (387)
<223> OTHER INFORMATION: N = A, C, G or T/U

<400> SEQUENCE: 169
```

```
cggccgctcc ctcggctgta gttgctgagc ttgtaggaat gactccagat tttctcacac    60
agaacagcag gtgtagggaa gtagaaagtg aagggatggc aggaggctcc cacagggcac   120
tcattatgcc ccgaggtcca gttccatccc ttgtgccagt tgctcttgca ggtaaaagag   180
ctcttgcagt cctcccacca cagcacacag tcttctttgc acagggaac atcaaggatc    240 cgctctttgc gccagctctg gtccacctgc tggatccagg gtcccaagtt cggggaacac   300
tcatagaggc aagtgtcttg gataaagtga cgtttgcact ccggggtcat agttccacag   360
tgattccagt tgaatcggta caggtangaa atgtccttat gtgcttggca tccatgcaga   420
cattgagaag ttcgcctcgt gccgaatt                                      448

<210> SEQ ID NO 170
<211> LENGTH: 435
<212> TYPE: DNA
<213> ORGANISM: RAT
<220> FEATURE:
<221> NAME/KEY: modified_base
<222> LOCATION: (378)
<223> OTHER INFORMATION: N = A, C, G, or T/U

<400> SEQUENCE: 170
tttttttttt ttttttaga tgtgtcatag atttattgaa aatgattgtt gtagaaaccc    60
caagccccaa catggatcag gaactggatg gcagaggaga ggggtggaag caggctcaag   120
acttccttat tctttgaaga gttgaaccaa ccgagaccaa gggtagctag aggagaagac   180
tggcctcagt cagggagcca taatgacagc actggggcca ggctgggcac aagaagtatt   240
gctgcatggt acacagtccc agatgtcata aggaagcat agaacttcac cacttcctca    300
ttgggattgc cctgggttga gtcaaaccac atctggatgc actggccact ccctctgcta   360
tagttgctga cccttgtanga gtgactccag agaccctcac aaaggctggc tggtgtcggg   420
aaatagtact gaaat                                                    435

<210> SEQ ID NO 171
<211> LENGTH: 429
<212> TYPE: DNA
<213> ORGANISM: RAT
<220> FEATURE:
<221> NAME/KEY: modified_base
<222> LOCATION: (387)
<223> OTHER INFORMATION: N = A, C, G or T/U

<400> SEQUENCE: 171
cggccgctcc ctcggctgta gttgctgagc ttgtaggagt gactccagat tttctcacac    60
agaacagcag gtgtagggaa gtagaaagtg aagggatggc aggaggctcc cacagggcac   120
tcattatgcc ccgaggtcca gttccatccc ttgtgccagt tgctcttgca ggtaaaagag   180
ctcttgcagt cctcccacca cagcacacag tcttctttgc acagggaac atcaaggatc    240 cgctctttgc gccagctctg gtccacctgc tggatccagg gtcccaagtt cggggaacac   300
tcatagaggc aggtgtcttg gataaagtga cgtttgcact ccggggtcat agttccacag   360
tgattccagt tgaatcggta caggtangaa atgtccttat gtgcttcctg gcttgtgttg   420
gtggagcag                                                           429

<210> SEQ ID NO 172
<211> LENGTH: 427
<212> TYPE: DNA
<213> ORGANISM: RAT

<400> SEQUENCE: 172
```

```
cggccactcc ctcggctgta gttgctgagc ttgtaggagt gactccagat tttctcacac        60
agaacagcag gtgtagggaa gtagaaagtg aagggatggc aggaggctcc cacagggcac       120
tcattatgcc ccgaggtcca gttccatccc ttgtgccagt tgctcttgca ggtaaaagag       180
ctcttgcagt cctcccacca cagcacacag tcttctttgc acaggggaac atcaaggatc       240
cgctctttgc gccagctctg gtccacctgc tggatccagg gtcccaagtt cggggaacac       300
tcatagaggc aggtgtcttg gataaagtga cgtttgcact ccggggtcat agttccacag       360
tgattccagt tgaatcggta caggtaggaa atgtccttat gtgcttcctg gcttgtgttg       420
gtggagc                                                                 427

<210> SEQ ID NO 173
<211> LENGTH: 382
<212> TYPE: DNA
<213> ORGANISM: RAT

<400> SEQUENCE: 173
cggccgctcc ctcggctgta gttgctgagc ttgtaggagt gactccagat tttctcacac        60
agaacagcag gtgtagggaa gtagaaagtg aagggatggc aggaggctcc cacagggcac       120
tcattatgcc ccgaggtcca gttccatccc ttgtgccagt tgctcttgca ggtaaaagag       180
ctcttgcagt cctcccacca cagcacacag tcttctttgc acaggggaac atcaaggatc       240
cgctctttgc gccagctctg gtccacctgc tggatccagg gtcccaagtt cggggaacac       300
tcatagaggc aggtgtcttg gataaagtga cgtttgcact ccggggtcat agttccacag       360
tgattccagt tgaatcggta ca                                                382

<210> SEQ ID NO 174
<211> LENGTH: 52
<212> TYPE: DNA
<213> ORGANISM: Homo sapiens

<400> SEQUENCE: 174
aaggcccggg aactcccatc aaaagttgtt agggcaaact ttcaaatggg tc                52

<210> SEQ ID NO 175
<211> LENGTH: 847
<212> TYPE: DNA
<213> ORGANISM: Mus musculus
<220> FEATURE:
<221> NAME/KEY: modified_base
<222> LOCATION: (520)..(717)
<223> OTHER INFORMATION: N = A, C, G or T/U

<400> SEQUENCE: 175
aattcggatc catgggctga tctggaagta taaacaagaa aggaggctga cggctctaga        60
agtccccaac ctgttgtgat cttcagtata caaacactcc tggtgtgtca caggattcag       120 ctctgttttcc taggccacta aacctcggcc ggctgtctcc tggaatgaag aaagcaaagg       180
aagcctatag tggagacaaa gaagcccgag gcactctgag agctgccatc ttttccttgt       240
ttgccgcctg acacttctca gcaggatcca catacccctaa ggagtggaag actccttggc       300
gcttggtgct tcaaccggac tgacttcctg tgcctggagt tggcgattag actctgcctt       360
cagggtctga catggctcac ctgatgactg tgcagttgtt gctcctggtg atgtggatgg       420
ccgaatgtgc tcagtccata gctactcggg ccaggactga acttctcaat gtctgcatgg       480
atgcctaaca ccacaaagat aaaccgtccc tgaggacatn tacacgacca gtgcagcccc       540
```

```
tgcaagacaa ttactgctgt tccactaaca caagccagga agcacataat gacatttcct      600
acctgtaccg tttcactgga accactgctg aactatgaca tcggaatgca tacggcacta      660
tatccaagac acttgctcta tgagtgttcc cccgacttgt gaccctgtat tcagcangtg      720
gaacatgact tgcgcatata cggatccttg atgttcccct gtgcaaagag gactgtcagc      780
attgatgtga tgactgccat agctctttac ctgtcagaac atttgtccat ggtatgtaac      840
tgttcct                                                                847

<210> SEQ ID NO 176
<211> LENGTH: 326
<212> TYPE: DNA
<213> ORGANISM: Homo sapiens

<400> SEQUENCE: 176
gggtcatttc cacatgcttt attccagcaa tcaaataat taaaaacatc tcaaattatt        60
atacacatac aaaataggta cagagtcttt tgcttcctcc caccccagg gggaaaaact       120 gctttgtgct ttgggaagtt gtctctgaaa cccggggaca gaggacgcag acagactag       180 gagggagccg ggaggatggg ctgcagctgt ggaggagggt ttcagaggag agaggtcgga     240
gagcagaggc ctgagaagcc tgattccccg tcacccgtgg tcaccatggt aggcacggca     300
actaccatcg aaagttgatg ggcaga                                            326

<210> SEQ ID NO 177
<211> LENGTH: 4409
<212> TYPE: DNA
<213> ORGANISM: Homo sapiens

<400> SEQUENCE: 177
actagttgtc tgttgctgca taacaaatca ttccataatt ttgtggtgta ttgctgcaga        60
caatgttaaa ctaagtggat gaaaaggata ttcacatagt ctcagagtgt ctccctacaa      120
ggtaggatta ctaacaaagg gaaactaata attatatagt aaggaaatct ccttaaccca      180
ataatcacca gcaataagat gcagcaaccc tcatcatgta cctcttgata tgatgcactg      240
acaaaagcac ctctcttctc taattttctt gccaaaatcg ataagctcaa gctaattaca      300
ggaaaatata gacaaaccca aattgaggga cattctgcaa ataactgaa cagtaattct       360 ccaaaagtgt caaggtcata aaagacaaag acattgagga ctgtcacaga ttggagggag     420 actaaggga catgacaact acatgcaacc tggaatcatg gactgaatcc tgggccagag      480
aaggacattg ggggggaact ggtgtaaagg gcataaagct tgtagattag ttaacagtat      540
tgcctcaata ttaattccct gattttttta agaactgggc tttggttaca aagatgcca       600 atattttgggg aagttgcata aaaacatacg ggaaatcttt tgacgatgtt ttgcagttt       660 tctgcaaatc taaaattatt tcaaaacaaa aagtttaaaa atcaaataca catagttgct      720
tgaaatagta actattttat tatattccaa gatgttgtga gtcaggaatt tggccaaaac     780
tcaggtgggc gattcttctg caaagacccc cacaacacat tcaaagtcac aggcagaggt     840
tgttggggga gggcattgaa aagaagagaa gagtcatagg tgggtgcaat ggagggaggg    900
cagagggctg ctgactatgt gcaggactca tccataatgg agccctgggg aggcaagggc    960
ttcataacta gacactggtc ttgtcacctc agactcacct gtagcaggac cagatactga   1020
ggtcagactg aaaacacagg ctctgcctca ggagaggctc tctactagct gagtaaatga   1080
tgacagtatt ggaaatgttc ccaacatcat aatgggaaaa catcacttca cactacataa   1140
gcaatacaca ggggcagtgc cggtcgtctt cccaggttag tagcagttct actgcctcca   1200
```

```
agagtgttgg agaaatacaa accaagcatt aggcactttt aacttgaaaa catgaagttc    1260
tctttcctaa ctttctttgt ttccttattt cttcttcttc ttcttcttct tcttcttctt    1320
cttcttcttc ttcttcttct tcttcttctt cttcttcttc ttcctcttct tcttcttctt    1380
cttctttctt cttcttctcc ttctccttt ccttcttctt tttttgctga gacagggtct     1440
cactctgaca gtacagtggt gccatcacag ctcactgcag cctcgacctc agggctcaa    1500 gcaatcctcc cagctcaccc tcccaaatgg ctgaaactac aagctcgcac caccatacgt    1560
ggctaatttt tctatttttg tgtgcagatg aagttttcct atgttgccca agtggtctca    1620
aactcctggg atcaagtgat ccatccacct caacctccca aaacgctggg attacaggtg    1680
taagccacca cacccagccc actaactttt ttatatcggc taatgaaata gttttaagtt    1740
tagaccctac gaggcataaa gaaataattt tagttatgtt atcagatgta cagtaatact    1800
caagtgtgca actgtggata acttgagttc atgaggtttt tgtttttttg tcaaaagaat    1860
aaatttatag tgaaactacc caaaaaagca aagtacagaa cagtatgcta ccatttgtgc    1920
acagaaatgg gatatatatg gtgtaactgc atcgaattta ctggatgtat gtccagggac    1980
cagaactctt ggtggcttca tgttcatact tttgcaagca catgtgtagt atccttaact    2040
taaaggtact gttgtataca ttctagtgtt atcaaaattt acatacatat tatcaagtca    2100
gagaggtcat tctgtgtctt agtattttca cttcatattt ggtatattta tgtatgtata    2160
cacacatacc tatatgtatt taaataagat ttatagtcac atggtccaaa aatcaaaaca    2220
atgtggaaag gtttacagag aaaagtctca agcctaatcc tgttctctac tgccaggtga    2280
ccatgttatt aatttctttt cataccttgc cacagaattt tcacctgcaa acacagatat    2340
tcttttcttt tttaatgaca gagtcacgtt ctgttatcca ggctggagtg cagtggcgtg    2400
atcttggctc actgcaaact cctcccgggt tcaagtgatt ctcctgtctc agcctcctga    2460
gtagctggga ttacaggcat gtgccaccac acccagctaa ttttgtatt tttagtacag     2520 atggggtttt atcatattga ccaggctgat gtcgaactcc tgacctcaag tgatccgcct    2580
gcctcggcct cccacagtgc tgggattaca ggcgtgagcc accacgccca gtcaacacag    2640
acattcttac tccttttta cagagaattt attattatta ttttttacat agcatttttc     2700
tgcacctttc tttttccact taacaatgca cttgaagatt tttccatatt tgtacatcag    2760
gagctttctc tttctttgtt accacattaa attccactgg gtagatgtac cataatttaa    2820
ctgggtcctt attgaaagac aattgagctg tctcctagac aaagccttgt gcaccttccc    2880
gaacagaggg tctaaccaag caggcaggat ggggttataa agtaggtggg gaggtgggag    2940
agactccacc ttcccaggtg ggctgagaat ggaggtaagg ccctgcaaca ggacagaggg    3000
aaaagtgggg atgagaggtg ggaggcgaga tagcgcccac tgttctcgct cagcccctc    3060 ctccgtttgc cgctgacctg ttggcctccc ccaacctctg agcctgcctc tgcctaggta    3120
atttcccaag acccagaagg ggtgaagggt gaggtgtgat tgcccccacc tccttgcctc    3180
ccgcagcatc tgctccggga ccatgaacaa tagctgacag ctccatggcc cttgctgtcc    3240
ccatctcagc ttccctgggc atctaaacct cagctgccat ggggtaggag gacaggctga    3300
ggaagcagaa gcctgaggct gtctagagtc tcactcctgc atcagcaggc caccacctgt    3360
ggttcctcct tgtgcaaatt tgaaaagaat tgcataaaac actggagaaa tccaagaggg    3420
gaagtccaca agggcggtgg ctccctacaa ggtcacagag caagctggtg tcagagcctg    3480
gacctacagc gctgttggtg gaggtcctgc ctccaggtag gggaagggct ccctctcacc    3540
```

```
tctacacgca gcgcatttct tggctcagct gccctgtagg ggatgcaggg tggggacagc    3600
agagatctgg gcctgggagg gagagagtac acaatcacat ggctgttgcc cctgtctcag    3660
gccttgtcta cctctgactg tggctctctg gcaggaatag atggacatgg cctggcagat    3720
gatgcagctg ctgcttctgg ctttggtgac tgctgcgggg agtgcccagc ccaggagtgc    3780
gcgggccagg acggacctgc tcaatgtctg catgaacgcc aagcaccaca agacacagcc    3840
cagccccgag gacgagctgt atggccaggt gagggcagcc tggtgtagga cagcatgcac    3900
acaggtcaga gggtgatggc acgagcaatg gcaggtccag tgtggtcaga accaagggtg    3960
ccgctgctga caaggaaggg gaggggcggc caggccacc atgccacagg taaggccact     4020
gaggcagctt ggggaatatg agctccaatt tgaactccag gctcaggagt gtgcttgtat    4080
ttcattcctc tggtctcctg gcctgctccc tacaaggttt cacattccca gagggctggg    4140
gatgtgccta gggagagact gtggcgtgga cacaatctgt gggttaaagc gaagacagga    4200
cagcctggaa gccccatgac atctgagtca ctcccaacat tccatttgct tattttttaaa   4260 tcggggttaa aaaaaaaaaa caaatacata acatacattt tccactttgg ccattttaa    4320 ctgtacggtt cagtggcatt aggtatgctc atgtggttgt gcaaccatca ccaccatcca    4380
tctcctgacc tctgtgattc tccaaaact                                      4409
```

<210> SEQ ID NO 178
<211> LENGTH: 847
<212> TYPE: DNA
<213> ORGANISM: Mus musculus
<220> FEATURE:
<221> NAME/KEY: modified_base
<222> LOCATION: (645) (712)
<223> OTHER INFORMATION: N = A, C, G, or T/U

<400> SEQUENCE: 178

```
aattcggatc catgggctga tctggaagta taaacaagaa aggaggctga cggctctaga      60
agtccccaac ctgttgtgat cttcagtaga caaacactcc tggtgtgtca caggattcag     120 ctctgttttcc taggccacta aacctcggcc ggctgtctcc tggaatgaag aaagcaaagg    180
aagcctagag tggagacaaa gaagcccgag gcactctgag agctgccatc ttttccttgt    240
ttgccgcctg acacttctca gcaggatcca catacccta ggagtggaag actccttggc    300
gcttggtgct tcaaccggac tgacttcctg ggcctggagt tggcgattag actctgcctt    360
cagggtctga catggctcac ctgatgactg tgcagttgtt gctcctggtg atgtggatgg    420
ccgaatgtgc tcagtccaga gctactcggg cccagactga acctctcatg tctgatggat    480
gccaaacacc acatagaata accgggccct gaggacaatt tacacgacca gtgcagcccc    540
tggaagacga aatcctgctg ttccacgaac acaagccagg aagcacataa ggacatttcc    600
tacctgtacc ggttcaactg gaaccactgc ggaactatga catcngcaat gcanacggca    660
ctttatccaa gacacctgcc tctatgagtg ttccccgaac ttgggacact gnatccagca    720
ggtgggacca aagcttgcgc caaagagcgg atcccttgat gtttcccctg gcaaagagg    780 actgtccagc agttgtgggg aggactgcca gaagctcttt tacctgccag agcaatttgc    840
accaggg                                                              847
```

<210> SEQ ID NO 179
<211> LENGTH: 541
<212> TYPE: DNA
<213> ORGANISM: Mus musculus

<400> SEQUENCE: 179

```
gtagttgctg agcttgtagg agtgactcca gatttcctca cacatagcag cagatgtggg    60
gaagtagaag gtgaagggat ggcaggaggc tcccacagga cactcgttat gccccgagga   120
ccagttccat cccttgtgcc aattgctctt gcaggtaaaa gagctctggc agtcctccca   180
ccactgctga cagtcctctt tgcacagggg aacatcaagg atccgctctt tgcgccagct   240
ctggtccacc tgctggatcc agggtcccaa gttcggggaa cactcataga ggcaggtgtc   300
ttggataaag tgccgtttgc attccgatgt catagttccg cagtggttcc agttgaaccg   360
gtacaggtag gaaatgtcct tatgtgcttc ctggcttgtg ttcgtggaac agcaggaatt   420
cgtcttccag gggctgcact ggtcgtgtaa attgtcctca gggcccggtt tttctttgtg   480
gtgtttggca tccatgcaga cattgagaag ttcagtcctg gcccgagtag ctctggactg   540
a                                                                   541
```

<210> SEQ ID NO 180
<211> LENGTH: 525
<212> TYPE: DNA
<213> ORGANISM: Mus musculus

<400> SEQUENCE: 180

```
acacagtagt tttcagatgt ggggaagtag aaggtgaagg gagggcagga tgctcccaca    60
ggacactcgt tatgccccga ggaccagttc catcccttgt gccaattgct cttgcaggta   120
aaagagctct ggcagtcctc ccaccactgc tgacagtcct ctttgcacag gggaacatca   180
aggatccgct ctttgcgcca gctctggtcc acctgctgga tccagggtcc caagttcggg   240
gaacactcat agaggcaggt gtcttggata agtgccgtt tgcattccga tgtcatagtt   300
ccgcagtggt tccagttgaa ccggtacagg taggaaatgt ccttatgtgc ttcctggctt   360
gtgttcgtgg aacagcagga attcgtcttc caggggctgc actggtcgtg taaattgtcc   420
tcagggcccg ttttctttt gtggtgtttg gcatccatgc agacattgag aagttcagtc   480
ctggcccgag tagctctgga ctgagcacat tcggccatcc acatc                   525
```

<210> SEQ ID NO 181
<211> LENGTH: 805
<212> TYPE: DNA
<213> ORGANISM: Mus musculus
<220> FEATURE:
<221> NAME/KEY: modified_base
<222> LOCATION: (535)..(740)
<223> OTHER INFORMATION: N = A, C, G or T/U

<400> SEQUENCE: 181

```
gtggacgaag actgtagaga ctacccagag tctgacctag ggagaggcca actcggatac    60
ccctatgtgc gctcccagaa gctaaggaca ttgagacaga aagacatggc ctggaaacag   120
acaccactct tgcttttggt ctacatggtc acaacaggca gtggccggga cagaacagac   180
ctactcaacg tttgcatgga tgccaaacac cataagacaa agccgggccc cgaggacaag   240
ctgcatgacc agtgtagtcc atggaagaaa aatgcctgtt gctcagtcaa caccagccag   300
gagctacaca aggctgactc ccgtctgtac ttcaactggg atcactgtgg caagatggag   360
cctgcctgta agagtcactt catccaagac tcctgcctgt atgagtgctc ccccaacctt   420
gggccttgga tccagcaagt ggaccagagt tggcgtaaag agcgttttct ggatgtgccc   480
ctatgcaaag aggactgtca ccagtggtgg aagcctgtc gtacctcctt taccntgcag   540
agagactggc atanaggctg ggactggtcc tcaggcatta acaagtgccc anacacagca   600
```

```
ccctgtcaca cgtntgagta ctacttcccg acaccagcca gcctttgcga gggtctctgg    660
agtcactcct acaaggtcag caaactacag cagaggagtg gccgctgcat ccagatgtgg    720
ttgactcacc ccanngcann tcgaaatgag acgtggtgaa gtttatgctt ctttatacat    780
ctgggatgtg cccatgcaca gtact                                         805
```

<210> SEQ ID NO 182
<211> LENGTH: 585
<212> TYPE: DNA
<213> ORGANISM: Mus musculus
<220> FEATURE:
<221> NAME/KEY: modified_base
<222> LOCATION: (511)..(513)
<223> OTHER INFORMATION: N = A, C, G or T/U

<400> SEQUENCE: 182

```
acacagagca gcagatgtgg ggaagtagaa ggtgaaggga tggcaggagg ctcccacagg     60
acactcgtta tgccccgagg accagttcca tcccttgtgc caattgctct tgcaggtaaa    120
agagctctgg cagtcctccc accactgctg acagtcctct ttgcacaggg gaacatcaag    180
gatccgctct ttgcgccagc tctggtccac ctgctggatc cagggtccca agttcgggga    240
acactcatag aggcaggtgt cttggataaa gtgccgtttg cattccgatg tcatagttcc    300
gcagtggttc cagttgaacc ggtacaggta ggaaatgtcc ttatgtgctt cctggcttgt    360
gttcgtggaa cagcaagaat tcgtcttcca ggggctgcac tggtcgtgta aattgtgctc    420
atggccctgg tcttctttag tgtgtttagc atccatgcag acatcgagaa gatcagtcct    480
ggtccgagta gctctggact gagcacagtc ngncattcac atcatccaga gcaacaactg    540
cacagtcatc aggtgagcca tgtcagaccc tgatgcagag tctaa                   585
```

<210> SEQ ID NO 183
<211> LENGTH: 584
<212> TYPE: DNA
<213> ORGANISM: Mus musculus
<220> FEATURE:
<221> NAME/KEY: modified_base
<222> LOCATION: (557)
<223> OTHER INFORMATION: N = A, C, G or T/U

<400> SEQUENCE: 183

```
tgggtcataa attgattgaa aatgattgta gaaaccccaa cccccaacat ggatcaggaa     60
ctggatgaca gaggagaggg gtggaagcag gctcaaaact tccttattct ttgaagagtt    120
gaaccagacc aagggtagat agaggagaaa tctaaagagg aagactgacc tctcagccag    180
ggagccataa tgacagcact ggggccaggc tgggcacaag aagtactgct gcatggggca    240
cagtcccaga tgtcataaag gaagcataaa acttcaccac gtcctcattc ggattgccct    300
gggttgagtc aaaccacatc tggatgcagc ggccactccc tctgctgtag ttgctgacct    360
tgtaggagtg actccagaga ccctcgcaaa ggctggcttg tgtcgggaag tagtactcaa    420
acgtgtgaca gggtgctgtt gttgggcacc ttgttaatgc ctgaggacca gtcccagcct    480
tattgcaatc tttccttgcag gtaaaggagg acgacaggct tccaccactg gtgcagtcct    540
ctttgataag ggacatncag aaacgctctt acgccactct ggtc                    584
```

<210> SEQ ID NO 184
<211> LENGTH: 85
<212> TYPE: DNA
<213> ORGANISM: Mus musculus

<400> SEQUENCE: 184

```
ctatccattc gaacgtgtgc catatcatct tctgatgtac caacccgtgc ctaccatgtg      60
gaccacgggt gactggcaat ccaga                                            85

<210> SEQ ID NO 185
<211> LENGTH: 70
<212> TYPE: DNA
<213> ORGANISM: Mus musculus
<220> FEATURE:
<221> NAME/KEY: modified_base
<222> LOCATION: (9)
<223> OTHER INFORMATION: N = A, C, G or T/U

<400> SEQUENCE: 185
attccccgnc cccggggtc accaggggag gcgcgggac taccattaaa agttgatagg        60
gcaaactttt                                                             70

<210> SEQ ID NO 186
<211> LENGTH: 576
<212> TYPE: DNA
<213> ORGANISM: Manduca sexta
<220> FEATURE:
<221> NAME/KEY: modified_base
<222> LOCATION: (187)..(530)
<223> OTHER INFORMATION: N = A, C, G or T/U

<400> SEQUENCE: 186
gaactagggc ggtatctaat cgccttcgaa cctctaactt tcgttcttga ttgatgaaaa      60
cacctttggc aaatgctttc gctgatgttc gtcttgcgac gatccaagaa tttcacctct     120
aacgtcgcaa tacgaatgcc cccagttatc cctattaatc attacctcgg agttctgaaa    180
accaacnaaa tagaaccgag atcatattct attattccat gcacgaaata ttcaagcagc    240
attttgagcc cgctttgagc actctaattt gttcaaagna aaattgtcgg cccatctcga    300
cactcaccga agagcaccgc gataggattt tgatattgaa ccgacgtttg ttacaacgcc    360
ggctcaccga cnatatgctc cgcagacgtg tcagtatcac cgcggatgcg gtgcaccgac    420
agcncggcgc acaaatgcan ctacnagctt tttaaccgca acaattttag tatacgctat    480
tggagctggg aattaccgcg gctgctggca ccagacttgc cctcaattgn cctcgttaaa    540
atatttaaag tgtctcattc cgattacgaa gcctcg                              576

<210> SEQ ID NO 187
<211> LENGTH: 295
<212> TYPE: DNA
<213> ORGANISM: Mus musculus
<220> FEATURE:
<221> NAME/KEY: modified_base
<222> LOCATION: (154)..(195)
<223> OTHER INFORMATION: N = A, C, G or T/U

<400> SEQUENCE: 187
cagcgagcct ttgcggggt gtctggagtg actcctacga ggtgagcgac tacagcagag      60
ggagtggccg ctgcgtccag atgtggtttg agtcagccca gggcgatccc aatgaggacg    120
tggtggagtt ttatgcttcc tttatgacat ctgngactgt gccccatgca gcagtagttc    180
ttgtgcccag cctnngccca gtgctgtcat tatagctccc tggctgagag gtcagtgttc    240
ctctctagat ttcgtcctct atctaccctt ggtgctggtt cagctcttca gagaa         295

<210> SEQ ID NO 188
<211> LENGTH: 85
<212> TYPE: DNA
```

```
<213> ORGANISM: Mus musculus

<400> SEQUENCE: 188
cagctcacct cctgttttac cttcacttct ctccacgccc caccctcgct tcgcgctcac    60
gcctcccagc tcccacgcct ccttt                                          85

<210> SEQ ID NO 189
<211> LENGTH: 88
<212> TYPE: DNA
<213> ORGANISM: Mus musculus

<400> SEQUENCE: 189
cctcccggct cctgcccgag ggtcgggcgc ctgcggcttt ggtgacttta gattacctcg    60
ggccgatcgc acgcccccg tggcggcg                                        88

<210> SEQ ID NO 190
<211> LENGTH: 369
<212> TYPE: DNA
<213> ORGANISM: Mus musculus
<220> FEATURE:
<221> NAME/KEY: modified_base
<222> LOCATION: (93)..(353)
<223> OTHER INFORMATION: N = A, C, G or T/U

<400> SEQUENCE: 190
gtctctctct ctcttctctt gcttcgctct cttgcttttc tctctctctt gcttttcgc     60 tctcttgctt ctcgctctct cttgcttctt gcnctctttt cctgaagatg taagaataaa   120
gctttgccgc agaagattct ggtctgtggt gttcttcctg gccggtcgtg anaacgcgtc   180
taataacaat tggtgccgaa ttccgggang anaaaatccg ggacgagaaa aaaactccgg   240
antggcgcag gagggatact tcattccagg aancagaact gcgaatcaag gttanaaggg   300
atcncgtnac acagattgat tgagaagnnn tccnactggc cgaattcnag aanctcatcg   360
cttggggaa                                                           369

<210> SEQ ID NO 191
<211> LENGTH: 332
<212> TYPE: DNA
<213> ORGANISM: Mus musculus
<220> FEATURE:
<221> NAME/KEY: modified_base
<222> LOCATION: (309)
<223> OTHER INFORMATION: N = A, C, G, or T/U

<400> SEQUENCE: 191
ggtttttcga gacagggttt ctctgtgtag ccctggctgt ccttgaactc actttgtaga    60
ccaggctggc ctcgaactca gaaatccgcc tgcctctgcc tcccaagtgc tgggattaaa   120
ggcattcgcc accaccaacc ggcgataaac aaatttttata cgaaagaaaa gaagcaagta   180
agattatgag aaacataagc tattttaaga gagtttagag aagatccttc aaatatttta   240
aaagagatct gaataaatca gaaagcatta ttcctggata aataatgggg agagaaataa   300
tagattaana tacaacctat caaaatttaa tc                                 332

<210> SEQ ID NO 192
<211> LENGTH: 331
<212> TYPE: DNA
<213> ORGANISM: Mus musculus
<220> FEATURE:
<221> NAME/KEY: modified_base
<222> LOCATION: (295)..(308)
<223> OTHER INFORMATION: N = A, C, G or T/U
```

<400> SEQUENCE: 192

```
cgagacaggg tttctctgtg cagtcctgga actcactctg tagaccaggc tggccttgaa      60
ctcagaaatc cacctgcctc tgcctcccaa gtgctgggat tgcaggcatg cgccaccact     120
gcctggctgc ctggtttttt aattactggc tttagcctaa atggcaaatt ctataactag     180
gttataagaa tagttttaaa agaaagagcc tcaggagagt gggaacagga acatggagaa     240
gtaagaggac acctgggctt tagtcaagat cctgtctaaa acaaaacaga ggggncggna     300
gagctngngc aatggctcag ttggttagag c                                    331
```

<210> SEQ ID NO 193
<211> LENGTH: 67
<212> TYPE: DNA
<213> ORGANISM: Homo sapiens

<400> SEQUENCE: 193

```
ccgccacggg ggggtcgcga tcggtccgag gttatctaga gtcaccaaag ccgccggcgt      60
cgtcccc                                                                67
```

<210> SEQ ID NO 194
<211> LENGTH: 593
<212> TYPE: DNA
<213> ORGANISM: Mus musculus
<220> FEATURE:
<221> NAME/KEY: modified_base
<222> LOCATION: (489)..(578)
<223> OTHER INFORMATION: N = A, C, G or T/U

<400> SEQUENCE: 194

```
ctctctccag gtattcctac ctaaccttaa cttttcctcg ggttcaagac ccttggaaag      60
gcctgtatac ttattttgtg aaccatattt tctctttgtt cctactcttt cttcccgctt     120
tacttctgat agcttgtcct gaatttcctc tagaattttc agcccatatct taaccactat    180
ataacatgtg aaaaggaaca aaagggcttc taacactaga aaaaattcaa ggccaaacat     240
aacttgtaaa gccatttttcc actttacttc tgatagactg tcttgaattt ccttagaaag    300
ttcaagatca gacttacctc gttccccagc tgaaaagttc tgaattcata cagttgaatc     360
ctcttaacag tctggcttta cgggaacctt atcaccgtcg ttccccagct ggatgagttc     420
tgaatcggca gttgaatcct tctcaacagt ctgtgttacg ggaaccttat aacctggatt     480
cgcagttcng ggttctggga aggaaagtaa tcccctcctg gcggccagtn ccgggagntt     540
ttttcctcgg tcccgggatt tttcctcggt ccccgggnaa ttcgggcacc caa             593
```

<210> SEQ ID NO 195
<211> LENGTH: 58
<212> TYPE: DNA
<213> ORGANISM: Homo sapiens

<400> SEQUENCE: 195

```
tgggtccgtt cctaaaacaa aaaaaaaaaa acagcggtcc tattccaata ttcctagc        58
```

<210> SEQ ID NO 196
<211> LENGTH: 22
<212> TYPE: DNA
<213> ORGANISM: Homo sapiens

<400> SEQUENCE: 196

```
tgggcagacg ttcgaatggg tc                                               22
```

<210> SEQ ID NO 197
<211> LENGTH: 324
<212> TYPE: DNA
<213> ORGANISM: Mus musculus

<400> SEQUENCE: 197

| | | |
|---|---|---|
| gacatcgagc tcactcagtc tccagcttct ttggctgtgt ctctagggca gagggccatc | 60 |
| atctcctgca aggccagcca aagtgtcagt tttgctggta ctagtttaat gcactggtac | 120 |
| caccagaaac caggacagca acccaaactc ctcatctatc gtgcatccaa cctagaagct | 180 |
| ggggttccta ccaggtttag tggcagtggg tctaagacag acttcaccct caatatccat | 240 |
| cctgtggagg aggaggatgc tgcaacctat tactgtcagc aaagtaggga atatccgtac | 300 |
| acgttcggag gggggacaaa gttg | 324 |

<210> SEQ ID NO 198
<211> LENGTH: 351
<212> TYPE: DNA
<213> ORGANISM: Mus musculus

<400> SEQUENCE: 198

| | | |
|---|---|---|
| caggtgcagc tgcagcagtc tggagctgag ctggtgaagc ctggggcttc agtgaagata | 60 |
| tcctgcaagg cttctggtta ctcatttact ggctacttta tgaactgggt gaagcagagc | 120 |
| catgaaaga gccttgagtg gattggacgt attcatcctt acgatggtga actttctac | 180 |
| aaccagaact tcaaggacaa ggccacattg actgtagaca atcctctaa cacagcccac | 240 |
| atggagctcc tgagcctgac atctgaggac tttgcagtct attattgtac aagatacgac | 300 |
| ggtagtcggg ctatggacta ctggggccaa gggaccacgg tcaccgtctc c | 351 |

<210> SEQ ID NO 199
<211> LENGTH: 360
<212> TYPE: DNA
<213> ORGANISM: Homo sapiens

<400> SEQUENCE: 199

| | | |
|---|---|---|
| caggtgcagc tggtggagtc tgggggaggc ttggtacagc cagggcggtc cctgagactc | 60 |
| tcctgcacaa cttctggatt cacttttggt gattatgcta tgatctgggc ccgccaggct | 120 |
| ccagggaagg ggctggagtg ggtctcatcc attagtagta gtagtagtta catatactac | 180 |
| gcagactcag tgaagggccg attcaccatc tccagagaca cgccaagaa ctcactgtat | 240 |
| ctgcaaatga acagcctgag agccgaggac acggctgtgt attactgtgc gagagaacga | 300 |
| tacgattttt ggagtggaat ggacgtctgg ggcaaaggga ccacggtcac cgtgtcgagt | 360 |

<210> SEQ ID NO 200
<211> LENGTH: 333
<212> TYPE: DNA
<213> ORGANISM: Homo sapiens

<400> SEQUENCE: 200

| | | |
|---|---|---|
| cagtctgccc tgactcagcc tgcctcagtg tccgggtctc ctggacagtc cgtctccatc | 60 |
| tcctgcactg gaaccatcaa tgatgttggt ggatataggt ttgtctcctg gtaccaacga | 120 |
| cgccccggca agcccccaa actcatcatt tctgatgtca ttaggcggcc atcagggggtc | 180 |
| cctgatcgct tctctagttc caagtctgac aacacggcct acctgaccat ctctgggctc | 240 |
| caggctgagg acgaggctga ttattactgc agctcatata caagcagcag cactctctat | 300 |
| gtcttcggaa ctgggaccaa ggtcaccgtc cta | 333 |

<210> SEQ ID NO 201
<211> LENGTH: 330
<212> TYPE: DNA
<213> ORGANISM: Homo sapiens

<400> SEQUENCE: 201
cagtctgccc tgactcagcc tgcctccgtg tctgggtctc ctggacagtc gatcaccatc      60
tcctgcactg gaaccagcag tgatgttggg agttataacc ttgtctcctg gtaccaacag     120
cacccaggca agcccccaa actcatgatt tatgagggca gtaagcggcc ctcaggggtt      180
tctaatcgct tctctggctc caagtctggc aacgcggcct ccctgacaat ctctgggctc     240
caggctgagg acgaggctga ttattactgc cagtcctatg acagcagcct gagtgtggta     300
ttcggcggag ggaccaagct gaccgtccta                                      330

<210> SEQ ID NO 202
<211> LENGTH: 349
<212> TYPE: DNA
<213> ORGANISM: Mus musculus

<400> SEQUENCE: 202
acacagagca gcagatgtgg ggaagtagaa ggtgaaggga tggcaggagg ctcccacagg      60
acactcgtta tgccccgagg accagttcca tcccttgtgc caattgctct tgcaggtaaa     120
agagctctgg cagtcctccc accactgctg acagtcctct ttgcacaggg aacatcaag      180 gatccgctct ttgcgccagc tctggtccac ctgctggatc cagggtccca agttcgggga     240
acactcatag aggcaggtgt cttggataaa gtgccgtttg cattccgatg tcatagttcc     300
gcagtggttc cagttgaacc ggtacaggta ggaaatgtcc tcctcgtgc                  349

<210> SEQ ID NO 203
<211> LENGTH: 276
<212> TYPE: DNA
<213> ORGANISM: Homo sapiens

<400> SEQUENCE: 203 tttttttta aattcatgtt tttaattggc ttaatacaaa ggtcccccag gaggccctgg       60 gaggagggg acagcctggg agaggcagag attcatggcc agcagcccac ccccacctgc     120
cacccactcc ccaacaaggg tcccagactc tttcaataat cctaaaaaaa ccgacgagag     180
cgcaggcaga tgaagagccc cttcatcctc aaacggcgac taccatcgaa agttgatagg    240
gcagacgttc gaatgggtcg tcgccgccac gggggg                               276

<210> SEQ ID NO 204
<211> LENGTH: 668
<212> TYPE: DNA
<213> ORGANISM: Mus musculus

<400> SEQUENCE: 204
gatccttcga ctccttggcg cttggtgctt caaccggact gacttcctgg gcctggagtt      60
ggcgattaga ggtctgacat ggctcacctg atgactgtgc agttgttgct cctggtgatg     120
tggatggccg aatgtgctca gtccagagct actcgggcca ggactgaact tctcaatgtc     180
tgcatggatg ccaaacacca caaagaaaaa ccgggccctg aggacaattt acacgaccag     240
tgcagcccct ggaagacgaa ttcctgctgt tccacgaaca caagccagga agcacataag     300
gacatttcct acctgtaccg gttcaactgg aaccactgcg gaactatgac atcggaatgc     360

```
aaacggcact ttatccaaga cacctgcctc tatgagtgtt ccccgaactt gggaccttgg    420
atccagcagg tggaccagag ctggcgcaaa gagcggatcc ttgattgttc ccctgtgcaa    480
agaggactgt catcagtggt gggaggactt gcagagctct tttccctgca agagcaattt    540
ggacaaggga tggaacttgg tctcggggca taacgagtgt cctgtggggc tccttgcaa     600 tccttcacgt tttatttccc agattggttg gtcttgttgt gaggaatctg gggttcactc    660
ttacagct                                                            668

<210> SEQ ID NO 205
<211> LENGTH: 73
<212> TYPE: DNA
<213> ORGANISM: Mus musculus

<400> SEQUENCE: 205
ccagctccaa taacgtatat gagagttgca gcagataagg ggcaagtagt agagtatgga    60
gagagggaga gcg                                                       73

<210> SEQ ID NO 206
<211> LENGTH: 542
<212> TYPE: DNA
<213> ORGANISM: Mus musculus

<400> SEQUENCE: 206
ctgtcaccag tggtgggaag cctgtcgtac ctcctttacc tgcaagagag actggcataa    60
aggctgggac tggtcctcag gcattaacaa gtgcccaaac acagcaccct gtcacacgtt    120
tgagtactac ttcccgacac cagccagcct tgcgagggt ctctggagtc actcctacaa     180
ggtcagcaac tacagcagag ggagtggccg ctgcatccag atgtggtttg actcaaccca    240
gggcaatccc aatgaggacg tggtgaagtt ttatgcttcc tttatgacat ctgggactgt    300
gccccatgca gcagtacttc ttgtgcccag cctggcccca gtgctgtcat tatggctccc    360
tggctgagag gtcagtcttc ctctctagat ttctcctcta tctacccttg gtctggttca    420
actcttcaaa gaataaggaa gtcttgagcc tggttccacc cctctcctct gtcatccagt    480
tcctgatcca tgttgggga tggggttct acatcatttc aataaactat gaacatctgg      540
gc                                                                   542

<210> SEQ ID NO 207
<211> LENGTH: 269
<212> TYPE: DNA
<213> ORGANISM: Mus musculus

<400> SEQUENCE: 207
gacatttcct aactgtaacg ggtcaactgg aagcactgcg gaaatatgac atcggaatgc    60
aaacgggact tttttcaaga cacctgcctc tatgagtgtt ccccgaattt ggaccttgat    120
tcagcaggtg gagcaaaact tgcgcaagaa ggggttcctg aagttcccct gtgcaaaaag    180
gactttcaca attggttgga ggatttccaa agctctttta cccgcaagag gaatttgcac    240
aagggtttga acatgtcctc ggggaataa                                      269

<210> SEQ ID NO 208
<211> LENGTH: 785
<212> TYPE: DNA
<213> ORGANISM: Mus musculus

<400> SEQUENCE: 208
attcggatcc ttcaaaccct ggccggctgt ctcctggaat gaagaaagca aaggaagcct    60
```

```
agagtggaga caaagaagcc cgaggactct gagagctgcc atctttttcct tgtttgccgc    120 ctgacacttc tcagcaggat ccacataccc taaggagtgg aagactcctt ggcgcttggt    180
gcttcaaccg gactgacttc ctgggcctgg agttggcgat tagaggtctg acatggctca    240
cctgatgact gtgcagttgt tgctcctggt gatgtggatg ccgaatgtg ctcagtccag     300 agctactcgg gccaggactg aacttctcaa tgtctgcatg gatgccaaac accacaaaga    360
aaaaccgggc cctgaggaca atttacacga ccagtcagc ccctggaaga cgaattcctg     420
ctgttccacg aacacaagcc aggaagcaca taaggacatt cctacctgt accggttcaa     480 ctggaaccac tgcggaacta tgacatcgga atgcaaacgg cactttatcc aagacacctg    540
cctctatgag tgttccccga acttgggacc ctggatccag caggtggacc agagctggcg    600
caaagagcgg atccttgatg ttccctgtg caagaggact gtcagcagtg gtgggaggac     660
tgccagagct ctttaccct gcagagcaat ggcacaagg gtggaatggt ccccgggca       720 taacgatttc ccgtggaggc ttctggaatc ccttaacctc taattcccaa tctgcggcct    780
gtgtg                                                                785

<210> SEQ ID NO 209
<211> LENGTH: 718
<212> TYPE: DNA
<213> ORGANISM: Mus musculus

<400> SEQUENCE: 209
attcggatcc ttcctggaag tataaacaag aaaggaggct gacggctcta gaagtcccaa     60
cctgttgtga tcttcagtag acaaacactc ctggtgtgtc acaggattca ggccactaaa    120
cctcggccgg ctgtctcctg gaatgaagaa agcaaaggaa gcctagagtg agacaaaga    180 agcccgaggc actctgagag ctgccatctt ttccttgttt gccgcctgac acttctcagc    240
aggatccaca tacccctaagg agtggaagac tccttggcgc ttggtgcttc aaccggactg    300
acttcctggg cctggagttg gcgattagag gtctgacatg gctcacctga tgactgtgca    360
gttgttgctc ctgctgatgt ggatggccga atgtgctcag tccagagcta ctcgggccag    420
gactgaactt ctcaatgtct gcatggatgc caaacaccac aaagaaaaac cgggccctga    480
ggacaattta cacgaccagt gcagcccctg gaagacgaat tcctgctgtt cacgaacac     540 aagccaggaa gcataagg acagttccta cctgtaccgg ttcaactggg accactgcgg     600
aactatgaca tcggaatgca acggcactt tatccagaaa cctgcctcta ttagtgttcc     660
cccacattgg gaccctggat tcaccagtgg gacaaagatg cgcgaaaaa acgggtcc      718

<210> SEQ ID NO 210
<211> LENGTH: 323
<212> TYPE: DNA
<213> ORGANISM: Mus musculus

<400> SEQUENCE: 210
attcggatcc ttcggaacta tgacatcgga atgcaaacgg cactttatcc aagacacctg     60
cctctatgag tgttccccga acttgggacc ctggatccag caggtggacc agagctggcg    120
caaagagcgg atccttgatg ttccctgtg caagaggac tgtcagcagt ggtgggagga     180
ctgccagagc ctttaccct gcaagagcaa ttggcacaag ggatggaact ggtcctcggg    240
gcataacgag tgtcctgtgg gagcctcctg ccatcccttc accttctact tccccacatc    300
tgctgctctg tgtgaggaaa tct                                            323
```

<210> SEQ ID NO 211
<211> LENGTH: 450
<212> TYPE: DNA
<213> ORGANISM: Mus musculus

<400> SEQUENCE: 211

| | | | | | | |
|---|---|---|---|---|---|---|
| attcggatcc | ttcctggaag | tataaaccag | aaaggaggct | gacggctcta | gaagtcccca | 60 |
| acctgttgtg | atcttcagta | gacaaacact | cctggtgtgt | cacaggattc | aggccactaa | 120 |
| acctcggccg | gctgtctcct | ggaatgaaga | aagcaaagga | agcctagagt | ggagacaaag | 180 |
| aagcccgagg | cactctgaga | gctggcatct | tttccttgtt | tgccgcctga | caattctcag | 240 |
| cagggtccac | atatcctaag | taagagtggg | agactccttt | gcgcttggtg | cttcaaccgg | 300 |
| actgaattcc | tgggcctgga | attggcgatt | agaggtccga | catggctcaa | ctgatgacct | 360 |
| tgcaattgtt | ggccccggtg | atgtggatgg | gcgaaagtgc | ttcagttcaa | gaagctactt | 420 |
| cgggccaagg | actgaaactt | tctcaaatgt | | | | 450 |

<210> SEQ ID NO 212
<211> LENGTH: 682
<212> TYPE: DNA
<213> ORGANISM: Mus musculus

<400> SEQUENCE: 212

| | | | | | | |
|---|---|---|---|---|---|---|
| gaagactcct | tggcgcttgg | tgcttcaacc | ggactgactt | cctgggcctg | gagttggcga | 60 |
| ttagaggtct | gacatggctc | acctgatgac | tgtgcagttg | ttgctcctgg | tgatgtggat | 120 |
| ggccgaatgt | gctcagtcca | gagctactcg | ggccaggact | gaacttctca | atgtctgcat | 180 |
| ggatgccaaa | caccacaaag | aaaaaccggg | ccctgaggac | aatttacacg | accagtgcag | 240 |
| cccctggaag | acgaattcct | gctgttccac | gaacacaagc | caggaagcac | ataaggacat | 300 |
| ttcctacctg | taccggttca | actggaacca | ctgcggaact | atgacatcgg | aatgcaaacg | 360 |
| gcactttatc | caagacacct | gcctctatga | gtgttcccccg | aacttgggac | cctggatcca | 420 |
| gcaggtggac | cagagctggc | gcaaagagcg | gatccttgat | gttcccctgt | gcaaagagga | 480 |
| ctgtcagcag | tggtgggagg | actgccagag | ctcttttacc | tgcaagagca | attggcacaa | 540 |
| gggatggaac | tggtcctcgg | ggcataacga | gtgtcctgtg | ggagcctcct | gccatccctt | 600 |
| caccttccta | cttcccaaca | tctgctgctc | tgtgtgagga | aatctggagt | cactcctcaa | 660 |
| gctcagcaac | tacagttcga | gg | | | | 682 |

<210> SEQ ID NO 213
<211> LENGTH: 411
<212> TYPE: DNA
<213> ORGANISM: Mus musculus

<400> SEQUENCE: 213

| | | | | | | |
|---|---|---|---|---|---|---|
| cgggccctga | ggacaattta | cacgaccagt | gcagcccctg | aagacgaat | tcctgctgtt | 60 |
| ccacgaacac | aagccaggaa | gcacataagg | acatttccta | cctgtaccgg | ttcaactgga | 120 |
| accactgcgg | aactatgaca | tcggaatgca | aacggcactt | tatccaagac | acctgcctct | 180 |
| atgagtgttc | cccgaacttg | ggaccctgga | tccagcaggt | ggaccagagc | tggcgcaaag | 240 |
| agcggatcct | tgatgttccc | ctgtgcaaag | aggactgtca | gcagtggacg | gaggactgcc | 300 |
| agagctcttt | tacctgcaag | agcaattggc | acaagggatg | gaactggtcc | tctgggcata | 360 |
| acgagtgtcc | tgtgggagcc | tcctgccatc | ccttcacctt | ctacttcccc | a | 411 |

<210> SEQ ID NO 214
<211> LENGTH: 653
<212> TYPE: DNA
<213> ORGANISM: Mus musculus

<400> SEQUENCE: 214

```
ctggagctga gcacacactt ggaggttcca cttaccttag ctctgccttc agggtctgac        60
atggctcacc tgatgactgt gcagttgtgg ctgctggtga tgtggatggc cgaatgtgct       120
cagtccagag ctactcgggc caggactgaa cttctcaatg tctgcatgga tgccaaacac       180
cacaaagaaa aaccgggccc tgaggacaat ttacacgacc agtgcagccc tggaagacg        240
aattcctgct gttccacgaa cacaagccag gaagcacata aggacatttc ctacctgtac       300
cggttcaact ggaaccactg cggaactatg acatcggaat gcaacggca ctttatccaa        360
gacacctggc tctatgagtg ttccccgaac ttgggaccct ggattcagca ggtggaccaa       420
agctggcgca agagagggat cctttatgtt ccctgtgc aaagaggact tgtcagcagt         480
tggtgggagg actgccagaa ctcgtgtacc tgccaggagc aattggcaca agggatggaa       540
ttggttcttc gggcataac gaagtgctct gtgtggagcc tcctgcagtc ctgtaacgtc        600
taattcccac atttggcggt ctgtgtaatg aatctcgggc actccacagg ctc              653
```

<210> SEQ ID NO 215
<211> LENGTH: 256
<212> TYPE: DNA
<213> ORGANISM: Homo sapiens

<400> SEQUENCE: 215

```
acacctgcct ctacgagtgc tcccccaact tggggccctg gatccagcag gtggatcaga        60
gctggcgcaa agagcgggta ctgaacgtgc ccctgtgcaa agaggactgt gagcaatggt       120
gggaagattg tcgcacctcc tacacctgca agagcaactg gcacaagggc tgcaactgga       180
cttcagggtt taacaagtgc gcagtgggag ctgcctgcca acctttccat ttctacttcc       240
ccacacccat tgcccg                                                       256
```

<210> SEQ ID NO 216
<211> LENGTH: 1282
<212> TYPE: DNA
<213> ORGANISM: Homo sapiens

<400> SEQUENCE: 216

```
gtgtccccag aagtggcctt gaaccgaata tctccaatgg acagggctgg ggagcccaca        60
gggctggtgc ggcgggagtc agtggaggcg aagatgcaga gtgccagctg aaggtcaga        120
atacgctcca ccaccatggc ctggccctgc gttgtgttgt tggtagagcg cgttgtctac       180
cctgtaccga agacagaggc tgtggggaca gccaggggc cctggatcta ttgcctactt       240
agagagaggc caactcagac acagccgtgt atgctcccag cagcaacgga ggttcagcac       300
cgcctgcagg gacagaaaga catggtctgg aaatggatgc cacttctgct gcttctggtc       360
tgtgtagcca ccatgtgcag tgcccaggac aggactgatc tcctcaatgt ctgtatggat       420
gccaagcacc acaagacaaa gccaggtcct gaggacaagc tgcatgacca atgcagtccc       480
tggaagaaga tgcctgctg cacagccagc accagccagg agctgcacaa ggacacctcc       540
cgcctgtaca actttaactg ggaccactgc ggcaagatgg agcccgcctg cagcgccact       600
tcatccagga cacctgtctc tatgagtgct caccaacctg gggccctgga tccagcaggt       660
gaatcagagc tggcggcaaa gaacgcttcc tggatgtgcc cttatgcaaa gagcactgtc       720
```

```
agcgctggtg ggaggattgt cacacctccc acacgtgcaa gagcaactgg cacagaggat    780
gggactggac ctcaggagtt aacaagtgcc cagctgggc tctctgccgc acctttgagt    840
cctacttccc cactccagct gcccttgtc aaggcctctg gagtcactca tacaaggtca    900
gcaactacag ccgagggagc ggccgctgca tccagatgtg gtttacttca gcccagggca    960 acccccaacga ggaagtggcg aggttctatg ctgcagccat gcatgtgaat gctggtgaga   1020
tgcttcatgg gactggggt ctcctgctca gtctggccct gatgctgacc ctctggctcc    1080
tcggctgcgt tcagtcctcc cagactacct gccctcagct tggataacca ggctgggctc   1140
agctcagctc ccacaaatga cagccccttta agcatgcttc tattagtcac ctaaccctct   1200
gtcacccagt ctgttgctgc tccatggtgg ggccaagagt cacttctaat aaacagactg   1260 tttttctaata aaaaaaaaaa aa                                           1282

<210> SEQ ID NO 217
<211> LENGTH: 211
<212> TYPE: DNA
<213> ORGANISM: Mus musculus

<400> SEQUENCE: 217
aggattctat gccgaggcca tgagtggagc tgggcttcat gggacctggc cactcttgtg     60
cagcctgtcc ttagtgctgc tctgggtgat cagctgagtt cctgttttac cttcagttgt    120
ctggagcgcc accctgcttg gctcagcctc ccagctccca gcctcctttg tggtggggct    180
ctgacagcct ctttaataaa ccagacattc c                                   211

<210> SEQ ID NO 218
<211> LENGTH: 559
<212> TYPE: DNA
<213> ORGANISM: Mus musculus

<400> SEQUENCE: 218
attaggatcc ttccttctca gcaggatcca catacccctaa ggagtggaag actccttggc    60
gcttggtgct tcaaccggac tgacttcctg ggcctggagt tggcgattag aggtctgaca   120
tggctcaact gatgactgtg cagttgttgc tcctggtgat gtggatggcc gaatgtgctc   180
agtccagagc tactcgggcc aggactgaac ttctcaatgt ctgcatggat gccaaacacc   240
acaaagaaaa accgggccct gaggacaatt tacacgacca gtgcagcccc tggaagacga   300
attcctgctg ttccacgaac acaagccagg aagcacataa ggacatttcc tacctgtacc   360
ggttcaactg gaaccactgc ggaaatatga atcggaatg caaacggcac tttatccaag   420
aaaccttgac tcaatgagtg ttacacgaaa cttgggacac tggataagca agtggaacag   480
agatgggcga aaagagcgga tacattgatg taaccctgtg acaagaggac tgttcagcag   540
tggtgggagg actgccaga                                                 559

<210> SEQ ID NO 219
<211> LENGTH: 661
<212> TYPE: DNA
<213> ORGANISM: Mus musculus

<400> SEQUENCE: 219
aattcggatc catgatctgg aagtataaac aagaaggag gctgacggct ctagaagtcc      60
ccaacctgtt gtgatcttca gtagacaaac actcctggtg tgtcacagga ttcaggccac   120
taaacctcgg ccggctgtct cctgaatga agaaagcaaa ggaagcctag agtggagaca   180
aagaagcccg aggcactctg agagctgcca tcttttcctt gtttgccgcc tgacacttct   240
```

```
cagcaggatc cacatacect aagcagggag tggagagagg cctgggctgg gccaggtttt      300
ctgggctttt tcctgtgctc cgagtaggtg ggttgtattt tacccagtag gagtggaaga      360
ctccttggcg cttggtgctt caaccggact gacttcctgg gcctggagtt ggcgattaga      420
ggtctgacat ggctcacctg atgactgtgc agttgttgct cctggtgatg tggatggccg      480
aatgtgctca gtccagagct actcgggcca ggactgaact tctcaatgtc tgcatggatg      540
ccaaacacca caaagaaaaa ccgggccctg aggacaattt acacgaccag tgcagcccct      600
ggaagacgaa ttcctgctgt tcaacgacac aagcaggaag cactaaggac ttttctactg      660
t                                                                      661

<210> SEQ ID NO 220
<211> LENGTH: 695
<212> TYPE: DNA
<213> ORGANISM: Mus musculus

<400> SEQUENCE: 220
ttcggatcct tctctggaag tataaacaag aaaggaggct gacggctcta gaagtcccca       60
acctgttgtg atcttcagta gacaaacact cctggtgtgt cacaggattc aggccactaa      120
acctcggccg gctgtctcct ggaatgaaga aagcaaagga agcctagagt ggagacaaag      180
aagcccgagg cactctgaga gctgccatct tttccttgtt tgccgcctga cacttctcag      240
caggatccac atacectaag gagtggaaga ctccttggcg cttggtgctt caaccggact      300
gacttcctgg gcctggagtt ggcgattaga ggtctgacat ggctcacctg atgactgtgc      360
agttgttgct cctggtgatg tggatggccg aatgtgctca gtccagagct actcggggcc      420
aggactgaac ttctcaatgt ctgcatggat gccaaacacc acaaagaaaa accgggccct      480
gaggacaatt tacacgacca gtgcagcccc tggaagacga attcctgctg ttccacgaac      540
acaagccagg aagcacataa ggacatttcc tacctgtacc ggttcaactg gaaccactgc      600
ggaactatga catcggaatg caaacggcac tttatccaag cacctgcct ctatgagtgt       660 tccccgaact tgggactgga ttcagcaggt ggacc                                 695

<210> SEQ ID NO 221
<211> LENGTH: 567
<212> TYPE: DNA
<213> ORGANISM: Mus musculus

<400> SEQUENCE: 221
tggaagactc cttggcgctt ggtgcttcaa ccggactgac ttcctgggcc tggagttggc       60
atttagaggt ctgacatggc tcacctgatg actgtgcagt tgttgctcct ggtgatgtgg      120
atggccgaat gtgctcagtc cagagctact cgggccagga ctgaacttct caatgtctgc      180
atggatgcca agcaccacaa agaaaaaccg ggccctgagg acaatttaca cgaccagtgc      240 agccctgga agacgaattc ctgctgttcc acgaacacaa gccaggaagc acataaggac       300
atttcctacc tgtaccggtt caactggaac cactgcggaa ctatgacatc ggaatggcaa      360
cggcactttt atcaaagaca cctgcctcta tgagtgttcc ccgaactttg ggaacctgga      420
ttccagaagt tggacagagc ctgcgcaaaa gagcggattc ttgatggttc cctgtgcaaa      480
gaggactgtc agcagtggtg ggagactgcc aagctctta cctgcaagag cattggcaca       540
aggatggaat ggtcctctgg caaacga                                          567

<210> SEQ ID NO 222
```

<211> LENGTH: 600
<212> TYPE: DNA
<213> ORGANISM: Mus musculus

<400> SEQUENCE: 222

```
atggctccct gatgactgtg cagttgttgc tcctgctgat gtggatggcc gaatgtgctc      60
agtccagagc tactcgggcc aggactgaac ttctcagtgt ctgcatggat gccagacacc     120
acaaagagaa accgggccct gaggacaatt tacacgacca gtgcagcccc tggaagacga     180
attcctgctg ttccacgaac acaagccagt aagcacataa ggacatttcc tacctgtacc     240
ggttcaactg gaaccactgc ggaactatga catcggaatg caaacggcac tttatccaag     300
acagctgcct ctatgagtgt tccccgaact tgggagcctg tatgcagcag gtggacgaga     360
gctgtcgcaa agagcggatc cttgatgtgc ccctgtgcaa agaggactgt cagcagtggt     420
gcgagtgctg cggagctctt gtacctgcag agaggaattt gcacagggga tggaactggt     480
tccctggggc ataacaagtg tcctgtggta gcctgccggc aggccgttag cgttgtagtt     540
tcgcggatcg gctggtcggg tgaagaagtt gtggggcatg ccacatgtca gtagtttgtt     600
```

<210> SEQ ID NO 223
<211> LENGTH: 582
<212> TYPE: DNA
<213> ORGANISM: Mus musculus

<400> SEQUENCE: 223

```
aattcgcatc cttcataaac aagacaggag gctgacggct ctagaagtcc ccaacctgtt      60
gtgatcttca gtagacaaac actcctggtg tgtcacagga ttcaggccac taaacctcgg     120
ccggctgtct cctggaatga agaaagcaaa ggaagcctag agtggagaca agaagcccg      180
aggcactctg agagctgcca tcttttcctt gtttgccgcc tgacacttct cagcaggatc     240
cacatacccct aaggagtgga agactccttg gcgcttggtg cttcaaccgg actgacttcc     300
tgggcctgga gttggcgatt agaggtctga catggctcac ctgatgactg tgcagttgtt     360
gctcctggtg atgttgatgg ccgaatgtgc tcagtccaga gctactcggg ccaggactga     420
acttctcaat gtctgcatgg atgccaaaca ccacaaagaa aaaccgggcc ctgaggacaa     480
tttacacgac cagtgcagcc cctggaagac gaatttctgc tgttccacga acacaagcca     540
ggaagcacat aaggacattt cctaactgta acggttcaat gg                        582
```

<210> SEQ ID NO 224
<211> LENGTH: 372
<212> TYPE: DNA
<213> ORGANISM: Mus musculus

<400> SEQUENCE: 224

```
tcccatttcc tacctgtacc ggttcaactg gaaccactgc ggaactatga catcggaatg      60
caaacggcac tttatccaag acacctgcct ctatgagtgt tccccgaact tgggaccctg     120
gatccagcag gtggaccaga gctggcgcaa agagcggatc cttgatgttc ccctgtgcaa     180
agaggactgt cagcagtggt gggaggactg ccagagctct tttacctgca gagcaattg     240
gcacaaggga tggaactggt cctcggggca taacgagtg cctgtgggag cctcctgcca     300
tcccttcacc ttctacttcc ccacatctgc tgctctgtgt gaggaaatct ggagtcactc     360
ctacgagctc ag                                                         372
```

<210> SEQ ID NO 225
<211> LENGTH: 375

```
<212> TYPE: DNA
<213> ORGANISM: Mus musculus

<400> SEQUENCE: 225
ctatcccatt tcctacctgt accggttcaa ctggaaccac tgcggaacta tgacatcgga      60
atgcaaacgg cactttatcc aagacacctg cctctatgag tgttccccga acttgggacc     120
ctggatccag caggtggacc agagctggcg caaagagcgg atccttgatg ttcccctgtg     180
caaagaggac tgtcagcagt ggtgggagga ctgccagagc tctttttacct gcaagagcaa    240 ttggcacaag ggatggaact ggtcctcggg gcataacgag tgtcctgtgg gagcctcctg     300
ccatcccttc accttctact tccccacatc tgctgctctg tgtgaggaaa tctggagtca     360
ctcctacaag ctcag                                                     375

<210> SEQ ID NO 226
<211> LENGTH: 440
<212> TYPE: DNA
<213> ORGANISM: Mus musculus

<400> SEQUENCE: 226
tatccctgag agctgccatc ttttccttgt ttgccgcctg acacttctca gcaggatcca      60 catacccta gggagtggag agaggcctgg gctgggccag gttttctggg cttttt cctg     120 tgctccagt cagtgggttg tattttaccc agtaggagtg aaagactcct tggcgcttgg      180
tgcttcaacc ggaactgact tcctgggcct ggagttggcg attagaggtc ctacatggct    240
cacctgatga ctgtgcaagt tgtgcccccg gtgatgttga atggcggatg tgctcagtcc    300
agaagtaatt tgggccaaga ctggacttct ccatggctgc attgatggca aacacccaa     360 aggaaaacgg ggccttgggg caattatcac ggccctgtaa cccttggaaa ccaattcccg   420
ggttccgaaa cacagccgga                                               440

<210> SEQ ID NO 227
<211> LENGTH: 544
<212> TYPE: DNA
<213> ORGANISM: Mus musculus

<400> SEQUENCE: 227
aattcggatc catgggctga tctggaagta taaacaagaa aggaggctga cggctctaga      60
agtccccaac ctgttgtgat cttcagtaga caaacactcc tggtgtgtca caggattcag     120
gccactaaac ctcggccggc tgtctcctgg aatgaagaaa gcaaaggaag cctagagtgg     180
agacaaagaa gcccgaggac tctgagagct gccatctttt ccttgtttgc cgcctgacac     240
ttctcagcag gatccacata ccctaaggga gtggagagag gcctgggctg gcaggttttt     300
ctgggctttt tcctgtgctc cgagtaggtg ggttgtattt tacccagtag gagtggaaga     360
ctccttggcg cttggtgctt caaccggact gacttcctgg gcctggagtt ggcgattaga     420
ggtctgacat ggctcacctg atgactgtgc agttgttgct cctggtgatg tggatggccg     480
aatgtgctca gtccagagct actcgggcca ggactgaact tctcaatgtc tgcatggatg     540
ccaa                                                                544

<210> SEQ ID NO 228
<211> LENGTH: 350
<212> TYPE: DNA
<213> ORGANISM: Mus musculus

<400> SEQUENCE: 228
```

```
ttggcatcca tgcagacatt gagaagttca gtcctggccc gagtagctct ggactgagca    60
cattcggcca tccacatcac caggagcaac aactgcacag tcatcaggtg agccatgtca   120
gacctctaat cgccaactcc aggcccagga agtcagtccg gttgaagcac aagcgccaa   180 ggagtcttcc actcctactg ggtaaaatac aacccaccta ctcggagcac aggaaaaagc   240
ccagaaaacc tggcccagcc caggcctctc tccactccct tagggtatgt ggatcctgct   300
gagaagtgtc aggcggcaaa caaggaaaag atggcagctc tcagagtgcc               350

<210> SEQ ID NO 229
<211> LENGTH: 563
<212> TYPE: DNA
<213> ORGANISM: Mus musculus

<400> SEQUENCE: 229
ttcggatcca tggtgctccg agtaggtggg ttgtattta cccagtagga gtggaagact     60
ccttggcgct tggtgcttca accgactga cttcctgggc ctggagttgg cgattagagg    120
tctgacatgg ctcacctgat gactgtgcag ttgttgctcc tggtgatgtg gatggccgaa   180
tgtgctcagt ccagagctac tcgggccagg actgaacttc tcaatgtctg catggatgcc   240
aaacaccaca agaaaaaacc gggccctgag gacaatttac acgaccagtg cagccctgg    300 aagacgaatt cctgctgttc cacgaacaca agccaggaag cacataagga catttcctac   360
ctgtaccggt tcaactggaa ccactgcgga actatgacat cggaatgcaa acggcacttt   420
atccaagaca cctgcctcta tgagtgttcc ccgaacttgg accctggat ccagcaagtg    480 gaccagagct ggcgcaagag cggatccttg aatgtccctg tgcaagagga ctgtcagcag   540
tggtgggaga ctgcagagct ctt                                             563

<210> SEQ ID NO 230
<211> LENGTH: 587
<212> TYPE: DNA
<213> ORGANISM: Mus musculus

<400> SEQUENCE: 230
aattcgggat ccatgggctg atctggaagt ataaacaaga aggaggctg acggctctag      60 aagtccccaa cctgttgtga tcttcagtag acaaacactc ctggtgtgtc acaggattca    120
gctctgtttc ctaggccact aaacctcggc cggctgtctc ctggaatgaa gaaagcaaag   180
gaagcctaga gtgagacaa agaagcccga ggcactctga gagctgccat cttttccttg    240
tttgccgcct gacacttctc agcaggatcc acatacccta aggagtggaa gactccttgg   300
cgcttggtgc ttcaaccgga ctgacttcct gggcctggag ttggcgatta gaggtctgac   360
atggctcacc tgatgactgt gcagttgttg ctcctggtga tgtggatggc cgaatgtgct   420
cagtccagag ctactcgggc caggactgaa cttctcaatg tctgcatgga tgccaaacac   480
cacaaagaaa aacccgggccc tgaggacaat ttacacgacc agtgcagccc ctggaagacg  540
aattcctgct gttccacgaa cacaagccag gaagcacata aggacat                   587

<210> SEQ ID NO 231
<211> LENGTH: 557
<212> TYPE: DNA
<213> ORGANISM: Mus musculus

<400> SEQUENCE: 231
attcggatcc acgtataaac aagaaaggag gctgacggct ctagaagtcc ccaacctgtt     60
gtgatcttca gtagacaaac actcctggtg tgtcacagga ttcagctctg tttcctaggc   120
```

```
cactaaacct cggccggctg tctcctggaa tgaagaaagc aaaggaagcc tagagtggag    180
acaaagaagc ccgaggcact ctgagagctg ccatcttttc cttgtttgcc gcctgacact    240
tctcagcagg atccacatac cctaagggag tggagagagg cctgggctgg gcaggttttc    300 tgggctttt cctgtgctcc gagtaggtgg gttgtatttt acccagtagg agtggaagac     360
tccttggcgc ttggtgcttc aaccggactg acttcctggg cctggagttg cgattagag     420 gtctgacatg gctcacctga tgactgtgca gttgttgctc ctggtgatgt ggatggccga    480
attggctcat ccaaagcta ctcgggccgg aactgaactc ctcaaggtct gcatggatgc     540
aaacgccaca agaaaa                                                    557

<210> SEQ ID NO 232
<211> LENGTH: 613
<212> TYPE: DNA
<213> ORGANISM: Mus musculus

<400> SEQUENCE: 232
gttcggatcc atgggctgat ctggaagtat aaacaagaaa ggaggctgac ggctctagaa    60
gtccccaacc tgttgtgatc ttcagtagac aaacactcct ggtgtgtcac aggattcagc    120
tctgtttcct aggccactaa acctcggccg gctgtctcct ggaatgaaga agcaaagga    180 agcctagagt gggacaaag aagcccgagg cactctgaga gctgccatct tttccttgtt    240
tgccgcctga cacttctcag caggatccac atacccctaag ggagtggaga gaggcctggg    300
ctgggccagg ttttctgggc ttttcctgtg ctccgagtag gtgggttgta ttttacccag    360
taggagtgga agactccttg gcgcttggtg cttcaaccgg actgacttcc tgggcctgga    420
gttggcgatt agaggtctga catggctcac ctgatgactg tgcagttgtt gctcctggtg    480
atgtggatgg cgaatgtgct cagtccagag ctactcgggc aagactgaa cttctcaatg    540 tctgcatgga tgccaacacc acaagaaaaa cggggcttga acaatttca cgacagtgca    600 gccctggaaa aga                                                       613

<210> SEQ ID NO 233
<211> LENGTH: 1230
<212> TYPE: DNA
<213> ORGANISM: Pig

<400> SEQUENCE: 233
gaattcgcgg ccgctccggg aagggggaa gggcacaact ccctcgggaa gctcgccgct     60
gcctcctgga gcagaaggca gacaaagcca tgccctggaa gctgacagcc cttctgctct    120
ttctggccgg ggtggtctcc gtgtgccgcg cccgggccag gacggacctg ctcaacgtct    180
gcatggatgc caagcaccac aaggtagagc caggccctga ggacgagctg cacgaccagt    240
gcgtcccctg gaagaagaac gcctgctgct ccgccagagt cagccacgag ctgcaccggg    300
acaagtcctc cctgtataac ttttcctggg agcactgcgg caggatggag ccggcctgca    360
agcgccactt cattcagaac aactgtctgt acgagtgctc gcccaacctg ggccctggt     420 tccaggaggt gaaccagaag tggcgcaaag agcggttcct gaacgtgccc ctctgcaaag    480
aggactgtct ggactggtgg gaagactgcc gcacctccta cacctgcaag agcagctggc    540
acaagggctg gaactggagc tcaggatcta accagtgtcc cacggggacc acctgcgaca    600
catttgagtc cttcttcccc acacccgcag cgctgtgtga gggcatctgg aatcacgatt    660
ataagttcac caactacagc cgggggcagcg gccgctgcat ccagatgtgg tttgacgcgg    720
```

```
ccgagggcaa ccccaacgag gaggtagcga ggttctacgc cttggccttg agtgcgggga      780
ccatgtccct tgggaccggg cctctcctgc tcagcgcagc cctgatgctg ccacttgggc      840
tccttgactg agtccggcgt ctccagacgg tccttctgcc tgtccccagc tttgatgacc      900
aggctggtct caactcagct cccaccaatg agggagccct aagcccgcct catctgttac      960
ccatccctct gtcatcaagt tcctgccgta gggtgggcct tggggtctct ctgacagcca     1020
gttctaacag gcagattaac agcactgtgt ctgatgggct gttttggttg tgagctggtg     1080
tgtggcagag gacagagccc atagcttttg gattccttca gcttagagaa atgagacctg     1140
ggtttgaatt ccagctctgc cactcactat gtcaagtgaa gcagttgcgc gacggctcta     1200
aaccataggc tcctcctcaa taaaatgaag                                      1230

<210> SEQ ID NO 234
<211> LENGTH: 317
<212> TYPE: DNA
<213> ORGANISM: Mus musculus

<400> SEQUENCE: 234
aatctggagt cactcctaca agctcagcaa ctacagtcga gggagcggcc gctgcattca       60
gatgtggttc gacccagccc agggcaaccc caacgaggaa gtggcgaggt tctatgccga      120
ggccatgagt ggagctgggt ttcatgggac ctggccactc ttgtgcagcc tgtccttagt      180
gctgctctgg gtgatcagct gagctcctgt tttaccttca gttgtctgga gcgccaccct      240
gcttggctca gcctcccagc tcccagcctc ctttgtggtg gggctctgac agcctcttta      300
ataaaccaga cattcca                                                    317

<210> SEQ ID NO 235
<211> LENGTH: 529
<212> TYPE: DNA
<213> ORGANISM: Mus musculus

<400> SEQUENCE: 235
cacgaacaca agccaggaag cacataagga catttcctac ctgtaccggt tcaactggaa       60
ccactgcgga actatgacat cggaatgcaa acggcacttt atccaagaca catgcctcta      120
tgagtattcc ccgaacttgg accctggat ccagcaggtg gaccagagct ggcgcaaaga      180
gcggatcctt gatgttcccc tgtgcaaaga ggactgtcag cagtggtggg aggactgcca      240
gagctctttt acctgcaaga gcaattggca aagggatgg aactggtcct cggggcataa      300
cgagtgtcct gtgtgagcct cctgccatcg cttcaccttc tacttcccca catctgctgc      360
tctgtgtgaa gaaatctgga gtcactccta caagcttaac aactacagtc gagggaagcg      420
gccgctgcag tcagatgtgg ttcgacccag ccatggcaaa cccagcgagg aagttgcgag      480
gtctatgccg aggcaatagt gagctggtgt ctggactgg gcactttgt                 529

<210> SEQ ID NO 236
<211> LENGTH: 557
<212> TYPE: DNA
<213> ORGANISM: Mus musculus

<400> SEQUENCE: 236
aagactgtag agactaccca gagtctgacc tagggacagg ccaactcgga taccccctatg       60 tgcgctccca gaagctaagg acattgagac agaaagacat ggcctggaaa cagacaccac      120
tcttgctttt ggtctacatg gtcacaacag gcagtggcgg gacagaacag acctactcaa      180
cgtttgcatg gatgccaaac accataagac aaagccgggc cccgaggaca agctgcatga      240
```

```
ccagtgtagt ccatggaaga aaaatgcctg ttgctcagtc aacaccagcc aggagctaca    300
caaggctgac tcccgtctgt acttcaactg ggatcactgt ggcaagatgg agcctgcctg    360
taagagtcac ttcatccaag actcctgcct gtatgattgt ttcccaaacc ttggcccttg    420
attcagtcaa gtggatcaag attgggctta aaaaggtttt cctgatgtgc ccctaatgca    480
agaagacctg tcaccagtgt tggaaagctt gtggtacctc ctttactggc agaagagact    540
ggcataaagc tcggact                                                   557
```

<210> SEQ ID NO 237
<211> LENGTH: 616
<212> TYPE: DNA
<213> ORGANISM: Mus musculus

<400> SEQUENCE: 237

```
attcggatcc atgggctgat ctggaagtat aaacaagaaa ggaggctgac ggctctagaa    60
gtcccaacct gttgtgatct tcagtagaca aacactcctg gtgtgtcaca ggattcagct   120
ctgtttccta ggccactaaa cctcggccgg ctgtctcctg aatgaagaa agcaaaggaa    180 gcctagagtg gagacaaaga agcccgaggc actctgagag ctgccatctt ttccttgttt   240
gccgcctgac acttctcagc aggatccaca taccctaagg agtggaagac tccttggcgc   300
ttggtgcttc aaccggactg acttcctggg cctggagttg gcgattagac tctgccttca   360
gggtctgaca tggctcacct gatgactgtg cagttgttgc tcctggtgat gtggatggcc   420
gaatgtgctc agtccagagc tactcgggcc aggactgaac ttctcaatgt ctgcatggat   480
gccaaacacc acagagaaag accgggccct gaggacaatt ttacacgaca gtgcagcccc   540
tggaagacga attcctgttg ttcacgaaca caagcaggat gacataggac atttctactg   600
taccgttcac tggaac                                                   616
```

<210> SEQ ID NO 238
<211> LENGTH: 648
<212> TYPE: DNA
<213> ORGANISM: Mus musculus
<220> FEATURE:
<221> NAME/KEY: modified_base
<222> LOCATION: (605)
<223> OTHER INFORMATION: N = A, C, G, or T/U

<400> SEQUENCE: 238

```
aattcggatc catgggctga tctggaagta taaacaagaa aggaggctga cggctctaga    60 gtccccaac ctgttgtgat cttcagtaga caaacactcc tggtgtgtca caggattcag   120
ctctgtttcc taggccacta aacctcggcc ggctgtctcc tggaatgaag aaagcaaagg   180
aagcctagag tggagacaaa gaagcccgag gcactctgag agctgccatc ttttccttgt   240
ttgccgcctg acacttctca gcaggatcca catacccta ggagtggaag actccttggc   300
gcttggtgct tcaaccggac tgacttcctg gcctggagt ggcgattag actctgcctt    360 cagggtctga catggctcac ctgatgactg tgcagttgtt gctcctggtg atgtggatgg   420
ccgaatgtgc tcagtccaga gctactcggg ccaggactga acttctcaat gtctgcatgg   480
atgccaaaca ccacaaagaa aaccgggcg ctgaggacaa tttacacgac cagtgcagca   540
cctggaagac gaattcctgg ctgttcacga gcacaagcta ggaagcacat aaggacattt   600
tctanctgta ccggttcaac tggacccact gcggactatg acatcgga               648
```

<210> SEQ ID NO 239

```
<211> LENGTH: 636
<212> TYPE: DNA
<213> ORGANISM: Mus musculus

<400> SEQUENCE: 239
attcggatcc atgcagctta gaagggcctc cagctttagg ctttatagat acctggccca      60
cccttcccca gtcagcaggc tgatctggaa gtataaacaa gaaaggaggc tgacggctct     120
agaagtcccc aacctgttgt gatcttcagt agacaaacac tcctggtgtg tcacaggatt     180
caggccacta aacctcggcc ggctgtctcc tggaatgaag aaagcaaagg aagcctagag     240
tggagacaaa gaagcccgag gcactctgag agctgccatc ttttccttgt ttgccgcctg     300
acacttctca gcaggatcca catacccta agtaggagtgg aagactcctt ggcgcttggt     360
gcttcaaccg gactgacttc ctgggcctgg agttggcgat tagaggtctg acatggctca     420
cctgatgact gtgcagttgt tgctcctggt gatgtggatg ggcgaatgtg ctcagtccag     480
agctactcgg gccaggactg aacttctcaa tgtctgcatg gatgtcaaac accacaaaga     540
aacaccgggc ctgaggacaa tttacacgac cagtgcagcc cctggaagac gaatcctgct     600
gttccagaaa caagcaggag cacataggcc attcct                               636

<210> SEQ ID NO 240
<211> LENGTH: 660
<212> TYPE: DNA
<213> ORGANISM: Mus musculus

<400> SEQUENCE: 240
attcggatcc atgggctgat ctggaagtat aaacaagaaa ggaggctgac ggctctagaa      60
gtccccaacc tgttgtgatc ttcagtagac aaacactcct ggtgtgtcac aggattcagg     120
ccactaaacc tcggccggct gtctcctgga atgaagaaag caaggaagc ctagagtgga     180
gacaagaag cccgaggcac tctgagagct gccatctttt ccttgtttgc cgcctgacac     240
ttctcagcag gatccacata ccctaaggag tggaagactc cttggcgctt ggtgcttcaa     300
ccggactgac ttcctgggcc tggagttggc gattagaggt ctgacatggc tcacctgatg     360
actgtgcagt tgttgctcct ggtgatgtgg atggccgaat gtgctcagtc cagagctact     420
cgggccagga ctgaacttct caatgtctgc atggatgcca acaccacaa agaaaaaccg     480
ggccctgagg acaatttaca cgaccagtgc atgccctgga gacgaattc ctgctgttcc     540
acgaacacaa gccaggaagc acatagagac atttcctgct gtaccggttc aactggacca     600
ctgcggaact atgacatcga atgcagacgc actttgccag acactggct ctatgagtgt     660

<210> SEQ ID NO 241
<211> LENGTH: 578
<212> TYPE: DNA
<213> ORGANISM: Mus musculus

<400> SEQUENCE: 241
aattcggatc catgggctct agaagtcccc aacctgttgt gatcttcagt agacaaacac      60
tccgtggtgt gtcacaggat tcaggccact aaacctcggc cggctgtctc ctggaatgaa     120
gaaagcaaag gaagcctaga gtggagacaa agaagcccga ggcactctga gctgccat     180
cttttccttg tttgccgcct gacacttctc agcaggatcc atacccta aggagtggaa     240
gactccttgg cgcttggtgc ttcaaccgga ctgacttcct gggcctggag ttggcgatta     300
gaggtctgac atggctcacc tgatgactgt gcagttgttg ctcctggtga tgtggatggc     360
cgaatgtgct aagtccagag ctactcgggc caggactgaa ctcctaaatg tctgcatgga     420
```

```
tgccaaacac cacaaggaaa aacgggcccc tgaggacaat tacacgacca gtgcaagccc    480
tggaagacga aattctgctg ttcaagacca caagccagta gcatagggg acattccaac    540 ctgtaccgtt caacttgaac actgcggaat atgactcg                           578
```

<210> SEQ ID NO 242
<211> LENGTH: 403
<212> TYPE: DNA
<213> ORGANISM: Mus musculus

<400> SEQUENCE: 242

```
ccactaacca cataaggaca tttcctacct gtaccggttg acctgcaacg actgccgaac    60
tatgacatcg caatgcacac gccactttat cgaccacacc tgcctctatg agtgttaccc   120
gaacttcgca ccctccatcc accaggtgca cgacagctgg cccacagagc gcatccttca   180
tgttcccctg tccacagacg actgtcagca gtcgtcccag cactcccaca gctctcttac   240
ctgcaacacc aattcccaca acggatgaa ctcgtcctcg cggcatcacg agtgtcctgt    300
agcaccctcc tgccatccct tcaccttcta cttccgcaca tctcgtgctc tgtgtgatga   360
actctggagt cactcctaga cactcagcaa ctacagtcga cgg                     403
```

<210> SEQ ID NO 243
<211> LENGTH: 477
<212> TYPE: DNA
<213> ORGANISM: Mus musculus

<400> SEQUENCE: 243

```
aattcggatc catgcatgga tccggatcca tggcccctgg aagacgaatt cctgctgttc    60
cacgaacaca agccaggaag cacataagga catttcctac ctgtaccggt tcaactggaa   120
ccactgcgga actatgacat cggaatgcaa acggcacttt atccaagaca cctgcctcta   180
tgagtgttcc ccgaacttgg gaccctggat ccagcaggtg gaccagagct ggcgcaaaga   240
gcggatcctt gatgttcccc tgtgcaaaga ggactgtcag cagtggtggg aggactgcca   300
gagctctttt acctgcaaga gcaattggca caagggatgg aactggtcct cggggcataa   360
cgagtgtcct gtgggagcct cctgccatcc cttcaccttc tacttcccac atctgctgct   420
ctgtgtgagg aatctggagt cactctacaa gctcagcact acagtcgagg agccgcc      477
```

<210> SEQ ID NO 244
<211> LENGTH: 643
<212> TYPE: DNA
<213> ORGANISM: Mus musculus

<400> SEQUENCE: 244

```
ctgagtctga ggccagctgg tcgacaaggg tctgacatgg ctcacctgat gactgtgcag    60
ttgttgctcc tggtgatgtg gatggccgaa tgtgctcagt ccagagctac tcgggccagg   120
actgaacttc tcaatgtctg catggatgcc aaacaccaca agaaaaacc gggccctgag    180 gacaatttac acgaccagtg cagcccctgg aagacgaatt cctgctgttc cacgaacaca   240
agccaggaag cacataagga catttcctac ctgtaccggt tcaactggaa ccactgcgga   300
actatgacat cggaatgcaa acggcacttt atccaagaca cctgcctcta tgagtgttcc   360
ccgaacttgg gaccctggat ccagcaggtg gaccagagct ggcgcaaaga gcggatcctt   420
gatgttcccc tgtgcaaaga ggactgtcag cagtggtggg aggactgcca gagctctttt   480
acctgcaaga gcaattggca caagggatgg aactggtcct cggggcataa cgagtgtcct   540
```

```
gtgggagcct cctgccatcc gttcacttct acttcgcaca tctgctgtct gtgtgaggaa    600
tctggagtca ctctacaagt ctagaataca gtcgaggacc ggc                      643

<210> SEQ ID NO 245
<211> LENGTH: 351
<212> TYPE: DNA
<213> ORGANISM: Mus musculus

<400> SEQUENCE: 245
aaccactgcg gaactatgac atcggaatgc aaacggcact ttatccaaga cacctgcctc     60
tatgagtgtt ccccgaactt gggaccctgg atccagcagg tggaccagag ctggcgcaaa    120
gagcggatcc ttgatgttcc cctgtgcaaa gaggactgtc agcagtggtg ggaggactgc    180
cagagctctt ttacctgcaa gagcaattgg cacaagggat ggaactggtc ctcgggggca    240
taacgagtgt cctgtgggag cctcctggca tcccttcagc ttctacttcc ccacatctgg    300
ctgctcctgt gttaggaaaa tcttggattc actcctacca agcttcagca a             351

<210> SEQ ID NO 246
<211> LENGTH: 423
<212> TYPE: DNA
<213> ORGANISM: Mus musculus

<400> SEQUENCE: 246
aattcggcac tagggaggc tgacggctct agaagtcccc aacctgttgt gatcttcagt      60
agacaaacac tcctggtgtg tcacaggatt cagctctgtt tcctaggcca ctaaacctcg    120
gccggctgtc tcctggaatg aagaaagcaa aggaagccta gagtggagac aaagaagccc    180
gaggcactct gagagctgcc atcttttcct tgtttgccgc ctgacacttc tcagcaggat    240
ccacataccc taaggagtgg aagactcctt ggcgcttagt gctgctctgg gtgatcagct    300
gagctcctgt tttaccttca gttgtctgga gcgccaccct gcttggctca gcctcccagc    360
tcccagcctc ctttgtggtg gggctctgac agcctcttta ataaaccaga cattccaaaa    420
aag                                                                  423

<210> SEQ ID NO 247
<211> LENGTH: 638
<212> TYPE: DNA
<213> ORGANISM: Mus musculus

<400> SEQUENCE: 247
gtggacgaag actgtagaga ctacccagag tctgacctag ggagaggcca actcggatac     60
ccctatgtgc gctcccagaa gctaaggaca ttgagacaga aagacatggc ctggaaacag    120
acaccactct tgcttttggt ctacatggtc acaacaggca gtggccggga cagaacagac    180
ctactcaacg tttgcatgga tgccaaacac cataagacaa agccgggccc cgaggacaag    240
ctgcatgacc agtgtagtcc atggaagaaa aatgcctgtt gctcagtcaa caccagccag    300
gagctacaca aggctgactc ccgtctgtac ttcaactggg atcactgtgg caagatggag    360
cctgcctgta agagtcactt catccaagac tcctgcctgt atgagtgctc cccaaccttt    420
gggccttgga tccagcaagt ggaccagagt tggcgtaaag agcgtttcct ggatgtgccc    480
ttatgcagag aggactgtca ccagtggtgg gaagcctgtc gtacctcctt tacctgcaag    540
agagactggc ataaaggctg ggaatggtcg tcaggcatgt acaagtgcgc aacacagcac    600
ctgtacacgt gtgagtactc ttccgaacca gcagctttt                           638
```

<210> SEQ ID NO 248
<211> LENGTH: 638
<212> TYPE: DNA
<213> ORGANISM: Mus musculus

<400> SEQUENCE: 248

```
gggctgtgga cgaagactgt agagactacc cagagtctga cctagggaga ggccaactcg      60
gatacccta tgtgcgctcc cagaagctaa ggacattgag acagaaagac atggcctgga     120
aacagacacc actcttgctt ttggtctaca tggtcacaac aggcagtggc cgggacagaa     180
cagacctact caacgtttgc atggatgcca acaccataa gacaaagccg ggccccgagg     240
acaagctgca tgaccagtgt agtccatgga agaaaaatgc ctgttgctca gtcaacacca     300
gccaggagct acacaaggct gactcccgtc tgtacttcaa ctgggatcac tgtggcaaga     360
tggagcctgc ctgtaagagt cacttcatcc aagactcctg cctgtatgag tgctccccca     420
accttgggcc ttggatccag caagtggacc agagttggcg taaagagcgt ttcctggatg     480
tgccttatgc aaagaggact gtcaccagtg gtgggaagcc tgtcgtacgt cctttacctg     540
caagagagac tggcataaag gctgggactg gtctcaggca ttaccagtgc caaacacagg     600
accctgtaaa cgttgagtac tattccgaaa cagcagcc                            638
```

<210> SEQ ID NO 249
<211> LENGTH: 502
<212> TYPE: DNA
<213> ORGANISM: Mus musculus

<400> SEQUENCE: 249

```
ttcggcacag ggggctgtgg acgaagactg tagagactac ccagagtctg acctagggag      60
aggccaactc ggatacccct atgtgcgctc ccagaagcta aggacattga dacagaaaga     120
catggcctgg aaacagacac cactcttgct ttggtctac atggtcacaa caggcagtgg     180
ccgggacaga acagacctac tcaacgtttg catggatgcc aaacaccata agacaaagcc     240
gggccccgag gacaagctgc atgaccagtg tagtccatgg aagaaaaatg cctgttgctc     300
agtcaacacc agccaggagc tacacaaggc tgactcccgt ctgtacttca actgggatca     360
ctgtggcaag atggagcctg cctgtaagag tcacttcatc aagactcct gcctgtatga     420
gtgctcccc aaccttgggc cttggatcca gcaagtggac cagagttggc gtaaagagcg     480
tttcctggat gtgcccttat gc                                             502
```

<210> SEQ ID NO 250
<211> LENGTH: 1325
<212> TYPE: DNA
<213> ORGANISM: Homo sapiens

<400> SEQUENCE: 250

```
ggaaaggatt ttctcagccc ccatctccag cactgtgtgt tggccgcacc catgagagcc      60
tcagcactct gaaggtgcag ggggcaaagg ccaaaagagc tctggcctga acttgggtgg     120
tccctactgt gtgacttggg gcatggcctc atctgtgctg aaatgattcc acaaagatta     180
aactggctat catttgttga tttccccctt cttacattta atccttgcag gagaaagcta     240
agcctcaaga tagtttgctt ctctttcccc caaggccaag gagaaggtgg agtgagggct     300
ggggtcggga caggttgaac gggaaccctg tgctctaaca gttagggccc gccgaggaac     360
tgaacccaaa ggatcacctg gtattccctg agagtacaga tttctccggc gtggccctca     420
agggacagac atggctcagc ggatgacaac acagctgctg ctccttctag tgtgggtggc     480
```

```
tgtagtaggg gaggctcaga caaggattgc atgggccagg actgagcttc tcaatgtctg    540
catgaacgcc aagcaccaca aggaaaagcc aggccccgag acaagttgc atgagcagtg    600
tcgaccctgg aggaagaatg cctgctgttc taccaacacc agccaggaag cccataagga    660
tgtttcctac ctatatagat tcaactgaa ccactgtgga gagatggcac ctgcctgcaa    720
acggcatttc atccaggaca cctgcctcta cgagtgctcc cccaacttgg ggccctggat    780
ccagcaggtg gatcagagct ggcgcaaaga gcgggtactg aacgtgcccc tgtgcaaaga    840
ggactgtgag caatggtggg aagattgtcg cacctcctac acctgcaaga gcaactggca    900
caagggctgg aactggactt cagggtttaa caagtgcgca gtgggagctg cctgccaacc    960
tttccatttc tacttcccca cacccactgt tctgtgcaat gaaatctgga ctcactccta   1020
caaggtcagc aactacagcc gagggagtgg ccgctgcatc cagatgtggt tcgacccagc   1080
ccagggcaac cccaatgagg aggtggcgag gttctatgct gcagccatga gtggggctgg   1140
gccctgggca gctggccttt cctgcttag cctggcccta atgctgctgt ggctgctcag   1200
ctgacctcct tttaccttct gatacctgaa aatccctgcc ctgttcagcc ccacagctcc   1260
caactatttg gttcctgctc catggtcggg cctctgacag ccactttgaa taaaccagac   1320
accgc                                                              1325

<210> SEQ ID NO 251
<211> LENGTH: 819
<212> TYPE: DNA
<213> ORGANISM: Homo sapiens

<400> SEQUENCE: 251
cgcaggaata gatggacatg gcctggcaga tgatgcagct gctgcttctg gctttggtga     60
ctgctgcggg gagtgcccag cccaggagtg cgcgggccag gacggacctg ctcaatgtct    120
gcatgaacgc caagcaccac aagacacagc ccagccccga ggacgagctg tatggccagt    180
gcagtccctg gaagaagaat gcctgctgca cggccagcac cagccaggag ctgcacaagg    240
acacctcccg cctgtacaac tttaactggg atcactgtgg taagatggaa cccacctgca    300
agcgccactt tatccaggac agctgtctct atgagtgctc acccaacctg ggccctgga    360
tccggcaggt caaccagagc tggcgcaaag agcgcattct gaacgtgccc ctgtgcaaag    420
aggactgtga gcgctggtgg gaggactgtc gcacctccta cacctgcaaa agcaactggc    480
acaaaggctg gaattggacc tcagggatta atgagtgtcc ggccggggcc ctctgcagca    540
cctttgagtc ctacttcccc actccagccg ccctttgtga aggcctctgg agccactcct    600
tcaaggtcag caactatagt cgagggagcg gccgctgcat ccagatgtgg tttgactcag    660
cccagggcaa ccccaatgag gaggtggcca agttctatgc tgcggccatg aatgctgggg    720
ccccgtctcg tgggattatt gattcctgat ccaagaaggg tcctctgggg ttcttccaac    780
aacctattct aatagacaaa tccacatgaa aaaaaaaa                            819

<210> SEQ ID NO 252
<211> LENGTH: 283
<212> TYPE: DNA
<213> ORGANISM: Homo sapiens
<220> FEATURE:
<221> NAME/KEY: modified_base
<222> LOCATION: (259)
<223> OTHER INFORMATION: N = A, C, G, or T/U

<400> SEQUENCE: 252
catgagcagt gtcgaccctg gaggaagaat gcctgctgtt ctaccaacac cagccaggaa     60
```

```
gcccataagg atgtttccta cctatataga ttcaactgga accactgtgg agagatggca      120
cctgcctgca aacggcattt catccaggac acctgcctct acgagtgctc ccccaacttg      180
gggccctgga tccagcaggt ggatcagagc tggcgcaaag agcgggtact gaacgtgccc      240
ctgtgcaaag aggactgtna gcaaatggtg gggaagattg tcg                         283

<210> SEQ ID NO 253
<211> LENGTH: 834
<212> TYPE: DNA
<213> ORGANISM: Homo sapiens

<400> SEQUENCE: 253
gaattccgga caaggattgc atgggccagg actgagcttc tcaatgtctg catgaacgcc       60
aagcaccaca aggaaaagcc aggccccgag gacaagttgc atgagcagtg tcgaccctgg      120
aggaagaatg cctgctgttc taccaacacc agccaggaag cccataagga tgtttcttac      180
ctatatagat tcaactggaa ccactgtgga gagatggcac ctgcctgcaa acggcatttc      240
atccaggaca cctgcctcta cgagtgctcc cccaacttgg ggccctggat ccagcaggtg      300
gatcagagct ggcgcaaaga gcgggtactg aacgtgcccc tgtgcaaaga ggactgtgag      360
caatggtggg aagattgtcg cacctcctac acctgcaaga gcaactggca aagggctgg      420 aactggactt cagggtttaa caagtgcgca gtgggagctg cctgccaacc tttccatttc      480
tacttcccct ctcccactgt tctgtgcaat gaaatctgga ctcactccta caggtcagc       540 aactacagcc agggagtgg ccgctgcatc cagatgtggt tcgacccagc ccagggcaac      600
cccaatgagg aggtggcgag gttctatgct gcagccatga gtggggctgg gccctgggca      660
gcctggcctt tcctgcttag cctggcctaa tgctgctgtg gctgctcagc tgacctcctt      720
ttaccttctg atacctggaa atccctgccc tgttcagccc cacagctccc aactatttgg      780
ttcctgctcc atggtcgggc ctctgacagc cattttgaat aaaccagaca ccgc            834

<210> SEQ ID NO 254
<211> LENGTH: 1067
<212> TYPE: DNA
<213> ORGANISM: Homo sapiens

<400> SEQUENCE: 254
cctgtgtctt cccgcatcca gtgtagtctc tggagaaaga atgcctgagc tttaccagca       60
ccacccagga agcccataag aatattccca tctatatgga ttcaactgga accactgtgg      120
agagatggta cctgcctgca aacggcactt tatccaggac acctgccttt acgagtgacc      180
ccccaacttg gggccctgga tccagcaggt atgcatggct tcctggcatc caagagctag      240
cagaggagct gaattttcca ggcgtctctg caggcagcaa cccagctcc acttctattc       300 agggctgggt tcctgggatt cttgagcctg agcccttctt ttctaccaaa atctcccagg      360
tggatcagag ctggtgcaaa gagtgggtgc tgaatgtgcc cctgtgcaaa gaggactgtg      420
agcaatggtg ggaagattgt cgcacctcct acacctgcaa gagcaatggg cacaagggct      480
ggaactggac ctcaggtgag ggctggggtg ggcaggaaag gagggatttg gaagtgaagg      540
tgtgttgggt gtggaacagg tgtgtgacat tttgggttg tagggctggc agaatcagag      600
acctttgggg cccagtggct aaaggtcttc cctcttccta cagggtctaa caagtgccag      660
gtggcagctg cctgactacc tttccatctc tactttctca cacccactgc tctgtgcagt      720
gaaatctgga ctcactccta cagggtcagc aactacaacc gagggagcag ccgctgcatc      780
```

```
cagatgtggt tcgacctggc ccagggcaac cccaatgagg aggtggcaag gttctatgct     840
gcagctctga gtggggctgg gccctgggca gcctggcctc tcctgctcaa cctggcccta     900
atgctgctgt ggctgctcag ctgacctcct tttaccttct gatacttgga catccctgcc     960
ctgtttagcc ccacagctcc caactatttg gttcctcttc tatggtcttg tctctgacag    1020
ccactttgaa taaaccacac accacacatg tatcttgaga attattt                  1067
```

<210> SEQ ID NO 255
<211> LENGTH: 900
<212> TYPE: DNA
<213> ORGANISM: chicken

<400> SEQUENCE: 255

```
gaattcctct agggagaagt ctcacccaga aggacagcaa aagaggaaaa gaagggaaca      60
acaatgctga ggtttgccat caccctcttt gctgtcatca catcatctac ctgccagcag     120
tatggatgtc tggaagggga cacccacaaa gcgaagccaa gtcctgagcc aaacatgcat     180
gaatgcactc tgtattctga atcttcctgt tgctatgcaa acttcacaga gcaattggct     240
cattccccaa taattaaagt aagcaacagc tactggaaca gatgtgggca gctcagtaaa     300
tcctgtgaag atttcacaaa gaaatcgag  tgcttttacc ggtgttctcc gcacgctgct     360
cgctggatcg atcccagata tactgctgct attcagtctg ttccactgtg tcagagcttc     420
tgtgatgact ggtatgaagc tgcaaagat  gattccattt gtgctcataa ctggctgacg     480
gactgggaac gggatgaaag tggagaaaac cactgtaaga gtaaatgcgt accatacagt     540
gagatgtatg caaatgggac cgacatgtgc cagagtatgt gggggggaatc ctttaaggtg     600
agcgaatcct cctgcctctg cttgcaaatg aacaagaagg acatggtggc aatcaagcac     660
ctcctctccg aaagctcaga ggaaagctcc agtatgagca gcagtgagga gcacgcctgc     720
caaaagaaac tcctgaagtt tgaggcactg cagcaagagg aaggggaaga gagaagatga     780
attttggtgg atgaatatca ggaggagagg aatcattgtg gaggttgtgc tcggggcatc     840
acagcagcct gtcttatccc tcacttctga gaacacaata aatcaatggt tggctatatt     900
```

<210> SEQ ID NO 256
<211> LENGTH: 1223
<212> TYPE: DNA
<213> ORGANISM: Mus musculus

<400> SEQUENCE: 256

```
gctttagagg cagatcaggg tgtagttttc agctagcgcc gtgccttccc caccatgttc      60
cttgccatga tgataatgta ctagacctct gaaactgtag cttctttgtt acagagtctc     120
cgtgaatctg gaattcacca attcggcgag tctgaaagcc tcagtgatct ctcaggctcc     180
atctgtctcc actcccagt  ggaaggcttg cagctgtgtc accgctccag acttcacaca     240
ggtgctggaa gactgaacta agacagaaag acatggcctg gaaacagaca ccactcttgc     300
ttttggtcta catggtcaca acaggcagtg gccgggacag aacagaccta tcaacgtttt     360
gcatggatgc caaacaccat aagacaaagc cgggccccga ggacaagctg catgaccagt     420
gtagtccatg gaagaaaaat gcctgttgct cagtcaacac cagccaggag ctacacaagg     480
ctgactcccg tctgtacttc aactgggatc actgtggcaa gatggagcct gcctgtaaga     540
gtcacttcat ccaagactcc tgcctgtatg agtgctcccc caaccttggg ccttggatcc     600
agcaagtgga ccagagttgg cgtaaagagc gtttcctgga tgtgcccta  tgcaaagagg     660
actgtcacca gtggtgggaa gcctgtcgta cctcctttac ctgcaagaga gactggcata     720
```

```
aaggctggga ctggtcctca ggcattaaca agtgcccaaa cacagcaccc tgtcacacgt      780
ttgagtacta cttcccgaca ccagccagcc tttgcgaggg tctctggagt cactcctaca      840
aggtcagcaa ctacagcaga gggagtggcc gctgcatcca gatgtggttt gactcaaccc      900
agggcaatcc caatgaggac gtggtgaagt tttatgcttc ctttatgaca tctgggactg      960
tgccccatgc agcagtactt cttgtgccca gcctggcccc agtgctgtca ttatggctcc     1020
ctggctgaga ggtcagtctt cctctctaga tttctcctct atctacccctt ggtctggttc     1080 aactcttcaa agaataagga agtcttgagc ctgcttccac ccctctcctc tgtcatccag     1140
ttcctgatcc atgttggggg ttggggtttc tacaatcatt tcaataaat ctatgacaca      1200 tctgggccta atgaaaaaaa aaa                                              1223

<210> SEQ ID NO 257
<211> LENGTH: 1565
<212> TYPE: DNA
<213> ORGANISM: Mus musculus

<400> SEQUENCE: 257
ggatccaaga gattttatac tgtccttcag cactgtcctt cagttctttt tgttttttg       60 ttttttgttt tgttttgttt tggttttttc gagacagggt ttctctgtgt agccctggct      120
gtcctggaac tcactctgta gaccaggctg gcctcgaact cagaaatcca cctgcctctg      180
cctcccaagt gctgggttta aggcatacg ccaccacagc ccggctcttc ggttctttag       240
gtcattattt tttggggtag ggggacaaac aaattctcac tatgtatcac agattggcct      300
agaccccaca agccttcccc cttcccgtcc tccatgtcct ggggttgcag gcgtgtctca      360
ccaattgcag ctgggcttgt tttgtgtgtt tccttttgag aggtttcggt cgggtcgggt      420
gcttttgctg cagatgccgc tgtcaggatg gctgtcagg gcagaatggc ttttggagaa       480
caggaaagga aaatactgag gaagcaaaac tttacaaagc agcactcttt cttgtgtacc      540
ctctaaccac accatcctgt gggctgtcac ttggtcctcc tgccaatctg agaacttgg       600 cagggctggg tcaccacctc cctcaggggct aacaggactt ctaggctgac atgatgaccc     660
agctgataca gagtggaatg ccgagaaacct cctgtgacag gatgaaggat ctgtgtgtcc     720
ctggcccttg tcaaggtagc aagcagcagg aacctgaact atttaactat gtgtcataaa     780
gtctggaaat aagatgaaag catggggcat cccatcttct ctaggttgga aagctttgct     840
tcttttataa ccccccctccc caatgccatg gggccatggg ataaaagagt ctccttgctg    900
acctctattc cagcttcagg gagcctgagg acatgaatgc tgaaggagaa gggactgatc     960
taatctttca ctatagggac agagagtctg agtcagggaa taaatgaagt ccctccccccc    1020 tctggtctag gtctccctaa ctttagctcc ctctgcacag acagaaagac atggcctgga    1080
aacagacacc actcttgctt ttggtctaca tggtcacaac aggcagtggc cgggacagaa     1140
cagacctact caacgtttgc atggatgcca aacaccataa gacaaagccg gccccgagg     1200 acaagctgca tgaccaggtt ctgtgccagt gtggtcctga tgggagggtg atagagggca    1260
gggtggggtt agtgagcagc cagacacacc cacaccctga gctcttgttg gcagagatgg     1320
cttggtggaa agtagtgagg tgattttctg agggctgtcc ccagaagagg acacagtagt     1380
ggcaatgaag cagttgatca ttagaagcct ctaattagag gccacgtgag gtcatgtgat     1440
gataatctct atatctctca aataagggcc cgtggaagca cagggactca ctctcacagg    1500
ttagacacac ctgattttt ttttttgag agcattggtg ttttgcctac atatgtgttg      1560
```

```
gatcc                                                                  1565

<210> SEQ ID NO 258
<211> LENGTH: 1000
<212> TYPE: DNA
<213> ORGANISM: Mus musculus

<400> SEQUENCE: 258
tctagaattt tcagccctat cttaagcact atataacatg tgaaaaggaa caaagggct      60
tctaacacta gaaaaaattt aaggccaaac ataacttgta aagccatttt ccactttact    120
tctgatagac tgtcttgaat ttccttagaa agttcaagat cagacttacc tcgttcccca    180
gctgaaaagt tctgaattca tacagttgaa tccttcttaa cagtctgctt tacgggaacc    240
tttatcaccg tcgttcccca gctgatgagt tctgaattcg gcagttgaat ccttctcaac    300
agtctgtgtt acgggaacct tataaccttg attcgcagtt ctggttctgg aatgagggat    360
cttccttgcg ccagtcccga gttttttctc gtcccggatt ttctcgtccc ggaattcggc    420
accaattgtt attcgacgcg ttctcacgac cggccaggaa gaacaccaca gaccagaatc    480
ttctgcgaca aagctttatt cttacatctt caggaaaaga gagcaagaag caagagagag    540
caagaagcaa gagagggaag caagagagag caagaagcaa gagagggaag caagagagag    600
caaagcaaga gagagagaaa aacgaaaccc cttctatttt aaagagaaca accattgcct    660
agggcgcatc actccctgat tggctgcagc ccatggccga gctgacgttc acgggaaaaa    720
cagagtacaa gtagtcgtaa ataccccttgg ctcatgcgca gattatttgt ttaccaactt    780
agaacacagg atgtcagcgc catcttgtga cggcgaatgt gggggcggct cccacaagg    840
ctccacccac tggagctgag cacacacttg gaggttccac ttaccttagc tctgccttca    900
gggtctgaca tggctcacct gatgactgtg cagttgttgc tcctggtgat gtggatggcc    960
gaatgtgctc agtccagagc tactcgggcc aggactgaac                         1000

<210> SEQ ID NO 259
<211> LENGTH: 1391
<212> TYPE: DNA
<213> ORGANISM: Mus musculus

<400> SEQUENCE: 259
actagttgtg tctagatcct attgcactga tggtcatgaa gttgaaacat ggggaaaat      60
gaactttata cccttcttca tgacttctgt ccttttgcct gcctcctttc tcatctccta    120
atattacagt cttggtttcc tctctaaatt tttagacttt taacccacac ctaaacctgt    180
atcagctttt ataaaaatct tttcaaaact tcacactgaa gcatctgcct ccaaaggttt    240
tgaatgtgaa cgtgggtaaa ctctgttttt gcaaatggcc catctcttat tttttaattg    300
ccctgtgtga gtctcaggac cactaagtct aacaggctgt gaccagtgat tgtctctagg    360
gcatctgagc ctcacagagt ctgggaagac tgacaggagg aggtgaccca aggtctgtga    420
gtgcaggctc cacccactgg agctgagcac acacttggag gttccactta ccttagctct    480
gccttcaggg tctgacatgg ctcacctgat gactgtgcag ttgttgctcc tggtgatgtg    540
gatggccgaa tgtgctcagt ccagagctac tcggccagg actgaacttc tcaatgtctg    600
catggatgcc aagcaccaca agaaaaaacc gggccctgag acaatttac acgaccaggt    660
aggacgaagg gtgatgtgtg gctgactaag ggctcgtggg tcaggagaaa gaagtatcta    720
gtcccagttt atggtggagg tggtcagacc tacctgagga gaccttcggt tctctctagt    780
gtgggtgact ttgacagtac atattggctg ccaactgcca gtgtgatatt atcagctcat    840
```

```
cttcctggta gctgaatttt gacgttgcat aagtaaggaa gtagattcaa ggaggaactt      900
gggaatggaa caggcaaacc attgtgatgg ttttagattt aaactgattg gggaggacgc      960
ctctgggagt ctcaggggag ggactgtatg ctgcccagtc acttttctgc cagcctttga     1020
agacttgaga aggagactct catatctgag aagcctttgg aggcaggcat ctagcgaaca     1080
cttggactgt ggtcctcagc ttgagggctg gagggcttga gggctctgtg ttataacagt     1140
tgtttgccat agtgctttta gtatcccaaa gctcactaaa catttaataa aatcagtgtg     1200
atgcaacaac tatgaagtca accagcagca ggtctgctat tggggaggta caatcagtgc     1260
agacaacaaa gtgggagggg ggtctcaaaa aagccaagat gagggctgga gagttggctc     1320
agtggttaaa agcacttgtt gagcttgcag aataccaagg tctgatccac aacatccaag     1380
gtggtggatc c                                                          1391
```

<210> SEQ ID NO 260
<211> LENGTH: 979
<212> TYPE: DNA
<213> ORGANISM: Mus musculus

<400> SEQUENCE: 260

```
tggagctgag cacacacttg gaggttccac ttaccttagc tctgccttca gggtctgaca       60
tggctcacct gatgactgtg cagttgttgc tcctggtgat gtggatggcc gaatgtgctc      120
agtccagagc tactcgggcc aggactgaac ttctcaatgt ctgcatggat gccaagcacc      180
acaaagaaaa accgggccct gaggacaatt tacacgacca gtgcagcccc tggaagacga      240
attcctgctg ttccacgaac acaagccagg aagcacataa ggacatttcc tacctgtacc      300
ggttcaactg gaaccactgc ggaactatga catcggaatg caaacggcac tttatccaag      360
acacctgcct ctatgagtgt tccccgaact tgggaccctg gatccagcag gtggaccaga      420
gctggcgcaa agagcggatc cttgatgttc ccctgtgcaa agaggactgt cagcagtggt      480
gggaggactg ccagagctct tttacctgca agagcaattg gcacaaggga tggaactggt      540
cctctgggca taacgagtgt cctgtgggag cctcctgcca tcccttcacc ttctacttcc      600
ccacatctgc tgctctgtgt gaggaaatct ggagtcactc ctacaagctc agcaactaca      660
gccgagggag cggccgctgc attcagatgt ggtttgaccc agcccagggc aaccccaacg      720
aggaagtggc gaggttctat gccgaggcca tgagtggagc tgggcttcat gggacctggc      780
cactcttgtg cagcctgtcc ttagtgctgc tctgggtgat cagctgagtt cctgttttac      840
cttcagttgt ctggagcgcc accctgcttg gctcagcctc ccagctccca gcctcctttg      900
tggtggggct ctgacagcct ctttaataaa ccagacattc cacatgtgcc ttatgaatta      960
aaaaaaaaaa aaaaaaaa                                                   979
```

<210> SEQ ID NO 261
<211> LENGTH: 66
<212> TYPE: DNA
<213> ORGANISM: Homo sapiens

<400> SEQUENCE: 261

```
acaaggattg catgggccag gactgagctt ctcaatgtct gcatgaacgc caagcaccac       60
aaggaa                                                                 66
```

<210> SEQ ID NO 262
<211> LENGTH: 1108
<212> TYPE: DNA

<213> ORGANISM: Homo sapiens

<400> SEQUENCE: 262

```
ctggaggcct ggctggtgct cacatacaat aattaactgc tgagtggcct tcgcccaatc    60
ccaggctcca ctcctgggct ccattcccac tccctgcctg tctcctaggc cactaaacca   120
cagctgtccc ctggaataag gcaaggggga gtgtagagca gagcagaagc ctgagccaga   180
cggagagcca cctcctctcc cagggacaga catggctcag cggatgacaa cacagctgct   240
gctccttcta gtgtgggtgg ctgtagtagg ggaggctcag acaaggattg catgggccag   300
gactgagctt ctcaatgtct gcatgaacgc caagcaccac aaggaaaagc caggccccga   360
ggacaagttg catgagcagt gtcgaccctg gaggaagaat gcctgctgtt ctaccaacac   420
cagccaggaa gcccataagg atgtttccta cctatataga ttcaactgga accactgtgg   480
agagatggca cctgcctgca acggcatttt catccaggac acctgcctct acgagtgctc   540
ccccaacttg gggccctgga tccagcaggt ggatcagagc tggcgcaaag agcgggtact   600
gaacgtgccc ctgtgcaaag aggactgtga gcaatggtgg aagattgtc gcacctccta   660
cacctgcaag agcaactggc acaagggctg gaactggact tcagggttta caagtgcgc   720
agtgggagct gcctgccaac cttccattt ctacttcccc acaccactg ttctgtgcaa   780
tgaaatctgg actcactcct acaaggtcag caactacagc cgagggagtg gccgctgcat   840
ccagatgtgt ttcgacccag cccagggcaa ccccaatgag gaggtggcga ggttctatgc   900
tgcagccatg agtggggctg ggccctgggc agcctggcct ttcctgctta gcctggccct   960
aatgctgctg tggctgctca gctgacctcc ttttaccttc tgatacctgg aaatccctgc  1020
cctgttcagc cccacagctc ccaactattt ggttcctgct ccatggtcgg gcctctgaca  1080
gccactttga ataaaccaga caccgcac                                      1108
```

<210> SEQ ID NO 263
<211> LENGTH: 991
<212> TYPE: DNA
<213> ORGANISM: Homo sapiens

<400> SEQUENCE: 263

```
ggagagccac ctcctctccc aggaactgaa cccaaaggat cacctggtat tccctgagag    60
tacagatttc tccggcgtgg ccctcaaggg acagacatgg ctcagcggat gacaacacag   120
ctgctgctcc ttctagtgtg ggtggctgta gtaggggagg ctcagacaag gattgcatgg   180
gccaggacta gcttctcaa tgtctgcatg aacgccaagc accacaagga aaagccaggc   240
cccgaggaca agttgcatga gcagtgtcga ccctggagga gaatgcctg ctgttctacc   300
aacaccagcc aggaagccca taaggatgtt tcctacctat atagattcaa ctggaaccac   360
tgtggagaga tggcacctgc ctgcaaacgg catttcatcc aggacacctg cctctacgag   420
tgctccccca acttggggcc ctggatccag caggtggatc agagctggcg caaagagcgg   480
gtactgaacg tgcccctgtg caaagaggac tgtgagcaat ggtgggaaga ttgtcgcacc   540
tcctacacct gcaagagcaa ctggcacaag ggctggaact ggacttcagg gtttaacaag   600
tgcgcagtgg gagctgcctg ccaaccttc catttctact tccccacacc cactgttctg   660
tgcaatgaaa tctggactca ctcctacaag gtcagcaact acagccgagg gagtggccgc   720
tgcatccaga tgtggttcga cccagcccag ggcaacccca tgaggaggt ggcgaggttc   780
tatgctgcag ccatgagtgg ggctgggccc tgggcagcct ggccttcct gcttagcctg   840
gccctaatgc tgctgtggct gctcagctga cctccttta ccttctgata cctggaaatc   900
```

```
cctgccctgt tcagccccac agctcccaac tatttggttc ctgctccatg gtcgggcctc    960
tgacagccac tttgaataaa ccagacaccg c                                    991

<210> SEQ ID NO 264
<211> LENGTH: 1230
<212> TYPE: DNA
<213> ORGANISM: Homo sapiens

<400> SEQUENCE: 264
gaatcaattc ctccaaaccg caagaacagt aacatttatt attcaaaaaa acaaaaacca     60
gattatagga tatgacattt ggtataacaa taatgttatt gaaaaatgga aaaatgatcc    120
attaatggct tgggctaaaa attcggggga cagcctaggg gcctggatct attgcctact    180
tagagagagg ccaactcaga cacagccgtg tatgctccca gcagcaacgg aggttcacgt    240
ccgcctgcag ggacagaaag acatggtctg gaaatggatg ccacttctgc tgcttctggt    300
ctgtgtagcc accatgtgca gtgcccagga caggactgat ctcctcaatg tctgtatgga    360
tgccaagcac cacaagacaa agccaggtcc tgaggacaag ctgcatgacc aatgcagtcc    420
ctggaagaag aatgcctgct gcacagccag caccagccag gagctgcaca aggacacctc    480
ccgcctgtac aactttaact gggaccactg cggcaagatg gagcccgcct gcaagcgcca    540
cttcatccag gacacctgtc tctatgagtg ctcacccaac ctggggccct ggatccagca    600
ggtgaatcag acgtggcgaa agaacgctt cctggatgtg cccttatgca agaggactg     660 tcagcgctgg tgggaggatt gtcacacctc ccacacgtgc aagagcaact ggcacagagg    720
atgggactgg acctcaggag ttaacaagtg cccagctggg gctctctgcc gcacctttga    780
gtcctacttc cccactccag ctgccctttg tgaaggcctc tggagtcact catacaaggt    840
cagcaactac agccgaggga gcggccgctg catccagatg tggtttgatt cagcccaggg    900
caaccccaac gaggaagtgg cgaggttcta tgctgcagcc atgcatgtga atgctggtga    960
gatgcttcat gggactgggg gtctcctgct cagtctggcc ctgatgctgc aactctggct   1020
ccttggctga gttcagtcct cccagactac ctgccctcag cttggataac caggctgggc   1080
tcagctcagc tcccacaaat gacagcccct taagcatgct tctattagtc acctaaccct   1140
ctgtcaccca gtctgttgct gctccatggt ggggccaaga gtcacttcta ataaacagac   1200
tgttttctaa taaaaaaaaa aaaaaaaaa                                    1230

<210> SEQ ID NO 265
<211> LENGTH: 819
<212> TYPE: DNA
<213> ORGANISM: Homo sapiens

<400> SEQUENCE: 265
cgcaggaata gatggacatg gcctggcaga tgatgcagct gctgcttctg gctttggtga     60
ctgctgcggg gagtgcccag cccaggagtg cgcgggccag gacggacctg ctcaatgtct    120
gcatgaacgc caagcaccac aagacacagc ccagccccga ggacgagctg tatggccagt    180
gcagtccctg gaagaagaat gcctgctgca cggccagcac cagccaggag ctgcacaagg    240
acacctcccg cctgtacaac tttaactggg atcactgtgg taagatggaa cccacctgca    300
agcgccactt tatccaggac agctgtctct atgagtgctc acccaacctg ggccctgga    360 tccggcaggt caaccagagc tggcgcaaag agcgcattct gaacgtgccc ctgtgcaaag    420
aggactgtga gcgctggtgg gaggactgtc gcacctccta cacctgcaaa agcaactggc    480
```

```
acaaaggctg gaattggacc tcagggatta atgagtgtcc ggccggggcc ctctgcagca    540
cctttgagtc ctacttcccc actccagccg ccctttgtga aggcctctgg agccactcct    600
tcaaggtcag caactatagt cgagggagcg gccgctgcat ccagatgtgg tttgactcag    660
cccagggcaa ccccaatgag gaggtggcca agttctatgc tgcggccatg aatgctgggg    720
ccccgtctcg tgggattatt gattcctgat ccaagaaggg tcctctgggg ttcttccaac    780
aacctattct aatagacaaa tccacatgaa aaaaaaaa                            819

<210> SEQ ID NO 266
<211> LENGTH: 1123
<212> TYPE: DNA
<213> ORGANISM: Homo sapiens

<400> SEQUENCE: 266
gaggagggta tggggaggca cttagttcct gtgtcttccc cacccagtgc agtccctgga     60
agaagaatgc ctgctgcaca gccagcacca gccaggagct gcacaaggac acctcccgcc    120
tgtacaactt taactgggac cactgcggca agatggagcc cgcctgcaag cgccacttca    180
tccaggacac ctgtctctat gagtgctcac ccaacctggg gccctggatc cagcaggtag    240
ggtgtctccc ccccacccac cccagcagac tgccatcccc ctcagtcact tcaaggcgat    300
ggctgccagc atccctggct gagaggagcc ctgcctcccc acctcccacc caggtgaatc    360
agacgtggcg caaagaacgc ttcctggatg tgcccttatg caaagaggac tgtcagcgct    420
ggtgggagga ttgtctcacc tcccacacgt gcaagagcaa ctggcacaga ggatgggact    480
ggacctcagg tgagggtgat tgagttgggg ttaggaaaaa ggagattgag gtagggtttg    540
gaaaatcctc aaggatttgg ggtggggtga agatttctgg gggtggccag aaatgagctt    600
tgggcccagg ggctgaaagt ctgtgtccac catgcctctc cctgcaggag ttaacaagtg    660
cccagctggg gctctctgcc gcacctttga gtcctacttc cccactccag ctgcccttttg   720 tgaaggcctc tggagtcact catacaaggt cagcaactac agccgaggga gcggccgctg    780
catccagatg tggtttgatt cagcccaggg caaccccaac gaggaagtgg cgaggttcta    840
tgctgcagcc atgcatgtga atgctggtga atgcttcat gggactgggg gtctcctgct     900
caggctggcc ctgatgctgc aactctggct ccttggctga gttcagtcct cccagactac    960
ctgccctcag cttggataac caggctgggc tcagctcagc tcccacaaat gccagccct    1020 taagcatgct tctattagtc acctaaccct ctgtcaccca gtctgttgct gctccatggt   1080
ggggccaaga gtcacttcta ataaacagac tgttttctaa taa                    1123

<210> SEQ ID NO 267
<211> LENGTH: 374
<212> TYPE: DNA
<213> ORGANISM: Homo sapiens

<400> SEQUENCE: 267
agcttcaggg ccccagcatc gaaggaacag ggtctgacct catttgccac cgtagggatg     60
gggagactga ggcaggaggt gaatggctcc cagcttggag ccctttcccc tcaggacttg    120
gtttccctac cctacgtccg cctgcaggga cagaaagaca tggtctggaa atggatgcca    180
cttctgctgc ttctggtctg tgtagccacc atgtgcagtg cccaggacag gactgatctc    240
ctcaatgtct gtatggatgc caagcaccac aagacaaagc caggtcctga ggacaagctg    300
catgaccaag tacggctgga gtgtgcctct gctaaggagg ggcttgttct aacagggagg    360
agaaagtcag gatg                                                     374
```

```
<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 268

Glu Ile Trp Thr His Ser Tyr Lys Val
 1               5

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 269

Leu Leu Ser Leu Ala Leu Met Leu Leu
 1               5

<210> SEQ ID NO 270
<211> LENGTH: 4
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 270

Ser Tyr Lys Val
 1

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 271

Phe Ile Trp Thr Phe Ser Thr Lys Val
 1               5
```